(12) United States Patent
Tchistiakova et al.

(10) Patent No.: US 7,501,121 B2
(45) Date of Patent: Mar. 10, 2009

(54) IL-13 BINDING AGENTS

(75) Inventors: Lioudmila Tchistiakova, Andover, MA (US); Marion T. Kasaian, Charlestown, MA (US); Debra D. Donaldson, Medford, MA (US); Xiang-Yang Tan, Reading, MA (US); Davinder Gill, Burlington, MA (US); Macy X. Jin, Reading, MA (US); Bruce Jacobson, Framingham, MA (US); Samuel J. Goldman, Acton, MA (US); John Knopf, Carlisle, MA (US); Angela M. Widom, Acton, MA (US)

(73) Assignee: Wyeth, Madison, NJ (US)

( * ) Notice: Subject to any disclaimer, the term of this patent is extended or adjusted under 35 U.S.C. 154(b) by 271 days.

(21) Appl. No.: 11/155,843

(22) Filed: Jun. 17, 2005

(65) Prior Publication Data

US 2006/0073148 A1 Apr. 6, 2006

Related U.S. Application Data

(63) Continuation-in-part of application No. 11/149,025, filed on Jun. 9, 2005.

(60) Provisional application No. 60/581,078, filed on Jun. 17, 2004.

(51) Int. Cl.
A61K 39/395 (2006.01)
C07K 16/24 (2006.01)

(52) U.S. Cl. .............. 424/139.1; 530/387.9; 530/387.3

(58) Field of Classification Search ...................... None
See application file for complete search history.

(56) References Cited

U.S. PATENT DOCUMENTS

| | | | |
|---|---|---|---|
| 4,023,449 A | 5/1977 | Boyadjieff | |
| 5,011,778 A | 4/1991 | Newman et al. | |
| 5,225,539 A | 7/1993 | Winter et al. | |
| 5,246,701 A | 9/1993 | Dugas et al. | |
| 5,359,037 A | 10/1994 | Wallach et al. | |
| 5,585,089 A | 12/1996 | Queen et al. | |
| 5,596,072 A | 1/1997 | Culpeper et al. | |
| 5,599,905 A | 2/1997 | Mosley et al. | |
| 5,624,821 A | 4/1997 | Winter et al. | |
| 5,648,260 A | 7/1997 | Winter et al. | |
| 5,652,123 A | 7/1997 | Caput et al. | |
| 5,677,165 A | 10/1997 | de Boer et al. | |
| 5,693,761 A | 12/1997 | Queen et al. | |
| 5,693,762 A | 12/1997 | Queen et al. | |
| 5,696,234 A | 12/1997 | Zurzwski et al. | |
| 5,705,154 A | 1/1998 | Dalie et al. | |
| 5,710,023 A | 1/1998 | Collins et al. | |
| 5,717,072 A | 2/1998 | Mosley et al. | |
| 5,747,037 A | 5/1998 | Noelle et al. | |
| 5,783,181 A | 7/1998 | Browne et al. | |
| 5,859,205 A | 1/1999 | Adair et al. | |
| 6,140,047 A | 10/2000 | Duff et al. | |
| 6,143,871 A | 11/2000 | Bonnefoy et al. | |
| 6,180,370 B1 | 1/2001 | Queen et al. | |
| 6,214,559 B1 | 4/2001 | Collins et al. | |
| 6,248,714 B1 | 6/2001 | Collins et al. | |
| 6,268,480 B1 | 7/2001 | Collins et al. | |
| 6,407,213 B1 | 6/2002 | Carter et al. | |
| 6,632,927 B2 | 10/2003 | Adair et al. | |
| 6,664,227 B1 | 12/2003 | Wynn et al. | |
| 6,703,360 B2 | 3/2004 | McCall et al. | |
| 6,746,838 B1 | 6/2004 | Choo et al. | |
| 6,811,780 B2 | 11/2004 | Furfine et al. | |
| 6,911,530 B1 | 6/2005 | Willson et al. | |
| 7,078,494 B1 | 7/2006 | Collins et al. | |
| 7,282,206 B2 | 10/2007 | Wynn et al. | |
| 2002/0136719 A1 | 9/2002 | Shenoy et al. | |
| 2003/0013851 A1 | 1/2003 | Powes et al. | |
| 2003/0023555 A1 | 1/2003 | Rees | |
| 2003/0031666 A1 | 2/2003 | Debinski et al. | |
| 2003/0040606 A1 | 2/2003 | Leung | |
| 2003/0166871 A1 | 9/2003 | Barbas et al. | |
| 2003/0175898 A1 | 9/2003 | Pantelidis | |
| 2003/0235555 A1 | 12/2003 | Shealey et al. | |
| 2004/0142372 A1 | 7/2004 | McCall et al. | |
| 2004/0234499 A1 | 11/2004 | Shealy et al. | |
| 2004/0248260 A1 | 12/2004 | Heavner et al. | |
| 2005/0019260 A1 | 1/2005 | Meeusen et al. | |
| 2005/0028496 A1 | 2/2005 | Sabbadini et al. | |
| 2005/0032175 A1 | 2/2005 | Stahl et al. | |
| 2005/0058645 A1 | 3/2005 | Dunlop et al. | |
| 2005/0065327 A1 | 3/2005 | Monk et al. | |
| 2005/0096268 A1 | 5/2005 | Wynn et al. | |
| 2005/0142105 A1 | 6/2005 | Puri et al. | |
| 2005/0154192 A1 | 7/2005 | Shirakzwa et al. | |
| 2005/0164323 A1 | 7/2005 | Chaudhary et al. | |
| 2005/0186146 A1 | 8/2005 | Gong et al. | |
| 2005/0260216 A1 | 11/2005 | Ashman et al. | |
| 2005/0266005 A1 | 12/2005 | Heavner et al. | |
| 2005/0277126 A1 | 12/2005 | Collins et al. | |
| 2005/0282216 A1 | 12/2005 | Caput et al. | |
| 2006/0024306 A1 | 2/2006 | Strober et al. | |
| 2006/0063228 A1 | 3/2006 | Kasaian et al. | |
| 2007/0048785 A1 | 3/2007 | Lin et al. | |

FOREIGN PATENT DOCUMENTS

EP 0 506 574 11/1995

(Continued)

OTHER PUBLICATIONS

Ahlers et al., "A push—pull approach to maximize vaccine efficacy: Abrogating suppression with an IL-13 inhibitor while augmenting help with granulocyte macrophage colony-stimulating factor and CD40L," PNAS, vol. 99, No. 20, pp. 13020-13025, 2002.

(Continued)

*Primary Examiner*—Prema Mertz
(74) *Attorney, Agent, or Firm*—Lowrie, Lando & Anastasi, LLP

(57) ABSTRACT

Agents (e.g., antibodies and fragments thereof) that bind specifically to IL 13 and modulate the ability of IL-13 to interact with IL-13 receptors and signaling mediators are disclosed.

41 Claims, 13 Drawing Sheets

FOREIGN PATENT DOCUMENTS

| | | |
|---|---|---|
| EP | 0812913 | 12/1997 |
| EP | 0 876 482 B1 | 11/1998 |
| EP | 1 141 286 B1 | 10/2006 |
| WO | WO 89/04838 | 6/1989 |
| WO | WO 91/09059 | 6/1991 |
| WO | WO 93/15766 | 8/1993 |
| WO | WO 94/04680 | 3/1994 |
| WO | WO 94/14975 | 7/1994 |
| WO | WO 95/14780 | 6/1995 |
| WO | WO 97/15663 | 5/1997 |
| WO | WO 97/20926 | 6/1997 |
| WO | WO 97/29131 | 8/1997 |
| WO | WO 97/31946 | 9/1997 |
| WO | WO 97/33913 | 9/1997 |
| WO | WO 97/47741 | 12/1997 |
| WO | WO 97/47742 | 12/1997 |
| WO | WO 98/10638 | 3/1998 |
| WO | WO 98/30240 | 8/1998 |
| WO | WO 99/29888 | 6/1999 |
| WO | WO 00/36103 | 6/2000 |
| WO | WO 00/64944 | 11/2000 |
| WO | WO 00/78336 | 12/2000 |
| WO | WO 01/23410 | 4/2001 |
| WO | WO 01/25282 | 4/2001 |
| WO | WO 01/62287 | 8/2001 |
| WO | WO 01/92340 | 12/2001 |
| WO | WO 02/018445 | 3/2002 |
| WO | WO 02/055100 | 7/2002 |
| WO | WO 02/101629 | 12/2002 |
| WO | WO 03/034984 | 5/2003 |
| WO | WO 03/035847 | 5/2003 |
| WO | WO 03/086451 | 10/2003 |
| WO | WO 2004/001655 | 12/2003 |
| WO | WO 2004/039956 | 5/2004 |
| WO | WO 2004/047728 | 6/2004 |
| WO | WO 2004/069274 | 8/2004 |
| WO | WO 2005/007699 | 1/2005 |
| WO | WO 2005/009464 | 2/2005 |
| WO | WO 2005/016962 | 2/2005 |
| WO | WO 2005/019258 | 3/2005 |
| WO | WO 2005/042028 | 5/2005 |
| WO | WO 2005/062967 | 7/2005 |
| WO | WO 2005/062972 | 7/2005 |
| WO | WO 2005/079755 | 9/2005 |
| WO | WO 2005/081873 | 9/2005 |
| WO | WO 2005/091853 | 10/2005 |
| WO | WO 2005/091856 | 10/2005 |
| WO | WO 2005/121177 | 12/2005 |
| WO | WO 2005/123126 | 12/2005 |
| WO | WO 2006/003407 | 1/2006 |

OTHER PUBLICATIONS

Bancroft et al., "Gastrointestinal nematode expulsion in IL-4 knock-out mice is IL-13 dependent," Eur. J. Immunol. vol. 30, pp. 2083-2091, 2000.
Blease et al., "Therapeutic Effect of IL-13 Immunoneutralization During Chronic Experimental Fungal Asthma," The Journal of Immunology, vol. 166, pp. 5219-5224, 2001.
Borish et al., "Interleukin-4 Receptor in Moderate Atopic Asthma," Am J Respir Crit Care Med, vol. 160, pp. 1816-1823, 1999.
Bost et al., "In vivo treatment with anti-interleukin-13 antibodies significantly reduces the humoral immune response against an oral immunogen in mice," Immunology, vol. 87, pp. 633-641, 1996.
Caput et al., "Cloning and Characterization of a Specific Interleukin (IL)-13 Binding Protein Structurally Related to the IL-5 Receptor alpha Chain," The Journal of Biological Chemistry, vol. 271, No. 28, pp. 16921-16926, 1996.
Carballido et al., "IL-4 Induces Human B Cell Maturation and IgE Synthesis in SCI-D-hu Mice," The Journal of Immunology, vol. 155, pp. 4162-4170, 1995.

Chiaramonte et al., "An IL-13 inhibitor blocks the development of hepatic fibrosis during a T-helper type 2-dominated inflammatory response," J. Clin. Invest. vol. 104, pp. 777-785, 1999.
Chiaramonte et al., "IL-13 Is a Key Regulatory Cytokine for Th2 Cell-Mediated Pulmonary Granuloma Formation and IgE Responses Induced by Schistosoma mansoni Eggs," The Journal of Immunology, vol. 162, pp. 920-930, 1999.
Chiaramonte et al., "Regulation and Function of the Interleukin 13 Receptor alpha 2 During a T Helper Cell Type 2-dominant Immune Response," The Journal of Experimental Medicine, vol. 197, No. 6, pp. 687-701, 2003.
Chiaramonte et al., "Studies of Murine Schistosomiasis Reveal Interleukin-13 Blockade as a Treatment for Established and Progressive Liver Fibrosis," Hepatology, vol. 34, pp. 273-282, 2001.
Donaldson et al., "The Murine IL-13 Receptor a2: Molecular Cloning, Characterization, and Comparison with Murine IL-13 Receptor alpha 1," The Journal of Immunology, vol. 161, pp. 2317-2324, 1998.
Economides et al., "Cytokine traps: multi-component, high-affinity blockers of cytokine action," Nature Medicine vol. 9, No. 1, pp. 47-52, 2003.
Finkelman et al., "The role of IL-13 in helminth-induced inflammation and protective immunity against nematode infections," Current Opinion in Immunology, vol. 11, pp. 420-426, 1999.
Fish et al., "IgE Generation and Mast Cell Effector Function in Mice Deficient in IL-4 and IL-13," The Journal of Immunology, vol. 174, pp. 7716-7724, 2005.
Ford et al., "IL-13 and IFN-g: Interactions in Lung Inflammation," The Journal of Immunology, vol. 167, pp. 1769-1777, 2001.
Gruenig et al., "Roles of Interleukin-13 and Interferon-gama in Lung Inflammation," Chest, Mar. 2002;121(3 Suppl.): 88S.
Hart et al., "Preclinical efficacy and safety of pascolizumab (SB 240683): a humanized anti-interleukin-4 antibody with therapeutic potential in asthma," Clin Exp Immunol, vol. 130, pp. 93-100, 2002.
Heller et al., "Oxazolone Colitis, a Th2 Colitis Model Resembling Ulcerative Colitis, Is Mediated by IL-13-Producing NK-T Cells," Immunity, vol. 17, pp. 629-638, Nov. 2002.
Henderson et al., "Soluble IL-4 Receptor Inhibits Airway Inflammation Following Allergen Challenge in a Mouse Model of Asthma," The Journal of Immunology vol. 164, pp. 1086-1095, 2000.
Leigh et al., "Is Interleukin-13 Critical in Maintaining Airway Hyper-resposiveness in Allergen-challenged Mice?," Am. J. Respir. Crit. Care. Med., vol. 170, pp. 851-856, 2004.
Lentsch et al., "Regulation of Acute Lung Inflammatory Injury by Endogenous IL-13," The Journal of Immunology, vol. 162, pp. 1071-1076, 1999.
Li et al., "Effects of Th2 Cytokines on Chemokine Expression in the Lung: IL-13 Potently Induces Eotaxin Expression by Airway Epithelial Cells1," The Journal of Immunology, vol. 162, pp. 2477-2487, 1999.
Ma et al., "Turmor cells secreting IL-13 but not IL-13Ralpha2 fusion protein have reduced tumorigenicity in vivo," International Immunology, vol. 16, No. 7, pp. 1009-1017, 2004.
Mentink-Kane et al., "IL-13 receptor alpha 2 down-modulates granulomatous inflammation and prolongs host survival in schistosomiasis," PNAS, vol. 101, No. 2, pp. 586-590, 2004.
Morse et al. "Effects of IL-13 on airway responses in the guinea pig," Am. J. Physiol. Lung. Cell. Mol. Physiol., vol. 282, pp. 44-49, 2002.
Obiri et al., "Receptor for Interleukin 13," The Journal of Biological Chemistry, vol. 270, No. 15, pp. 8797-8804, 1995.
Padilla et al., "IL-13 Regulates the Immune Response to Inhaled Antigens," The Journal of Immunology, vol. 174, pp. 8097-8105, 2005.
Park et al., "Respiratory syncytial virus—induced airway hyper-responsiveness is independent of IL-13 compared with that induced by allergen,"J. Allergy Clin Immunol, vol. 112, pp. 1078-1087, 2003.
Park et al., "Unmasking immunosurveillance against a syngeneic colon cancer by elimination of CD4 NKT regulatory cells and IL-13," Int. J. Cancer, vol. 114, pp. 80-87, 2005.
Proust et al., "Persistence of bronchopulmonary hyper-reactivity and eosinophilic lung inflammation after anti-IL-5 or -IL-13 treatment in allergic BALB/c and IL-4Rαknockout nice," Clin Exp Allergy vol. 33, pp. 119-131, 2003.

Taube et al., "Mast Cells, FcεRI, and IL-13 Are Required for Development of Airway Hyperresponsiveness after Aerosolized Allergen Exposure in the Absence of Adjuvant," The Journal of Immunology, vol. 172, pp. 6398-6406, 2004.

Taube et al., "The Role of IL-13 in Established Allergic Airway Disease," The Journal of Immunology, vol. 169, pp. 6482-6489, 2002.

Tekkanat et al., "IL-13-Induced Airway Hyperreactivity During Respiratory Syncytial Virus Infection Is STAT6 Dependent," The Journal of Immunology, vol. 166, pp. 3542-3548, 2001.

Terabe et al., "NKT cell—mediated repression of tumor immunosurveillance by IL-13 and the IL-4R-STAT6 pathway," Nature Immunology, vol. 1, No. 6, pp. 515-520, 2000.

Tomkinson et al., "A Murine IL-4 Receptor Antagonist That Inhibits IL-4- and IL-13-Induced Responses Prevents Antigen-Induced Airway Eosinophilia and Airway Hyperresponsiveness," The Journal of Immunology, vol. 166, pp. 5792-5800, 2001.

Urban et al., "IL-13-Mediated Worm Expulsion Is B7 Independent and IFN-gama Sensitive," The Journal of Immunology, vol. 164, pp. 4250-4256, 2000.

Vita et al., "Characterization and Comparison of the Interleukin 13 Receptor with the Interleuking 4 receptor on Several Cell Types," The Journal of Biological Chemistry, vol. 270, No. 8, pp. 3512-3517, 1995.

Vogel, "Interleukin-13's Key Role in Asthma Shown," Science, vol. 282, p. 2168, 1998.

Walter et al., "Critical Role for IL-13 in the Development of Allergen-Induced Airway Hyperreactivity," The Journal of Immunology, vol. 167, pp. 4668-4675, 2001.

Webb et al., "Antigen-specific production of interleukin (IL)-13 and IL-5 cooperate to mediate IL-4Ralpha -independent airway hyperreactivity," Eur. J. Immunol., vol. 33, pp. 3377-3385, 2003.

Wills-Karp et al., "Polymorphisms Not Foud in the IL-13 Gene Promotor," Science, vol. 284, p. 1431, 1999.

Wills-Karp et al., "Interleukin-13: Central Mediator of Allergic Asthma", Science, vol. 282, No. 5397, pp. 2258-2261, 18, 1998.

Wood et al., "Enhanced Interleukin (IL)-13 Responses in Mice Lacking IL-13 Receptor alpha 2," J. Exp. Med., vol. 197, No. 6, pp. 703-709, 2003.

Wood et al., "IL-21 eVects on human IgE production in response to IL-4 or IL-13," Cellular Immunology, vol. 231, pp. 133-145, 2004.

Zurawski et al., "The Primary Binding Subunit of the Human Interleukin-4 Receptor Is Also a Component of the Interleukin-13 Receptor," The Journal of Biological Chemistry, vol. 270, No. 23, pp. 13869-13878, 1995.

Al Ghamdi et al., "IL-4 and IL-13 expression in chronic sinusitis: relationship with cellular infiltrate and effect of topical corticosteroid treatment," J. Otolaryngol. 26:160-166 (1997).

Aversa et al., "An interleukin 4 mulant protein inhibits both IL-4 or IL-13 induced human immunoglobulin G4 and IgE synthesis and B cell proliferation: support for a common component shared by IL-4 and IL-13 receptors," J. Exp. Med. 178:2213-18 (1993).

Bellanti, "Cytokines and allergic diseases: clinical aspects," Allergy Asthma Proc. 19:337-341 (1998).

Blundell et al., "High-Throughput Crystallography for Lead Discovery in Drug Design," Nature Reviews 1(1):45-54 (2002).

Bouma et al., "The Immunological and Genetic Basis of Inflammatory Bowel Disease," Nature Reviews 3(7):521-532 (2003).

Casolaro et al., "Biology and genetics of atopic disease," Curr. Opin. Immunol. 8:796-803 (1996).

Cocks et al., "IL-13 induces proliferation and differentiation of human B cells activated by the CD40 ligand," Int. Immunol. 5:657-663 (1993).

de Vries and Yssel, "Modulation of the human IgE response," Eur. Respir. J. Suppl. 22:58s-62s (1996).

de Vries, "Novel fundamental approaches to intervening in IgE-mediated allergic diseases," J. Invest. Dermatol. 102:141-144 (1994).

Doucet et al., "Interleukin (IL) 4 and IL-13 act on human lung fibroblasts. Implication in asthma," J. Clin. Invest. 101:2129-39 (1998).

Gabrielsson et al., "Increased frequencies of allergen-induced interleukin-13-producing cells in atopic individuals during the pollen season," Scand. J. Immunol. 48:429-35 (1998).

Ghaffar et al., "IL-13 mRNA and immunoreactivity in allergen-induced rhinitis: comparison with IL-4 expression and modulation by topical glucocorticoid therapy," Am. J. Respir. Cell. Mol. Biol. 17:17-24 (1997).

Gruenig et al., "Requirement of IL-13 independently of IL-4 in experimental asthma," Science 282:2261-63 (1998).

Grunewald et al., "An antagonistic IL-4 mutant prevents type I allergy in the mouse: inhibition of the IL-4/IL-13 receptor system completely abrogates humoral immune response to allergen and development of allergic symptoms in vivo," J. Immunol. 160:4004-09 (1998).

Hamid et al., "In vivo expression of IL-12 and IL-13 in atopic dermatitis," J. Allergy Clin. Immunol. 98:225-31 (1996).

Hilton et al., "Cloning and characterization of a binding subunit of the interleukin 13 receptor that is also a component of the interleukin 4 receptor," Proc. Natl. Acad. Sci. USA 93:497-501 (1996).

Huang et al., "IL-13 expression at the sites of allergen challenge in patients with asthma," J. Immunol. 155:2688-94 (1995).

Humbert et al., "Elevated expression of messenger ribonucleic acid encoding IL-13 in the bronchial mucosa of atopic and nonatopic subjects with asthma," J. Allergy Clin. Immunol. 99:657-665 (1997).

Kimata et al., "Involvement of interleukin (IL)-13, but not IL-4, in spontaneous IgE and IgG4 production in nephrotic syndrome," Eur. J. Immunol. 25:1497-1501 (1995).

Kotsimbos et al., "Interleukin-13 and interleukin-4 are coexpressed in atopic asthma," Proc. Assoc. Am. Physicians 108:368-373 (1996).

Kroegel et al., "Endobronchial secretion of interleukin-13 following local allergen challenge in atopic asthma: relationship to interleukin-4 and eosinophil counts," Eur. Resp. J. 9:899-904 (1996).

Maini et al., "Interleukin-13 receptors on human prostate carcinoma cell lines represent a novel target for a chimeric protein composed of IL-13 and a mutated form of Pseudomonas exotoxin," J. Urol. 158:948-953 (1997).

Marsh et al., "Linkage analysis of IL4 and other chromosome 5q31.1 markers and total serum immunoglobulin E concentrations," Science. 264:1152-56 (1994).

McKenzie et al., "Interleukin-13, a T-cell-derived cytokine that regulates human monocyte and B-cell function," Proc. Natl. Acad. Sci. USA 90:3735-39 (1993).

Mentik-Kane and Wynn, "Opposing roles for IL-13 and IL-13 receptor alpha 2 in health and disease," Immunol. Rev. 202:191-202 (2004).

Minty et al., "Interleukin-13 is a new human lymphokine regulating inflammatory and immune responses," Nature 362:248-250 (1993).

Moy et al., "Solution structure of human IL-13 and implication for receptor binding," J. Mol. Biol. 310:219-230 (2001).

Naseer et al., "Expression of IL-12 and IL-13 mRNA in asthma and their modulation in response to steroid therapy," Am. J. Respir. Crit. Care Med. 155:845-851 (1997).

Pawankar et al., "Nasal mast cells in perennial allergic rhinitics exhibit increased expression of the FcεRI, CD40L, IL-4, and IL-13, and can induce IgE synthesis in B cells," J. Clin. Invest. 99:1492-99 (1997).

Postma et al., "Genetic susceptibility to asthma—bronchial hyperresponsiveness coinherited with a major gene for atopy," N. Engl. J. Med. 333:894-900 (1995).

Punnonen and de Vries, Oct. 1998, In: *Allergy and Allergic Diseases*, J.A. Denburg ed., Human Press Inc., Totowa, New Jersey, pp. 13-40.

Punnonen et al., "IL-13 induces proliferation, Ig isotype switching, and Ig synthesis by immature human fetal B cells," J. Immunol., 152:1094-1102 (1994).

Punnonen et al., "Interleukin 13 induces interleukin 4-independent IgG4 and IgE synthesis and CD23 expression by human B cells," Proc. Natl. Acad. Sci. USA 90:3730-34 (1993).

Punnonen et al., "The relative contribution of IL-4 and IL-13 to human IgE synthesis induced by activated $CD4^+$ or $CD8^+$ cells," J. Allergy Clin. Immunol. 100(6):792-801 (1997).

Shanafelt et al., "An immune cell-selective interleukin 4 agonist," Proc. Natl. Acad. Sci. USA 95:9454-58 (1998).

Van der Pouw Kraan et al., "The role of IL-13 in IgE synthesis by allergic asthma patients," Clin. Exp. Immunol. 111:129-135 (1998).

Warner, "Bronchial hyperresponsiveness, atopy, airway inflammation, and asthma," Pediatr. Allergy Immunol. 9:56-60 (1998).

Yssel et al., "The role of IgE in asthma," Clin. Exp. Allergy 28(Suppl. 5):104-109 (1998).

Zurawski et al., "Receptors for interleukin-13 and interleukin-4 are complex and share a novel component that functions in signal transduction," EMBO J. 12:2663-70 (1993).

Andrews, A. L. et al., "Kinetic Analysis of the Interleukin-13 Receptor Complex," Journal of Biological Chemistry, 277 (48):46073-8 (2002).

Berger, R. et al., "IL-4 and IL-13 regulation of ICAm-1 expression and eosinophil recruitment in *Onchocera volvulus* keratitus," Investigative Ophthalmology and Visual Science, 43(9):2992-7 (2002).

Bree, A. et al., "Il-13 blockade reduces lung inflammation after Ascaris Suum challenge in Cynomolgus monkeys," Journal of Allergy and Clinical Immunology. 119(5):1251-7 (2007).

Cetre, C. et al., "Interleukin-13 and IgE production in rat experimental schistosomiasis," European Cytokine Network, 11(2):241-9 (2000).

Fichter-Feigl, S. et al., "IL-13 signaling through the IL-13-alpha2 receptor is involved in induction of TGF-β1 production and fibrosis," Nature Medicine, 12(1):99-106 (2006).

Hahn, C. et al., "Inhibition of the IL-4/IL-13 receptor system prevents allergic sensitization without affecting established allergy in a mouse model for allergic asthma," Journal of Allergy and Clinical Immunology, 111(6):1361-9 (2003).

Kasaian, M. et al., "Efficacy of IL-13 Neutralization in a sheep model of experimental asthma," American Journal of Respiratory Cell and Molecular Biology, 36:368-76 (2007).

Lee, S.H., et al., "Inhibitory effect of DA-9201, and extract of *Oryza sativa* L., on airway inflammation and bronchial hyperresponsiveness in mouse asthma model," Medicinal and Aromatic Plants Abstracts, 28(5):1148 (2006).

Li, X. et al., "The Chinese herbal medicine formula MSSM-002 suppresses allergic airway hyperreactivity and modulates TH1/TH2 responses in a murine model of allergic asthma," Journal of Allergy and Clinical Immunology, 106(4):660-8 (2000).

Tekkanat, K. et al., "IL-13-induced airway hyperreactivity during respiratory syncytial virus infection is STAT6 dependent," Journal of Immunology, 166(3542-8 (2001).

Vugmeyster, Y. et al., "Preclinical pharmacokinetics, interspecies scaling, and tissue distribution of humanized monoclonal anti-IL-13 neutralization mechanisms," International Immunopharmacology, 8(3):477-83 (2008).

Appeal Brief of Opposition to EP 1 141 286 B1, filed by Genentech, Inc. and received by the European Patent Office on Jul. 9, 2007.

Appeal Brief of Opposition to EP 1 141 286 B1, filed by George W. Schlich and received by the European Patent Office on Jul. 9, 2007.

Appeal Brief of Opposition to EP 1 141 286 B1, filed by UCB Pharma S.A. and received by the European Patent Office on Jul. 16, 2007.

Appeal Brief of Opposition to EP 1 141 286 B1, filed by AstraZeneca AB and received by the European Patent Office on Jul. 16, 2007.

Appeal Brief of Opposition to EP 1 141 286 B1, filed by Glaxo Group Limited and received by the European Patent Office on Jul. 19, 2007.

Proprietor's Brief in the Opposition of EP 1 141 286 B1, received by the European Patent Office on Jul. 7, 2008.

International Search Report in related International Application PCT/US99/29493, dated Apr. 25, 2000.

International Search Report in corresponding International Application PCT/US05/21454, dated May 21, 2008.

International Search Report in related International Application PCT/US07/025418, dated Jul. 14, 2008.

FIG. 1A

```
human  MALLLTTVIALTCLGGFASPGPVPPSTALRELIEELVNITQNQKA  45   SEQ ID NO:178
cyno   MALLLTMVIALTCLGGFASPSPVPPSTALKELIEELVNITQNQKA       SEQ ID NO:24 human  PLCNGSMVWSINLTAGMYCAALESLINVSGCSAIEKTQRMLSGF  89
cyno   PLCNGSMVWSINLTAGVYCAALESLINVSGCSAIEKTQRMINGF human  CPHKVSAGQFSSLHVRDTKIEVAQFVKDLLHLKKLFREGRFN  132
cyno   CPHKVSAGQFSSLRVRDTKIEVAQFVKDLLVHLKKLFREGQFN
```

FIG. 1B

```
peptide 1    MALLLTMVIALTC                SEQ ID NO:179
peptide 2    LGGFASPSPVPP                 SEQ ID NO:180
peptide 3    SPSPVPPSTALKELIEE            SEQ ID NO:181
peptide 4    TALKELIEELVNITQNQKA          SEQ ID NO:182
peptide 5    NQKAPLCNGSMVWSINLTAGVY       SEQ ID NO:183
peptide 6    INLTAGVYCAALESLINVSGC        SEQ ID NO:184
peptide 7    SLINVSGCSAIEKTQRMINGF        SEQ ID NO:185
peptide 8    GFCPHKVSAGQFSSLRVR           SEQ ID NO:186
peptide 9    VRDTKIEVAQFVKDLLVHLK         SEQ ID NO:187
peptide 10   FVKDLLVHLKKLFREGQFN          SEQ ID NO:188
```

FIG. 12

```
DPK 18        DVVMTQSPLSLPVTLGQPASISCRSSQSLVYSDGNTYLNWFQQRPGQSPR  50   (SEQ ID NO:126)
              ||||||||||||||||||||||||||||||||||||||||||||||||||
hMJ2-7VLV3    DVVMTQSPLSLPVTLGQPASISCRSSQSLVYSDGNTYLNWFQQRPGQSPR  50   (SEQ ID NO:190)

DPK 18        RLIYKVSNRDSGVPDRFSGSGSGTDFTLKISRVEAEDVGVYYCMQGTHWP  100
              |||||||||||||||||||||||||||||||||||||||||| ||| |
hMJ2-7VLV3    RLIYKVSNRDSGVPDRFSGSGSGTDFTLKISRVEAEDLGVYYCFQGSHIP  100

DPK 18        P..........  101
              |
hMJ2-7VLV3    YTFGGGTKVEIK  112
```

FIG. 13A

PGPVPPSTALRELIEELVNITQNQKAPLCNGSMVWSINLTAGM
YCAALESLINVSGCSAIEKTQRMLSGFCPHKVSAGQFSSLHVR
DTKIEVAQFVKDLLLHLKKLFREGRFN (SEQ ID NO:124)

FIG. 13B

MEWPARLCGLWALLLCAGGGGGGAAPTETQPPVTNLSVSVENLCTVIWTWNPPE
GASSNCSLWYFSHFGDKQDKKIAPETRRSIEVPLNERICLQVGSQCSTNESEKPSI
LVEKCISPPEGDPESAVTELQCIWHNLSYMKCSWLPGRNTSPDTNYTLYWHRSLE
KIHQCENIFREGQYFGCSFDLTKVKDSSFEQHSVQIMVKDNAGKIKPSFNIVPLTS
RVKPDPPHIKNLSFHNDDLYVQWENPQNFISRCLFYEVEVNNSQTETHNVFYVQEA
KCENPEFERNVENTSCFMVPGVLPDTLNTVRIRVKTNKLCYEDDKLWSNWSQEMSI
GKKRNSTLYITMLLIVPVIVAGAIIVLLLYLKRLKIIIFPPIPDPGKIFKEMFGDQ
NDDTLHWKKYDIYEKQTKEETDSVVLIENLKKASQ (SEQ ID NO:125)

IL-13 BINDING AGENTS

CROSS-REFERENCE TO RELATED APPLICATIONS

This application claims priority to U.S. Patent Application Ser. No. 60/581,078, filed on Jun. 17, 2004, under 35 U.S.C. 119, and is a continuation-in-part of U.S. patent application Ser. No. 11/149,025, filed on Jun. 9, 2005. The contents of the aforementioned applications are hereby incorporated by reference. This application also incorporates by reference a PCT/US2005/021454, filed with the U.S. Receiving Office on Jun. 17, 2005.

SEQUENCE LISTING

This application incorporates the sequence listing by reference ASCII text file identified by the name 16158-020001.txt, containing 178 KB of data, and created on Nov. 15, 2005, filed in computer-readable format (CRF) and encoded on the CD-ROM.

BACKGROUND

Interleukin-13 (IL-13) is a cytokine secreted by T lymphocytes and mast cells (McKenzie et al. (1993) *Proc. Natl. Acad. Sci. USA* 90:3735-39; Bost et al. (1996) *Immunology* 87:663-41). IL-13 shares several biological activities with IL-4. For example, either IL-4 or IL-13 can cause IgE isotype switching in B cells (Tomkinson et al. (2001) *J. Immunol.* 166:5792-5800). Additionally, increased levels of cell surface CD23 and serum CD23 (sCD23) have been reported in asthmatic patients (Sanchez-Guerrero et al. (1994) *Allergy* 49:587-92; DiLorenzo et al. (1999) *Allergy Asthma Proc.* 20:119-25). In addition, either IL-4 or IL-13 can upregulate the expression of MHC class II and the low-affinity IgE receptor (CD23) on B cells and monocytes, which results in enhanced antigen presentation and regulated macrophage function (Tomkinson et al., supra). Importantly, either IL-4 or IL-13 can increase the expression of VCAM-1 on endothelial cells, which facilitates preferential recruitment of eosinophils (and T cells) to the airway tissues (Tomkinson et al., supra). Either IL-4 or IL-13 can also increase airway mucus secretion, which can exacerbate airway responsiveness (Tomkinson et al., supra). These observations suggest that although IL-13 is not necessary for, or even capable of, inducing Th2 development, IL-13 may be a key player in the development of airway eosinophilia and AHR (Tomkinson et al., supra; Wills-Karp et al. (1998) *Science* 282:2258-61).

SUMMARY

We have discovered, inter alia, IL-13 binding agents, in particular, anti-IL-13 antibody molecules can bind to human IL-13 and/or cynomolgus monkey IL-13, with high affinity and specificity. In one embodiment, the antibody molecules reduce at least one IL-13-associated activity, e.g., modulation of an inflammatory condition. For example, the anti-IL-13 antibody molecules can bind to IL-13 and modulate, e.g., inhibit, an interaction (e.g., binding) between IL-13 and an IL-13 receptor, e.g., IL-13 receptor α1 ("IL-13Rα1"), IL-13 receptor α2 ("IL-13Rα2"), and/or the interleukin-4 receptor alpha chain ("IL-4Rα"), thereby reducing or preventing signal transduction.

An IL-13 binding agent, such as an anti-IL-13 antibody molecule can be used to modulate (e.g., inhibit) at least one IL-13-associated activity in vivo. The IL-13 binding agent can be used to treat or prevent an IL-13 associated-disorder, or to ameliorate at least one symptom thereof. Exemplary IL-13 associated disorders include inflammatory disorders (e.g., lung inflammation), respiratory disorders (e.g., asthma, including allergic and non-allergic asthma, chronic obstructive pulmonary disease (COPD)), as well as conditions involving airway inflammation, eosinophilia, fibrotic disorders (e.g., cystic fibrosis, liver fibrosis, and pulmonary fibrosis), scleroderma, excess mucus production; atopic disorders (e.g., atopic dermatitis, urticaria, eczema, allergic rhinitis, and allergic enterogastritis), an IL-13 associated cancer (e.g., a leukemia, glioblastoma, or lymphoma, e.g., Hodgkin's lymphoma), gastrointestinal disorders (e.g., inflammatory bowel diseases), liver disorders(e.g., cirrhosis), and viral infections.

An IL-13 binding agent can be a protein, e.g., an antibody molecule, a peptide, or a scaffold domain, that interacts with, e.g., binds to and/or inhibits IL-13, in particular, mammalian IL-13, e.g., human or nonhuman primate IL-13. The antibody molecule can be an isolated antibody molecule. In one embodiment, the binding agent is an antagonist, e.g., a binding agent that neutralizes, reduces and/or inhibits one or more IL-13-associated activities, including but not limited to, induction of CD23 expression; production of IgE by human B cells; phosphorylation of a transcription factor, e.g., STAT protein (e.g., STAT6 protein); antigen-induced eosinophilia in vivo; antigen-induced bronchoconstriction in vivo; or drug-induced airway hyperreactivity in vivo, among others. For example, the binding agent has a statistically significant effect in one or more assays described herein. Beside anti-IL-13 antibody molecules, other IL-13 binding agents that can be used include IL-13 receptor-Fc fusions, other soluble forms of the IL-13 receptor, soluble forms of IL-4Rα, antibodies that bind to IL-13R, and other molecules that inhibit the interaction between IL-13 and one of its receptors.

In one aspect, the invention features an IL-13 binding agent that that binds to IL-13, e.g., with an affinity corresponding to a $K_D$ of less than $5\times10^{-7}$ M, $1\times10^{-7}$ M, $5\times10^{-8}$, $1\times10^{-8}$, $5\times10^{-9}$, $1\times10^{-9}$ M, more typically less than $5\times10^{-10}$, $1\times10^{-10}$, $5\times10^{-11}$ M, $1\times10^{-11}$ M, or better. The IL-13 binding agent can be, for example, an antibody molecule that includes first and second immunoglobulin variable domain sequences that include at least a sufficient portion of an immunoglobulin variable domain to form an antigen-binding site that binds to IL-13. Typically, the first and second immunoglobulin variable domain sequences correspond to immunoglobulin variable domain sequences of a heavy and light chain, e.g., a paired or otherwise compatible heavy and light chain.

In one embodiment, the IL-13 binding agent binds to one or more of the following peptides:

FVKDLLVHLKKLFREGQ$_{130}$FN (SEQ ID NO:1),
FVKDLLVHLKKLFREGR$_{130}$FN (SEQ ID NO:2),
FVKDLLLHLKKLFREGQ$_{130}$FN (SEQ ID NO:3),
FVKDLLLHLKKLFREGR$_{130}$FN (SEQ ID NO:4),
FVKDLLVHLKKLFREG (SEQ ID NO:5), and
FVKDLLLHLKKLFREG (SEQ ID NO:6), e.g., as isolated peptides, or to an amino acid within such a peptide when the peptide is folded in the structure of a mature IL-13 protein.

For example, the IL-13 binding agent can bind to a peptide or to an IL-13 with comparable affinity (e.g., affinities that differ by less than a factor of 8, 5, 4, or 2), regardless of whether R or Q is present at position 130. In particular, the IL-13 binding agent may bind with equal affinity to the peptide or the IL-13 regardless of whether R or Q is present at position 130.

The IL-13 binding agent may bind to one or more of the following peptides:

KDLLVHLKKLFREGQFN (SEQ ID NO:7),
KDLLVHLKKLFREGRFN (SEQ ID NO:8),
KDLLLHLKKLFREGQFN (SEQ ID NO:9),
KDLLLHLKKLFREGRFN (SEQ ID NO:10),
KDLLVHLKKLFRE (SEQ ID NO:11),
KDLLLHLKKLFRE (SEQ ID NO:12), and
HLKKLFRE (SEQ ID NO:13), e.g., as isolated peptides, or to an amino acid within such a peptide when the peptide is folded in the structure of a mature IL-13 protein. The IL-13 binding agent can bind to an epitope on IL-13 that includes at least one (e.g., one, two, three or four) amino acid residues from a peptide sequence recited herein (e.g., in FIG. 1B), or a corresponding peptide which differs by at least one, but no more than one, two or three amino acid residues, e.g., a corresponding peptide from human IL-13.

In one embodiment, the IL-13 binding agent contacts (e.g., makes a van der Waals contact with) an amino acid residue in helix D (amino acid residues 114-130) of full-length IL-13 (SEQ ID NO:24 or SEQ ID NO:178), e.g., one or more of the following amino acid residues: residue 116, 117, 118, 122, 123, 124, 125, 126, 127, or 128 of SEQ ID NO:24 or SEQ ID NO:178. In one embodiment, the IL-13 binding agent binds to an epitope on helix D, or an epitope that includes at least one amino acid residue (e.g., at least one, two, three, or four) on helix D, and/or may inhibit interaction of IL-13 with one or both of IL-13Rα1 and/or IL-13Rα2. Helix D corresponds to amino acid residues 95-111 of mature, processed IL-13 (SEQ ID NO:14 or SEQ ID NO:124).

In one embodiment, the IL-13 binding agent specifically binds to an epitope, e.g., a linear or a conformational epitope, of IL-13, e.g., mammalian, e.g., human IL-13. For example, the IL-13 binding agent competes with MJ 2-7 and/or C65 for binding to IL-13, e.g., to human IL-13. The IL-13 binding agent may competitively inhibit binding of MJ 2-7 and/or C65 to IL-13. The IL-13 binding agent may specifically bind at least one amino acid in an epitope defined by MJ 2-7 binding to human IL-13 or an epitope defined by C65 binding to human IL-13. In one embodiment, the IL-13 binding agent may bind to an epitope that overlaps with that of MJ 2-7 or C65, e.g., includes at least one, two, three, or four amino acids in common, or an epitope that, when bound, sterically prevents interaction with MJ 2-7 or C65.

In still another embodiment, the IL-13 binding agent specifically binds at least one amino acid in an epitope defined by IL-13Rα1 binding to human IL-13 or an epitope defined by IL-13Rα2 binding to human IL-13, or an epitope that overlaps with such epitopes. The IL-13 binding agent may compete with IL-13Rα1 and/or IL-13Rα2 for binding to IL-13, e.g., to human IL-13. The IL-13 binding agent may competitively inhibit binding of IL-13Rα1 and/or IL-13Rα2 to IL-13. The IL-13 binding agent may interact with an epitope on IL-13 which, when bound, sterically prevents interaction with IL-13Rα1 and/or IL-13Rα2.

In one embodiment, the IL-13 binding agent has a functional activity comparable to IL-13Rα2, e.g., the IL-13 binding agent reduces or inhibits IL-13 interaction with IL-13Rα1. The IL-13 binding agent may prevent formation of a complex between IL-13 and IL-13Rα1 or disrupt or destabilize a complex between IL-13 and IL-13Rα1. In one embodiment, the IL-13 binding agent inhibits ternary complex formation, e.g., formation of a complex between IL 13, IL-13Rα1 and IL4-R.

In one embodiment, the IL-13 binding agent can inhibit one or more IL-13-associated activities with an $IC_{50}$ of about 50 nM to 5 pM, typically about 100 to 250 pM or less, e.g., better inhibition. Agents that inhibit at least one activity of IL-13 are considered IL-13 antagonists. In one embodiment, the IL-13 binding agent can associate with IL-13 with kinetics in the range of $10^3$ to $10^8$ $M^{-1}s^{-1}$, typically $10^4$ to $10^7 M^{-1}s^{-1}$. In yet another embodiment, the IL-13 binding agent has dissociation kinetics in the range of $10^{-2}$ to $10^{-6}$ $s^{-1}$, typically $10^{-2}$ to $10^{-5}s^{-1}$. In one embodiment, the IL-13 binding agent binds to IL-13, e.g., human IL-13, with an affinity and/or kinetics similar (e.g., within a factor 20, 10, or 5) to monoclonal antibody MJ 2-7 or C65, or modified forms thereof, e.g., chimeric forms or humanized forms thereof (e.g., a humanized form described herein). The affinity and binding kinetics of an IL-13 binding agent can be tested using, e.g., biosensor technology (BIACORE™).

The IL-13 binding agent can be an antibody molecule, e.g., an antigen-binding fragment of an antibody (such as a Fab, F(ab')2, Fv or a single chain Fv fragment) or an antibody that includes an Fc domain. Typically, an anti-IL-13 antibody molecule is monoclonal or a mono-specific.

The IL-13 binding agent, particularly an anti-IL-13 antibody molecule, can be an effectively human, human, humanized, CDR-grafted, chimeric, mutated, affinity matured, deimmunized, synthetic or otherwise in vitro-generated protein. In one embodiment, the IL-13 binding agent is a humanized antibody. In one embodiment, the IL-13 binding agent is not antigenic in humans or does not cause a HAMA response.

In one embodiment, the IL-13 antibody molecule includes a heavy and light chain. The heavy and light chains of an anti-IL-13 antibody molecule can be substantially full-length (e.g., an antibody molecule can include at least one, and preferably two heavy chains, and at least one, and preferably two light chains) or can include an antigen-binding fragment (e.g., a Fab, F(ab')2, Fv or a single chain Fv fragment). In yet other embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the heavy chain constant regions of IgG1, IgG2, IgG3, and IgG4, more particularly, the heavy chain constant regions IgG1 (e.g., human IgG1). Typically the heavy chain constant region is human or a modified form of a human constant region (e.g., as described in Example 5). In another embodiment, the antibody molecule has a light chain constant region chosen from, e.g., the light chain constant regions of kappa or lambda, preferably kappa (e.g., human kappa). In one embodiment, the constant region is altered, e.g., mutated, to modify the properties of the antibody molecule (e.g., to increase or decrease one or more of: Fc receptor binding, antibody glycosylation, the number of cysteine residues, effector cell function, or complement function). For example, the human IgG1 constant region can be mutated at one or more residues, e.g., one or more of residues 234 and 237, as described in Example 5.

In one embodiment, the IL-13 binding agent (e.g., the anti-IL-13 binding molecule) includes at least one, two and preferably three CDRs from the light or heavy chain variable domain of an antibody disclosed herein, e.g., MJ 2-7. For example, the protein includes one or more of the following sequences within a CDR region:

GFNIKDTYIH (SEQ ID NO:15),
RIDPANDNIKYDPKFQG (SEQ ID NO:16),
SEENWYDFFDY (SEQ ID NO:17),
RSSQSIVHSNGNTYLE (SEQ ID NO:18),
KVSNRFS (SEQ ID NO:19), and
FQGSHIPYT (SEQ ID NO:20), or a CDR having an amino acid sequence that differs by no more than 4, 3, 2.5, 2, 1.5, 1, or 0.5 alterations (e.g., substitutions, insertions or deletions) for every 10 amino acids (e.g., the number of differences being proportional to the CDR length) relative to a sequence listed above, e.g., at least one alteration but not more than two, three, or four per CDR.

For example, the IL-13 binding agent can include, in the light chain variable domain sequence, at least one, two, or three of the following sequences within a CDR region:

RSSQSIVHSNGNTYLE (SEQ ID NO:18),
KVSNRFS (SEQ ID NO:19), and
FQGSHIPYT (SEQ ID NO:20), or an amino acid sequence that differs by no more than 4, 3, 2.5, 2, 1.5, 1, or 0.5 substitutions, insertions or deletions for every 10 amino acids relative to a sequence listed above.

The IL-13 binding agent can include, in the heavy chain variable domain sequence, at least one, two, or three of the following sequences within a CDR region:

GFNIKDTYIH (SEQ ID NO:15),
RIDPANDNIKYDPKFQG (SEQ ID NO:16), and
SEENWYDFFDY (SEQ ID NO:17), or an amino acid sequence that differs by no more than 4, 3, 2.5, 2, 1.5, 1, or 0.5 substitutions, insertions or deletions for every 10 amino acids relative to a sequence listed above. The heavy chain CDR3 region can be less than 13 or less than 12 amino acids in length, e.g., 11 amino acids in length (either using Chothia or Kabat definitions).

In another example, the IL-13 binding agent can include, in the light chain variable domain sequence, at least one, two, or three of the following sequences within a CDR region (amino acids in parentheses represent alternatives for a particular position):

(i)  (RK)-S-S-Q-S-(LI)-(KV)-H-S-     (SEQ ID NO: 25)
     (ND)-G-N-(TN)-Y-L-(EDNQYAS)
     or (RK)-S-S-Q-S-(LI)-(KV)-H-S-     (SEQ ID NO: 26)
     (ND)-G-N-(TN)-Y-L-E, or (RK)-S-S-Q-S-(LI)-(KV)-H-S-     (SEQ ID NO: 21)
     N-G-N-T-Y-L-(EDNQYAS), (ii) K-(LVI)-S-(NY)-(RW)-(FD)-S,     (SEQ ID NO: 27)
     or

K-(LV)-S-(NY)-R-F-S, and        (SEQ ID NO: 22)

(iii) Q-(GSA)-(ST)-(HEQ)-I-P,        (SEQ ID NO: 28)

F-Q-(GSA)-(SIT)-(HEQ)-(IL)-     (SEQ ID NO: 23)
     P, or

Q-(GSA)-(ST)-(HEQ)-I-P-Y-T,     (SEQ ID NO: 194)
     or

F-Q-(GSA)-(SIT)-(HEQ)-(IL)-     (SEQ ID NO: 29)
     P-Y-T.

In one preferred embodiment, the IL-13 binding agent includes all six CDR's from MJ 2-7 or closely related CDRs, e.g., CDRs which are identical or which have at least one amino acid alteration, but not more than two, three or four alterations (e.g., substitutions, deletions, or insertions). The IL-13 binding agent can include at least two, three, four, five, six, or seven IL-13 contacting amino acid residues of MJ 2-7

In still another example, the IL-13 binding agent includes at least one, two, or three CDR regions that have the same canonical structures and the corresponding CDR regions of MJ 2-7, e.g., at least CDR1 and CDR2 of the heavy and/or light chain variable domains of MJ 2-7.

The IL-13 binding agent can include one of the following sequences:

```
                                              (SEQ ID NO: 30)
DIVMTQTPLSLPVTPGEPASISCRSSQSIVHSNGNTYLEWYLQKPGQSP
QLLIYKVSNRFSGVPDRFSGSGSGTDFTLKISRVEAEDVGVYYC
FQGSHIPYT (SEQ ID NO: 31)
DVVMTQSPLSLPVTLGQPASISCRSSQSIVHSNGNTYLEWFQQRPGQSP
RRLIYKVSNRFSGVPDRFSGSGSGTDFTLKISRVEAEDVGVYYC
FQGSHIPYT (SEQ ID NO: 32)
DIVMTQTPLSLSVTPGQPASISCRSSQSIVHSNGNTYLEWYLQKPGQSP
QLLIYKVSNRFSGVPDRFSGSGSGTDFTLKISRVEAEDVGVYYC
FQGSHIPYT (SEQ ID NO: 33)
DIVMTQTPLSLSVTPGQPASISCRSSQSIVHSNGNTYLEWYLQKPGQPP
QLLIYKVSNRFSGVPDRFSGSGSGTDFTLKISRVEAEDVGVYYC
FQGSHIPYT (SEQ ID NO: 34)
DIVMTQSPLSLPVTPGEPASISCRSSQSIVHSNGNTYLEWYLQKPGQSP
QLLIYKVSNRFSGVPDRFSGSGSGTDFTLKISRVEAEDVGVYYC
FQGSHIPYT (SEQ ID NO: 35)
DIVMTQTPLSSPVTLGQPASISCRSSQSIVHSNGNTYLEWLQQRPGQPP
RLLIYKVSNRFSGVPDRFSGSGAGTDFTLKISRVEAEDVGVYYC
FQGSHIPYT (SEQ ID NO: 36)
DIQMTQSPSSLSASVGDRVTITCRSSQSIVHSNGNTYLEWYQQKPGKAP
KLLIYKVSNRFSGVPSRFSGSGSGTDFTLTISSLQPEDFATYYC
FQGSHIPYT (SEQ ID NO: 37)
DVVMTQSPLSLPVTLGQPASISCRSSQSLVYSDGNTYLNWFQQRPGQSP
RRLIYKVSNRFSGVPDRFSGSGSGTDFTLKISRVEAEDVGVYYC
FQGSHIPYT (SEQ ID NO: 38)
DVLMTQTPLSLPVSLGDQASISCRSSQSIVHSNGNTYLEWYLQKPGQSP
KLLIYKVSNRFSGVPDRFSGSGSGTDFTLKISRVEAEDLGVYYC
FQGSHIPYT
``` or a sequence that has fewer than eight, seven, six, five, four, three, or two alterations (e.g., substitutions, insertions or deletions, e.g., conservative substitutions or a substitution for an amino acid residue at a corresponding position in MJ 2-7). Exemplary substitutions are at one of the following Kabat positions: 2, 4, 6, 35, 36, 38, 44, 47, 49, 62, 64-69, 85, 87, 98, 99, 101, and 102. The substitutions can, for example, substitute an amino acid at a corresponding position from MJ 2-7 into a human framework region.

The IL-13 binding agent may also include one of the following sequences:

```
                                              (SEQ ID NO: 39)
DIVMTQTPLSLPVTPGEPASISC-(RK)-S-S-Q-S-(LI)-(KV)-H-
S-(ND)-G-N-(TN)-Y-L-(EDNQYAS)WYLQKPGQSPQLLIYK-
(LVI)-S-(NY)-(RW)-(FD)-
SGVPDRFSGSGSGTDFTLKISRVEAEDVGVYYC F-Q-(GSA)-
(SIT)-(HEQ)-(IL)-P (SEQ ID NO: 40)
DVVMTQSPLSLPVTLGQPASISC-(RK)-S-S-Q-S-(LI)-(KV)-H-
S-(ND)-G-N-(TN)-Y-L-(EDNQYAS)WFQQRPGQSPRRLIYK-
(LVI)-S-(NY)-(RW)-(FD)-
SGVPDRFSGSGSGTDFTLKISRVEAEDVGVYYCF-Q-(GSA)-(SIT)-
(HEQ)-(IL)-P
```

-continued (SEQ ID NO: 41)
DIVMTQTPLSLSVTPGQPASISC-(RK)-S-S-Q-S-(LI)-(KV)-H-
S-(ND)-G-N-(TN)-Y-L-(EDNQYAS)WYLQKPGQSPQLLIYK-
(LVI)-S-(NY)-(RW)-(FD)-
SGVPDRFSGSGSGTDFTLKISRVEAEDVGVYYCF-Q-(GSA)-(SIT)-
(HEQ)-(IL)-P (SEQ ID NO: 42)
DIVMTQTPLSLSVTPGQPASISC(RK)-S-S-Q-S-(LI)-(KV)-H-
S-(ND)-G-N-(TN)-Y-L-(EDNQYAS)WYLQKPGQPPQLLIYK-
(LVI)-S-(NY)-(RW)-(FD)-
SGVPDRFSGSGSGTDFTLKISRVEAEDVGVYYCF-Q-(GSA)-(SIT)-
(HEQ)-(IL)-P (SEQ ID NO: 43)
DIVMTQSPLSLPVTPGEPASISC(RK)-S-S-Q-S-(LI)-(KV)-H-
S-(ND)-G-N-(TN)-Y-L-(EDNQYAS)WYLQKPGQSPQLLIYK-
(LVI)-S-(NY)-(RW)-(FD)-
SGVPDRFSGSGSGTDFTLKISRVEAEDVGXTYYCF-Q-(GSA)-(SIT)-
(HEQ)-(IL)-P (SEQ ID NO: 44)
DIVMTQTPLSSPVTLGQPASISC(RK)-S-S-Q-S-(LI)-(KV)-H-
S-(ND)-G-N-(TN)-Y-L-(EDNQYAS)WLQQRPGQPPRLLIYK-
(LVI)-S-(NY)-(RW)-(FD)-
SGVPDRFSGSGAGTDFTLKISRVEAEDVGVYYCF-Q-(GSA)-(SIT)-
(HEQ)-(IL)-P (SEQ ID NO: 45)
DIQMTQSPSSLSASVGDRVTITC(RK)-S-S-Q-S-(LI)-(KV)-H-
S-(ND)-G-N-(TN)-Y-L-(EDNQYAS)WYQQKPGKAPKLLIYK-
(LVI)-S-(NY)-(RW)-(FD)-
SGVPSRFSGSGSGTDFTLTISSLQPEDFATYYCF-Q-(GSA)-(SIT)-
(HEQ)-(IL)-P (SEQ ID NO: 46)
DVLMTQTPLSLPVSLGDQASISC(RK)-S-S-Q-S-(LI)-(KV)-H-
S-(ND)-G-N-(TN)-Y-L-(EDNQYAS)WYLQKPGQSPKLLIYK-
(LVI)-S-(NY)-(RW)-(FD)-
SGVPDRFSGSGSGTDFTLKISRVEAEDLGVYYCF-Q-(GSA)-(SIT)-
(HEQ)-(IL)-P or a sequence that has fewer than eight, seven, six, five, four, three, or two alterations (e.g., substitutions, insertions or deletions, e.g., conservative substitutions or a substitution for an amino acid residue at a corresponding position in MJ 2-7) in the framework region. Exemplary substitutions are at one or more of the following Kabat positions: 2, 4, 6, 35, 36, 38, 44, 47, 49, 62, 64-69, 85, 87, 98, 99, 101, and 102. The substitutions can, for example, substitute an amino acid at a corresponding position from MJ 2-7 into a human framework region. The sequences may also be followed by the dipeptide Tyr-Thr. The FR4 region can include, e.g., the sequence FGGGTKVEIKR (SEQ ID NO:47).

In another example, the IL-13 binding agent can include, in the heavy chain variable domain sequence, at least one, two, or three of the following sequences within a CDR region (amino acids in parentheses represent alternatives for a particular position):

(i) G-(YF)-(NT)-I-K-D-T-Y-(MI)-H (SEQ ID NO:48),
(ii) (WR)-I-D-P-(GA)-N-D-N-I-K-Y-(SD)-(PQ)-K-F-Q-G (SEQ ID NO:49), and
(iii) SEENWYDFFDY (SEQ ID NO:17).

The IL-13 binding agent can include one of the following sequences:

(SEQ ID NO: 50)
QVQLVQSGAEVKKPGASVKVSCKASGFNIKDTYIHWVRQAPGQGLEWMG
RIDPANDNIKYDPKFQGRVTMTRDTSISTAYMELSRLRSDDTAVYYCAR
SEENWYDFFDY (SEQ ID NO: 51)
QVQLVQSGAEVKKPGASVKVSCKASGFNIKDTYIHWVRQAPGQRLEWMG
RIDPANDNIKYDPKFQGRVTITRDTSASTAYMELSSLRSEDTAVYYCAR
SEENWYDFFDY (SEQ ID NO: 52)
QVQLVQSGAEVKKPGASVKVSCKASGFNIKDTYIHWVRQATGQGLEWMG
RIDPANDNIKYDPKFQGRVTMTRNTSISTAYMELSSLRSEDTAVYYCAR
SEENWYDFFDY (SEQ ID NO: 53)
QVQLVQSGAEVKKPGASVKVSCKASGFNIKDTYIHWVRQAPGQGLEWMG
RIDPANDNIKYDPKFQGRVTMTTDTSTSTAYMELRSLRSDDTAVYYCAR
SEENWYDFFDY (SEQ ID NO: 54)
QVQLVQSGAEVKKPGASVKVSCKVSGFNIKDTYIHWVRQAPGKGLEWMG
RIDPANDNIKYDPKFQGRVTMTEDTSTDTAYMELSSLRSEDTAVYYCAT
SEENWYDFFDY (SEQ ID NO: 55)
QMQLVQSGAEVKKTGSSVKVSCKASGFNIKDTYIHWVRQAPGQALEWMG
RIDPANDNIKYDPKFQGRVTITRDRSMSTAYMELSSLRSEDTAMYYCAR
SEENWYDFFDY (SEQ ID NO: 56)
QVQLVQSGAEVKKPGASVKVSCKASGFNIKDTYIHWVRQAPGQGLEWMG
RIDPANDNIKYDPKFQGRVTMTRDTSTSTVYMELSSLRSEDTAVYYCAR
SEENWYDFFDY (SEQ ID NO: 57)
QMQLVQSGPEVKKPGTSVKVSCKASGFNIKDTYIHWVRQARGQRLEWIG
RIDPANDNIKYDPKFQGRVTITRDMSTSTAYMELSSLRSEDTAVYYCAA
SEENWYDFFDY (SEQ ID NO: 58)
EVQLVESGGGLVQPGGSLRLSCAASGFNIKDTYIHWVRQAPGKGLEWVA
RIDPANDNIKYDPKFQGRFTISRDNAKNSLYLQMNSLRAEDTAVYYCAR
SEENWYDFFDY (SEQ ID NO: 59)
EVQLVESGGGLVQPGRSLRLSCAASGFNIKDTYIHWVRQAPGKGLEWVS
RIDPANDNIKYDPKFQGRFTISRDNAKNSLYLQMNSLRAEDTALYYCAK
DSEENWYDFFDY (SEQ ID NO: 60)
QVQLVESGGGLVKPGGSLRLSCAASGFNIKDTYIHWIRQAPGKGLEWVS
RIDPANDNIKYDPKFQGRFTISRDNAKNSLYLQMNSLPAEDTAVYYCAR
SEENWYDFFDY (SEQ ID NO: 61)
EVQLVESGGGLVKPGGSLRLSCAASGFNIKDTYIHWVRQAPGKGLEWVG
RIDPANDNIKYDPKFQGRFTISRDDSKNTLYLQMNSLKTEDTAVYYCTT
SEENWYDFFDY (SEQ ID NO: 62)
EVQLVESGGGVVRPGGSLRLSCAASGFNIKDTYIHWVRQAPGKGLEWVS
RIDPANDNIKYDPKFQGRFTISRDNAKNSLYLQMNSLRAEDTALYHCAR
SEENWYDFFDY (SEQ ID NO: 63)
EVQLVESGGGLVKPGGSLRLSCAASGFNIKDTYIHWVRQAPGKGLEWVS
RIDPANDNIKYDPKFQGRFTISRDNAKNSLYLQMNSLRAEDTAVYYCAR
SEENWYDFFDY (SEQ ID NO: 64)
EVQLLESGGGLVQPGGSLRLSCAASGFNIKDTYIHWVRQAPGKGLEWVS
RIDPANDNIKYDPKFQGRFTISRDNSKNTLYLQMNSLRAEDTAVYYCAK
SEENWYDFFDY (SEQ ID NO: 65)
QVQLVESGGGVVQPGRSLRLSCAASGFNIKDTYIHWVRQAPGKGLEWVA
RIDPANDNIKYDPKFQGRFTISRDNSKNTLYLQMNSLRAEDTAVYYCAK
SEENWYDFFDY (SEQ ID NO: 66)
QVQLVESGGGVVQPGRSLRLSCAASGFNIKDTYIHWVRQAPGKGLEWVA
RIDPANDNIKYDPKFQGRFTISRDNSKNTLYLQMNSLRAEDTAVYYCAR
SEENWYDFFDY

-continued (SEQ ID NO: 67)
EVQLVESGGVVVQPGGSLRLSCAASGFNIKDTYIHWVRQAPGKGLEWVS
RIDPANDNIKYDPKFQGRFTISRDNSKNSLYLQMNSLRTEDTALYYCAK
DSEENWYDFFDY (SEQ ID NO: 68)
EVQLVESGGGLVQPGGSLRLSCAASGFNIKDTYIHWVRQAPGKGLEWVS
RIDPANDNIKYDPKFQGRFTISRDNAKNSLYLQMNSLRDEDTAVYYCAR
SEENWYDFFDY (SEQ ID NO: 69)
EVQLVESGGGLVQPGRSLRLSCTASGFNIKDTYIHWFRQAPGKGLEWVG
RIDPANDNIKYDPKFQGRFTISRDGSKSIAYLQMNSLKTEDTAVYYCTR
SEENWYDFFDY (SEQ ID NO: 70)
EVQLVESGGGLVQPGGSLRLSCAASGFNIKDTYIHWVRQAPGKGLEYVS
RIDPANDNIKYDPKFQGRFTISRDNSKNTLYLQMGSLRAEDMAVYYCAR
SEENWYDFFDY (SEQ ID NO: 71)
EVQLVESGGGLVQPGGSLRLSCAASGFNIKDTYIHWVRQAPGKGLEWIG
RIDPANDNIKYDPKFQGRFTISRDNAKNSLYLQMNSLRAEDTAVYYCAR
SEENWYDFFDY (SEQ ID NO: 72)
EVQLVESGGGLVQPGGSLRLSCAASGFNIKDTYIHWVRQAPGKGLEWVA
RIDPANDNIKYDPKFQGKATISRDNAKNSLYLQMNSLRAEDTAVYYCAR
SEENWYDFFDY (SEQ ID NO: 73)
EVQLVESGGGLVQPGGSLRLSCAASGFNIKDTYIHWVRQAPGKGLEWVA
RIDPANDNIKYDPKFQGRFTISADNAKNSLYLQMNSLRAEDTAVYYCAR
SEENWYDFFDY (SEQ ID NO: 74)
EVQLVESGGGLVQPGGSLRLSCAASGFNIKDTYIHWVRQAPGKGLEWVG
RIDPANDNIKYDPKFQGRFTISRDNAKNSLYLQMNSLPAEDTAVYYCAR
SEENWYDFFDY (SEQ ID NO: 75)
EVQLVESGGGLVQPGGSLRLSCAASGFNIKDTYIHWVRQAPGKGLEWVA
RIDPANDNIKYDPKFQGKATISADNAKNSLYLQMNSLRAEDTAVYYCAR
SEENWYDFFDY (SEQ ID NO: 76)
EVQLVESGGGLVQPGGSLRLSCAASGFNIKDTYIHWVRQAPGKGLEWIG
RIDPANDNIKYDPKFQGRFTISADNAKNSLYLQMNSLRAEDTAVYYCAR
SEENWYDFFDY (SEQ ID NO: 77)
EVQLVESGGGLVQPGGSLRLSCAASGFNIKDTYIHWVRQAPGKGLEWVG
RIDPANDNIKYDPKFQGRFTISADNAKNSLYLQMNSLRAEDTAVYYCAR
SEENWYDFFDY (SEQ ID NO: 78)
EVQLVESGGGLVQPGGSLRLSCAASGFNIKDTYIHWVRQAPGKGLEWVA
RIDPANDNIKYDPKFQGRFTISRDNAKNSAYLQMNSLRAEDTAVYYCAR
SEENWYDFFDY (SEQ ID NO: 79)
EVQLVESGGGLVQPGGSLRLSCAASGFNIKDTYIHWVRQAPGKGLEWVG
RIDPANDNIKYDPKFQGRFTISADNAKNSAYLQMNSLRAEDTAVYYCAR
SEENWYDFFDY (SEQ ID NO: 80)
EVQLVESGGGLVQPGGSLRLSCAASGFNIKDTYIHWVRQAPGKGLEWIG
RIDPANDNIKYDPKFQGRFTISADNAKNSAYLQMNSLPAEDTAVYYCAR
SEENWYDFFDY (SEQ ID NO: 81)
EVQLVESGGGLVQPGGSLRLSCTGSGFNIKDTYIHWVRQAPGKGLEWIG
RIDPANDNIKYDPKFQGRFTISADNAKNSLYLQMNSLPAEDTAVYYCAR
SEENWYDFFDY (SEQ ID NO: 82)
EVQLQQSGAELVKPGASVKLSCTGSGFNIKDTYIHWVKQRPEQGLEWIG
RIDPANDNIKYDPKFQGKATITADTSSNTAYLQLNSLTSEDTAVYYCAR
SEENWYDFFDY or a sequence that has fewer than eight, seven, six, five, four, three, or two alterations (e.g., substitutions, insertions or deletions, e.g., conservative substitutions or a substitution for an amino acid residue at a corresponding position in MJ 2-7). Exemplary substitutions are at one or more of the following Kabat positions: 2, 4, 6, 25, 36, 37, 39, 47, 48, 93, 94, 103, 104, 106, and 107. Exemplary substitutions can also be at one or more of the following positions (accordingly to sequential numbering): 48, 49, 67, 68, 72, and 79. The substitutions can, for example, substitute an amino acid at a corresponding position from MJ 2-7 into a human framework region. In one embodiment, the sequence includes (accordingly to sequential numbering) one or more of the following: Ile at 48, Gly at 49, Lys at 67, Ala at 68, Ala at 72, and Ala at 79; preferably, e.g., Ile at 48, Gly at 49, Ala at 72, and Ala at 79.

Further, the frameworks of the heavy chain variable domain sequence can include: (i) at a position corresponding to 49, Gly; (ii) at a position corresponding to 72, Ala; (iii) at positions corresponding to 48, Ile, and to 49, Gly; (iv) at positions corresponding to 48, Ile, to 49, Gly, and to 72, Ala; (v) at positions corresponding to 67, Lys, to 68, Ala, and to 72, Ala; and/or (vi) at positions corresponding to 48, Ile, to 49, Gly, to 72, Ala, to 79, Ala.

The IL-13 binding agent may also include one of the following sequences:

(SEQ ID NO: 83)
QVQLVQSGAEVKKPGASVKVSCKASG-(YF)-(NT)-I-K-D-T-Y-
(MI)-H,WVRQAPGQGLEWMG(WR)-I-D-P-(GA)-N-D-N-I-K-Y-
(SD)-(PQ)-K-F-Q-GRVTMTRDTSISTAYMELSRLRSDDTAVYYCAR
SEENWYDFFDY (SEQ ID NO: 84)
QVQLVQSGAEVKKPGASVKVSCKASG-(YF)-(NT)-I-K-D-T-Y-
(MI)-H,WVRQAPGQRLEWMG(WR)-I-D-P-(GA)-N-D-N-I-K-Y-
(SD)-(PQ)-K-F-Q-GRVTITRDTSASTAYMELSSLRSEDTAVYYCAR
SEENWYDFFDY (SEQ ID NO: 85)
QVQLVQSGAEVKKPGASVKVSCKASG-(YF)-(NT)-I-K-D-T-Y-
(MI)-H,WVRQATGQGLEWMG(WR)-I-D-P-(GA)-N-D-N-I-K-Y-
(SD)-(PQ)-K-F-Q-GRVTMTRNTSISTAYMELSSLRSEDTAVYYCAR
SEENWYDFFDY (SEQ ID NO: 86)
QVQLVQSGAEVKKPGASVKVSCKASG-(YF)-(NT)-I-K-D-T-Y-
(MI)-H,WVRQAPGQGLEWMG(WR)-I-D-P-(GA)-N-D-N-I-K-Y-
(SD)-(PQ)-K-F-Q-GRVTMTTDTSTSTAYMELRSLRSDDTAVYYCAR
SEENWYDFFDY (SEQ ID NO: 87)
QVQLVQSGAEVKKPGASVKVSCKVSG-(YF)-(NT)-I-K-D-T-Y-
(MI)-H,WVRQAPGKGLEWMG(WR)-I-D-P-(GA)-N-D-N-I-K-Y-
(SD)-(PQ)-K-F-Q-GRVTMTEDTSTDTAYMELSSLRSEDTAVYYCAT
SEENWYDFFDY (SEQ ID NO: 88)
QMQLVQSGAEVKKTGSSVKVSCKASG-(YF)-(NT)-I-K-D-T-Y-
(MI)-H,WVRQAPGQALEWMG(WR)-I-D-P-(GA)-N-D-N-I-K-Y-
(SD)-(PQ)-K-F-Q-GRVTITRDRSMSTAYMELSSLRSEDTAMYYCAR
SEENWYDFFDY (SEQ ID NO: 89)
QVQLVQSGAEVKKPGASVKVSCKASG-(YF)-(NT)-I-K-D-T-Y-
(MI)-H,WVRQAPGQGLEWMG(WR)-I-D-P-(GA)-N-D-N-I-K-Y-
(SD)-(PQ)-K-F-Q-GRVTMTRDTSTSTVYMELSSLRSEDTAVYYCAR
SEENWYDFFDY (SEQ ID NO: 90)
QMQLVQSGPEVKKPGTSVKVSCKASG-(YF)-(NT)-I-K-D-T-Y-
(MI)-H,WVRQARGQRLEWIG(WR)-I-D-P-(GA)-N-D-N-I-K-Y-
(SD)-(PQ)-K-F-Q-GRVTITRDMSTSTAYMELSSLRSEDTAVYYCAA
SEENWYDFFDY (SEQ ID NO: 91)
EVQLVESGGGLVQPGGSLRLSCAASG-(YF)-(NT)-I-K-D-T-Y-
(MI)-H,WVRQAPGKGLEWVA(WR)-I-D-P-(GA)-N-D-N-I-K-Y-
(SD)-(PQ)-K-F-Q-GRFTISRDNAKNSLYLQMNSLRAEDTAVYYCAR
SEENWYDFFDY (SEQ ID NO: 92)
EVQLVESGGGLVQPGRSLRLSCAASG-(YF)-(NT)-I-K-D-T-Y-
(MI)-H,WVRQAPGKGLEWVS(WR)-I-D-P-(GA)-N-D-N-I-K-Y-
(SD)-(PQ)-K-F-Q-GRFTISRDNAKNSLYLQMNSLPAEDTALYYCAK
DSEENWYDFFDY (SEQ ID NO: 93)
QVQLVESGGGLVKPGGSLRLSCAASG-(YF)-(NT)-I-K-D-T-Y-
(MI)-H,WIRQAPGKGLEWVS(WR)-I-D-P-(GA)-N-D-N-I-K-Y-
(SD)-(PQ)-K-F-Q-GRFTISRDNAKNSLYLQMNSLRAEDTAVYYCAR
SEENWYDFFDY (SEQ ID NO: 94)
EVQLVESGGGLVKPGGSLRLSCAASG-(YF)-(NT)-I-K-D-T-Y-
(MI)-H,WVRQAPGKGLEWVG(WR)-I-D-P-(GA)-N-D-N-I-K-Y-
(SD)-(PQ)-K-F-Q-GRFTISRDDSKNTLYLQMNSLKTEDTAVYYCTT
SEENWYDFFDY (SEQ ID NO: 95)
EVQLVESGGGVVRPGGSLRLSCAASG-(YF)-(NT)-I-K-D-T-Y-
(MI)-H,WVRQAPGKGLEWVS(WR)-I-D-P-(GA)-N-D-N-I-K-Y-
(SD)-(PQ)-K-F-Q-GRFTISRDNAKNSLYLQMNSLPAEDTALYHCAR
SEENWYDFFDY (SEQ ID NO: 96)
EVQLVESGGGLVKPGGSLRLSCAASG-(YF)-(NT)-I-K-D-T-Y-
(MI)-H,WVRQAPGKGLEWVS(WR)-I-D-P-(GA)-N-D-N-I-K-Y-
(SD)-(PQ)-K-F-Q-GRFTISRDNAKNSLYLQMNSLRAEDTAVYYCAR
SEENWYDFFDY (SEQ ID NO: 97)
EVQLLESGGGLVQPGGSLRLSCAASG-(YF)-(NT)-I-K-D-T-Y-
(MI)-H,WVRQAPGKGLEWVS(WR)-I-D-P-(GA)-N-D-N-I-K-Y-
(SD)-(PQ)-K-F-Q-GRFTISRDNSKNTLYLQMNSLRAEDTAVYYCAK
SEENWYDFFDY (SEQ ID NO: 98)
QVQLVESGGGVVQPGRSLRLSCAASG-(YF)-(NT)-I-K-D-T-Y-
(MI)-H,WVRQAPGKGLEWVA(WR)-I-D-P-(GA)-N-D-N-I-K-Y-
(SD)-(PQ)-K-F-Q-GRFTISRDNSKNTLYLQMNSLRAEDTAVYYCAK
SEENWYDFFDY (SEQ ID NO: 99)
QVQLVESGGGVVQPGRSLRLSCAASG-(YF)-(NT)-I-K-D-T-Y-
(MI)-H,WVRQAPGKGLEWVA(WR)-I-D-P-(GA)-N-D-N-I-K-Y-
(SD)-(PQ)-K-F-Q-GRFTISRDNSKNTLYLQMNSLRAEDTAVYYCAR
SEENWYDFFDY (SEQ ID NO: 100)
EVQLVESGGVVVQPGGSLRLSCAASG-(YF)-(NT)-I-K-D-T-Y-
(MI)-H,WVRQAPGKGLEWVS(WR)-I-D-P-(GA)-N-D-N-I-K-Y-
(SD)-(PQ)-K-F-Q-GRFTISRDNSKNSLYLQMNSLRTEDTALYYCAK
DSEENWYDFFDY (SEQ ID NO: 101)
EVQLVESGGGLVQPGGSLRLSCAASG-(YF)-(NT)-I-K-D-T-Y-
(MI)-H,WVRQAPGKGLEWVS(WR)-I-D-P-(GA)-N-D-N-I-K-Y-
(SD)-(PQ)-K-F-Q-GRFTISRDNAKNSLYLQMNSLRDEDTAVYYCAR
SEENWYDFFDY (SEQ ID NO: 102)
EVQLVESGGGLVQPGRSLRLSCTASG-(YF)-(NT)-I-K-D-T-Y-
(MI)-H,WFRQAPGKGLEWVG(WR)-I-D-P-(GA)-N-D-N-I-K-Y-
(SD)-(PQ)-K-F-Q-GRFTISRDGSKSIAYLQMNSLKTEDTAVYYCTR
SEENWYDFFDY (SEQ ID NO: 103)
EVQLVESGGGLVQPGGSLRLSCAASG-(YF)-(NT)-I-K-D-T-Y-
(MI)-H,WVRQAPGKGLEYVS(WR)-I-D-P-(GA)-N-D-N-I-K-Y-
(SD)-(PQ)-K-F-Q-GRFTISRDNSKNTLYLQMGSLRAEDMAVYYCAR
SEENWYDFFDY (SEQ ID NO: 104)
EVQLVESGGGLVQPGGSLRLSCAASG-(YF)-(NT)-I-K-D-T-Y-
(MI)-H,WVRQAPGKGLEWIG(WR)-I-D-P-(GA)-N-D-N-I-K-Y-
(SD)-(PQ)-K-F-Q-GRFTISRDNAKNSLYLQMNSLRAEDTAVYYCAR
SEENWYDFFDY (SEQ ID NO: 105)
EVQLVESGGGLVQPGGSLRLSCAASG-(YF)-(NT)-I-K-D-T-Y-
(MI)-H,WVRQAPGKGLEWVA(WR)-I-D-P-(GA)-N-D-N-I-K-Y-
(SD)-(PQ)-K-F-Q-GKATISRDNAKNSLYLQMNSLRAEDTAVYYCAR
SEENWYDFFDY (SEQ ID NO: 106)
EVQLVESGGGLVQPGGSLRLSCAASG-(YF)-(NT)-I-K-D-T-Y-
(MI)-H,WVRQAPGKGLEWVA(WR)-I-D-P-(GA)-N-D-N-I-K-Y-
(SD)-(PQ)-K-F-Q-GRFTISADNAKNSLYLQMNSLRAEDTAVYYCAR
SEENWYDFFDY (SEQ ID NO: 107)
EVQLVESGGGLVQPGGSLRLSCAASG-(YF)-(NT)-I-K-D-T-Y-
(MI)-H,WVRQAPGKGLEWVG(WR)-I-D-P-(GA)-N-D-N-I-K-Y-
(SD)-(PQ)-K-F-Q-GRFTISRDNAKNSLYLQMNSLPAEDTAVYYCAR
SEENWYDFFDY (SEQ ID NO: 108)
EVQLVESGGGLVQPGGSLRLSCAASG-(YF)-(NT)-I-K-D-T-Y-
(MI)-H,WVRQAPGKGLEWVA(WR)-I-D-P-(GA)-N-D-N-I-K-Y-
(SD)-(PQ)-K-F-Q-GKATISADNAKNSLYLQMNSLPAEDTAVYYCAR
SEENWYDFFDY (SEQ ID NO: 109)
EVQLVESGGGLVQPGGSLRLSCAASG-(YF)-(NT)-I-K-D-T-Y-
(MI)-H,WVRQAPGKGLEWIG(WR)-I-D-P-(GA)-N-D-N-I-K-Y-
(SD)-(PQ)-K-F-Q-GRFTISADNAKNSLYLQMNSLRAEDTAVYYCAR
SEENWYDFFDY (SEQ ID NO: 110)
EVQLVESGGGLVQPGGSLRLSCAASG-(YF)-(NT)-I-K-D-T-Y-
(MI)-H,WVRQAPGKGLEWVG(WR)-I-D-P-(GA)-N-D-N-I-K-Y-
(SD)-(PQ)-K-F-Q-GRFTISADNAKNSLYLQMNSLRAEDTAVYYCAR
SEENWYDFFDY (SEQ ID NO: 111)
EVQLVESGGGLVQPGGSLRLSCAASG-(YF)-(NT)-I-K-D-T-Y-
(MI)-H,WVRQAPGKGLEWVA(WR)-I-D-P-(GA)-N-D-N-I-K-Y-
(SD)-(PQ)-K-F-Q-GRFTISRDNAKNSAYLQMNSLRAEDTAVYYCAR
SEENWYDFFDY (SEQ ID NO: 112)
EVQLVESGGGLVQPGGSLRLSCAASG-(YF)-(NT)-I-K-D-T-Y-
(MI)-H,WVRQAPGKGLEWVG(WR)-I-D-P-(GA)-N-D-N-I-K-Y-
(SD)-(PQ)-K-F-Q-GRFTISADNAKNSAYLQMNSLRAEDTAVYYCAR
SEENWYDFFDY (SEQ ID NO: 113)
EVQLVESGGGLVQPGGSLRLSCAASG-(YF)-(NT)-I-K-D-T-Y-
(MI)-H,WVRQAPGKGLEWIG(WR)-I-D-P-(GA)-N-D-N-I-K-Y-
(SD)-(PQ)-K-F-Q-GRFTISADNAKNSAYLQMNSLRAEDTAVYYCAR
SEENWYDFFDY (SEQ ID NO: 114)
EVQLVESGGGLVQPGGSLRLSCTGSG-(YF)-(NT)-I-K-D-T-Y-
(MI)-H,WVRQAPGKGLEWIG(WR)-I-D-P-(GA)-N-D-N-I-K-Y-
(SD)-(PQ)-K-F-Q-GRFTISADNAKNSLYLQMINSLRAEDTAVYYCAR
SEENWYDFFDY (SEQ ID NO: 115)
EVQLQQSGAELVKPGASVKLSCTGSG-(YF)-(NT)-I-K-D-T-Y-
(MI)-H,WVKQRPEQGLEWIG(WR)-I-D-P-(GA)-N-D-N-I-K-Y-
(SD)-(PQ)-K-F-Q-(KV)-H-GKATITADTSSNTAYLQLNSLTSED-
TAVYYCAR
SEENWYDFFDY or a sequence that has fewer than eight, seven, six, five, four, three, or two alterations (e.g., substitutions, insertions or deletions, e.g., conservative substitutions or a substitution for an amino acid residue at a corresponding position in MJ 2-7) in the framework region. Exemplary substitutions are at one or more of the following Kabat positions: 2, 4, 6, 25, 36, 37, 39, 47, 48, 93, 94, 103, 104, 106, and 107. The substitutions can, for example, substitute an amino acid at a corresponding position from MJ 2-7 into a human framework region. The FR4 region can include, e.g., the sequence WGQGTTLTVSS (SEQ ID NO:116) or WGQGTLVTVSS (SEQ ID NO:117).

In one embodiment, the heavy chain variable domain sequence is at least 90, 92, 93, 94, 95, 96, 97, 98, 99% identical or identical to the heavy chain variable domain of V2.1, V2.2, V2.3, V2.4, V2.5, V2.6, V2.7, V2.11, or other heavy chain variable domain described herein. In one embodiment, the heavy chain variable domain sequence includes variable domain sequence comprises a sequence encoded by a nucleic acid that hybridizes under high stringency conditions to the complement of a nucleic acid encoding the heavy chain variable domain of V2.1, V2.2, V2.3, V2.4, V2.5, V2.6, V2.7, V2.11, or other heavy chain variable domain described herein. In one embodiment, the light chain variable domain sequence is at least 90, 92, 93, 94, 95, 96, 97, 98, 99% identical or identical to the light chain variable domain of V2.11 or other light chain variable domain described herein. In one embodiment, the light chain variable domain sequence comprises a sequence encoded by a nucleic acid that hybridizes under high stringency conditions to the complement of a nucleic acid encoding the light chain variable domain of V2.11 or other light chain variable domain described herein.

In one embodiment, the heavy chain framework (e.g., FR1, FR2, FR3, individually, or a sequence encompassing FR1, FR2, and FR3, but excluding CDRs) includes an amino acid sequence, which is at least 80%, 85%, 90%, 95%, 97%, 98%, 99% or higher identical to the heavy chain framework of one of the following germline V segment sequences: DP-25, DP-1, DP-12, DP-9, DP-7, DP-31, DP-32, DP-33, DP-58, or DP-54, or another V gene which is compatible with the canonical structure class 1-3 (see, e.g., Chothia et al. (1992) J. Mol. Biol. 227:799-817; Tomlinson et al. (1992) J. Mol. Biol. 227:776-798). Other frameworks compatible with the canonical structure class 1-3 include frameworks with the one or more of the following residues according to Kabat numbering: Ala, Gly, Thr, or Val at position 26; Gly at position 26; Tyr, Phe, or Gly at position 27; Phe, Val, Ile, or Leu at position 29; Met, Ile, Leu, Val, Thr, Trp, or Ile at position 34; Arg, Thr, Ala, Lys at position 94; Gly, Ser, Asn, or Asp at position 54; and Arg at position 71.

In one embodiment, the light chain framework (e.g., FR1, FR2, FR3, individually, or a sequence encompassing FR1, FR2, and FR3, but excluding CDRs) includes an amino acid sequence, which is at least 80%, 85%, 90%, 95%, 97%, 98%, 99% or higher identical to the light chain framework of a Vκ II subgroup germline sequence or one of the following germline V segment sequences: A17, A1, A18, A2, A19/A3, or A23 or another V gene which is compatible with the canonical structure class 4-1 (see, e.g., Tomlinson et al. (1995) EMBO J. 14:4628). Other frameworks compatible with the canonical structure class 4-1 include frameworks with the one or more of the following residues according to Kabat numbering: Val or Leu or Ile at position 2; Ser or Pro at position 25; Ile or Leu at position 29; Gly at position 31d; Phe or Leu at position 33; and Phe at position 71.

In another embodiment, the light chain framework (e.g., FR1, FR2, FR3, individually, or a sequence encompassing FR1, FR2, and FR3, but excluding CDRs) includes an amino acid sequence, which is at least 80%, 85%, 90%, 95%, 97%, 98%, 99% or higher identical to the light chain framework of a Vκ I subgroup germline sequence, e.g., a DPK9 sequence.

In another embodiment, the heavy chain framework (e.g., FR1, FR2, FR3, individually, or a sequence encompassing FR1, FR2, and FR3, but excluding CDRs) includes an amino acid sequence, which is at least 80%, 85%, 90%, 95%, 97%, 98%, 99% or higher identical to the light chain framework of a VH I subgroup germline sequence, e.g., a DP-25 sequence or a VH III subgroup germline sequence, e.g., a DP-54 sequence.

In one embodiment, the IL-13 binding agent includes at least one, two and preferably three CDR's from the light or heavy chain variable domain of an antibody disclosed herein, e.g., C65. For example, the IL-13 binding agent includes one or more of the following sequences within a CDR region:

QASQGTSINLN (SEQ ID NO:118),
GASNLED (SEQ ID NO:119), and
LQHSYLPWT (SEQ ID NO:120)
GFSLTGYGVN (SEQ ID NO:121),
IIWGDGSTDYNSAL (SEQ ID NO:122), and
DKTFYYDGFYRGRMDY (SEQ ID NO:123), or a CDR having an amino acid sequence that differs by no more than 4, 3, 2.5, 2, 1.5, 1, or 0.5 substitutions, insertions or deletions for every 10 amino acids (e.g., the number of differences being proportional to the CDR length) relative to a sequence listed above, e.g., at least one alteration but not more than two, three, or four per CDR. For example, the protein can include, in the light chain variable domain sequence, at least one, two, or three of the following sequences within a CDR region:

QASQGTSINLN (SEQ ID NO:118),
GASNLED (SEQ ID NO:119), and
LQHSYLPWT (SEQ ID NO:120), or an amino acid sequence that differs by no more than 4, 3, 2.5, 2, 1.5, 1, or 0.5 substitutions, insertions or deletions for every 10 amino acids relative to a sequence listed above.

The IL-13 binding agent can include, in the heavy chain variable domain sequence, at least one, two, or three of the following sequences within a CDR region:

GFSLTGYGVN (SEQ ID NO:121),
IIWGDGSTDYNSAL (SEQ ID NO:122), and
DKTFYYDGFYRGRMDY (SEQ ID NO:123), or an amino acid sequence that differs by no more than 4, 3, 2.5, 2, 1.5, 1, or 0.5 substitutions, insertions or deletions for every 10 amino acids relative to a sequence listed above.

In one preferred embodiment, the IL-13 binding agent includes all six CDRs from C65 or closely related CDRs, e.g., CDRs which are identical or which have at least one amino acid alteration, but not more than two, three or four alterations (e.g., substitutions, deletions, or insertions).

In still another embodiment, the IL-13 binding agent includes at least one, two or three CDR regions that have the same canonical structures and the corresponding CDR regions of C65, e.g., at least CDR1 and CDR2 of the heavy and/or light chain variable domains of C65.

In one embodiment, the heavy chain framework (e.g., FR1, FR2, FR3, individually, or a sequence encompassing FR1, FR2, and FR3, but excluding CDRs) includes an amino acid sequence, which is at least 80%, 85%, 90%, 95%, 97%, 98%, 99% or higher identical to the heavy chain framework of one of the following germline V segment sequences: DP-71 or DP-67 or another V gene which is compatible with the canonical structure class of C65 (see, e.g., Chothia et al. (1992) J. Mol. Biol. 227:799-817; Tomlinson et al. (1992) J. Mol. Biol. 227:776-798).

In one embodiment, the light chain framework (e.g., FR1, FR2, FR3, individually, or a sequence encompassing FR1, FR2, and FR3, but excluding CDRs) includes an amino acid sequence, which is at least 80%, 85%, 90%, 95%, 97%, 98%, 99% or higher identical to the light chain framework of DPK-1 or DPK-9 germline sequence or another V gene which is compatible with the canonical structure class of C65 (see, e.g., Tomlinson et al. (1995) *EMBO J.* 14:4628).

In another embodiment, the light chain framework (e.g., FR1, FR2, FR3, individually, or a sequence encompassing FR1, FR2, and FR3, but excluding CDRs) includes an amino acid sequence, which is at least 80%, 85%, 90%, 95%, 97%, 98%, 99% or higher identical to the light chain framework of a Vκ I subgroup germline sequence, e.g., a DPK-9 or DPK-1 sequence.

In another embodiment, the heavy chain framework (e.g., FR1, FR2, FR3, individually, or a sequence encompassing FR1, FR2, and FR3, but excluding CDRs) includes an amino acid sequence, which is at least 80%, 85%, 90%, 95%, 97%, 98%, 99% or higher identical to the light chain framework of a VH IV subgroup germline sequence, e.g., a DP-71 or DP-67 sequence.

In one embodiment, the light or the heavy chain variable framework (e.g., the region encompassing at least FR1, FR2, FR3, and optionally FR4) can be chosen from: (a) a light or heavy chain variable framework including at least 80%, 85%, 90%, 95%, or 100% of the amino acid residues from a human light or heavy chain variable framework, e.g., a light or heavy chain variable framework residue from a human mature antibody, a human germline sequence, a human consensus sequence, or a human antibody described herein; (b) a light or heavy chain variable framework including from 20% to 80%, 40% to 60%, 60% to 90%, or 70% to 95% of the amino acid residues from a human light or heavy chain variable framework, e.g., a light or heavy chain variable framework residue from a human mature antibody, a human germline sequence, a human consensus sequence; (c) a non-human framework (e.g., a rodent framework); or (d) a non-human framework that has been modified, e.g., to remove antigenic or cytotoxic determinants, e.g., deimmunized, or partially humanized. In one embodiment, the heavy chain variable domain sequence includes human residues or human consensus sequence residues at one or more of the following positions (preferably at least five, ten, twelve, or all): (in the FR of the variable domain of the light chain) 4L, 35L, 36L, 38L, 43L, 44L, 58L, 46L, 62L, 63L, 64L, 65L, 66L, 67L, 68L, 69L, 70L, 71L, 73L, 85L, 87L, 98L, and/or (in the FR of the variable domain of the heavy chain) 2H, 4H, 24H, 36H, 37H, 39H, 43H, 45H, 49H, 58H, 60H, 67H, 68H, 69H, 70H, 73H, 74H, 75H, 78H, 91H, 92H, 93H, and/or 103H (according to the Kabat numbering).

In one embodiment, the IL-13 binding agent includes at least one non-human CDR, e.g., a murine CDR, e.g., a CDR from MJ 2-7 or C65, or a mutant thereof, and at least one framework which differs from a framework of MJ 2-7 or C65 by at least one amino acid, e.g., at least 5, 8, 10, 12, 15, or 18 amino acids. For example, the proteins include one, two, three, four, five, or six such non-human CDRs and includes at least one amino acid difference in at least three of HC FR1, HC FR2, HC FR3, LC FR1, LC FR2, and LC FR3.

In one embodiment, the heavy or light chain variable domain sequence of the anti-IL-13 antibody molecule includes an amino acid sequence, which is at least 80%, 85%, 90%, 95%, 97%, 98%, 99% or higher identical to a variable domain sequence of an antibody described herein, e.g., MJ 2-7 or C65; or which differs at at least 1 or 5 residues, but less than 40, 30, 20, or 10 residues, from a variable domain sequence of an antibody described herein, e.g., MJ 2-7 or C65. In one embodiment, the heavy or light chain variable domain sequence of the protein includes an amino acid sequence encoded by a nucleic acid sequence described herein or a nucleic acid that hybridizes to a nucleic acid sequence described herein or its complement, e.g., under low stringency, medium stringency, high stringency, or very high stringency conditions.

In one embodiment, one or both of the variable domain sequences include amino acid positions in the framework region that are variously derived from both a non-human antibody (e.g., a murine antibody such as mAb13.2) and a human antibody or germline sequence. For example, a variable domain sequence can include a number of positions at which the amino acid residue is identical to both the non-human antibody and the human antibody (or human germline sequence) because the two are identical at that position. Of the remaining framework positions where the non-human and human differ, at least 50, 60, 70, 80, or 90% of the positions of the variable domain are preferably identical to the human antibody (or human germline sequence) rather than the non-human. For example, none, or at least one, two, three, or four of such remaining framework position may be identical to the non-human antibody rather than to the human. For example, in HC FR1, one or two such positions can be non-human; in HC FR2, one or two such positions can be non-human; in FR3, one, two, three, or four such positions can be non-human; in LC FR1, one, two, three, or four such positions can be non-human; in LC FR2, one or two such positions can be non-human; in LC FR3, one or two such positions can be non-human. The frameworks can include additional non-human positions.

The IL-13 binding agent, e.g., anti-IL-13 antibody molecule, can be derivatized or linked to another functional molecule, e.g., another peptide or protein (e.g., an Fab fragment). For example, the binding agent can be functionally linked (e.g., by chemical coupling, genetic fusion, noncovalent association or otherwise) to one or more other molecular entities, such as another antibody molecule (e.g., to form a bispecific or a multispecific antibody molecule), toxins, radioisotopes, cytotoxic or cytostatic agents, among others.

In another embodiment, the IL-13 binding agent, e.g., anti-IL-13 antibody molecule, interferes with the interaction of IL-13 with the receptor IL-13Rα1. In one embodiment, the IL-13 binding agent can interfere with the interaction of Phe107 of IL-13 (SEQ ID NO:124; FIG. 13A) with a hydrophobic pocket of IL-13Rα1 formed by the side chains of residues Leu319, Cys257, Arg256, and Cys320 (SEQ ID NO:125; FIG. 13B), e.g., by direct binding to these residues or steric hindrance. In another embodiment, the IL-13 binding agent can interfere with van der Waals interactions between amino acid residues Ile254, Ser255, Arg256, Lys318, Cys320, and Tyr321 of IL-13Rα1 (SEQ ID NO:125) and amino acid residues Arg11, Glu12, Leu13, Ile14, Glu15, Lys104, Lys105, Leu106, Phe107, and Arg108 of IL-13 (SEQ ID NO:124), e.g., by direct binding to these residues or steric hindrance.

In one embodiment, the IL-13 binding agent, e.g., the anti-IL-13 antibody, molecule has no significant cross-reactivity when screened against at least half, two-thirds, three-quarter, 90%, or all the tissues on the "suggested list of human tissues to be used for immunohistochemical investigations of cross-reactivity" in Annex II of the DC CPMP Guideline III/5271/94 Draft 5, "Production and quality control of monoclonal antibodies" and at least half, two-thirds, three-quarter, 90%, or all of the tissues recommended in Table 2 of the 1997 US FDA/CBER "Points to Consider in the Manufacture and Testing of Monoclonal Antibody Products for Human Use."

In one embodiment, the IL-13 binding agent, e.g., the anti-IL-13 antibody, specifically binds to IL-13, e.g., a mammalian IL-13, e.g., human or non-human primate IL-13. For example, the binding agent binds to IL-13 with an affinity that is at least two-fold, 10-fold, 50-fold, 100-fold, or better (smaller $K_d$) than its affinity for binding to a non-specific antigen (e.g., BSA, casein) other than IL-13, or with an affinity that is at least two-fold, 10-fold, 50-fold, 100-fold, or better (smaller $K_d$) than its affinity for binding to another human interleukin other than IL-13. In some embodiments, the IL-13 binding agent only detects a single prominent band when blotted against the crude sample of human IL-13 described in Example 1 ("Quaternary Screen"). In some embodiments, a precipitate made by pulling down proteins from that crude sample using beads to which the IL-13 binding agent is immobilized is a composition in which IL-13 is at least 5%, 10%, 50%, or 80% pure.

In another aspect, an IL-13 binding agent, e.g., an anti-IL-13 antibody molecule, or a pharmaceutical composition thereof, is administered to treat or prevent an IL-13-associated disorder. Treating refers to improving or maintaining (or so attempting) the condition of subject. In a typical case, treating improves the condition of the subject to an extent discernable to a physician or prevents worsening of the condition. Examples of IL-13-associated disorders include, but are not limited to, disorders chosen from one or more of: respiratory disorders, e.g., asthma (e.g., allergic and nonallergic asthma (e.g., asthma due to infection with, e.g., respiratory syncytial virus (RSV), e.g., in younger children)), chronic obstructive pulmonary disease (COPD), and other conditions involving airway inflammation, eosinophilia, fibrosis and excess mucus production, e.g., cystic fibrosis and pulmonary fibrosis; atopic disorders, e.g., resulting from an increased sensitivity to IL-13, (e.g., atopic dermatitis, urticaria, eczema, allergic rhinitis, and allergic enterogastritis); inflammatory and/or autoimmune conditions of, the skin (e.g., atopic dermatitis), gastrointestinal disorders (e.g., inflammatory bowel diseases (IBD), such as ulcerative colitis and/or Crohn's disease), liver (e.g., cirrhosis, hepatocellular carcinoma), and scleroderma; tumors or cancers (e.g., soft tissue or solid tumors), such as leukemia, glioblastoma, and lymphoma, e.g., Hodgkin's lymphoma; viral infections (e.g., from HTLV-1); fibrosis of other organs, e.g., fibrosis of the liver, (e.g., fibrosis caused by a hepatitis B and/or C virus); and suppression of expression of protective type 1 immune responses, (e.g., during vaccination), e.g., as described herein.

The IL-13 binding agent (e.g., the anti-IL-13 antibody molecule, such as one described herein) can be in administered in an amount effective to treat or prevent the disorder. In the case of prophylactic use (e.g., to prevent onset or delay onset), the subject may or may not have one or more symptoms of the disorder. The amount can also be selected to be effective to ameliorate at least one symptom of the disorder. Preferably, the subject is a mammal, e.g., a human suffering from an IL-13-associated disorder as described herein. For respiratory disorders, e.g., asthma, the IL-13 binding agent can be delivered by inhalation.

In one embodiment, the method includes administering doses of an antibody molecule that binds to IL-13. For example, the antibody molecule inhibits or neutralizes IL-13. In one embodiment, each dose is administered subcutaneously, e.g., in an amount of about 0.5-10 mg/kg (e.g., 0.7-3.3 mg/kg) at a frequency of no more than once per week, e.g., every other week or once or twice monthly. In one embodiment, the antibody is an antibody described herein. For example, the antibody is an antibody that inhibits binding of IL-13Rα1. The antibody can, e.g., confers a post-injection protective effect against exposure to Ascaris antigen in a sheep model at least 6 weeks after injection.

In one embodiment, the IL-13 binding agent is administered in combination with another therapeutic agent. The combination therapy can include an IL-13 binding agent, e.g., an anti-IL-13 antibody molecule, coformulated with and/or coadministered with one or more additional therapeutic agents, e.g., one or more cytokine and growth factor inhibitors, immunosuppressants, anti-inflammatory agents (e.g., systemic anti-inflammatory agents), metabolic inhibitors, enzyme inhibitors, and/or cytotoxic or cytostatic agents, as described in more herein. The IL-13 binding agent and the other therapeutic can also be administered separately.

Examples of preferred additional therapeutic agents that can be coadministered and/or coformulated with an IL-13 binding agent include: inhaled steroids; beta-agonists, e.g., short-acting or long-acting beta-agonists; antagonists of leukotrienes or leukotriene receptors; combination drugs such as ADVAIR®; IgE inhibitors, e.g., anti-IgE antibodies (e.g., XOLAIR®); phosphodiesterase inhibitors (e.g., PDE4 inhibitors); xanthines; anticholinergic drugs; mast cell-stabilizing agents such as cromolyn; IL-4 inhibitors; IL-5 inhibitors; eotaxin/CCR3 inhibitors; and antihistamines. Such combinations can be used to treat asthma and other respiratory disorders. Additional examples of therapeutic agents that can be coadministered and/or coformulated with an IL-13 binding agent include one or more of: TNF antagonists (e.g., a soluble fragment of a TNF receptor, e.g., p55 or p75 human TNF receptor or derivatives thereof, e.g., 75 kd TNFR-IgG (75 kD TNF receptor-IgG fusion protein, ENBREL™)); TNF enzyme antagonists, e.g., TNFα converting enzyme (TACE) inhibitors; muscarinic receptor antagonists; TGF-β antagonists; interferon gamma; perfenidone; chemotherapeutic agents, e.g., methotrexate, leflunomide, or a sirolimus (rapamycin) or an analog thereof, e.g., CCI-779; COX2 and cPLA2 inhibitors; NSAIDs; immunomodulators; p38 inhibitors, TPL-2, Mk-2 and NFκB inhibitors, among others.

In another aspect, this application provides compositions, e.g., pharmaceutical compositions, that include a pharmaceutically acceptable carrier and at least one IL-13 binding agent, e.g., an anti-IL-13 antibody molecule. In one embodiment, the compositions, e.g., pharmaceutical compositions, comprise a combination of two or more IL-13 binding agents, e.g., two or more anti-IL-13 antibody molecules. Combinations of the IL-13 binding agent, e.g., the anti-IL-13 antibody molecule, and a drug, e.g., a therapeutic agent (e.g., one or more cytokine and growth factor inhibitors, immunosuppressants, anti-inflammatory agents (e.g., systemic anti-inflammatory agents), metabolic inhibitors, enzyme inhibitors, and/or cytotoxic or cytostatic agents, as described herein, can also be used.

This application also features nucleic acids that include nucleotide sequences that encode an IL-13 binding agent described herein or a component thereof, e.g., a heavy and/or light chain variable domain sequence of an anti-IL-13 antibody molecule, e.g., an antibody molecule described herein. For example, the application features a first and second nucleic acid encoding heavy and light chain variable domain sequences, respectively, of an anti-IL-13 antibody chosen from one or more of, e.g., MJ 2-7 or C65, e.g., as described herein. In another aspect, the application features host cells and vectors containing the nucleic acids described herein.

The invention also features the epitope of IL-13, e.g., human IL-13, recognized by one or more of, e.g., MJ 2-7 or C65. For example, proteins and peptides that include the epitope can be used to generate or screen for other binding compounds that interact with the epitope, e.g., proteins such as antibodies or small molecules. For example, a peptide that includes the epitope can be used as an immunogen or as a target for screening an expression library. It is also possible to evaluate compounds for ability to interact with the peptide, or, by mapping or structure determination, to evaluate compounds for ability to interact with the epitope, e.g., in the context of a mature IL-13.

In another aspect, this application features a method of modulating, e.g., interfering with (e.g., inhibiting, blocking or otherwise reducing), an interaction, e.g., binding, between IL-13 and a cognate IL-13 binding protein, e.g., an IL-13 receptor complex, e.g., a complex comprising IL-13Rα1 and IL-4Rα, or a subunit thereof. The modulating can be effected in vivo or in vitro. In other embodiments, the IL-13 binding agent, e.g., the anti-IL-13 antibody molecule, binds to IL-13, and interferes with (e.g., inhibits, blocks or otherwise reduces) an interaction, e.g., binding, between IL-13 and a subunit of the IL-13 receptor complex, e.g., IL-13Rα1 or IL-4Rα, individually. In yet another embodiment, the IL-13 binding agent, e.g., the anti-IL-13 antibody molecule, binds to IL-13, and interferes with (e.g., inhibits, blocks or otherwise reduces) an interaction, e.g., binding, between IL-13 and IL-13Rα1. In another embodiment, the IL-13 binding agent, e.g., the anti-IL-13 antibody molecule, binds to IL-13, and interferes with (e.g., inhibits, blocks or otherwise reduces) an interaction, e.g., binding, between IL-13 and IL-13Rα1. Typically, the anti-IL-13 antibody molecule interferes with (e.g., inhibits, blocks or otherwise reduces) an interaction, e.g., binding, of IL-13 and IL-13Rα1.

In another aspect, this application features a method of modulating interaction between IL-13 and an IL-13 receptor protein, e.g., IL-13Rα1 or IL-13Rα2. For example, an IL-13 binding agent, e.g., an agent described herein, can be used to reduce or inhibit binding, between IL-13 and IL-13Rα1 or IL-13Rα2, or to reduce formation of a complex that includes IL-13Rα1 and IL-4Rα (e.g., a complex as described herein). The method comprises contacting IL-13 or a complex that contains IL-13 with an IL-13 binding agent, e.g., a protein described herein.

The subject methods can be used on cells in vitro (e.g., in a cell-free system), in culture, e.g. in vitro or ex vivo. For example, IL-13 receptor-expressing cells can be cultured in vitro in culture medium and the contacting step can be effected by adding an IL-13 binding agent to the culture medium. Alternatively, the method can be performed on cells present in a subject, e.g., as part of an in vivo (e.g., therapeutic or prophylactic) protocol. For example, the IL-13 binding agent can be delivered locally or systemically.

The method can include contacting IL-13 with the IL-13 receptor complex, or subunit thereof, under conditions that allow an interaction between IL-13 and the IL-13 receptor complex, or subunit thereof, to occur to thereby form an IL-13/IL-13 receptor mixture. Generally, the IL-13 binding agent is provided in an effective amount, e.g., so that contacting the IL-13/IL-13 receptor mixture modulates, e.g., interferes with (e.g., inhibits, blocks or otherwise reduces) the interaction between IL-13 and the receptor protein or at least one function of IL-13, e.g., IL-13 mediated signaling.

In another aspect, this application provides a method for detecting the presence of IL-13 in a sample in vitro (e.g., a biological sample, such as serum, plasma, tissue, biopsy). The subject method can be used to diagnose a disorder, e.g., an immune cell-associated disorder. The method includes: (i) contacting the sample or a control sample with an IL-13 binding agent, e.g., an anti-IL-13 antibody molecule, e.g., as described herein; and (ii) detecting formation of a complex between the IL-13 binding agent and the sample or the control sample, wherein a statistically significant change in the formation of the complex in the sample relative to the control sample is indicative of the presence of the IL-13 in the sample.

In yet another aspect, this application provides a method for detecting the presence of IL-13 in vivo (e.g., in vivo imaging in a subject). The subject method can be used to diagnose a disorder, e.g., an IL-13-associated disorder. The method includes: (i) administering an IL-13 binding agent, e.g., an anti-IL-13 antibody molecule, e.g., as described herein, to a subject or a control subject under conditions that allow binding of the binding agent to IL-13; and (ii) detecting formation of a complex between the binding agent and IL-13, wherein a statistically significant change in the formation of the complex in the subject relative to the control subject is indicative of the presence of IL-13.

For example, the antibody molecule is directly or indirectly labeled with a detectable substance to facilitate detection of the bound or unbound antibody. Suitable detectable substances include various enzymes, prosthetic groups, fluorescent materials, luminescent materials and radioactive materials.

Methods for delivering or targeting an agent, e.g., a therapeutic or a cytotoxic agent, to an IL-13-expressing cell in vivo are also disclosed.

In one aspect, the invention features a polypeptide that comprises the sequence, or a functional fragment thereof:

```
SPVPPSTALKELIEELVNITQNQKAPLCNGSMVWSINLTAGVYCAALESLINVSGCSAI  (SEQ ID NO: 14)

EKTQRMLNGFCPHKVSAGQFSSLRVRDTKIEVAQFVKDLLVHLKKLFREGQFN
```

The polypeptide can further include:

```
MALLLTMVIALTCLGGFASP,      (SEQ ID NO: 127)
``` e.g., as an N-terminal signal sequence. For example, the polypeptide is an IL-13 protein from cynomolgus monkey (herein, "NHP-IL-13"). The, NHP-IL-13 can be a mature IL-13 protein or an unprocessed full length IL-13 protein. Peptides of the above sequence, e.g., peptides that differ from corresponding peptides in human IL-13, can be used, e.g., as an immunogen or target compound.

Also featured are related polypeptides that differ from human IL-13 at one or more of the boldfaced positions above but are identical to human IL-13 at the non-boldface positions above. For example, one or more of the boldfaced positions can be an alanine, or a conservative substitution of the corresponding residue in the cynomolgus sequence (above) or the corresponding residue in the human sequence. The invention also features peptides, e.g., of at least 5 or 6 amino acids from the above sequence. The peptides can be included in a heterologous protein (e.g., a protein other than an IL-13), a chimeric protein (e.g., a human IL-13) or can be in an isolated peptide, e.g., one that does not include other sequences. The peptides can also be fused or conjugated to other compounds, e.g., a carrier. In one embodiment, the peptide includes at least one amino acid residue that differs from human IL-13. Exemplary peptides are described below.

Also featured are nucleic acids encoding the cynomolgus IL-13 sequence and variants thereof. The polypeptide can be used to provide an IL-13 binding agent that binds the cynomolgus monkey IL-13, and, optionally, also an IL-13 protein from another species, e.g., a human IL-13.

In one aspect, the invention features a method of providing a target binding molecule that specifically binds to a human target protein. For example, the target binding molecule is an antibody molecule. The method includes: providing a target protein that comprises at least a portion of a non-human protein, the portion being homologous to (at least 70, 75, 80, 85, 87, 90, 92, 94, 95, 96, 97, or 98% identical to) a corresponding portion of a human target protein, but differing by at least one amino acid (e.g., at least one, two, three, four, five, six, seven, eight, or nine amino acids); obtaining a binding agent that specifically binds to the antigen; and evaluating if the binding agent specifically binds to the human target protein or evaluating efficacy of the binding agent in modulating activity of the human target protein. The method can further include administering the binding agent (e.g., an antibody molecule) or a derivative (e.g., a humanized antibody molecule) to a human subject. In one embodiment, the human target protein is a cytokine, e.g., an interleukin, e.g., IL-13 or IL-4. The non-human protein can be from a non-human primate, e.g., a rhesus monkey, a cynomolgus monkey, or a pigtail macaque.

In one embodiment, the step of obtaining comprises using a protein expression library, e.g., a phage or ribosome display library. For example, the library displays antibody molecules such as Fab's or scFv's. In one embodiment, the step of obtaining comprises immunizing an animal using the antigen as an immunogen. For example, the animal can be a rodent, e.g., a mouse or rat. The animal can be a transgenic animal that has at least one human immunoglobulin gene.

All publications, patent applications, patents, and other references mentioned herein are incorporated by reference in their entirety.

DEFINITIONS

The term "IL-13 binding agent, " as used herein, refers to any compound, such as a protein (e.g., a multi-chain polypeptide, a polypeptide) or a peptide, that includes an interface that binds to an IL-13 protein, e.g., a mammalian IL-13, particularly a human or non-human primate IL-13. The binding agent generally binds with a Kd of less than $5\times10^{-7}$ M. An exemplary IL-13 binding agent is a protein that includes an antigen binding site, e.g., an antibody molecule.

As used herein, the term "antibody molecule" refers to a protein comprising at least one immunoglobulin variable domain sequence. The term antibody molecule includes, for example, full-length, mature antibodies and antigen-binding fragments of an antibody. For example, an antibody molecule can include a heavy (H) chain variable domain sequence (abbreviated herein as VH), and a light (L) chain variable domain sequence (abbreviated herein as VL). In another example, an antibody molecule includes two heavy (H) chain variable domain sequences and two light (L) chain variable domain sequence, thereby forming two antigen binding sites. Examples of antigen-binding fragments include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment, which consists of a VH domain; (vi) a camelid or camelized variable domain; and (vii) a single chain Fv (scFv).

The VH and VL regions can be further subdivided into regions of hypervariability, termed "complementarity determining regions" (CDR), interspersed with regions that are more conserved, termed "framework regions" (FR). The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) J. Mol. Biol. 196:901-917; and the AbM definition used by Oxford Molecular's AbM antibody modelling software. See, generally, e.g., *Protein Sequence and Structure Analysis of Antibody Variable Domains. In: Antibody Engineering Lab Manual (Ed.: Duebel, S. and Kontermann, R., Springer-Verlag, Heidelberg). Generally, unless specifically indicated, the following definitions are used: AbM definition of CDR*1 of the heavy chain variable domain and Kabat definitions for the other CDRs. In addition, embodiments of the invention described with respect to Kabat or AbM CDRs may also be implemented using Chothia hypervariable loops. Each VH and VL typically includes three CDRs and four FRs, arranged from amino-terminus to carboxy-terminus in the following order: FR1, CDR1, FR2, CDR2, FR3, CDR3, FR4.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

The term "antigen-binding site" refers to the part of an IL-13 binding agent that comprises determinants that form an interface that binds to the IL-13, e.g., a mammalian IL-13, e.g., human or non-human primate IL-13, or an epitope thereof. With respect to proteins (or protein mimetics), the antigen-binding site typically includes one or more loops (of at least four amino acids or amino acid mimics) that form an interface that binds to IL-13. Typically, the antigen-binding site of an antibody molecule includes at least one or two CDRs, or more typically at least three, four, five or six CDRs.

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

An "effectively human" protein is a protein that does not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Saleh et al., *Cancer Immunol. Immunother.,* 32:180-190 (1990)) and also because of potential allergic reactions (see, e.g., LoBuglio et al., *Hybridoma,* 5:5117-5123 (1986)).

The term "isolated" refers to a molecule that is substantially free of its natural environment. For instance, an isolated protein is substantially free of cellular material or other proteins from the cell or tissue source from which it is derived. The term refers to preparations where the isolated protein is sufficiently pure to be administered as a therapeutic composition, or at least 70% to 80% (w/w) pure, more preferably, at least 80%-90% (w/w) pure, even more preferably, 90-95% pure; and, most preferably, at least 95%, 96%, 97%, 98%, 99%, or 100% (w/w) pure. A "separated" compound refers to a compound that is removed from at least 90% of at least one component of a sample from which the compound was obtained. Any compound described herein can be provided as an isolated or separated compound.

An "epitope" refers to the site on a target compound that is bound by a binding agent, e.g., an antibody molecule. An epitope can be a linear or conformational epitope, or a combination thereof. In the case where the target compound is a protein, for example, an epitope may refer to the amino acids that are bound by the binding agent. Overlapping epitopes include at least one common amino acid residue.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6. Aqueous and nonaqueous methods are described in that reference and either can be used. Specific hybridization conditions referred to herein are as follows: 1) low stringency hybridization conditions in 6×sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5 M sodium phosphate, 7% SDS at 65° C., followed by one or more washes at 0.2×SSC, 1% SDS at 65° C. Very high stringency conditions (4) are the preferred conditions and the ones that are used unless otherwise specified.

An "IL-13 associated disorder" is one in which IL-13 contributes to a pathology or symptom of the disorder. Accordingly, an IL-13 binding agent, e.g., an IL-13 binding agent that is an antagonist of one or more IL-13 associated activities, can be used to treat or prevent the disorder.

The term "IL-13" includes the full length unprocessed form of the cytokines known in the art as IL-13 (irrespective of species origin, and including mammalian, e.g., human and non-human primate IL-13) as well as mature, processed forms thereof, as well as any fragment (of at least 5 amino acids) or variant of such cytokines. Positions within the IL-13 sequence can be designated in accordance to the numbering for the full length, unprocessed human IL-13 sequence. For an exemplary full-length monkey IL-13, see SEQ ID NO:24; for mature, processed monkey IL-13, see SEQ ID NO:14; for full-length human IL-13, see SEQ ID NO:178, and for mature, processed human IL-13, see SEQ ID NO:124. An exemplary sequence is recited as follows:

For example, position 130 is a site of a common polymorphism.

Exemplary sequences of IL-13 receptor proteins (e.g., IL-13Rα1 and IL-13Rα2) are described, e.g., in Donaldson et al. (1998) *J Immunol*. 161:2317-24; U.S. Pat. Nos. 6,214,559; 6,248,714; and 6,268,480.

BRIEF DESCRIPTION OF THE DRAWINGS

FIG. 1A is an alignment of full-length human and cynomolgus monkey IL-13, SEQ ID NO:178 and SEQ ID NO:24, respectively.

FIG. 1B is a list of exemplary peptides from cynomolgus monkey IL-13, (SEQ ID NOs: 179-188, respectively).

```
MALLLTTVIALTCLGGFASPGPVPPSTALRELIEELVNITQNQKAPLCNGSMVWSI    (SEQ ID NO: 178)

NLTAGMYCAALESLINVSGCSAIEKTQRMLSGFCPHKVSAGQFSSLHVRDTKIEV

Figure 11B:
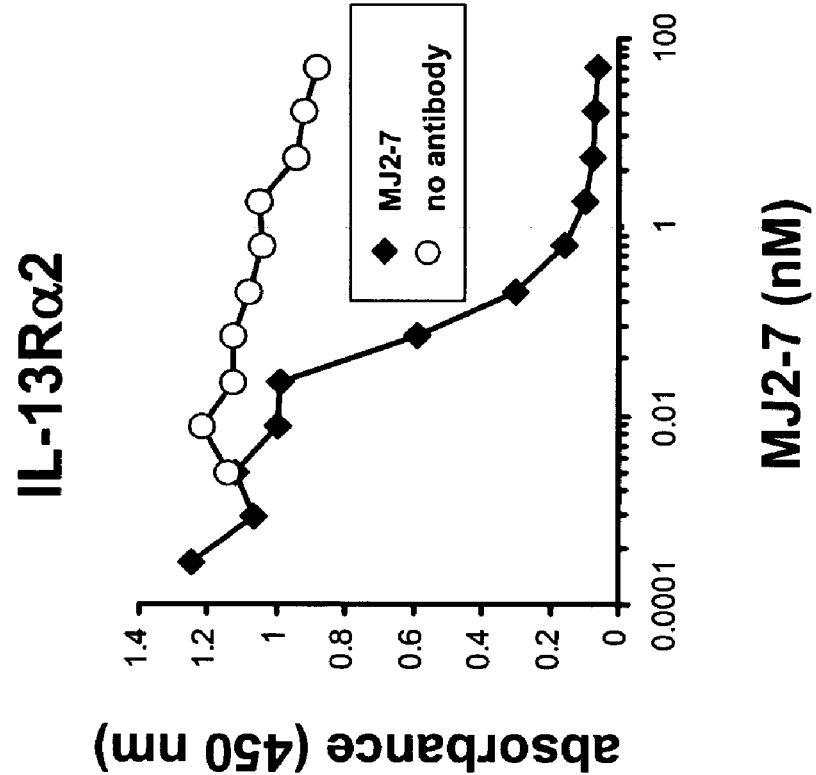
FIGS. 11A and 11B are graphs depicting inhibition of binding of IL-13 to immobilized IL-13 receptor by MJ2-7 antibody, as measured by ELISA. Binding is depicted as absorbance at 450 nm (y-axis). Concentration of MJ2-7 anti-
Figure 11A:
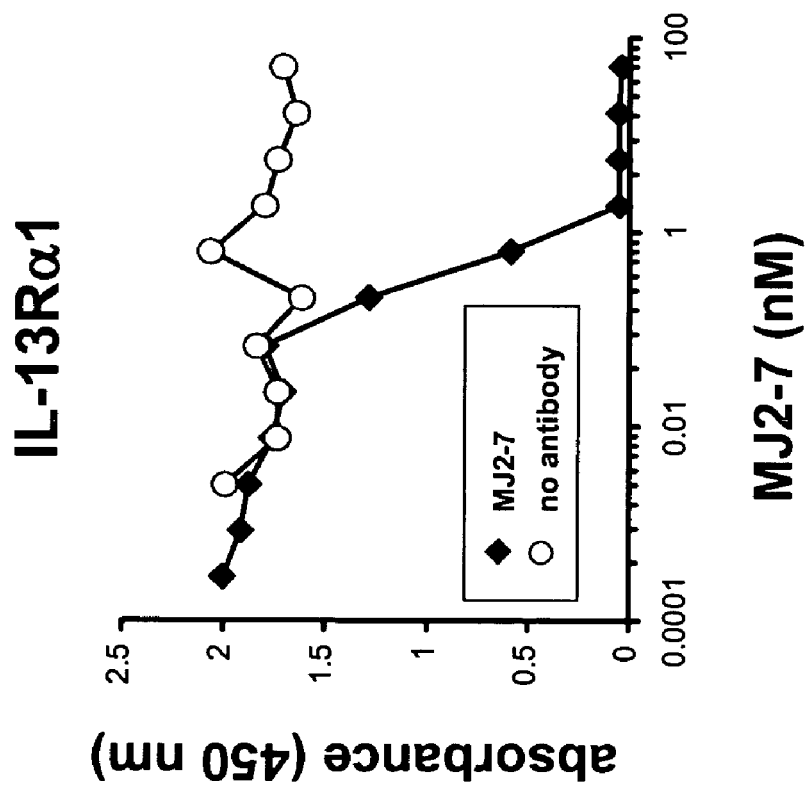

AQFVKDLLLHLKKLFREGRFN
``` body is depicted on the x-axis. FIG. 11A depicts binding to IL-13Rα1. FIG. 11B depicts binding to IL-13Rα2.

FIG. 12 is an alignment of DPK18 germline amino acid sequence (SEQ ID NO:126) and humanized MJ2-7 Version 3 VL (SEQ ID NO:190).

FIG. 13A is an amino acid sequence (SEQ ID NO:124) of mature, processed human IL-13.

FIG. 13B is an amino acid sequence (SEQ ID NO:125) of human IL-13Rα1.

DETAILED DESCRIPTION

Binding agents (e.g., anti-IL13 antibody molecules) that bind specifically to IL-13 and modulate the ability of IL-13 to interact with IL-13 receptors and signaling mediators are disclosed. The agents can be used to modulate (e.g., inhibit) one or more IL-13-associated activities. IL-13 binding agents, e.g., as described herein, can be used to modulate one or more IL-13-associated activities, e.g., in vivo, e.g., to treat or prevent IL-13-mediated disorders (e.g., asthma, airway inflammation, atopic disorders, allergic responses, eosinophilia, fibrosis, and IL-13 associated cancers).

Anti-IL-13 Antibody Molecules

Numerous methods are available for obtaining antibody molecules. One exemplary method includes screening protein expression libraries, e.g., phage or ribosome display libraries. Phage display is described, for example, in Ladner et al., U.S. Pat. No. 5,223,409; Smith (1985) *Science* 228: 1315-1317; WO 92/18619; WO 91/17271; WO 92/20791; WO 92/15679; WO 93/01288; WO 92/01047; WO 92/09690; and WO 90/02809. In addition to the use of display libraries, other methods can be used to obtain an anti-IL-13 antibody molecule. For example, an IL-13 protein or a peptide thereof can be used as an antigen in a non-human animal, e.g., a rodent, e.g., a mouse, hamster, or rat.

In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See, e.g., XENOMOUSE™, Green et al. (1994) *Nature Genetics* 7:13-21, US 2003-0070185, WO 96/34096, published Oct. 31, 1996, and PCT Application No. PCT/US96/05928, filed Apr. 29, 1996.

In another embodiment, a monoclonal antibody is obtained from the non-human animal, and then modified, e.g., humanized or deimmunized. Winter describes an exemplary CDR-grafting method that may be used to prepare the humanized antibodies described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

Humanized antibodies can be generated by replacing sequences of the Fv variable domain that are not directly involved in antigen binding with equivalent sequences from human Fv variable domains. Exemplary methods for generating humanized antibody molecules are provided by Morrison (1985) *Science* 229:1202-1207; by Oi et al. (1986) *BioTechniques* 4:214; and by U.S. Pat. Nos. 5,585,089; 5,693, 761; 5,693,762; 5,859,205; and U.S. Pat. No. 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

An IL-13-binding antibody molecule may also be modified by specific deletion of human T cell epitopes or "deimmunization" by the methods disclosed in WO 98/52976 and WO 00/34317. Briefly, the heavy and light chain variable domains of an antibody can be analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the $V_H$ and $V_L$ sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. Human germline sequences, e.g., are disclosed in Tomlinson, et al. (1992) *J. Mol. Biol.* 227:776-798; Cook, G. P. et al. (1995) *Immunol. Today* Vol. 16 (5): 237-242; Chothia, D. et al. (1992) *J. Mol. Biol.* 227:799-817; and Tomlinson et al. (1995) *EMBO J.* 14:4628-4638. The V BASE directory provides a comprehensive directory of human immunoglobulin variable region sequences (compiled by Tomlinson, I. A. et al. MRC Centre for Protein Engineering, Cambridge, UK). These sequences can be used as a source of human sequence, e.g., for framework regions and CDRs. Consensus human framework regions can also be used, e.g., as described in U.S. Pat. No. 6,300,064.

Additionally, chimeric, humanized, and single-chain antibody molecules (e.g., proteins that include both human and nonhuman portions), may be produced using standard recombinant DNA techniques. Humanized antibodies may also be produced, for example, using transgenic mice that express human heavy and light chain genes, but are incapable of expressing the endogenous mouse immunoglobulin heavy and light chain genes.

Additionally, the antibody molecules described herein also include those that bind to IL-13, interfere with the formation of a functional IL-13 signaling complex, and have mutations in the constant regions of the heavy chain. It is sometimes desirable to mutate and inactivate certain fragments of the constant region. For example, mutations in the heavy constant region can be made to produce antibodies with reduced binding to the Fc receptor (FcR) and/or complement; such mutations are well known in the art. An example of such a mutation to the amino sequence of the constant region of the heavy chain of IgG is provided in SEQ ID NO:128. Certain active fragments of the CL and CH subunits (e.g., CH1) are covalently link to each other. A further aspect provides a method for obtaining an antigen-binding site that is specific for a surface of IL-13 that participates in forming a functional IL-13 signaling complex.

Exemplary antibody molecules can include sequences of VL chains as set forth in SEQ ID NOs:30-46, and/or of VH chains as set forth in and SEQ ID NOs: 50-115, but also can include variants of these sequences that retain IL-13 binding ability. Such variants may be derived from the provided sequences using techniques well known in the art. Amino acid substitutions, deletions, or additions, can be made in either the FRs or in the CDRs. Whereas changes in the framework regions are usually designed to improve stability and reduce immunogenicity of the antibody molecule, changes in the CDRs are usually designed to increase affinity of the antibody molecule for its target. Such affinity-increasing changes are typically determined empirically by altering the CDR region and testing the antibody molecule. Such alterations can be made according to the methods described in Antibody Engineering, 2nd. ed. (1995), ed. Borrebaeck, Oxford University Press.

An exemplary method for obtaining a heavy chain variable domain sequence that is a variant of a heavy chain variable domain sequence described herein, includes adding, deleting, substituting, or inserting one or more amino acids in a heavy chain variable domain sequence described herein, optionally combining the heavy chain variable domain sequence with one or more light chain variable domain sequences, and testing a protein that includes the modified heavy chain variable domain sequence for specific binding to IL-13, and (preferably) testing the ability of such antigen-binding domain to modulate one or more IL-13-associated activities. An analogous method may be employed using one or more sequence variants of a light chain variable domain sequence described herein.

Variants of antibody molecules can be prepared by creating libraries with one or more varied CDRs and screening the libraries to find members that bind to IL-13, e.g., with improved affinity. For example, Marks et al. (*Bio/Technology* (1992) 10:779-83) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. The repertoire may be combined with a CDR3 of a particular antibody. Further, the CDR3-derived sequences may be shuffled with repertoires of VH or VL domains lacking a CDR3, and the shuffled complete VH or VL domains combined with a cognate VL or VH domain to provide specific antigen-binding fragments. The repertoire may then be displayed in a suitable host system such as the phage display system of WO 92/01047, so that suitable antigen-binding fragments can be selected. Analogous shuffling or combinatorial techniques are also disclosed by Stemmer (*Nature* (1994) 370:389-91). A further alternative is to generate altered VH or VL regions using random mutagenesis of one or more selected VH and/or VL genes to generate mutations within the entire variable domain. See, e.g., Gram et al. *Proc. Nat. Acad. Sci. USA* (1992) 89:3576-80.

Another method that may be used is to direct mutagenesis to CDR regions of VH or VL genes. Such techniques are disclosed by, e.g., Barbas et al. (*Proc. Nat. Acad. Sci. USA* (1994) 91:3809-13) and Schier et al. (*J. Mol. Biol.* (1996) 263:551-67). Similarly, one or more, or all three CDRs may be grafted into a repertoire of VH or VL domains, or even some other scaffold (such as a fibronectin domain). The resulting protein is evaluated for ability to bind to IL-13.

In one embodiment, a binding agent that binds to a target is modified, e.g., by mutagenesis, to provide a pool of modified binding agents. The modified binding agents are then evaluated to identify one or more altered binding agents which have altered functional properties (e.g., improved binding, improved stability, lengthened stability in vivo). In one implementation, display library technology is used to select or screen the pool of modified binding agents. Higher affinity binding agents are then identified from the second library, e.g., by using higher stringency or more competitive binding and washing conditions. Other screening techniques can also be used.

In some embodiments, the mutagenesis is targeted to regions known or likely to be at the binding interface. If, for example, the identified binding agents are antibody molecules, then mutagenesis can be directed to the CDR regions of the heavy or light chains as described herein. Further, mutagenesis can be directed to framework regions near or adjacent to the CDRs, e.g., framework regions, particular within 10, 5, or 3 amino acids of a CDR junction. In the case of antibodies, mutagenesis can also be limited to one or a few of the CDRs, e.g., to make step-wise improvements.

In one embodiment, mutagenesis is used to make an antibody more similar to one or more germline sequences. One exemplary germlining method can include: identifying one or more germline sequences that are similar (e.g., most similar in a particular database) to the sequence of the isolated antibody. Then mutations (at the amino acid level) can be made in the isolated antibody, either incrementally, in combination, or both. For example, a nucleic acid library that includes sequences encoding some or all possible germline mutations is made. The mutated antibodies are then evaluated, e.g., to identify an antibody that has one or more additional germline residues relative to the isolated antibody and that is still useful (e.g., has a functional activity). In one embodiment, as many germline residues are introduced into an isolated antibody as possible.

In one embodiment, mutagenesis is used to substitute or insert one or more germline residues into a CDR region. For example, the germline CDR residue can be from a germline sequence that is similar (e.g., most similar) to the variable domain being modified. After mutagenesis, activity (e.g., binding or other functional activity) of the antibody can be evaluated to determine if the germline residue or residues are tolerated. Similar mutagenesis can be performed in the framework regions.

Selecting a germline sequence can be performed in different ways. For example, a germline sequence can be selected if it meets a predetermined criteria for selectivity or similarity, e.g., at least a certain percentage identity, e.g., at least 75, 80, 85, 90, 91, 92, 93, 94, 95, 96, 97, 98, 99, or 99.5% identity. The selection can be performed using at least 2, 3, 5, or 10 germline sequences. In the case of CDR1 and CDR2, identifying a similar germline sequence can include selecting one such sequence. In the case of CDR3, identifying a similar germline sequence can include selecting one such sequence, but may including using two germline sequences that separately contribute to the amino-terminal portion and the carboxy-terminal portion. In other implementations more than one or two germline sequences are used, e.g., to form a consensus sequence.

In other embodiments, the antibody may be modified to have an altered glycosylation pattern (i.e., altered from the original or native glycosylation pattern). As used in this context, "altered" means having one or more carbohydrate moieties deleted, and/or having one or more glycosylation sites added to the original antibody. Addition of glycosylation sites to the presently disclosed antibodies may be accomplished by altering the amino acid sequence to contain glycosylation site consensus sequences; such techniques are well known in the art. Another means of increasing the number of carbohydrate moieties on the antibodies is by chemical or enzymatic coupling of glycosides to the amino acid residues of the antibody. These methods are described in, e.g., WO 87/05330, and Aplin and Wriston (1981) *CRC Crit. Rev. Biochem.* 22:259-306. Removal of any carbohydrate moieties present on the antibodies may be accomplished chemically or enzymatically as described in the art (Hakimuddin et al. (1987) *Arch. Biochem. Biophys.* 259:52; Edge et al. (1981) *Anal. Biochem.* 118:131; and Thotakura et al. (1987) *Meth. Enzymol.* 138:350). See, e.g., U.S. Pat. No. 5,869,046 for a modification that increases in vivo half life by providing a salvage receptor binding epitope.

In one embodiment, an antibody molecule has CDR sequences that differ only insubstantially from those of MJ 2-7 or C65. Insubstantial differences include minor amino acid changes, such as substitutions of 1 or 2 out of any of typically 5-7 amino acids in the sequence of a CDR, e.g., a Chothia or Kabat CDR. Typically, an amino acid is substituted by a related amino acid having similar charge, hydrophobic, or stereochemical characteristics. Such substitutions are within the ordinary skills of an artisan. Unlike in CDRs, more substantial changes in structure framework regions (FRs) can be made without adversely affecting the binding properties of an antibody. Changes to FRs include, but are not limited to, humanizing a nonhuman-derived framework or engineering certain framework residues that are important for antigen contact or for stabilizing the binding site, e.g., changing the class or subclass of the constant region, changing specific amino acid residues which might alter an effector function such as Fc receptor binding (Lund et al. (1991) *J. Immunol.* 147:2657-62; Morgan et al. (1995) *Immunology* 86:319-24), or changing the species from which the constant region is derived. Antibodies may have mutations in the CH2 region of the heavy chain that reduce or alter effector function, e.g., Fc receptor binding and complement activation. For example, antibodies may have mutations such as those described in U.S. Pat. Nos. 5,624,821 and 5,648,260. In the IgG1 or IgG2 heavy chain, for example, such mutations may be made to resemble the amino acid sequence set forth in SEQ ID NO:17. Antibodies may also have mutations that stabilize the disulfide bond between the two heavy chains of an immunoglobulin, such as mutations in the hinge region of IgG4, as disclosed in the art (e.g., Angal et al. (1993) *Mol. Immunol.* 30:105-08).

The IL-13 binding agents can be in the form of intact antibodies, antigen-binding fragments of antibodies, e.g., Fab, F(ab')$_2$, Fd, dAb, and scFv fragments, and intact antibodies and fragments that have been mutated either in their constant and/or variable domain (e.g., mutations to produce chimeric, partially humanized, or fully humanized antibodies, as well as to produce antibodies with a desired trait, e.g., enhanced IL-13 binding and/or reduced FcR binding).

Antibody Production. Some antibody molecules, e.g., Fabs, can be produced in bacterial cells, e.g., *E. coli* cells. For example, if the Fab is encoded by sequences in a phage display vector that includes a suppressible stop codon between the display entity and a bacteriophage protein (or fragment thereof), the vector nucleic acid can be transferred into a bacterial cell that cannot suppress a stop codon. In this case, the Fab is not fused to the gene III protein and is secreted into the periplasm and/or media.

Antibody molecules can also be produced in eukaryotic cells. In one embodiment, the antibodies (e.g., scFv's) are expressed in a yeast cell such as *Pichia* (see, e.g., Powers et al. (2001) *J Immunol Methods.* 251:123-35), *Hanseula*, or *Saccharomyces*.

In one preferred embodiment, antibody molecules are produced in mammalian cells. Preferred mammalian host cells for expressing the clone antibodies or antigen-binding fragments thereof include Chinese Hamster Ovary (CHO cells) (including dhfr⁻ CHO cells, described in Urlaub and Chasin (1980) *Proc. Natl. Acad. Sci. USA* 77:4216-4220, used with a DHFR selectable marker, e.g., as described in Kaufman and Sharp (1982) *Mol. Biol.* 159:601-621), lymphocytic cell lines, e.g., NS0 myeloma cells and SP2 cells, COS cells, and a cell from a transgenic animal, e.g., a transgenic mammal. For example, the cell is a mammary epithelial cell.

In addition to the nucleic acid sequences encoding the antibody molecule, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin, or methotrexate, on a host cell into which the vector has been introduced.

In an exemplary system for recombinant expression of an antibody molecule, a recombinant expression vector encoding both the antibody heavy chain and the antibody light chain is introduced into dhfr⁻ CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells can be cultured to allow for expression of the antibody heavy and light chains and intact antibody is recovered from the culture medium. Standard molecular biology techniques can be used to prepare the recombinant expression vector, transfect the host cells, select for transformants, culture the host cells and recover the antibody molecule from the culture medium. For example, some antibody molecules can be isolated by affinity chromatography with a Protein A or Protein G coupled matrix.

For antibody molecules that include an Fc domain, the antibody production system preferably synthesizes antibodies in which the Fc region is glycosylated. For example, the Fc domain of IgG molecules is glycosylated at asparagine 297 in the CH2 domain. This asparagine is the site for modification with biantennary-type oligosaccharides. It has been demonstrated that this glycosylation is required for effector functions mediated by Fcγ receptors and complement C1q (Burton and Woof (1992) *Adv. Immunol.* 51:1-84; Jefferis et al. (1998) *Immunol. Rev.* 163:59-76). In one embodiment, the Fc domain is produced in a mammalian expression system that appropriately glycosylates the residue corresponding to asparagine 297. The Fc domain can also include other eukaryotic post-translational modifications.

Antibody molecules can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody molecule and a signal sequence for secretion. The milk produced by females of such transgenic mammals includes, secreted-therein, the antibody of interest. The antibody molecule can be purified from the milk, or for some applications, used directly.

Characterization

The binding properties of a binding agent may be measured by any method, e.g., one of the following methods: BIA-CORE™ analysis, Enzyme Linked Immunosorbent Assay (ELISA), x-ray crystallography, sequence analysis and scanning mutagenesis. The ability of a protein to neutralize and/or inhibit one or more IL-13-associated activities may be measured by the following methods: assays for measuring the proliferation of an IL-13 dependent cell line, e.g. TFI; assays for measuring the expression of IL-13-mediated polypeptides, e.g., flow cytometric analysis of the expression of CD23; assays evaluating the activity of downstream signaling molecules, e.g., STAT6; assays evaluating production of tenascin; assays testing the efficiency of an antibody described herein to prevent asthma in a relevant animal model, e.g., the cynomolgus monkey, and other assays. An IL-13 binding agent, particularly an IL-13 antibody molecule, can have a statistically significant effect in one or more of these assays. Exemplary assays for binding properties include the following.

The binding interaction of a IL-13 binding agent and a target (e.g., IL-13) can be analyzed using surface plasmon resonance (SPR). SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface. The changes in the refractivity generate a detectable signal, which are measured as an indication of real-time reactions between biological molecules. Methods for using SPR are described, for example, in U.S. Pat. No. 5,641,640; Raether (1988) *Surface Plasmons* Springer Verlag; Sjolander and Urbaniczky (1991) *Anal. Chem.* 63:2338-2345; Szabo et al. (1995) *Curr. Opin. Struct. Biol.* 5:699-705 and on-line resources provide by BIAcore International AB (Uppsala, Sweden).

Information from SPR can be used to provide an accurate and quantitative measure of the equilibrium dissociation constant ($K_d$), and kinetic parameters, including $K_{on}$ and $K_{off}$, for the binding of a molecule to a target. Such data can be used to compare different molecules. Information from SPR can also be used to develop structure-activity relationships (SAR). For example, the kinetic and equilibrium binding parameters of different antibody molecule can be evaluated. Variant amino acids at given positions can be identified that correlate with particular binding parameters, e.g., high affinity and slow $K_{off}$. This information can be combined with structural modeling (e.g., using homology modeling, energy minimization, or structure determination by x-ray crystallography or NMR). As a result, an understanding of the physical interaction between the protein and its target can be formulated and used to guide other design processes.

Respiratory Disorders

IL-13 binding agents, e.g., anti-IL-13 antibody molecules, can be used to treat or prevent respiratory disorders including, but are not limited to asthma (e.g., allergic and nonallergic asthma (e.g., due to infection, e.g., with respiratory syncytial virus (RSV), e.g., in younger children)); bronchitis (e.g., chronic bronchitis); chronic obstructive pulmonary disease (COPD) (e.g., emphysema (e.g., cigarette-induced emphysema); conditions involving airway inflammation, eosinophilia, fibrosis and excess mucus production, e.g., cystic fibrosis, pulmonary fibrosis, and allergic rhinitis. For example, an IL-13 binding agent (e.g., an anti-IL-13 antibody molecule) can be administered in an amount effective to treat or prevent the disorder or to ameliorate at least one symptom of the disorder.

Asthma can be triggered by myriad conditions, e.g., inhalation of an allergen, presence of an upper-respiratory or ear infection, etc. (Opperwall (2003) *Nurs. Clin. North Am.* 38:697-711). Allergic asthma is characterized by airway hyperresponsiveness (AHR) to a variety of specific and non-specific stimuli, elevated serum immunoglobulin E (IgE), excessive airway mucus production, edema, and bronchial epithelial injury (Wills-Karp, supra). Allergic asthma begins when the allergen provokes an immediate early airway response, which is frequently followed several hours later by a delayed late-phase airway response (LAR) (Henderson et al. (2000) *J. Immunol.* 164:1086-95). During LAR, there is an influx of eosinophils, lymphocytes, and macrophages throughout the airway wall and the bronchial fluid. (Henderson et al., supra). Lung eosinophilia is a hallmark of allergic asthma and is responsible for much of the damage to the respiratory epithelium (Li et al. (1999) *J. Immunol.* 162:2477-87).

CD4$^+$ T helper (Th) cells are important for the chronic inflammation associated with asthma (Henderson et al., supra). Several studies have shown that commitment of CD4+ cells to type 2 T helper (Th2) cells and the subsequent production of type 2 cytokines (e.g., IL-4, IL-5, IL-10, and IL-13) are important in the allergic inflammatory response leading to AHR (Tomkinson et al. (2001) *J. Immunol.* 166: 5792-5800, and references cited therein). First, CD4$^+$ T cells have been shown to be necessary for allergy-induced asthma in murine models. Second, CD4$^+$ T cells producing type 2 cytokines undergo expansion not only in these animal models but also in patients with allergic asthma. Third, type 2 cytokine levels are increased in the airway tissues of animal models and asthmatics. Fourth, Th2 cytokines have been implicated as playing a central role in eosinophil recruitment in murine models of allergic asthma, and adoptively transferred Th2 cells have been correlated with increased levels of eotaxin (a potent eosinophil chemoattractant) in the lung as well as lung eosinophilia (Wills-Karp et al., supra; Li et al., supra).

The methods for treating or preventing asthma described herein include those for extrinsic asthma (also known as allergic asthma or atopic asthma), intrinsic asthma (also known as non-allergic asthma or non-atopic asthma) or combinations of both, which has been referred to as mixed asthma. Extrinsic or allergic asthma includes incidents caused by, or associated with, e.g., allergens, such as pollens, spores, grasses or weeds, pet danders, dust, mites, etc. As allergens and other irritants present themselves at varying points over the year, these types of incidents are also referred to as seasonal asthma. Also included in the group of extrinsic asthma is bronchial asthma and allergic bronchopulmonary aspergillosis.

Disorders that can be treated or alleviated by the agents described herein include those respiratory disorders and asthma caused by infectious agents, such as viruses (e.g., cold and flu viruses, respiratory syncytial virus (RSV), paramyxovirus, rhinovirus and influenza viruses. RSV, rhinovirus and influenza virus infections are common in children, and are one leading cause of respiratory tract illnesses in infants and young children. Children with viral bronchiolitis can develop chronic wheezing and asthma, which can be treated using the methods described herein. Also included are the asthma conditions which may be brought about in some asthmatics by exercise and/or cold air. The methods are useful for asthmas associated with smoke exposure (e.g., cigarette-induced and industrial smoke), as well as industrial and occupational exposures, such as smoke, ozone, noxious gases, sulfur dioxide, nitrous oxide, fumes, including isocyanates, from paint, plastics, polyurethanes, varnishes, etc., wood, plant or other organic dusts, etc. The methods are also useful for asthmatic incidents associated with food additives, preservatives or pharmacological agents. Also included are methods for treating, inhibiting or alleviating the types of asthma referred to as silent asthma or cough variant asthma.

The methods disclosed herein are also useful for treatment and alleviation of asthma associated with gastroesophageal reflux (GERD), which can stimulate bronchoconstriction. GERD, along with retained bodily secretions, suppressed cough, and exposure to allergens and irritants in the bedroom can contribute to asthmatic conditions and have been collectively referred to as nighttime asthma or nocturnal asthma. In methods of treatment, inhibition or alleviation of asthma associated with GERD, a pharmaceutically effective amount of the IL-13 binding agent can be used as described herein in combination with a pharmaceutically effective amount of an agent for treating GERD. These agents include, but are not limited to, proton pump inhibiting agents like PROTONIX® brand of delayed-release pantoprazole sodium tablets, PRILOSEC® brand omeprazole delayed release capsules, ACIPHEX® brand rebeprazole sodium delayed release tablets or PREVACID® brand delayed release lansoprazole capsules.

Atopic Disorders and Symptoms Thereof

It has been observed that cells from atopic patients have enhanced sensitivity to IL-13. Accordingly, an IL-13 binding agent (e.g., an IL-13 binding agent such as an antibody molecule described herein) can be administered in an amount effective to treat or prevent an atopic disorder. "Atopic" refers to a group of diseases in which there is often an inherited tendency to develop an allergic reaction.

Examples of atopic disorders include allergy, allergic rhinitis, atopic dermatitis, asthma and hay fever. Asthma is a phenotypically heterogeneous disorder associated with intermittent respiratory symptoms such as, e.g., bronchial hyperresponsiveness and reversible airflow obstruction. Immunohistopathologic features of asthma include, e.g., denudation of airway epithelium, collagen deposition beneath the basement membrane; edema; mast cell activation; and inflammatory cell infiltration (e.g., by neutrophils, eosinophils, and lymphocytes). Airway inflammation can further contribute to airway hyperresponsiveness, airflow limitation, acute bronchoconstriction, mucus plug formation, airway wall remodeling, and other respiratory symptoms. An IL-13 binding agent (e.g., an IL-13 binding agent such as an antibody molecule described herein) can be administered in an amount effective to ameliorate one or more of these symptoms.

Symptoms of allergic rhinitis (hay fever) include itchy, runny, sneezing, or stuffy nose, and itchy eyes. An IL-13 binding agent can be administered to ameliorate one or more of these symptoms. Atopic dermatitis is a chronic (long-lasting) disease that affects the skin. Information about atopic dermatitis is available, e.g., from NIH Publication No. 03-4272. In atopic dermatitis, the skin can become extremely itchy, leading to redness, swelling, cracking, weeping clear fluid, and finally, crusting and scaling. In many cases, there are periods of time when the disease is worse (called exacerbations or flares) followed by periods when the skin improves or clears up entirely (called remissions). Atopic dermatitis is often referred to as "eczema," which is a general term for the several types of inflammation of the skin. Atopic dermatitis is the most common of the many types of eczema. Examples of atopic dermatitis include: allergic contact eczema (dermatitis: a red, itchy, weepy reaction where the skin has come into contact with a substance that the immune system recognizes as foreign, such as poison ivy or certain preservatives in creams and lotions); contact eczema (a localized reaction that includes redness, itching, and burning where the skin has come into contact with an allergen (an allergy-causing substance) or with an irritant such as an acid, a cleaning agent, or other chemical); dyshidrotic eczema (irritation of the skin on the palms of hands and soles of the feet characterized by clear, deep blisters that itch and burn); neurodermatitis (scaly patches of the skin on the head, lower legs, wrists, or forearms caused by a localized itch (such as an insect bite) that become intensely irritated when scratched); nummular eczema (coin-shaped patches of irritated skin-most common on the arms, back, buttocks, and lower legs-that may be crusted, scaling, and extremely itchy); seborrheic eczema (yellowish, oily, scaly patches of skin on the scalp, face, and occasionally other parts of the body). Additional particular symptoms include stasis dermatitis, atopic pleat (Dennie-Morgan fold), cheilitis, hyperlinear palms, hyperpigmented eyelids (eyelids that have become darker in color from inflammation or hay fever), ichthyosis, keratosis pilaris, lichenification, papules, and urticaria. An IL-13 binding agent can be administered to ameliorate one or more of these symptoms.

An exemplary method for treating allergic rhinitis or other allergic disorder can include initiating therapy with an IL-13 binding agent prior to exposure to an allergen, e.g., prior to seasonal exposure to an allergen, e.g., prior to allergen blooms. Such therapy can include one or more doses, e.g., doses at regular intervals.

Cancer

IL-13 and its receptors may be involved in the development of at least some types of cancer, e.g., a cancer derived from hematopoietic cells or a cancer derived from brain or neuronal cells (e.g., a glioblastoma). For example, blockade of the IL-13 signaling pathway, e.g., via use of a soluble IL-13 receptor or a STAT6 —/—deficient mouse, leads to delayed tumor onset and/or growth of Hodgkins lymphoma cell lines or a metastatic mammary carcinoma, respectively (Trieu et al. (2004) *Cancer Res.* 64: 3271-75; Ostrand-Rosenberg et al. (2000) *J. Immunol.* 165: 6015-6019). Cancers that express IL-13R(2 (Husain and Puri (2003) *J. Neurooncol.* 65:37-48; Mintz et al. (2003) *J. Neurooncol.* 64:117-23) can be specifically targeted by anti-IL-13 antibodies described herein. IL-13 binding agents, e.g., anti-IL-13 antibody molecules, can be useful to inhibit cancer cell proliferation or other cancer cell activity. A cancer refers to one or more cells that has a loss of responsiveness to normal growth controls, and typically proliferates with reduced regulation relative to a corresponding normal cell.

Examples of cancers against which IL-13 binding agents (e.g., an IL-13 binding agent such as an antibody or antigen binding fragment described herein) can be used for treatment include leukemias, e.g., B-cell chronic lymphocytic leukemia, acute myelogenous leukemia, and human T-cell leukemia virus type 1 (HTLV-1) transformed T cells; lymphomas, e.g. T cell lymphoma, Hodgkin's lymphoma; glioblastomas; pancreatic cancers; renal cell carcinoma; ovarian carcinoma; and AIDS-Kaposi's sarcoma. For example, an IL-13 binding agent (e.g., an anti-IL-13 antibody molecule) can be administered in an amount effective to treat or prevent the disorder, e.g., to reduce cell proliferation, or to ameliorate at least one symptom of the disorder.

Fibrosis

IL-13 binding agents can also be useful in treating inflammation and fibrosis, e.g., fibrosis of the liver. IL-13 production has been correlated with the progression of liver inflammation (e.g., viral hepatitis) toward cirrhosis, and possibly, hepatocellular carcinoma (de Lalla et al. (2004) *J. Immunol.* 173:1417-1425). Fibrosis occurs, e.g., when normal tissue is replaced by scar tissue, often following inflammation. Hepatitis B and hepatitis C viruses both cause a fibrotic reaction in the liver, which can progress to cirrhosis. Cirrhosis, in turn, can evolve into severe complications such as liver failure or hepatocellular carcinoma. Blocking IL-13 activity using the IL-13 binding agents, e.g., anti-IL-13 antibodies, described herein can reduce inflammation and fibrosis, e.g., the inflammation, fibrosis, and cirrhosis associated with liver diseases, especially hepatitis B and C. For example, an IL-13 binding agent (e.g., an anti-IL-13 antibody molecule) can be administered in an amount effective to treat or prevent the disorder or to ameliorate at least one symptom of the inflammatory and/or fibrotic disorder.

Inflammatory Bowel Disease

Inflammatory bowel disease (IBD) is the general name for diseases that cause inflammation of the intestines. Two examples of inflammatory bowel disease are Crohn's disease and ulcerative colitis. IL-13/STAT6 signaling has been found to be involved in inflammation-induced hypercontractivity of mouse smooth muscle, a model of inflammatory bowel disease (Akiho et al. (2002) *Am. J. Physiol. Gastrointest. Liver Physiol.* 282:G226-232). For example, an IL-13 binding agent (e.g., an anti-IL-13 antibody molecule) can be administered in an amount effective to treat or prevent the disorder or to ameliorate at least one symptom of the inflammatory bowel disorder.

Additional IL-13 Binding Agents

Also provided are binding agents, other than binding agents that are antibodies and fragments thereof, that bind to IL-13, particularly binding agents that compete with MJ2-7 or C65 and other antibodies described herein for binding to IL-13. For example, the binding agents can bind to the same epitope or an overlapping epitope as MJ2-7 or C65 on IL-13. The binding agents preferably inhibit or neutralize IL-13 activity. For example, the binding agents inhibit binding of IL-13 to IL 13Rα1 and, e.g., does not prevent binding of IL-13 to IL-4Rα,. Such binding agents can be used in the methods described herein, e.g., the methods of treating and preventing disorders. All embodiments described herein can be adapted for use with IL-13 binding agents.

Binding agents can be identified by a number of means, including modifying a variable domain described herein or grafting one or more CDRs of a variable domain described herein onto another scaffold domain. Binding agents can also be identified from diverse libraries, e.g., by screening. One method for screening protein libraries uses phage display. Particular regions of a protein are varied and proteins that interact with IL-13 are identified, e.g., by retention on a solid support or by other physical association. To identify particular binding agents that bind to the same epitope or an overlapping epitope as MJ2-7 or C65 on IL-13, binding agents can be eluted by adding MJ2-7 or C65 (or related antibody), or binding agents can be evaluated in competition experiments with MJ2-7 or C65 (or related antibody). It is also possible to deplete the library of agents that bind to other epitopes by contacting the library to a complex that contains IL-13 and MJ2-7 or C65 (or related antibody). The depleted library can then be contacted to IL-13 to obtain a binding agent that binds to IL-13 but not to IL-13 when it is bound by MJ 2-7 or C65. It is also possible to use peptides from IL-13 that contain the MJ 2-7 or C65 epitope as a target.

Phage display is described, for example, in U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; WO 90/02809; WO 94/05781; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J* 12:725-734; Hawkins et al. (1992) *J Mol Biol* 226: 889-896; Clackson et al. (1991) *Nature* 352:624-628; Gram et al. (1992) *PNAS* 89:3576-3580; Garrard et al. (1991) *Bio/Technology* 9:1373-1377; Rebar et al. (1996) *Methods Enzymol.* 267:129-49; and Barbas et al. (1991) *PNAS* 88:7978-7982. Yeast surface display is described, e.g., in Boder and Wittrup (1997) *Nat. Biotechnol.* 15:553-557. Another form of display is ribosome display. See, e.g., Mattheakis et al. (1994) *Proc. Natl. Acad. Sci. USA* 91:9022 and Hanes et al. (2000) *Nat Biotechnol.* 18:1287-92; Hanes et al. (2000) *Methods Enzymol.* 328:404-30. and Schaffitzel et al. (1999) *J Immunol Methods.* 231(1-2):119-35.

Binding agents that bind to IL-13 can have structural features of one scaffold proteins, e.g., a folded domain. An exemplary scaffold domain, based on an antibody, is a "minibody" scaffold has been designed by deleting three beta strands from a heavy chain variable domain of a monoclonal antibody (Tramontano et al., 1994, *J Mol. Recognit.* 7:9; and Martin et al., 1994, *EMBO J.* 13:5303-5309). This domain includes 61 residues and can be used to present two hypervariable loops, e.g., one or more hypervariable loops of a variable domain described herein or a variant described herein. In another approach, the binding agent includes a scaffold domain that is a V-like domain (Coia et al. WO 99/45110). V-like domains refer to a domain that has similar structural features to the variable heavy (VH) or variable light (VL) domains of antibodies. Another scaffold domain is derived from tendamistatin, a 74 residue, six-strand beta sheet sandwich held together by two disulfide bonds (McConnell and Hoess, 1995, *J Mol. Biol.* 250:460). This parent protein includes three loops. The loops can be modified (e.g., using CDRs or hypervariable loops described herein) or varied, e.g., to select domains that bind to IL-13. WO 00/60070 describes a β-sandwich structure derived from the naturally occurring extracellular domain of CTLA-4 that can be used as a scaffold domain.

Still another scaffold domain for an IL-13 binding agent is a domain based on the fibronectin type III domain or related fibronectin-like proteins. The overall fold of the fibronectin type III (Fn3) domain is closely related to that of the smallest functional antibody fragment, the variable domain of the antibody heavy chain. Fn3 is a β-sandwich similar to that of the antibody VH domain, except that Fn3 has seven β-strands instead of nine. There are three loops at the end of Fn3; the positions of BC, DE and FG loops approximately correspond to those of CDR1, 2 and 3 of the VH domain of an antibody. Fn3 is advantageous because it does not have disulfide bonds. Therefore, Fn3 is stable under reducing conditions, unlike antibodies and their fragments (see WO 98/56915; WO 01/64942; WO 00/34784). An Fn3 domain can be modified (e.g., using CDRs or hypervariable loops described herein) or varied, e.g., to select domains that bind to IL-13.

Still other exemplary scaffold domains include: T-cell receptors; MHC proteins; extracellular domains (e.g., fibronectin Type III repeats, EGF repeats); protease inhibitors (e.g., Kunitz domains, ecotin, BPTI, and so forth); TPR repeats; trifoil structures; zinc finger domains; DNA-binding proteins; particularly monomeric DNA binding proteins; RNA binding proteins; enzymes, e.g., proteases (particularly inactivated proteases), RNase; chaperones, e.g., thioredoxin, and heat shock proteins; and intracellular signaling domains (such as SH2 and SH3 domains). US 20040009530 describes examples of some alternative scaffolds.

Examples of small scaffold domains include: Kunitz domains (58 amino acids, 3 disulfide bonds), *Cucurbida maxima* trypsin inhibitor domains (31 amino acids, 3 disulfide bonds), domains related to guanylin (14 amino acids, 2 disulfide bonds), domains related to heat-stable enterotoxin IA from gram negative bacteria (18 amino acids, 3 disulfide bonds), EGF domains (50 amino acids, 3 disulfide bonds), kringle domains (60 amino acids, 3 disulfide bonds), fungal carbohydrate-binding domains (35 amino acids, 2 disulfide bonds), endothelin domains (18 amino acids, 2 disulfide bonds), and Streptococcal G IgG-binding domain (35 amino acids, no disulfide bonds). Examples of small intracellular scaffold domains include SH2, SH3, and EVH domains. Generally, any modular domain, intracellular or extracellular, can be used.

Exemplary criteria for evaluating a scaffold domain can include: (1) amino acid sequence, (2) sequences of several homologous domains, (3) 3-dimensional structure, and/or (4) stability data over a range of pH, temperature, salinity, organic solvent, oxidant concentration. In one embodiment, the scaffold domain is a small, stable protein domains, e.g., a protein of less than 100, 70, 50, 40 or 30 amino acids. The domain may include one or more disulfide bonds or may chelate a metal, e.g., zinc.

Still other binding agents are based on peptides, e.g., proteins with an amino acid sequence that are less than 30, 25, 24, 20, 18, 15, or 12 amino acids. Peptides can be incorporated in a larger protein, but typically a region that can independently bind to IL-13, e.g., to an epitope described herein. Peptides can be identified by phage display. See, e.g., US 20040071705.

An IL-13 binding agent may include non-peptide linkages and other chemical modification. For example, part or all of the binding agent may be synthesized as a peptidomimetic, e.g., a peptoid (see, e.g., Simon et al. (1992) *Proc. Natl. Acad. Sci. USA* 89:9367-71 and Horwell (1995) *Trends Biotechnol.* 13:132-4). A binding agent may include one or more (e.g., all) non-hydrolyzable bonds. Many non-hydrolyzable peptide bonds are known in the art, along with procedures for synthesis of peptides containing such bonds. Exemplary non-hydrolyzable bonds include —[CH$_2$NH]— reduced amide peptide bonds, —[COCH$_2$]— ketomethylene peptide bonds, —[CH(CN)NH]— (cyanomethylene)amino peptide bonds, —[CH$_2$CH(OH)]— hydroxyethylene peptide bonds, —[CH$_2$O]—peptide bonds, and —[CH$_2$S]— thiomethylene peptide bonds (see e.g., U.S. Pat. No. 6,172,043).

Pharmaceutical Compositions

The IL-13 binding agents, e.g. antibody molecules that bind to IL-13 (such as those described herein) can be used in vitro, ex vivo, or in vivo. They can be incorporated into a pharmaceutical composition, e.g., by combining the IL-13 binding agent with a pharmaceutically acceptable carrier. Such a composition may contain, in addition to the IL-13 binding agent and carrier, various diluents, fillers, salts, buffers, stabilizers, solubilizers, and other materials well known in the art. Pharmaceutically acceptable materials is generally a nontoxic material that does not interfere with the effectiveness of the biological activity of an IL-13 binding agent. The characteristics of the carrier can depend on the route of administration.

The pharmaceutical composition described herein may also contain other factors, such as, but not limited to, other anti-cytokine antibody molecules or other anti-inflammatory agents as described in more detail below. Such additional factors and/or agents may be included in the pharmaceutical composition to produce a synergistic effect with an IL-13 binding agent, e.g., anti-IL-13 antibody molecule, described herein. For example, in the treatment of allergic asthma, a pharmaceutical composition described herein may include anti-IL-4 antibody molecules or drugs known to reduce an allergic response.

The pharmaceutical composition described herein may be in the form of a liposome in which an IL-13 binding agent, e.g., an anti-IL-13 antibody molecule, such as one described herein is combined, in addition to other pharmaceutically acceptable carriers, with amphipathic agents such as lipids that exist in aggregated form as micelles, insoluble monolayers, liquid crystals, or lamellar layers while in aqueous solution. Suitable lipids for liposomal formulation include, without limitation, monoglycerides, diglycerides, sulfatides, lysolecithin, phospholipids, saponin, bile acids, and the like. Exemplary methods for preparing such liposomal formulations include methods described in U.S. Pat. Nos. 4,235,871; 4,501,728; 4,837,028; and 4,737,323.

As used herein, the term "therapeutically effective amount" means the total amount of each active component of the pharmaceutical composition or method that is sufficient to show a meaningful patient benefit, e.g., amelioration of symptoms of, healing of, or increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use, a therapeutically effective amount of IL-13 binding agent, e.g., an anti-IL-13 antibody molecule, e.g., an antibody molecule that binds to IL-13 and interferes with the formation of a functional IL-13 signaling complex (and, e.g., neutralizes or inhibits one or more IL-13-associated activities), is administered to a subject, e.g., mammal (e.g., a human). An IL-13 binding agent, e.g., an anti-IL-13 antibody molecule, may be administered in accordance with a method described herein either alone as well as in combination with other therapies such as treatments employing cytokines, lymphokines or other hematopoietic factors, cancer therapeutics, or anti-inflammatory agents. When coadministered with one or more agents, an IL-13 binding agent, e.g., an anti-IL-13 antibody molecule, may be administered either simultaneously with the second agent, or sequentially. If administered sequentially, a physician can select an appropriate sequence for administering the IL-13 binding agent in combination with other agents.

Administration of an IL-13 binding agent, e.g., an anti-IL-13 antibody molecule, used in the pharmaceutical composition can be carried out in a variety of conventional ways, such as oral ingestion, inhalation, or cutaneous, subcutaneous, or intravenous injection. When a therapeutically effective amount of an IL-13 binding agent, e.g., an anti-IL-13 antibody molecule, is administered by intravenous, cutaneous or subcutaneous injection, the binding agent can be prepared as a pyrogen-free, parenterally acceptable aqueous solution. The composition of such parenterally acceptable protein solutions can be adapted in view factors such as pH, isotonicity, stability, and the like, e.g., to optimize the composition for physiological conditions, binding agent stability, and so forth. A pharmaceutical composition for intravenous, cutaneous, or subcutaneous injection can contain, e.g., an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition may also contain stabilizers, preservatives, buffers, antioxidants, or other additive.

The amount of an IL-13 binding agent, e.g., an anti-IL-13 antibody molecule, in the pharmaceutical composition can depend upon the nature and severity of the condition being treated, and on the nature of prior treatments that the patient has undergone. The pharmaceutical composition can be administered to normal patients or patients who do not show symptoms, e.g., in a prophylactic mode. An attending physician may decide the amount of IL-13 binding agent, e.g., an anti-IL-13 antibody molecule, with which to treat each individual patient. For example, an attending physician can administer low doses of antagonist and observe the patient's response. Larger doses of antagonist may be administered until the optimal therapeutic effect is obtained for the patient, and at that point the dosage is not generally increased further. For example, a pharmaceutical may contain between about 0.1 mg to 50 mg antibody per kg body weight, e.g., between about 0.1 mg and 5 mg or between about 8 mg and 50 mg antibody per kg body weight. In one embodiment in which the antibody is delivered subcutaneously at a frequency of no more than twice per month, e.g., every other week or monthly, the composition includes an amount of about 0.7-3.3, e.g., 1.0-3.0 mg/kg, e.g., about 0.8-1.2, 1.2-2.8, or 2.8-3.3 mg/kg.

The duration of therapy using the pharmaceutical composition may vary, depending on the severity of the disease being treated and the condition and potential idiosyncratic response of each individual patient. In one embodiment, the IL-13 binding agent, e.g., an anti-IL-13 antibody molecule, can also be administered via the subcutaneous route, e.g., in the range of once a week, once every 24, 48, 96 hours, or not more frequently than such intervals. Exemplary dosages can be in the range of 0.1-20 mg/kg, more preferably 1-10 mg/kg. The agent can be administered, e.g., by intravenous infusion at a rate of less than 20, 10, 5, or 1 mg/min to reach a dose of about 1 to 50 mg/m$^2$ or about 5 to 20 mg/m$^2$.

In one embodiment, an administration of a IL-13 binding agent to the patient includes varying the dosage of the protein, e.g., to reduce or minimize side effects. For example, the subject can be administered a first dosage, e.g., a dosage less than a therapeutically effective amount. In a subsequent interval, e.g., at least 6, 12, 24, or 48 hours later, the patient can be administered a second dosage, e.g., a dosage that is at least 25, 50, 75, or 100% greater than the first dosage. For example, the second and/or a comparable third, fourth and fifth dosage can be at least about 70, 80, 90, or 100% of a therapeutically effective amount.

Inhalation

A composition that includes an IL-13 binding agent, e.g., an anti-IL-13 antibody molecule, can be formulated for inhalation or other mode of pulmonary delivery. Accordingly, the IL-13 binding agent can be administered by inhalation to pulmonary tissue. The term "pulmonary tissue" as used herein refers to any tissue of the respiratory tract and includes both the upper and lower respiratory tract, except where otherwise indicated. An IL-13 binding agent, e.g., an anti-IL-13 antibody molecule, can be administered in combination with one or more of the existing modalities for treating pulmonary diseases.

In one example the IL-13 binding agent is formulated for a nebulizer. In one embodiment, the IL-13 binding agent can be stored in a lyophilized form (e.g., at room temperature) and reconstituted in solution prior to inhalation. It is also possible to formulate the IL-13 binding agent for inhalation using a medical device, e.g., an inhaler. See, e.g., U.S. Pat. No. 6,102,035 (a powder inhaler) and U.S. Pat. No. 6,012,454 (a dry powder inhaler). The inhaler can include separate compartments for the IL-13 binding agent at a pH suitable for storage and another compartment for a neutralizing buffer and a mechanism for combining the IL-13 binding agent with a neutralizing buffer immediately prior to atomization. In one embodiment, the inhaler is a metered dose inhaler.

The three common systems used to deliver drugs locally to the pulmonary air passages include dry powder inhalers (DPIs), metered dose inhalers (MDIs) and nebulizers. MDIs, the most popular method of inhalation administration, may be used to deliver medicaments in a solubilized form or as a dispersion. Typically MDIs comprise a Freon or other relatively high vapor pressure propellant that forces aerosolized medication into the respiratory tract upon activation of the device. Unlike MDIs, DPIs generally rely entirely on the inspiratory efforts of the patient to introduce a medicament in a dry powder form to the lungs. Nebulizers form a medicament aerosol to be inhaled by imparting energy to a liquid solution. Direct pulmonary delivery of drugs during liquid ventilation or pulmonary lavage using a fluorochemical medium has also been explored. These and other methods can be used to deliver an IL-13 binding agent, e.g., anti-IL-13 antibody molecule. In one embodiment, the IL-13 binding agent is associated with a polymer, e.g., a polymer that stabilizes or increases half-life of the compound.

For example, for administration by inhalation, an IL-13 binding agent, e.g., an anti-IL-13 antibody molecule, is delivered in the form of an aerosol spray from pressured container or dispenser which contains a suitable propellant or a nebulizer. The IL-13 binding agent may be in the form of a dry particle or as a liquid. Particles that include the IL-13 binding agent can be prepared, e.g., by spray drying, by drying an aqueous solution of the IL-13 binding agent, e.g., an anti-IL-13 antibody molecule, with a charge neutralizing agent and then creating particles from the dried powder or by drying an aqueous solution in an organic modifier and then creating particles from the dried powder.

The IL-13 binding agent may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges for use in an inhaler or insufflator may be formulated containing a powder mix of an IL-13 binding agent, e.g., an anti-IL-13 antibody molecule, and a suitable powder base such as lactose or starch, if the particle is a formulated particle. In addition to the formulated or unformulated compound, other materials such as 100% DPPC or other surfactants can be mixed with the IL-13 binding agent to promote the delivery and dispersion of formulated or unformulated compound. Methods of preparing dry particles are described, for example, in WO 02/32406.

An IL-13 binding agent, e.g., an anti-IL-13 antibody molecule, can be formulated for aerosol delivery, e.g., as dry aerosol particles, such that when administered it can be rapidly absorbed and can produce a rapid local or systemic therapeutic result. Administration can be tailored to provide detectable activity within 2 minutes, 5 minutes, 1 hour, or 3 hours of administration. In some embodiments, the peak activity can be achieved even more quickly, e.g., within one half hour or even within ten minutes. An IL-13 binding agent, e.g., an anti-IL-13 antibody molecule, can be formulated for longer biological half-life (e.g., by association with a polymer such as PEG) for use as an alternative to other modes of administration, e.g., such that the IL-13 binding agent enters circulation from the lung and is distributed to other organs or to a particular target organ.

In one embodiment, the IL-13 binding agent, e.g., an anti-IL-13 antibody molecule, is delivered in an amount such that at least 5% of the mass of the polypeptide is delivered to the lower respiratory tract or the deep lung. Deep lung has an extremely rich capillary network. The respiratory membrane separating capillary lumen from the alveolar air space is very thin ($\leq 0\,\mu m$) and extremely permeable. In addition, the liquid layer lining the alveolar surface is rich in lung surfactants. In other embodiments, at least 2%, 3%, 5%, 10%, 20%, 30%, 40%, 50%, 60%, 70%, or 80% of the composition of an IL-13 binding agent, e.g., an anti-IL-13 antibody molecule, is delivered to the lower respiratory tract or to the deep lung. Delivery to either or both of these tissues results in efficient absorption of the IL-13 binding agent and high bioavailability. In one embodiment, the IL-13 binding agent is provided in a metered dose using, e.g., an inhaler or nebulizer. For example, the IL-13 binding agent is delivered in a dosage unit form of at least about 0.02, 0.1, 0.5, 1, 1.5, 2, 5, 10, 20, 40, or 50 mg/puff or more. The percent bioavailability can be calculated as follows:

the percent bioavailability=($AUC_{non-invasive}$/$AUC_{i.v.\ or\ s.c.}$)×($dose_{i.v.\ or\ s.c.}$/$dose_{non-invasive}$)×100.

Although not necessary, delivery enhancers such as surfactants can be used to further enhance pulmonary delivery. A "surfactant" as used herein refers to a IL-13 binding agent having a hydrophilic and lipophilic moiety, which promotes absorption of a drug by interacting with an interface between two immiscible phases. Surfactants are useful in the dry particles for several reasons, e.g., reduction of particle agglomeration, reduction of macrophage phagocytosis, etc. When coupled with lung surfactant, a more efficient absorption of the IL-13 binding agent can be achieved because surfactants, such as DPPC, will greatly facilitate diffusion of the compound. Surfactants are well known in the art and include but are not limited to phosphoglycerides, e.g., phosphatidylcholines, L-alpha-phosphatidylcholine dipalmitoyl (DPPC) and diphosphatidyl glycerol (DPPG); hexadecanol; fatty acids; polyethylene glycol (PEG); polyoxyethylene-9—; auryl ether; palmitic acid; oleic acid; sorbitan trioleate (Span 85); glycocholate; surfactin; poloxomer; sorbitan fatty acid ester; sorbitan trioleate; tyloxapol; and phospholipids.

Stabilization

In one embodiment, an IL-13 binding agent, e.g., an anti-IL-13 antibody molecule, is physically associated with a moiety that improves its stabilization and/or retention in circulation, e.g., in blood, serum, lymph, bronchopulmonary lavage, or other tissues, e.g., by at least 1.5, 2, 5, 10, or 50 fold.

For example, an IL-13 binding agent, e.g., an anti-IL-13 antibody molecule, can be associated with a polymer, e.g., a substantially non-antigenic polymers, such as polyalkylene oxides or polyethylene oxides. Suitable polymers will vary substantially by weight. Polymers having molecular number average weights ranging from about 200 to about 35,000 (or about 1,000 to about 15,000, and 2,000 to about 12,500) can be used.

For example, an IL-13 binding agent, e.g., an anti-IL-13 antibody molecule, can be conjugated to a water soluble polymer, e.g., hydrophilic polyvinyl polymers, e.g. polyvinylalcohol and polyvinylpyrrolidone. A non-limiting list of such polymers includes polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextran sulfate, dextran, dextrins, glycogen, or the polysaccharide subunit of acid mucopolysaccharides, e.g. hyaluronic acid; polymers of sugar alcohols such as polysorbitol and polymannitol; heparin or heparan.

The conjugates of an IL-13 binding agent, e.g., an anti-IL-13 antibody molecule, and a polymer can be separated from the unreacted starting materials, e.g., by gel filtration or ion exchange chromatography, e.g., HPLC. Heterologous species of the conjugates are purified from one another in the same fashion. Resolution of different species (e.g. containing one or two PEG residues) is also possible due to the difference in the ionic properties of the unreacted amino acids. See, e.g., WO 96/34015.

Use of IL-13 Binding Agents to Modulate one or more IL-13-Associated Activities in vivo In yet another aspect, the invention features a method for modulating (e.g., decreasing, neutralizing and/or inhibiting) one or more associated activities of IL-13 in vivo by administering an IL-13 binding agent, e.g., an anti-IL-13 antibody molecule, described herein in an amount sufficient to inhibit its activity. An IL-13 binding agent can also be administered to subjects for whom inhibition of an IL-13-mediated inflammatory response is required. These conditions include, e.g., airway inflammation, asthma, fibrosis, eosinophilia and increased mucus production.

The efficacy of an IL-13 binding agent, e.g., an anti-IL-13 antibody molecule, described herein can be evaluated, e.g., by evaluating ability of the antagonist to modulate airway inflammation in cynomolgus monkeys exposed to an *Ascaris suum* allergen. An IL-13 binding agent, particularly one that inhibits at least one IL-13 activity, can be used to neutralize or inhibit one or more IL-13-associated activities, e.g., to reduce IL-13 mediated inflammation in vivo, e.g., for treating or preventing IL-13-associated pathologies, including asthma and/or its associated symptoms.

In one embodiment, an IL-13 binding agent, e.g., an anti-IL-13 antibody molecule, e.g., pharmaceutical compositions thereof, is administered in combination therapy, i.e., combined with other agents, e.g., therapeutic agents, that are useful for treating pathological conditions or disorders, such as allergic and inflammatory disorders. The term "in combination" in this context means that the agents are given substantially contemporaneously, either simultaneously or sequentially. If given sequentially, at the onset of administration of the second compound, the first of the two compounds is preferably still detectable at effective concentrations at the site of treatment.

For example, the combination therapy can include one or more IL-13 binding agents, e.g., anti-IL-13 antibodies and fragments thereof, e.g., that bind to IL-13 and interfere with the formation of a functional IL-13 signaling complex, coformulated with, and/or coadministered with, one or more additional therapeutic agents, e.g., one or more cytokine and growth factor inhibitors, immunosuppressants, anti-inflammatory agents, metabolic inhibitors, enzyme inhibitors, and/or cytotoxic or cytostatic agents, as described in more detail below. Furthermore, one or more an IL-13 binding agent, e.g., an anti-IL-13 antibody molecule, may be used in combination with two or more of the therapeutic agents described herein. Such combination therapies may advantageously utilize lower dosages of the administered therapeutic agents, thus avoiding possible toxicities or complications associated with the various monotherapies. Moreover, the therapeutic agents disclosed herein act on pathways that differ from the IL-13/

IL-13-receptor pathway, and thus are expected to enhance and/or synergize with the effects of the IL-13 binding agents.

Therapeutic agents that interfere with different triggers of asthma or airway inflammation, e.g., therapeutic agents used in the treatment of allergy, upper respiratory infections, or ear infections, may be used in combination with an IL-13 binding agent, e.g., an anti-IL-13 antibody molecule. In one embodiment, one or more IL-13 binding agents, e.g., anti-IL-13 antibodies and fragments thereof, may be coformulated with, and/or coadministered with, one or more additional agents, such as other cytokine or growth factor antagonists (e.g., soluble receptors, peptide inhibitors, small molecules, adhesins), antibody molecules that bind to other targets (e.g., antibodies that bind to other cytokines or growth factors, their receptors, or other cell surface molecules), and anti-inflammatory cytokines or agonists thereof. Nonlimiting examples of the agents that can be used in combination with IL-13 binding agents, e.g., anti-IL-13 antibodies and fragments thereof, include, but are not limited to, inhaled steroids; beta-agonists, e.g., short-acting or long-acting beta-agonists; antagonists of leukotrienes or leukotriene receptors; combination drugs such as ADVAIR®; IgE inhibitors, e.g., anti-IgE antibodies (e.g., XOLAIR®); phosphodiesterase inhibitors (e.g., PDE4 inhibitors); xanthines; anticholinergic drugs; mast cell-stabilizing agents such as cromolyn; IL-4 inhibitors; IL-5 inhibitors; eotaxin/CCR3 inhibitors; and antihistamines.

In other embodiments, one or more IL-13 binding agents, e.g., anti-IL-13 antibody molecules, can be coformulated with, and/or coadministered with, one or more anti-inflammatory drugs, immunosuppressants, or metabolic or enzymatic inhibitors. Examples of the drugs or inhibitors that can be used in combination with the IL-13 binding agents, e.g., anti-IL-13 antibodies and fragments thereof, include, but are not limited to, one or more of: Additional examples of therapeutic agents that can be coadministered and/or coformulated with one or more anti-IL-13 antibodies or fragments thereof include one or more of: TNF antagonists (e.g., a soluble fragment of a TNF receptor, e.g., p55 or p75 human TNF receptor or derivatives thereof, e.g., 75 kd TNFR-IgG (75 kD TNF receptor-IgG fusion protein, ENBREL™)); TNF enzyme antagonists, e.g., TNFα converting enzyme (TACE) inhibitors; muscarinic receptor antagonists; TGF-β antagonists; interferon gamma; perfenidone; chemotherapeutic agents, e.g., methotrexate, leflunomide, or a sirolimus (rapamycin) or an analog thereof, e.g., CCI-779; COX2 and cPLA2 inhibitors; NSAIDs; immunomodulators; p38 inhibitors, TPL-2, Mk-2 and NFκB inhibitors, among others.

Vaccine Formulations

In another aspect, the invention features a method of modifying an immune response associated with immunization. An IL-13 binding agent (e.g., an anti-IL-13 antibody molecule), can be used to increase the efficacy of immunization by inhibiting IL-13 activity. IL-13 binding agents can be administered before, during, or after delivery of an immunogen, e.g., administration of a vaccine. In one embodiment, the immunity raised by the vaccination is a cellular immunity, e.g., an immunity against cancer cells or virus infected, e.g., retrovirus infected, e.g., HIV infected, cells. In one embodiment, the vaccine formulation contains one or more IL-13 binding agents and an antigen, e.g., an immunogen. In another embodiment, the IL-13 binding agent and the immunogen are administered separately, e.g., within one hour, three hours, one day, or two days of each other. The IL-13 binding agent can be one that neutralizes or inhibits one or more IL-13 activities.

Inhibition of IL-13 can improve the efficacy of, e.g., cellular vaccines, e.g., vaccines against diseases such as cancer and viral infection, e.g., retroviral infection, e.g., HIV infection. Induction of $CD8^+$ cytotoxic T lymphocytes (CTL) by vaccines is down modulated by $CD4^+$ T cells, likely through the cytokine IL-13. Inhibition of IL-13 has been shown to enhance vaccine induction of CTL response (Ahlers et al. (2002) *Proc. Natl. Acad. Sci. USA* 99:13020-10325). An IL-13 binding agent, e.g., an anti-IL-13 antibody molecule, an antibody described herein, can be used in conjunction with a vaccine to increase vaccine efficacy. Cancer and viral infection (such as retroviral (e.g., HIV) infection) are exemplary disorders against which a cellular vaccine response can be effective. Vaccine efficacy is enhanced by blocking IL-13 signaling at the time of vaccination (Ahlers et al. (2002) *Proc. Nat. Acad. Sci. USA* 99:13020-25). A vaccine formulation may be administered to a subject in the form of a pharmaceutical or therapeutic composition.

Methods for Diagnosing, Prognosing, and Monitoring Disorders

IL-13 binding agents can be used in vitro and in vivo as diagnostic agents. One exemplary method includes: (i) administering the IL-13 binding agent (e.g., an IL-13 antibody molecule) to a subject; and (ii) detecting the IL-13 binding agent in the subject. The detecting can include determining location of the IL-13 binding agent in the subject. Another exemplary method includes contacting an IL-13 binding agent to a sample, e.g., a sample from a subject. The presence or absence of IL-13 or the level of IL-13 (either qualitative or quantitative) in the sample can be determined.

In another aspect, the present invention provides a diagnostic method for detecting the presence of a IL-13, in vitro (e.g., a biological sample, such as tissue, biopsy) or in vivo (e.g., in vivo imaging in a subject).

The method includes: (i) contacting a sample with IL-13 binding agent; and (ii) detecting formation of a complex between the IL-13 binding agent and the sample. The method can also include contacting a reference sample (e.g., a control sample) with the binding agent, and determining the extent of formation of the complex between the binding agent an the sample relative to the same for the reference sample. A change, e.g., a statistically significant change, in the formation of the complex in the sample or subject relative to the control sample or subject can be indicative of the presence of IL-13 in the sample.

Another method includes: (i) administering the IL-13 binding agent to a subject; and (ii) detecting formation of a complex between the IL-13 binding agent and the subject. The detecting can include determining location or time of formation of the complex.

The IL-13 binding agent can be directly or indirectly labeled with a detectable substance to facilitate detection of the bound or unbound protein. Suitable detectable substances include various enzymes, prosthetic groups, fluorescent materials, luminescent materials and radioactive materials.

Complex formation between the IL-13 binding agent and IL-13 can be detected by measuring or visualizing either the binding agent bound to the IL-13 or unbound binding agent. Conventional detection assays can be used, e.g., an enzyme-linked immunosorbent assays (ELISA), a radioimmunoassay (RIA) or tissue immunohistochemistry. Further to labeling the IL-13 binding agent, the presence of IL-13 can be assayed in a sample by a competition immunoassay utilizing standards labeled with a detectable substance and an unlabeled IL-13 binding agent. In one example of this assay, the biological sample, the labeled standards and the IL-13 binding agent are combined and the amount of labeled standard bound to the unlabeled binding agent is determined. The amount of IL-13 in the sample is inversely proportional to the amount of labeled standard bound to the IL-13 binding agent.

Methods for Diagnosing Prognosing, and/or Monitoring Asthma

The binding agents described herein can be used, e.g., in methods for diagnosing, prognosing, and monitoring the progress of asthma by measuring the level of IL-13 in a biological sample. In addition, this discovery enables the identification of new inhibitors of IL-13 signaling, which will also be useful in the treatment of asthma.

Such methods for diagnosing allergic and nonallergic asthma can include detecting an alteration (e.g., a decrease or increase) of IL-13 in a biological sample, e.g., serum, plasma, bronchoalveolar lavage fluid, sputum, etc. "Diagnostic" or "diagnosing" means identifying the presence or absence of a pathologic condition. Diagnostic methods involve detecting the presence of IL-13 by determining a test amount of IL-13 polypeptide in a biological sample, e.g., in bronchoalveolar lavage fluid, from a subject (human or nonhuman mammal), and comparing the test amount with a normal amount or range (i.e., an amount or range from an individual(s) known not to suffer from asthma) for the IL-13 polypeptide. While a particular diagnostic method may not provide a definitive diagnosis of asthma, it suffices if the method provides a positive indication that aids in diagnosis.

Methods for prognosing asthma and/or atopic disorders can include detecting upregulation of IL-13, at the mRNA or protein level. "Prognostic" or "prognosing" means predicting the probable development and/or severity of a pathologic condition. Prognostic methods involve determining the test amount of IL-13 in a biological sample from a subject, and comparing the test amount to a prognostic amount or range (i.e., an amount or range from individuals with varying severities of asthma) for IL-13. Various amounts of the IL-13 in a test sample are consistent with certain prognoses for asthma. The detection of an amount of IL-13 at a particular prognostic level provides a prognosis for the subject.

The present application also provides methods for monitoring the course of asthma by detecting the upregulation of IL-13. Monitoring methods involve determining the test amounts of IL-13 in biological samples taken from a subject at a first and second time, and comparing the amounts. A change in amount of IL-13 between the first and second time can indicate a change in the course of asthma and/or atopic disorder, with a decrease in amount indicating remission of asthma, and an increase in amount indicating progression of asthma and/or atopic disorder. Such monitoring assays are also useful for evaluating the efficacy of a particular therapeutic intervention (e.g., disease attenuation and/or reversal) in patients being treated for an IL-13 associated disorder.

Fluorophore- and chromophore-labeled binding agents can be prepared. The fluorescent moieties can be selected to have substantial absorption at wavelengths above 310 nm, and preferably above 400 nm. A variety of suitable fluorescers and chromophores are described by Stryer (1968) *Science,* 162:526 and Brand, L. et al. (1972) *Annual Review of Biochemistry,* 41:843-868. The binding agents can be labeled with fluorescent chromophore groups by conventional procedures such as those disclosed in U.S. Pat. Nos. 3,940,475, 4,289,747, and 4,376,110. One group of fluorescers having a number of the desirable properties described above is the xanthene dyes, which include the fluoresceins and rhodamines. Another group of fluorescent compounds are the naphthylamines. Once labeled with a fluorophore or chromophore, the binding agent can be used to detect the presence or localization of the IL-13 in a sample, e.g., using fluorescent microscopy (such as confocal or deconvolution microscopy).

Histological Analysis. Immunohistochemistry can be performed using the binding agents described herein. For example, in the case of an antibody, the antibody can be synthesized with a label (such as a purification or epitope tag), or can be detectably labeled, e.g., by conjugating a label or label-binding group. For example, a chelator can be attached to the antibody. The antibody is then contacted to a histological preparation, e.g., a fixed section of tissue that is on a microscope slide. After an incubation for binding, the preparation is washed to remove unbound antibody. The preparation is then analyzed, e.g., using microscopy, to identify if the antibody bound to the preparation. The antibody (or other polypeptide or peptide) can be unlabeled at the time of binding. After binding and washing, the antibody is labeled in order to render it detectable.

Protein Arrays. An IL-13 binding agent (e.g., a protein that is an IL-13 binding agent) can also be immobilized on a protein array. The protein array can be used as a diagnostic tool, e.g., to screen medical samples (such as isolated cells, blood, sera, biopsies, and the like). The protein array can also include other binding agents, e.g., ones that bind to IL-13 or to other target molecules.

Methods of producing protein arrays are described, e.g., in De Wildt et al. (2000) *Nat. Biotechnol.* 18:989-994; Lueking et al. (1999) *Anal. Biochem.* 270:103-111; Ge (2000) *Nucleic Acids Res.* 28, e3, I-VII; MacBeath and Schreiber (2000) *Science* 289:1760-1763; WO 01/40803 and WO 99/51773A1. Polypeptides for the array can be spotted at high speed, e.g., using commercially available robotic apparati, e.g., from Genetic MicroSystems or BioRobotics. The array substrate can be, for example, nitrocellulose, plastic, glass, e.g., surface-modified glass. The array can also include a porous matrix, e.g., acrylamide, agarose, or another polymer. For example, the array can be an array of antibodies, e.g., as described in De Wildt, supra. Cells that produce the protein can be grown on a filter in an arrayed format. proteins production is induced, and the expressed protein are immobilized to the filter at the location of the cell.

A protein array can be contacted with a sample to determine the extent of IL-13 in the sample. If the sample is unlabeled, a sandwich method can be used, e.g., using a labeled probe, to detect binding of the IL-13. Information about the extent of binding at each address of the array can be stored as a profile, e.g., in a computer database. The protein array can be produced in replicates and used to compare binding profiles, e.g., of different samples.

Flow Cytometry. The IL-13 binding agent can be used to label cells, e.g., cells in a sample (e.g., a patient sample). The binding agent can be attached (or attachable) to a fluorescent compound. The cells can then be analyzed by flow cytometry and/or sorted using fluorescent activated cell sorted (e.g., using a sorter available from Becton Dickinson Immunocytometry Systems, San Jose Calif.; see also U.S. Pat. Nos. 5,627,037; 5,030,002; and 5,137,809). As cells pass through the sorter, a laser beam excites the fluorescent compound while a detector counts cells that pass through and determines whether a fluorescent compound is attached to the cell by detecting fluorescence. The amount of label bound to each cell can be quantified and analyzed to characterize the sample. The sorter can also deflect the cell and separate cells bound by the binding agent from those cells not bound by the binding agent. The separated cells can be cultured and/or characterized.

In vivo Imaging. In still another embodiment, the invention provides a method for detecting the presence of a IL-13 within a subject in vivo. The method includes (i) administering to a subject (e.g., a patient having an IL-13 associated disorder) an anti-IL-13 antibody, conjugated to a detectable marker; (ii) exposing the subject to a means for detecting the detectable marker. For example, the subject is imaged, e.g., by NMR or other tomographic means.

Examples of labels useful for diagnostic imaging include radiolabels such as $^{131}$I, $^{111}$In, $^{123}$I, $^{99m}$Tc, $^{32}$P, $^{33}$P, $^{125}$I, $^{3}$H, $^{14}$C, and $^{188}$Rh, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes can also be employed. The binding agent can be labeled with such reagents using known techniques. For example, see Wensel and Meares (1983) *Radioimmunoimaging and Radioimmunotherapy*, Elsevier, New York for techniques relating to the radiolabeling of antibodies and Colcher et al. (1986) *Meth. Enzymol.* 121: 802-816. A radiolabeled binding agent can also be used for in vitro diagnostic tests. The specific activity of a isotopically-labeled binding agent depends upon the half-life, the isotopic purity of the radioactive label, and how the label is incorporated into the antibody. Procedures for labeling polypeptides with the radioactive isotopes (such as $^{14}$C, $^{3}$H, $^{35}$S, $^{125}$I, $^{99m}$Tc, $^{32}$P, $^{33}$P, and $^{131}$I) are generally known. See, e.g., U.S. Pat. No. 4,302,438; Goding, J. W. (*Monoclonal antibodies : principles and practice : production and application of monoclonal antibodies in cell biology, biochemistry, and immunology* 2nd ed. London; Orlando: Academic Press, 1986. pp 124-126) and the references cited therein; and A. R. Bradwell et al., "Developments in Antibody Imaging", *Monoclonal Antibodies for Cancer Detection and Therapy*, R. W. Baldwin et al., (eds.), pp 65-85 (Academic Press 1985).

IL-13 binding agents described herein can be conjugated to Magnetic Resonance Imaging (MRI) contrast agents. Some MRI techniques are summarized in EP-A-0 502 814. Generally, the differences in relaxation time constants T1 and T2 of water protons in different environments is used to generate an image. However, these differences can be insufficient to provide sharp high resolution images. The differences in these relaxation time constants can be enhanced by contrast agents. Examples of such contrast agents include a number of magnetic agents paramagnetic agents (which primarily alter T1) and ferromagnetic or superparamagnetic (which primarily alter T2 response). Chelates (e.g., EDTA, DTPA and NTA chelates) can be used to attach (and reduce toxicity) of some paramagnetic substances (e.g., $Fe^{3+}$, $Mn^{2+}$, $Gd^{3+}$). Other agents can be in the form of particles, e.g., less than 10 μm to about 10 nm in diameter) and having ferromagnetic, antiferromagnetic, or superparamagnetic properties. The IL-13 binding agents can also be labeled with an indicating group containing the NMR active $^{19}$F atom, as described by Pykett (1982) *Scientific American,* 246:78-88 to locate and image IL-13 distribution.

Also within the scope described herein are kits comprising an IL-13 binding agent and instructions for diagnostic use, e.g., the use of the IL-13 binding agent (e.g., an antibody molecule or other polypeptide or peptide) to detect IL-13, in vitro, e.g., in a sample, e.g., a biopsy or cells from a patient having an IL-13 associated disorder, or in vivo, e.g., by imaging a subject. The kit can further contain a least one additional reagent, such as a label or additional diagnostic agent. For in vivo use the binding agent can be formulated as a pharmaceutical composition.

Kits

An IL-13 binding agent, e.g., an anti-IL-13 antibody molecule, can be provided in a kit, e.g., as a component of a kit. For example, the kit includes (a) an IL-13 binding agent, e.g., an anti-IL-13 antibody molecule, and, optionally (b) informational material. The informational material can be descriptive, instructional, marketing or other material that relates to a method, e.g., a method described herein. The informational material of the kits is not limited in its form. In one embodiment, the informational material can include information about production of the compound, molecular weight of the compound, concentration, date of expiration, batch or production site information, and so forth. In one embodiment, the informational material relates to using the IL-13 binding agent to treat, prevent, diagnose, prognose, or monitor a disorder described herein.

In one embodiment, the informational material can include instructions to administer an IL-13 binding agent, e.g., an anti-IL-13 antibody molecule, in a suitable manner to perform the methods described herein, e.g., in a suitable dose, dosage form, or mode of administration (e.g., a dose, dosage form, or mode of administration described herein). In another embodiment, the informational material can include instructions to administer an IL-13 binding agent, e.g., an anti-IL-13 antibody molecule, to a suitable subject, e.g., a human, e.g., a human having, or at risk for, allergic asthma, non-allergic asthma, or an IL-13 mediated disorder, e.g., an allergic and/or inflammatory disorder, or HTLV-1 infection. IL-13 production has been correlated with HTLV-1 infection (Chung et al., (2003) *Blood* 102: 4130-36).

For example, the material can include instructions to administer an IL-13 binding agent, e.g., an anti-IL-13 antibody molecule, to a patient, a patient with or at risk for allergic asthma, non-allergic asthma, or an IL-13 mediated disorder, e.g., an allergic and/or inflammatory disorder, or HTLV-1 infection.

The kit can include one or more containers for the composition containing an IL-13 binding agent, e.g., an anti-IL-13 antibody molecule. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of an IL-13 binding agent, e.g., anti-IL-13 antibody molecule. For example, the kit includes a plurality of syringes, ampules, foil packets, atomizers or inhalation devices, each containing a single unit dose of an IL-13 binding agent, e.g., an anti-IL-13 antibody molecule, or multiple unit doses.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In a preferred embodiment, the device is an implantable device that dispenses metered doses of the binding agent.

The Examples that follow are set forth to aid in the understanding of the inventions but are not intended to, and should not be construed to, limit its scope in any way.

EXAMPLES

Example 1

(a) Cloning of NHP-IL-13 and Homology to Human IL-13

The cynomolgus monkey IL-13 (NHP IL-13) was cloned using hybridization probes. A comparison of the cynomolgus monkey IL-13 amino acid sequence to that of human IL-13 is shown in FIG. 1A. There is 94% amino acid identity between the two sequences, due to 8 amino acid differences. One of these differences, R130Q, represents a common human polymorphism preferentially expressed in asthmatic subjects (Heinzmann et al. (2000) *Hum. Mol. Genet.* 9:549-559).

(b) Binding of NHP-IL-13 to Human IL13Rα2

Human IL-13 binds with high affinity to the alpha2 form of IL-13 receptor (IL13Rα2). A soluble form of this receptor was expressed with a human IgG1 Fc tail (sIL13Rα2-Fc). By binding to IL-13 and sequestering the cytokine from the cell surface IL13Rα1-IL4R signaling complex, sIL13Rα2-Fc can act as a potent inhibitor of human IL-13 bioactivity. sIL13Rα2-Fc was shown to bind to NHP-IL-13 produced by CHO cells or *E. coli*.

(c) Bioactivity of NHP-IL-13 on Human Monocytes (i) CD23 expression on human monocytes. cDNA encoding cynomolgus monkey IL-13 was expressed in *E. coli* and refolded to maintain bioactivity. Reactivity of human cells to cynomolgus IL-13 was demonstrated using a bioassay in which normal peripheral blood mononuclear cells from healthy donors were treated with IL-13 overnight at 37° C. This induced up-regulation of CD23 expression on the surface of monocytes. Results showed that cynomolgus IL-13 had bioactivity on primary human monocytes.

(ii) STAT6 phosphorylation on HT-29 cells. The human HT-29 epithelial cell line responds to IL-13 by undergoing STAT6 phosphorylation, a consequence of signal transduction through the IL-13 receptor. To assay the ability of recombinant NHP-IL-13 to induce STAT6 phosphorylation, HT-29 cells were challenged with the NHP-IL-13 for 30 minutes at 37° C., then fixed, permeabilized, and stained with fluorescent antibody to phospho-STAT6. Results showed that cynomolgus IL-13 efficiently induced STAT6 phosphorylation in this human cell line.

(d) Generation of Antibodies that bind to NHP-IL-13

Mice or other appropriate animals may be immunized and boosted with cynomolgus IL-13, e.g., using one or more of the following methods. One method for immunization may be combined with either the same or different method for boosting:

(i) Immunization with cynomolgus IL-13 protein expressed in *E. coli*, purified from inclusion bodies, and refolded to preserve biological activity. For immunization, the protein is emulsified with complete Freund's adjuvant (CFA), and mice are immunized according to standard protocols. For boosting, the same protein is emulsified with incomplete Freund's adjuvant (IFA).

(ii) Immunization with peptides spanning the entire sequence of mature cynomolgus IL-13. Each peptide contains at least one amino acid that is unique to cynomolgus IL-13 and not present in the human protein. See FIG. 1B. Where the peptide has a C-terminal residue other than cysteine, a cysteine is added for conjugation to a carrier protein. The peptides are conjugated to an immunogenic carrier protein such as KLH, and used to immunize mice according to standard protocols. For immunization, the protein is emulsified with complete Freund's adjuvant (CFA), and mice are immunized according to standard protocols. For boosting, the same protein is emulsified with incomplete Freund's adjuvant (IFA).

(iii) Immunization with NHP-IL-13- encoding cDNA expressed. The cDNA encoding NHP-IL-13, including leader sequence, is cloned into an appropriate vector. This DNA is coated onto gold beads which are injected intradermally by gene gun.

(iv) The protein or peptides can be used as a target for screening a protein library, e.g., a phage or ribosome display library. For example, the library can display varied immunoglobulin molecules, e.g., Fab's, scFv's, or Fd's.

(e) Selection of Antibody Clones Cross-Reactive with NHP and Optionally a Human IL-13, e.g., a Native Human IL-13.

Primary Screen

The primary screen for antibodies was selection for binding to recombinant NHP-IL-13 by ELISA. In this ELISA, wells are coated with recombinant NHP IL-13. The immune serum was added in serial dilutions and incubated for one hour at room temperature. Wells were washed with PBS containing 0.05% TWEEN®-20 (PBS-Tween). Bound antibody was detected using horseradish peroxidase (HRP)-labeled anti-mouse IgG and tetramethylbenzidene (TMB) substrate. Absorbance was read at 450 nm. Typically, all immunized mice generated high titers of antibody to NHP-IL-13.

Secondary Screen

The secondary screen was selection for inhibition of binding of recombinant NHP-IL-13 to sIL-13Rα1-Fc by ELISA. Wells were coated with soluble IL-13Rα1-Fc, to which FLAG-tagged NHP-IL-13 could bind. This binding was detected with anti-FLAG antibody conjugated to HRP. Hydrolysis of TMB substrate was read as absorbance at 450 nm. In the assay, the FLAG-tagged NHP-IL-13 was added together with increasing concentrations of immune serum. If the immune serum contained antibody that bound to NHP-IL-13 and prevented its binding to the sIL13Rα1-Fc coating the wells, the ELISA signal was decreased. All immunized mice produced antibody that competed with sIL13Rα1-Fc binding to NHP-IL-13, but the titers varied from mouse to mouse. Spleens were selected for fusion from animals whose serum showed inhibited sIL13Rα1-Fc binding to NHP-IL-13 at the highest dilution.

Tertiary Screen

The tertiary screen tested for inhibition of NHP-IL-13 bioactivity. Several bioassays were available to be used, including the TF-1 proliferation assay, the monocyte CD23 expression assay, and the HT-29 cell STAT6 phosphorylation assay. Immune sera were tested for inhibition of NHP-IL-13- mediated STAT6 phosphorylation. The HT-29 human epithelial cell line was challenged for 30 minutes at 37° C. with recombinant NHP-IL-13 in the presence or absence of the indicated concentration of mouse immune serum. Cells were then fixed, permeabilized, and stained with ALEXA™ Fluor 488-conjugated mAb to phospho-STAT6 (Pharmingen). The percentage of cells responding to IL-13 by undergoing STAT6 phosphorylation was determined by flow cytometry. Spleens of mice with the most potent neutralization activity, determined as the strongest inhibition of NHP-IL-13 bioactivity at a high serum dilution, were selected for generation of hybridomas.

Quaternary Screen

A crude preparation containing human IL-13 was generated from human umbilical cord blood mononuclear cells (BioWhittaker/Cambrex). The cells were cultured in a 37° C. incubator at 5% $CO_2$, in RPMI media containing 10% heat-inactivated FCS, 50 U/ml penicillin, 50 mg/ml streptomycin, and 2 mM L-glutamine. Cells were stimulated for 3 days with the mitogen PHA-P (Sigma), and skewed toward Th2 with recombinant human IL-4 (R&D Systems) and anti-human IL-12. The Th2 cells were expanded for one week with IL-2, then activated to produce cytokine by treatment with phorbol 12-myristate 13-acetate (PMA) and ionomycin for three days. The supernatant was collected and dialyzed to remove PMA and ionomycin. To deplete GM-CSF and IL-4, which could interfere with bioassays for IL-13, the supernatant was treated with biotinylated antibodies to GM-CSF and IL-4 (R&D Systems, Inc), then incubated with streptavidin-coated magnetic beads (Dynal). The final concentration of IL-13 was determined by ELISA (Biosource), and for total protein by Bradford assay (Bio-Rad). The typical preparation contains <0.0005% IL-13 by weight.

Selection of Hybridoma Clones

Using established methods, hybridomas were generated from spleens of mice selected as above, fused to the P3X63_AG8.653 myeloma cell line (ATCC). Cells were plated at limiting dilution and clones were selected according to the screening criteria described above. Data was collected for the selection of clones based on ability to compete for NHP-IL-13 binding to sIL13Rα1-Fc by ELISA. Clones were further tested for ability to neutralize the bioactivity of NHP-IL-13. Supernatants of the hybridomas were tested for competition of STAT-6 phosphorylation induced by NHP-IL-13 in the HT-29 human epithelial cell line.

Example 2

MJ 2-7 Antibody

Total RNA was prepared from MJ 2-7 hybridoma cells using the QIAGEN RNEASY™ Mini Kit (Qiagen). RNA was reverse transcribed to cDNA using the SMART™ PCR Synthesis Kit (BD Biosciences Clontech). The variable region of MJ 2-7 heavy chain was extrapolated by PCR using SMART™ oligonucleotide as a forward primer and mIgG1 primer annealing to DNA encoding the N-terminal part of CH1 domain of mouse IgG1 constant region as a reverse primer. The DNA fragment encoding MJ 2-7 light chain variable region was generated using SMART™ and mouse kappa specific primers. The PCR reaction was performed using DEEP VENT™ DNA polymerase (New England Biolabs) and 25 nM of dNTPs for 24 cycles (94° C. for 1 minute, 60° C. for 1 minute, 72° C. for 1 minute). The PCR products were subcloned into the pED6 vector, and the sequence of the inserts was identified by DNA sequencing. N-terminal protein sequencing of the purified mouse MJ 2-7 antibody was used to confirm that the translated sequences corresponded to the observed protein sequence.

Exemplary nucleotide and amino acid sequences of mouse monoclonal antibody MJ 2-7 which interacts with NHP IL-13 and which has characteristics which suggest that it may interact with human IL-13 are as follows:

An exemplary nucleotide sequence encoding the heavy chain variable domain includes:

```
GAG GTTCAGCTGC AGCAGTCTGG        (SEQ ID NO: 129)
GGCAGAGCTT GTGAAGCCAG

GGGCCTCAGT CAAGTTGTCC TGCACAGGTT
CTGGCTTCAA CATTAAAGAC

ACCTATATAC ACTGGGTGAA GCAGAGGCCT
GAACAGGGCC TGGAGTGGAT

TGGAAGGATT GATCCTGCGA ATGATAATAT
TAAATATGAC CCGAAGTTCC

AGGGCAAGGC CACTATAACA GCAGACACAT
CCTCCAACAC AGCCTACCTA

CAGCTCAACA GCCTGACATC TGAGGACACT
GCCGTCTATT ACTGTGCTAG

ATCTGAGGAA AATTGGTACG ACTTTTTTGA
CTACTGGGGC CAAGGCACCA

CTCTCACAGT CTCCTCA
```

An exemplary amino acid sequence for the heavy chain variable domain includes:

EVQLQQSGAELVKPGASVKLSCTGSGFNIKDTYIHWVKQRPEQGLEWIGRIDPA (SEQ ID NO: 130)

NDNIKYDPKFQGKATITADTSSNTAYLQLNSLTSEDTAVYYCARSEENWYDFF

DYWGQGTTLTVSS

CDRs are underlined. The variable domain optionally is preceded by a leader sequence. e.g., MKCSWVIFFLMAVVTGVNS (SEQ ID NO:131). An exemplary nucleotide sequence encoding the light chain variable domain includes:

```
GAT GTTTTGATGA CCCAAACTCC        (SEQ ID NO: 132)
ACTCTCCCTG CCTGTCAGTC

TTGGAGATCA AGCCTCCATC TCTTGCAGGT
CTAGTCAGAG CATTGTACAT

AGTAATGGAA ACACCTATTT AGAATGGTAC
CTGCAGAAAC CAGGCCAGTC

TCCAAAGCTC CTGATCTACA AAGTTTCCAA
CCGATTTTCT GGGGTCCCAG

ACAGGTTCAG TGGCAGTGGA TCAGGGACAG
ATTTCACACT CAAGATTAGC

AGAGTGGAGG CTGAGGATCT GGGAGTTTAT
TACTGCTTTC AAGGTTCACA

TATTCCGTAC ACGTTCGGAG GGGGGACCAA
GCTGGAAATA AAA
```

An exemplary amino acid sequence for the light chain variable domain includes:

```
DVLMTQTPLSLPVSLGDQASISCRSSQSIVHSNGNTYLEWYLQKPGQSP    (SEQ ID NO: 133)

KLLIYKVSNRFSGVPDRFSGSGSGTDFTLKISRVEAEDLGVYYCFQGSHIPYTFG

GGTKLEIK
```

CDRs are underlined. The amino acid sequence optionally is preceded by a leader sequence, e.g., MKLPVRLLVLMF-WIPASSS (SEQ ID NO:134). The term "MJ 2-7" is used interchangeably with the term "mAb7.1.1," herein.

Example 3

C65 Antibody

Exemplary nucleotide and amino acid sequences of mouse monoclonal antibody C65, which interacts with NHP IL-13 and which has characteristics that suggest that it may interact with human IL-13 are as follows:

An exemplary nucleic acid sequence for the heavy chain variable domain includes:

```
  1   ATGGCTGTCC TGGCATTACT    (SEQ ID NO: 135)
      CTTCTGCCTG GTAACATTCC
      CAAGCTGTAT

51   CCTTTCCCAG GTGCAGCTGA
      AGGAGTCAGG ACCTGGCCTG
      GTGGCGCCCT

101   CACAGAGCCT GTCCATCACA
      TGCACCGTCT CAGGGTTCTC
      ATTAACCGGC

151   TATGGTGTAA ACTGGGTTCG
      CCAGCCTCCA GGAAAGGGTC
      TGGAGTGGCT

201   GGGAATAATT TGGGGTGATG
      GAAGCACAGA CTATAATTCA
      GCTCTCAAAT

251   CCAGACTGAT CATCAACAAG
      GACAACTCCA AGAGCCAAGT
      TTTCTTAAAA

301   ATGAACAGTC TGCAAACTGA
      TGACACAGCC AGGTACTTCT
      GTGCCAGAGA

351   TAAGACTTTT TACTACGATG
      GTTTCTACAG GGGCAGGATG
      GACTACTGGG

401   GTCAAGGAAC CTCAGTCACC
      GTCTCCTCA
```

An exemplary amino acid sequence for the heavy chain variable domain includes:

```
QVQLKESGPGL VAPSQSLSIT CTVSGFSLTG    (SEQ ID NO: 136)
YGVNWVRQPP GKGLEWLGII

WGDGSTDYNS ALKSRLIINK DNSKSQVFLK
MNSLQTDDTA RYFCARDKTF

YYDGFYRGRM DYWGQGTSVT VSS
```

CDRs are underlined. The amino acid sequence optionally is preceded by a leader sequence, e.g., MAVLALLFCL VTFP-SCILS (SEQ ID NO:137).

An exemplary nucleotide sequence encoding the light chain variable domain includes:

```
  1   ATGAACACGA GGGCCCCTGC    (SEQ ID NO: 138)
      TGAGTTCCTT GGGTTCCTGT
      TGCTCTGGTT

51   TTTAGGTGCC AGATGTGATG
      TCCAGATGAT TCAGTCTCCA
      TCCTCCCTGT

101   CTGCATCTTT GGGAGACATT
      GTCACCATGA CTTGCCAGGC
      AAGTCAGGGC

151   ACTAGCATTA ATTTAAACTG
      GTTTCAGCAA AAACCAGGGA
      AAGCTCCTAA

201   GCTCCTGATC TTTGGTGCAA
      GCAACTTGGA AGATGGGGTC
      CCATCAAGGT

251   TCAGTGGCAG TAGATATGGG
      ACAAATTTCA CTCTCACCAT
      CAGCAGCCTG

301   GAGGATGAAG ATATGGCAAC
      TTATTTCTGT CTACAGCATA
      GTTATCTCCC

351   GTGGACGTTC GGTGGCGGCA
      CCAAACTGGA AATCAAA
```

An exemplary amino acid sequence for the light chain variable domain includes:

```
DVQMIQSP SSLSASLGDI                  (SEQ ID NO: 139)
VTMTCQASQG TSINLNWFQQ KPGKAPKLLI

FGASNLEDGV PSRFSGSRYG TNFTLTISSL
EDEDMATYFC LQHSYLPWTF GGGTKLEIK
```

CDRs are underlined. The amino acid sequence optionally is preceded by a leader sequence, e.g., MNTRAPAEFLG-FLLLWFLGARC (SEQ ID NO:140).

Example 4

Cynomolgus Monkey Model

The efficacy of an antibody to neutralize one or more IL-13-associated activities in vivo can be tested using a model of antigen-induced airway inflammation in cynomolgus monkeys naturally allergic to *Ascaris suum*. In this model, challenge of an allergic monkey with *Ascaris suum* antigen results in an influx of inflammatory cells, especially eosinophils, into the airways. To test the ability of an antibody to prevent this influx of cells, the antibody can be administered 24 hours prior to challenge with *Ascaris suum* antigen. On the day of challenge, a baseline bronchoalveolar lavage (BAL) sample can be taken from the left lung. The antigen can then be instilled intratracheally into the right lung. Twenty-four hours later, the right lung is lavaged, and the BAL fluid from animals treated intravenously with 10 mg/kg recombinant antibody expressed from CHO cells are compared to BAL fluid from untreated animals. If the antibody reduces airway inflammation, an increase in percent BAL eosinophils may be observed among the untreated group, but not for the antibody-treated group. These assays can be used to confirm that the antibody effectively prevents airway eosinophilia in allergic animals challenged with an allergen.

Example 5

Fc Sequences

The Ser at position #1 of SEQ ID NO:128 represents amino acid residue #119 in a first exemplary full length antibody numbering scheme in which the Ser is preceded by residue #118 of a heavy chain variable domain. In the first exemplary full length antibody numbering scheme, mutated amino acids are at numbered 234 and 237, and correspond to positions 116 and 119 of SEQ ID NO:128. Thus, the following sequence represents an Fc domain with two mutations: L234A and G237A, according to the first exemplary full length antibody numbering scheme.

```
STKGPSVFPLAPSSKSTSGGTAALGCLVKDYFPEPVTVSWNSGALTSGVHTFPAV    (SEQ ID NO: 128)
LQSSGLYSLSSVVTVPSSSLGTQTYICNVNHKPSNTKVDKKVEPKSCDKTHTCPP
CPAPEALGAPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKSLSLS
PGK
```

The following is another exemplary human Fc domain sequence:

```
STKGPSVFPLAPSSKSTSGGTAALGCLVKDYFPEPVTVSWNSGALTSGVHTFPAV    (SEQ ID NO: 141)
LQSSGLYSLSSVVTVPSSSLGTQTYICNVNHKPSNTKVDKKVEPKSCDKTHTCPP
CPAPELLGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTIS
KAKGQPREPQVYTLPPSREEMTKNQVSLTCLVKGFYPSDLAVEWESNGQPENNY
KTTPPVLDSDGSFFLYSKLTVDKSRWQQGNVFSCSVMHEALHNHYTQKSLSLSP
GK
```

Other exemplary alterations that can be used to decrease effector function include L234A;L235A), (L235A;G237A), and N297A.

Example 6

IL-13 and IgE in Mice

IL-13 is involved in the production of IgE, an important mediator of atopic disease. Mice deficient in IL-13 had partial reductions in serum IgE and mast cell IgE responses, whereas mice lacking the natural IL-13 binding agent, IL-13Rα2—/—, had enhanced levels of IgE and IgE effector function.

BALB/c female mice were obtained from Jackson Laboratories (Bar Harbor, Me.). IL-13Rα2−/− mice are described, e.g., in Wood et al. (2003) *J. Exp. Med.* 197:703-9. Mice deficient in IL-13 are described, e.g., in McKenzie et al. (1998) *Immunity* 9:423-32. All mutant strains were on the BALB/c background.

Serum IgE levels were measured by ELISA. ELISA plates (MaxiSorp; Nunc, Rochester, N.Y.) were coated overnight at 4° C. with rat anti-mouse IgE (BD Biosciences, San Diego, Calif.). Plates were blocked for 1 hour at room temperature with 0.5% gelatin in PBS, washed in PBS containing 0.05% TWEEN®-20 (PBS-Tween), and incubated for six hours at room temperature with purified mouse IgE (BD Biosciences) as standards or with serum dilutions. Binding was detected with biotinylated anti-mouse IgE (BD Biosciences) using mouse IgG (Sigma-Aldrich, St. Louis, Mo.) as a blocker. Binding was detected with peroxidase-linked streptavidin (Southern Biotechnology Associates, Inc., Birmingham, Ala.) and SURE BLUE™ substrate (KPL Inc., Gaithersburg, Md.).

In order to investigate the requirement for IL-13 to support resting IgE levels in naive mice, serum was examined in the absence of specific immunization from wild-type mice and from mice genetically deficient in IL-13 and IL-13Rα2. Mice deficient in IL-13 had virtually undetectable levels of serum IgE. In contrast, mice lacking the inhibitory receptor IL-13Rα2 displayed elevated levels of serum IgE. These results demonstrate that blocking IL-13 can be useful for treating or preventing atopic disorders.

Example 7

IL-13 and Atopic Disorders

The ability of MJ2-7 to inhibit the bioactivity of native human IL-13 (at 1 ng/ml) was evaluated in an assay for STAT6 phosphorylation. MJ2-7 inhibited the activity of native human IL-13 with an IC50 of about 0.293 nM in this assay. An antibody with the murine heavy chain of MJ2-7 and a humanized light chain inhibited the activity of native human IL-13 with an IC50 of about 0.554 nM in this assay.

The ability of MJ2-7 to inhibit non-human primate IL-13 (at 1 ng/ml) was evaluated in an assay for CD23 expression. The MJ2-7 inhibited the activity of non-human primate IL-13 with an IC50 of about 0.242 nM in this assay. An antibody with the murine heavy chain of MJ2-7 and a humanized light chain inhibited the activity of non-human primate IL-13 with an IC50 of about 0.308 nM in this assay.

Example 8

Nucleotide and Amino Acid Sequences of Mouse MJ 2-7 Antibody

The nucleotide sequence encoding the heavy chain variable region (with an optional leader) is as follows:

```
  1   ATGAAATGCA GCTGGGTTAT           (SEQ ID NO: 142)
      CTTCTTCCTG ATGGCAGTGG
      TTACAGGGGT

51   CAATTCAGAG GTTCAGCTGC
      AGCAGTCTGG GGCAGAGCTT
      GTGAAGCCAG

101   GGGCCTCAGT CAAGTTGTCC
      TGCACAGGTT CTGGCTTCAA
      CATTAAAGAC

151   ACCTATATAC ACTGGGTGAA
      GCAGAGGCCT GAACAGGGCC
      TGGAGTGGAT

201   TGGAAGGATT GATCCTGCGA
      ATGATAATAT TAAATATGAC
      CCGAAGTTCC

251   AGGGCAAGGC CACTATAACA
      GCAGACACAT CCTCCAACAC
      AGCCTACCTA

301   CAGCTCAACA GCCTGACATC
      TGAGGACACT GCCGTCTATT
      ACTGTGCTAG

351   ATCTGAGGAA AATTGGTACG
      ACTTTTTTGA CTACTGGGGC
      CAAGGCACCA

401   CTCTCACAGT CTCCTCA
```

The amino acid sequence of the heavy chain variable region with an optional leader (underscored) is as follows:

```
  1   MKCSWVIFFL MAVVTGVNSE          (SEQ ID NO: 143)
      VQLQQSGAEL VKPGASVKLS
      CTGSGFNIKD

51   TYIHWVKQRP EQGLEWIGRI
      DPANDNIKYD PKFQGKATIT
      ADTSSNTAYL

101   QLNSLTSEDT AVYYCARSEE
      NWYDFFDYWG QGTTLTVSS
```

The nucleotide sequence encoding the light chain variable region is as follows:

```
  1   ATGAAGTTGC CTGTTAGGCT           (SEQ ID NO: 144)
      GTTGGTGCTG ATGTTCTGGA
      TTCCTGCTTC

51   CAGCAGTGAT GTTTTGATGA
      CCCAAACTCC ACTCTCCCTG
      CCTGTCAGTC

101   TTGGAGATCA AGCCTCCATC
      TCTTGCAGGT CTAGTCAGAG
      CATTGTACAT

151   AGTAATGGAA ACACCTATTT
      AGAATGGTAC CTGCAGAAAC
      CAGGCCAGTC

201   TCCAAAGCTC CTGATCTACA
      AAGTTTCCAA CCGATTTTCT
      GGGGTCCCAG

251   ACAGGTTCAG TGGCAGTGGA
      TCAGGGACAG ATTTCACACT
      CAAGATTAGC

301   AGAGTGGAGG CTGAGGATCT
      GGGAGTTTAT TACTGCTTTC
      AAGGTTCACA

351   TATTCCGTAC ACGTTCGGAG
      GGGGGACCAA GCTGGAAATA AAA
```

The amino acid sequence of the light chain variable region with an optional leader (underscored) is as follows:

```
  1   MKLPVRLLVL MFWIPASSSD          (SEQ ID NO: 145)
      VLMTQTPLSL PVSLGDQASI
      SCRSSQSIVH

51   SNGNTYLEWY LQKLPGQSPKL
      LIYKVSNRFS GVPDRFSGSG
      SGTDFTLKIS

101   RVEAEDLGVY YCFQGSHIPY
      TFGGGTKLEI K
```

Example 9

Nucleotide and Amino Acid Sequences of Exemplary First Humanized Variants of the MJ 2-7 Antibody Humanized antibody Version 1 (V1) is based on the closest human germline clones. The nucleotide sequence of hMJ 2-7 V1 heavy chain variable region (hMJ 2-7 VH V1) (with a sequence encoding an optional leader sequence) is as follows:

```
  1  ATGGATTGGA CCTGGCGCAT      (SEQ ID NO: 146)
     CCTGTTCCTG GTGGCCGCTG
     CCACCGGCGC

51  TCACTCTCAG GTGCAGCTGG
     TGCAGTCTGG CGCCGAGGTG
     AAGAAGCCTG

101  GCGCTTCCGT GAAGGTGTCC
     TGTAAGGCCT CCGGCTTCAA
     CATCAAGGAC

151  ACCTACATCC ACTGGGTGCG
     GCAGGCTCCC GGCCAGCGGC
     TGGAGTGGAT

201  GGGCCGGATC GATCCTGCCA
     ACGACAACAT CAAGTACGAC
     CCCAAGTTTC

251  AGGGCCGCGT GACCATCACC
     CGCGATACCT CCGCTTCTAC
     CGCCTACATG

301  GAGCTGTCTA GCCTGCGGAG
     CGAGGATACC GCCGTGTACT
     ACTGCGCCCG

351  CTCCGAGGAG AACTGGTACG
     ACTTCTTCGA CTACTGGGGC
     CAGGGCACCC

401  TGGTGACCGT GTCCTCT
```

The amino acid sequence of the heavy chain variable region (hMJ 2-7 V1) is based on a CDR grafted to DP-25, VH-1, 1-03. The amino acid sequence with an optional leader (first underscored region; CDRs based on AbM definition shown in subsequent underscored regions) is as follows:

```
  1  MDWTWRILFL VAAATGAHS -      (SEQ ID NO: 147)
     Q VQLVQSGAEV KKPGASVKVS
     CKASGFNIKD

51  TYIHWVRQAP GQRLEWMGRI
     DPANDNIKYD PKFQGRVTIT
     RDTSASTAYM

101  ELSSLRSEDT AVYYCARSEE
     NWYDFFDYWG QGTLVTVSSG ESCR
```

The nucleotide sequence of the hMJ 2-7 V1 light chain variable region (hMJ 2-7 VL V1) (with a sequence encoding an optional leader sequence) is as follows:

```
  1  ATGCGGCTGC CCGCTCAGCT      (SEQ ID NO: 148)
     GCTGGGCCTG CTGATGCTGT
     GGGTGCCCGG

51  CTCTTCCGGC GACGTGGTGA
     TGACCCAGTC CCCTCTGTCT
     CTGCCCGTGA

101  CCCTGGGCCA GCCCGCTTCT
     ATCTCTTGCC GGTCCTCCCA
     GTCCATCGTG

151  CACTCCAACG GCAACACCTA
     CCTGGAGTGG TTTCAGCAGA
     GACCCGGCCA

201  GTCTCCTCGG CGGCTGATCT
     ACAAGGTGTC CAACCGCTTT
     TCCGGCGTGC

251  CCGATCGGTT CTCCGGCAGC
     GGCTCCGGCA CCGATTTCAC
     CCTGAAGATC

301  AGCCGCGTGG AGGCCGAGGA
     TGTGGGCGTG TACTACTGCT
     TCCAGGGCTC

351  CCACATCCCT TACACCTTTG
     GCGGCGGAAC CAAGGTGGAG ATCAAG
```

This version is based on a CDR graft to DPK18, V kappaII. The amino acid sequence of hMJ 2-7 V1 light chain variable region (hMJ 2-7 VL V1) (with optional leader as first underscored region; CDRs based on AbM definition in subsequent underscored regions) is as follows:

```
  1  MRLPAQLLGL LMLWVPGSSG      (SEQ ID NO: 149)
     -DVVMTQSPLS LPVTLGQPAS
     ISCRSSQSIV

51  HSNGNTYLEW FQQRPGQSPR
     RLIYKVSNRF SGVIPDRFSGS
     GSGTDFTLKI

101  SRVEAEDVGV YYCFQGSHIP
     YTFGGGTKVE IK
```

Example 10

Nucleotide and Amino Acid Sequences of Exemplary Second Humanized Variants of the MJ 2-7 Antibody The following heavy chain variable region is based on a CDR graft to DP-54, VH-3, 3-07. The nucleotide sequence of hMJ 2-7 Version 2 (V2) heavy chain variable region (hMJ 2-7 VH V2) (with a sequence encoding an optional leader sequence) is as follows:

```
  1  ATGGAGCTGG GGCTGTCTTG      (SEQ ID NO: 150)
     GGTGTTCCTG GTGGCTATCC
     TGGAGGGCGT

51  GCAGTGCGAG GTGCAGCTGG
     TGGAGTCTGG CGGCGGACTG
     GTGCAGCCTG

101  GCGGCTCTCT GCGGCTGTCT
     TGCGCCGCTT CCGGCTTCAA
     CATCAAGGAC

151  ACCTACATCC ACTGGGTGCG
     GCAGGCTCCC GGCAAGGGCC
     TGGAGTGGGT

201  GGCCCGGATC GATCCTGCCA
     ACGACAACAT CAAGTACGAC
     CCCAAGTTCC

251  AGGGCCGGTT CACCATCTCT
     CGCGACAACG CCAAGAACTC
     CCTGTACCTC

301  CAGATGAACT CTCTGCGCGC
     CGAGGATACC GCCGTGTACT
     ACTGCGCCCG

351  GAGCGAGGAG AACTGGTACG
     ACTTCTTCGA CTACTGGGGC
     CAGGGCACCC

401  TGGTGACCGT GTCCTCT
```

The amino acid sequence of hMJ 2-7 V2 heavy chain variable region (hMJ 2-7 VH V2) with an optional leader (first underscored region; CDRs based on AbM definition shown in subsequent underscored regions) is as follows:

```
  1  MELGLSWVFL VAILEGVQC- E    (SEQ ID NO: 151)
     VQLVESGGGL VQPGGSLRLS
     CAASGFNIKD

51  TYIHWVRQAP GKGLEWVARI
     DPANDNIKYD PKFQGRFTIS
     RDNAKNSLYL

101  QMNSLRAEDT AVYYCARSEE
     NWYDFFDYWG QGTLVTVSS
```

The hMJ 2-7 V2 light chain variable region was based on a CDR graft to DPK9, V kappaI, O2. The nucleotide sequence of hMJ 2-7 V2 light chain variable region (hMJ 2-7 VL V2) (with a sequence encoding an optional leader sequence) is as follows:

```
  1  ATGGATATGC GCGTGCCCGC       (SEQ ID NO: 152)
     TCAGCTGCTG GGCCTGCTGC
     TGCTGTGGCT

51  GCGCGGAGCC CGCTGCGATA
     TCCAGATGAC CCAGTCCCCT
     TCTTCTCTGT

101  CCGCCTCTGT GGGCGATCGC
     GTGACCATCA CCTGTCGGTC
     CTCCCAGTCC

151  ATCGTGCACT CCAACGGCAA
     CACCTACCTG GAGTGGTATC
     AGCAGAAGCC

201  CGGCAAGGCC CCTAAGCTGC
     TGATCTACAA GGTGTCCAAC
     CGCTTTTCCG

251  GCGTGCCTTC TCGGTTCTCC
     GGCTCCGGCT CCGGCACCGA
     TTTCACCCTG

301  ACCATCTCCT CCCTCCAGCC
     CGAGGATTTC GCCACCTACT
     ACTGCTTCCA

351  GGGCTCCCAC ATCCCTTACA
     CCTTTGGCGG CGGAACCAAG
     GTGGAGATCA

401  AGCGT
```

The amino acid sequence of the light chain variable region of hMJ 2-7 V2 light chain variable region (hMJ 2-7 VL V2) (with optional leader peptide underscored and CDRs based on AbM definition shown in subsequent underscored regions) is as follows:

```
  1  MDMRVPAQLL GLLLLWLRGA RC     (SEQ ID NO: 153)
     -DIQMTQSP SSLSASVGDR VTITCRSSQS

51  IVHSNGNTYL EWYQQKPGKA
     PKLLIYKVSN RFSGVPSRFS
     GSGSGTDFTL

101  TISSLQPEDF ATYYCFQGSH
     IPYTFGGGTK VEIKR
```

Additional humanized versions of MJ 2-7 V2 heavy chain variable region were made. These versions included backmutations that have murine amino acids at selected framework positions.

The nucleotide sequence encoding the heavy chain variable region "Version 2.1" or V2.1 with the back mutations V48I,A29G is as follows:

```
  1  GAGGTGCAGC TGGTGGAGTC       (SEQ ID NO: 154)
     TGGCGGCGGA CTGGTGCAGC
     CTGGCGGCTC

51  TCTGCGGCTG TCTTGCGCCG
     CTTCCGGCTT CAACATCAAG
     GACACCTACA

101  TCCACTGGGT GCGGCAGGCT
     CCCGGCAAGG GCCTGGAGTG
     GATCGGCCGG

151  ATCGATCCTG CCAACGACAA
     CATCAAGTAC GACCCCAAGT
     TCCAGGGCCG

201  GTTCACCATC TCTCGCGACA
     ACGCCAAGAA CTCCCTGTAC
     CTCCAGATGA

251  ACTCTCTGCG CGCCGAGGAT
     ACCGCCGTGT ACTACTGCGC
     CCGGAGCGAG

301  GAGAACTGGT ACGACTTCTT
     CGACTACTGG GGCCAGGGCA
     CCCTGGTGAC

351  CGTGTCCTCT
```

The amino acid sequence of the heavy chain variable region of V2.1 (CDRs based on AbM definition shown in subsequent underscored regions) is as follows:

```
  1  EVQLVESGGG LVQPGGSLRL       (SEQ ID NO: 155)
     SCAASGFNIK DTYIHWVRQA
     PGKGLEWIGR

51  IDPANDNIKY DPKFQGRFTI
     SRDNAKNSLY LQMNSLRAED
     TAVYYCARSE

101  ENWYDFFDYW GQGTLVTVSS
```

The nucleotide sequence encoding the heavy chain variable region V2.2 with the back mutations (R67K,F68A) is as follows:

```
  1  GAGGTGCAGC TGGTGGAGTC       (SEQ ID NO: 156)
     TGGCGGCGGA CTGGTGCAGC
     CTGGCGGCTC

51  TCTGCGGCTG TCTTGCGCCG
     CTTCCGGCTT CAACATCAAG
     GACACCTACA

101  TCCACTGGGT GCGGCAGGCT
     CCCGGCAAGG GCCTGGAGTG
     GGTGGCCCGG

151  ATCGATCCTG CCAACGACAA
     CATCAAGTAC GACCCCAAGT
     TCCAGGGCAA

201  GGCCACCATC TCTCGCGACA
     ACGCCAAGAA CTCCCTGTAC
     CTCCAGATGA
```

```
251  ACTCTCTGCG CGCCGAGGAT
     ACCGCCGTGT ACTACTGCGC
     CCGGAGCGAG

301  GAGAACTGGT ACGACTTCTT
     CGACTACTGG GGCCAGGGCA
     CCCTGGTGAC

351  CGTGTCCTCT
```

The amino acid sequence of the heavy chain variable region of V2.2 (CDRs based on AbM definition shown in subsequent underscored regions) is as follows:

```
  1  EVQLVESGGG LVQPGGSLRL      (SEQ ID NO: 157)
     SCAASGFNIK DTYIHWVRQA
     PGKGLEWVAR

51  IDPANDNIKY DPKFQGKATI
     SRDNAKNSLY LQMNSLRAED
     TAVYYCARSE

102  ENWYDFFDYW GQGTLVTVSS
```

The nucleotide sequence encoding the heavy chain variable region V2.3 with the back mutations (R72A):

```
  1  GAGGTGCAGC TGGTGGAGTC      (SEQ ID NO: 158)
     TGGCGGCGGA CTGGTGCAGC
     CTGGCGGCTC

51  TCTGCGGCTG TCTTGCGCCG
     CTTCCGGCTT CAACATCAAG
     GACACCTACA

101  TCCACTGGGT GCGGCAGGCT
     CCCGGCAAGG GCCTGGAGTG
     GGTGGCCCGG

151  ATCGATCCTG CCAACGACAA
     CATCAAGTAC GACCCCAAGT
     TCCAGGGCCG

201  GTTCACCATC TCTGCCGACA
     ACGCCAAGAA CTCCCTGTAC
     CTCCAGATGA

251  ACTCTCTGCG CGCCGAGGAT
     ACCGCCGTGT ACTACTGCGC
     CCGGAGCGAG

301  GAGAACTGGT ACGACTTCTT
     CGACTACTGG GGCCAGGGCA
     CCCTGGTGAC

351  CGTGTCCTCT
```

The amino acid sequence of the heavy chain variable region of V2.3 (CDRs based on AbM definition shown in subsequent underscored regions) is as follows:

```
  1  EVQLVESGGG LVQPGGSLRL      (SEQ ID NO: 159)
     SCAASGFNIK DTYIHWVRQA
     PGKGLEWVAR

51  IDPANDNIKY DPKFQGRFTI
     SADNAKNSLY LQMNSLRAED
     TAVYYCARSE

103  ENWYDFFDYW GQGTLVTVSS
```

The nucleotide sequence encoding the heavy chain variable region V2.4 with the back mutations (A49G) is as follows:

```
  1  GAGGTGCAGC TGGTGGAGTC      (SEQ ID NO: 160)
     TGGCGGCGGA CTGGTGCAGC
     CTGGCGGCTC

51  TCTGCGGCTG TCTTGCGCCG
     CTTCCGGCTT CAACATCAAG
     GACACCTACA

101  TCCACTGGGT GCGGCAGGCT
     CCCGGCAAGG GCCTGGAGTG
     GGTGGGCCGG

151  ATCGATCCTG CCAACGACAA
     CATCAAGTAC GACCCCAAGT
     TCCAGGGCCG

201  GTTCACCATC TCTCGCGACA
     ACGCCAAGAA CTCCCTGTAC
     CTCCAGATGA

251  ACTCTCTGCG CGCCGAGGAT
     ACCGCCGTGT ACTAGTGCGC
     CCGGAGCGAG

301  GAGAACTGGT ACGACTTCTT
     CGACTACTGG GGCCAGGGCA
     CCCTGGTGAC

351  CGTGTCCTCT
```

The amino acid sequence of the heavy chain variable region of V2.4 (CDRs based on AbM definition shown in subsequent underscored regions) is as follows:

```
  1  EVQLVESGGG LVQPGGSLRL      (SEQ ID NO: 161)
     SCAASGFNIK DTYIHWVRQA
     PGKGLEWVGR

51  IDPANDNIKY DPKFQGRFTI
     SRDNAKNSLY LQMNSLRAED
     TAVYYCARSE

104  ENWYDFFDYW GQGTLVTVSS
```

The nucleotide sequence encoding the heavy chain variable region V2.5 with the back mutations (R67K;F68A; R72A) is as follows:

```
  1  GAGGTGCAGC TGGTGGAGTC      (SEQ ID NO: 162)
     TGGCGGCGGA CTGGTGCAGC
     CTGGCGGCTC

51  TCTGCGGCTG TCTTGCGCCG
     CTTCCGGCTT CAACATCAAG
     GACACCTACA

101  TCCACTGGGT GCGGCAGGCT
     CCCGGCAAGG GCCTGGAGTG
     GGTGGCCCGG

151  ATCGATCCTG CCAACGACAA
     CATCAAGTAC GACCCCAAGT
     TCCAGGGCAA

201  GGCCACCATC TCTGCCGACA
     ACGCCAAGAA CTCCCTGTAC
     CTCCAGATGA

251  ACTCTCTGCG CGCCGAGGAT
     ACCGCCGTGT ACTACTGCGC
     CCGGAGCGAG

301  GAGAACTGGT ACGACTTCTT
     CGACTACTGG GGCCAGGGCA
     CCCTGGTGAC

352  CGTGTCCTCT
```

The amino acid sequence of the heavy chain variable region of V2.5 (CDRs based on AbM definition shown in subsequent underscored regions) is as follows:

```
  1   EVQLVESGGG LVQPGGSLRL    (SEQ ID NO: 163)
      SCAASGFNIK DTYIHWVRQA
      PGKGLEWVAR

51   IDPANDNIKY DPKFQGKATI
      SADNAKNSLY LQMNSLRAED
      TAVYYCARSE

105   ENWYDFFDYW GQGTLVTVSS
```

The nucleotide sequence encoding the heavy chain variable region V2.6 with the back mutations (V48I;A49G; R72A) is as follows:

```
  1   GAGGTGCAGC TGGTGGAGTC    (SEQ ID NO: 164)
      TGGCGGCGGA CTGGTGCAGC
      CTGGCGGCTC

51   TCTGCGGCTG TCTTGCGCCG
      CTTCCGGCTT CAACATCAAG
      GACACCTACA

101   TCCACTGGGT GCGGCAGGCT
      CCCGGCAAGG GCCTGGAGTG
      GATCGGCCGG

151   ATCGATCCTG CCAACGACAA
      CATCAAGTAC GACCCCAAGT
      TCCAGGGCCG

201   GTTCACCATC TCTGCCGACA
      ACGCCAAGAA CTCCCTGTAC
      CTCCAGATGA

251   ACTCTCTGCG CGCCGAGGAT
      ACCGCCGTGT ACTACTGCGC
      CCGGAGCGAG

301   GAGAACTGGT ACGACTTCTT
      CGACTACTGG GGCCAGGGCA
      CCCTGGTGAC

351   CGTGTCCTCT
```

The amino acid sequence of the heavy chain variable region of V2.6 (CDRs based on AbM definition shown in subsequent underscored regions) is as follows:

```
  1   EVQLVESGGG LVQPGGSLRL    (SEQ ID NO: 165)
      SCAASGFNIK DTYIHWVRQA
      PGKGLEWIGR

51   IDPANDNIKY DPKFQGRFTI
      SADNAKNSLY LQMNSLRAED
      TAVYYCARSE

106   ENWYDFFDYW GQGTLVTVSS
```

The nucleotide sequence encoding the heavy chain variable region V2.7 with the back mutations (A49G;R72A) is as follows:

```
  1   GAGGTGCAGC TGGTGGAGTC    (SEQ ID NO: 166)
      TGGCGGCGGA CTGGTGCAGC
      CTGGCGGCTC

51   TCTGCGGCTG TCTTGCGCCG
      CTTCCGGCTT CAACATCAAG
      GACACCTACA

101   TCCACTGGGT GCGGCAGGCT
      CCCGGCAAGG GCCTGGAGTG
      GGTGGGCCGG

151   ATCGATCCTG CCAACGACAA
      CATCAAGTAC GACCCCAAGT
      TCCAGGGCCG

201   GTTCACCATC TCTGCCGACA
      ACGCCAAGAA CTCCCTGTAC
      CTCCAGATGA

251   ACTCTCTGCG CGCCGAGGAT
      ACCGCCGTGT ACTACTGCGC
      CCGGAGCGAG

301   GAGAACTGGT ACGACTTCTT
      CGACTACTGG GGCCAGGGCA
      CCCTGGTGAC

351   CGTGTCCTCT
```

The amino acid sequence of the heavy chain variable region of V2.7 (CDRs based on AbM definition shown in subsequent underscored regions) is as follows:

```
  1   EVQLVESGGG LVQPGGSLRL    (SEQ ID NO: 167)
      SCAASGFNIK DTYIHWVRQA
      PGKGLEWVGR

51   IDPANDNIKY DPKFQGRFTI
      SADNAKNSLY LQMNSLRAED
      TAVYYCARSE

107   ENWYDFFDYW GQGTLVTVSS
```

The nucleotide sequence encoding the heavy chain variable region V2.8 with the back mutations (L79A) is as follows:

```
  1   GAGGTGCAGC TGGTGGAGTC    (SEQ ID NO: 168)
      TGGCGGCGGA CTGGTGCAGC
      CTGGCGGCTC

51   TCTGCGGCTG TCTTGCGCCG
      CTTCCGGCTT CAACATCAAG
      GACACCTACA

101   TCCACTGGGT GCGGCAGGCT
      CCCGGCAAGG GCCTGGAGTG
      GGTGGGCCGG

151   ATCGATCCTG CCAACGACAA
      CATCAAGTAC GACCCCAAGT
      TCCAGGGCCG

201   GTTCACCATC TCTGCGACA
      ACGCCAAGAA CTCCGCCTAC
      CTCCAGATGA

251   ACTCTCTGCG CGCCGAGGAT
      ACCGCCGTGT ACTACTGCGC
      CCGGAGCGAG

301   GAGAACTGGT ACGACTTCTT
      CGACTACTGG GGCCAGGGCA
      CCCTGGTGAC

351   CGTGTCCTCT
```

The amino acid sequence of the heavy chain variable region of V2.8 (CDRs based on AbM definition shown in subsequent underscored regions) is as follows:

```
  1  EVQLVESGGG LVQPGGSLRL       (SEQ ID NO: 169)
     SCAASGFNIK DTYIHWYRQA
     PGKGLEWVAR

51  IDPANDNIKY DPKFQGRFTI
     SRDNAKNSAY LQMNSLRAED
     TAVYYCARSE

108  ENWYDFFDYW GQGTLVTVSS
```

The nucleotide sequence encoding the heavy chain variable region V2.10 with the back mutations (A49G;R72A; L79A) is as follows:

```
  1  GAGGTGCAGC TGGTGGAGTC       (SEQ ID NO: 170)
     TGGCGGCGGA CTGGTGCAGC
     CTGGCGGCTC

51  TCTGCGGCTG TCTTGCGCCG
     CTTCCGGCTT CAACATCAAG
     GACACCTACA

101  TCCACTGGGT GCGGCAGGCT
     CCCGGCAAGG GCCTGGAGTG
     GGTGGGCCGG

151  ATCGATCCTG CCAACGACAA
     CATCAAGTAC GACCCCAAGT
     TCCAGGGCCG

201  GTTCACCATC TCTGCCGACA
     ACGCCAAGAA CTCCGCCTAC
     CTCCAGATGA

251  ACTCTCTGCG CGCCGAGGAT
     ACCGCCGTGT ACTACTGCGC
     CCGGAGCGAG

301  GAGAACTGGT ACGACTTCTT
     CGACTACTGG GGCCAGGGCA
     CCCTGGTGAC

351  CGTGTCCTCT
```

The amino acid sequence of the heavy chain variable region of V2.10 (CDRs based on AbM definition shown in subsequent underscored regions) is as follows:

```
  1  EVQLVESGGG LVQPGGSLRL       (SEQ ID NO: 171)
     SCAASGFNIK DTYIHWVRQA
     PGKGLEWVGR

51  IDPANDNIKY DPKFQGRFTI
     SADNAKNSAY LQMNSLRAED
     TAVYYCARSE

109  ENWYDFFDYW GQGTLVTVSS
```

The nucleotide sequence encoding the heavy chain variable region V2.11 with the back mutations (V48I;A49G; R72A;L79A) is as follows:

```
  1  GAGGTGCAGC TGGTGGAGTC       (SEQ ID NO: 172)
     TGGCGGCGGA CTGGTGCAGC
     CTGGCGGCTC

51  TCTGCGGCTG TCTTGCGCCG
     CTTCCGGCTT CAACATCAAG
     GACACCTACA

101  TCCACTGGGT GCGGCAGGCT
     CCCGGCAAGG GCCTGGAGTG
     GATCGGCCGG

151  ATCGATCCTG CCAACGACAA
     CATCAAGTAC GACCCCAAGT
     TCCAGGGCCG

201  GTTCACCATC TCTGCCGACA
     ACGCCAAGAA CTCCGCCTAC
     CTCCAGATGA

251  ACTCTCTGCG CGCCGAGGAT
     ACCGCCGTGT ACTACTGCGC
     CCGGAGCGAG

301  GAGAACTGGT ACGACTTCTT
     CGACTACTGG GGCCAGGGCA
     CCCTGGTGAC

351  CGTGTCCTCT
```

The amino acid sequence of the heavy chain variable region of V2.11 (CDRs based on AbM definition shown in subsequent underscored regions) is as follows:

```
  1  EVQLVESGGG LVQPGGSLRL       (SEQ ID NO: 173)
     SCAASGFNIK DTYIHWVRQA
     PGKGLEWIGR

51  IDPANDNIKY DPKFQGRFTI
     SADNAKNSAY LQMNSLRAED
     TAVYYCARSE

110  ENWYDFFDYW GQGTLVTVSS
```

The nucleotide sequence encoding the heavy chain variable region V2.16 with the back mutations (V48I;A49G; R72A) is as follows:

```
  1  GAGGTGCAGC TGGTGGAGTC       (SEQ ID NO: 174)
     TGGCGGCGGA CTGGTGCAGC
     CTGGCGGCTC

51  TCTGCGGCTG TCTTGCACCG
     GCTCCGGCTT CAACATCAAG
     GACACCTACA

101  TCCACTGGGT GCGGCAGGCT
     CCCGGCAAGG GCCTGGAGTG
     GATCGGCCGG

151  ATCGATCCTG CCAACGACAA
     CATCAAGTAC GACCCCAAGT
     TCCAGGGCCG

201  GTTCACCATC TCTGCCGACA
     ACGCCAAGAA CTCCCTGTAC
     CTCCAGATGA

251  ACTCTCTGCG CGCCGAGGAT
     ACCGCCGTGT ACTACTGCGC
     CCGGAGCGAG

301  GAGAACTGGT ACGACTTCTT
     CGACTACTGG GGCCAGGGCA
     CCCTGGTGAC

351  CGTGTCCTCT
```

The amino acid sequence of the heavy chain variable region of V2.16 (CDRs based on AbM definition shown in subsequent underscored regions) is as follows:

```
  1  EVQLVESGGG LVQPGGSLRL       (SEQ ID NO: 175)
     SCTGSGFNIK DTYIHWVRQA
     PGKGLEWIGR
```

```
 51  IDPANDNIKY DPKFQGRFTI
     SADNAKNSLY LQMNSLRAED
     TAVYYCARSE

111  ENWYDFFDYW GQGTLVTVSS
```

The following is the amino acid sequence of a humanized MH 2-7 V2.11 IgG1 with a mutated CH2 domain:

```
EVQLVESGGGLVQPGGSLRLSCAASGFNIKDTYIHWVRQAPGKGLEWIGRIDPA    (SEQ ID NO: 176)

NDNIKYDPKFQGRFTISADNAKNSAYLQMNSLRAEDTAVYYCARSEENWYDFF

DYWGQGTLVTVSSASTKGPSVFPLAPSSKSTSGGTAALGCLVKDYFPEPVTVSW

NSGALTSGVHTFPAVLQSSGLYSLSSVVTVPSSSLGTQTYICNVNHKPSNTKVDK

KVEPKSCDKTHTCPPCPAPEALGAPSVFLFPPKPKDTLMISRTPEVTCVVVDVSHE

DPEVKFNWYVDGVEVHNAKTKPREEQYNSTYRVVSVLTVLHQDWLNGKEYKC

KVSNKALPAPIEKTISKAKGQPREPQVYTLPPSREEMTKNQVSLTCLVKGFYPSDI

AVEWESNGQPENNYKTFITPPVLDSDGSFFLYSKLTVDKSRWQQGNVFSCSVMHE

ALHNHYTQKSLSLSPGK
```

The variable domain is at amino acids 1-120; CH1 at 121-218; hinge at 219-233; CH2 at 234-343; and CH3 at 344-450. The light chain includes the following sequence with variable domain at 1-133.

```
DIQMTQSPSSLSASVGDRVTITCRSSQSIVHSNGNTYLEWYQQKPGKAPKLLIYK    (SEQ ID NO: 177)

VSNRFSGVPSRFSGSGSGTDFTLTISSLQPEDFATYYCFQGSHIPYTFGGGTKVEIK

RTVAAPSVFIFPPSDEQLKSGTASVVCLLNNFYPREAKVQWKVDNALQSGNSQE

SVTEQDSKDSTYSLSSTLTLSKADYEKHKVYACEVTHQGLSSPVTKSFNRGEC
```

Example 11

Functional Assays of Exemplary Variants of MJ2-7

We evaluated the ability of the MJ2-7 antibody and humanized variants to inhibit human IL-13 in assays for IL-13 activity.

STAT6 Phosphorylation Assay

HT-29 human colonic epithelial cells (ATCC) were grown as an adherent monolayer in McCoy's 5A medium containing 10% FBS, Pen-Strep, glutamine, and sodium bicarbonate. For assay, the cells were dislodged from the flask using trypsin, washed into fresh medium, and distributed into 12×75 mm polystyrene tubes. Recombinant human IL-13 (R&D Systems, Inc.) was added at concentrations ranging from 100-0.01 ng/ml. For assays testing the ability of antibody to inhibit the IL-13 response, 1 ng/ml recombinant human IL-13 was added along with dilutions of antibody ranging from 500-0.4 ng/ml. Cells were incubated in a 37° C. water bath for 30-60 minutes, then washed into ice-cold PBS containing 1% BSA. Cells were fixed by incubating in 1% paraformaldehyde in PBS for 15 minutes at 37° C., then washed into PBS containing 1% BSA. To permeabilize the nucleus, cells were incubated overnight at −20° C. in absolute methanol. They were washed into PBS containing 1% BSA, then stained with ALEXA™ Fluor 488-labeled antibody to STAT6 (BD Biosciences). Fluorescence was analyzed with a FACSCAN™ and CELLQUEST™ software (BD Biosciences).

CD23 Induction on Human Monocytes

Mononuclear cells were isolated from human peripheral blood by layering over HISTOPAQUE® (Sigma). Cells were washed into RPMI containing 10% heat-inactivated FCS, 50 U/ml penicillin, 50 mg/ml streptomycin, 2 mM L-glutamine, and plated in a 48-well tissue culture plate (Costar/Corning). Recombinant human IL-13 (R&D Systems, Inc.) was added at dilutions ranging from 100-0.01 ng/ml. For assays testing the ability of antibody to inhibit the IL-13 response, 1 ng/ml recombinant human IL-13 was added along with dilutions of antibody ranging from 500-0.4 ng/ml. Cells were incubated overnight at 37° C. in a 5% CO$_2$ incubator. The next day, cells were harvested from wells using non-enzymatic Cell Dissociation Solution (Sigma), then washed into ice-cold PBS containing 1% BSA. Cells were incubated with phycoerythrin (PE)-labeled antibody to human CD23 (BD Biosciences, San Diego, Calif.), and Cy-Chrome-labeled antibody to human CD11b (BD Biosciences). Monocytes were gated based on high forward and side light scatter, and expression of CD11b. CD23 expression on monocytes was determined by flow cytometry using a FACSCAN™ (BD Biosciences), and the percentage of CD23$^+$ cells was analyzed with CELLQUEST™ software (BD Biosciences).

TF-1 Cell Proliferation

TF-1 cells are a factor-dependent human hemopoietic cell line requiring interleukin 3 (IL-3) or granulocyte/macrophage colony-stimulating factor (GM-CSF) for their long-term growth. TF-1 cells also respond to a variety of other cytokines, including interleukin 13 (IL-13). TF-1 cells (ATCC) were maintained in RPMI medium containing 10% heat-inactivated FCS, 50 U/ml penicillin, 50 mg/ml streptomycin, 2 mM L-glutamine, and 5 ng/ml recombinant human GM-CSF (R&D Systems). Prior to assay, cells were starved of GM-CSF overnight. For assay, TF-1 cells were plated in duplicate at 5000 cells/well in 96-well flat-bottom microtiter plates (Costar/Corning), and challenged with human IL-13

(R&D Systems), ranging from 100-0.01 ng/ml. After 72 hours in a 37° C. incubator with 5% $CO_2$, the cells were pulsed with 1 μCi/well $^3$H-thymidine (Perkin Elmer/New England Nuclear). They were incubated an additional 4.5 hours, then cells were harvested onto filter mats using a TOMTEK™ harvester. $^3$H-thymidine incorporation was assessed by liquid scintillation counting.

Tenascin Production Assay

BEAS-2B human bronchial epithelial cells (ATCC) were maintained BEGM media with supplements (Clonetics). Cells were plated at 20,000 per well in a 96-well flat-bottom culture plate overnight. Fresh media is added containing IL-13 in the presence or absence of the indicated antibody. After overnight incubation, the supernatants are harvested, and assayed for the presence of the extracellular matrix component, tenascin C, by ELISA. ELISA plates are coated overnight with 1 ug/ml of murine monoclonal antibody to human tenascin (IgG1, k; Chemicon International) in PBS. Plates are washed with PBS containing 0.05% TWEEN®-20 (PBS-Tween), and blocked with PBS containing 1% BSA. Fresh blocking solution was added every 6 minutes for a total of three changes. Plates were washed 3× with PBS-Tween. Cell supernatants or human tenascin standard (Chemicon International) were added and incubated for 60 minutes at 37° C. Plates were washed 3× with PBS-Tween. Tenascin was detected with murine monoclonal antibody to tenascin (IgG2a, k; Biohit). Binding was detected with HRP-labeled antibody to mouse IgG2a, followed by TMB substrate. The reaction was stopped with 0.01 N sulfuric acid. Absorbance was read at 450 nm.

The HT 29 human epithelial cell line can be used to assay STAT6 phosphorylation. HT 29 cells are incubated with 1 ng/ml native human IL-13 crude preparation in the presence of increasing concentrations of the test antibody for 30 minutes at 37° C. Western blot analysis of cell lysates with an antibody to phosphorylated STAT6 can be used to detect dose-dependent IL 13-mediated phosphorylation of STAT6. Similarly, flow cytometric analysis can detect phosphorylated STAT6 in HT 29 cells that were treated with a saturating concentration of IL-13 for 30 minutes at 37° C., fixed, permeabilized, and stained with an ALEXA™ Fluor 488-labeled mAb to phospho-STAT6. An exemplary set of results is set forth in the Table 1. The inhibitory activity of V2.11 was comparable to that of sIL-13Ra2-Fc.

TABLE 1

| Construct | | Backmutations | Expression μg/ml/ | Native hIL-13 STAT6 assay |
|---|---|---|---|---|
| VH | VL | VH | COS; 48 h | IC 50, nM |
| V2.0 | V2 CDR graft | None, CDR grafted | 8-10 | >100 |
| V2.1 | V2 | V48I; A49G | 9-14 | 2.8 |
| V2.2 | V2 | R67K; F68A | 5-6 | >100 |
| V2.3 | V2 | R72A | 8-9 | 1.67-2.6 |
| V2.4 | V2 | A49G | 10 | 17.5 |
| V2.5 | V2 | R67K; F68A; R72A | 4-5 | 1.75 |
| V2.6 | V2 | V48I; A49G:R72A | 11-12 | 1.074-3.37 |
| V2.7 | V2 | A49G; R72A | 10-11 | 1.7 |
| V2.11 | V2 | V48I; A49G:R72A:L79A | 24 | 0.25-0.55 |

Example 12

Binding Interaction Site Between IL-13 and IL-13Rα1

A complex of IL-13, the extracellular domain of IL-13Rα1 (residues 27-342 of SEQ ID NO:125), and an antibody that binds human IL-13 was studied by x-ray crystallography. See, e.g., 16163-029001. Two points of substantial interaction were found between IL-13 and IL-13Rα1. The interaction between Ig domain 1 of IL-13Rα1 and IL-13 results in the formation of an extended beta sheet spanning the two molecules. Residues Thr88 [Thr107], Lys89 [Lys108], Ile90 [Ile109], and Glu91 [Glu110] of IL-13 (SEQ ID NO:124, mature sequence [full-length sequence (SEQ ID NO:178)]) form a beta strand that interacts with residues Lys76, Lys77, Ile78 and Ala79 of the receptor (SEQ ID NO:125). Additionally, the side chain of Met33 [Met52] of IL-13 (SEQ ID NO:124 [SEQ ID NO:178]) extends into a hydrophobic pocket that is created by the side chains of these adjoining strands.

The predominant feature of the interaction with Ig domain 3 is the insertion of a hydrophobic residue (Phe107 [Phe126]) of IL-13 (SEQ ID NO:124 [SEQ ID NO:178]) into a hydrophobic pocket in Ig domain 3 of the receptor IL-13Rα1. The hydrophobic pocket of IL-13Rα1 is formed by the side chains of residues Leu319, Cys257, Arg256, and Cys320 (SEQ ID NO:125). The interaction with Phe107 [Phe126] of IL-13 (SEQ ID NO:124 [SEQ ID NO:178]) results in an extensive set of van der Waals interactions between amino acid residues Ile254, Ser255, Arg256, Lys318, Cys320, and Tyr321 of IL-13Rα1 (SEQ ID NO:125) and amino acid residues Arg11 [Arg30], Glu12 [Glu31], Leu13 [Leu32], Ile14 [Ile33], Glu15 [Ile34], Lys104 [Lys123], Lys105 [Lys124], Leu106 [Leu125], Phe107 [Phe126], and Arg108 [Arg 127] of IL-13 (SEQ ID NO:124 [SEQ ID NO:178]). These results demonstrate that an IL-13 binding agent that binds to the regions of IL-13 involved in interaction with IL-13Rα1 can be used to inhibit IL-13 signaling.

Example 13

Expression of Humanized MJ 2-7 Antibody in COS Cells

To evaluate the production of chimeric anti-NHP IL13 antibodies in the mammalian recombinant system, the variable regions of mouse MJ 2-7 antibody were subcloned into a pED6 expression vector containing human kappa and IgG1mut constant regions. Monkey kidney COS-1 cells were grown in DME media (Gibco) containing 10% heat-inactivated fetal bovine serum, 1 mM glutamine and 0.1 mg/ml Penicillin/Streptomycin. Transfection of COS cells was performed using TRANSITIT™-LT1 Transfection reagent (Mirus) according to the protocol suggested by the reagent supplier. Transfected COS cells were incubated for 24 hours at 37° C. in the presence of 10% $CO_2$, washed with sterile PBS, and then grown in serum-free media R1CD1 (Gibco) for 48 hours to allow antibody secretion and accumulation in the conditioned media. The expression of chMJ 2-7 antibody was quantified by total human IgG ELISA using purified human IgG1/kappa antibody as a standard.

The production of chimeric MJ 2-7 antibody in COS cells was significantly lower then the control chimeric antibody (Table 2). Therefore, optimization of Ab expression was included in the MJ 2-7 humanization process. The humanized MJ 2-7 V1 was constructed by CDR grafting of mouse MJ 2-7 heavy chain CDRs onto the most homologous human germline clone, DP 25, which is well expressed and represented in typical human antibody response. The CDRs of light chain were subcloned onto human germline clone DPK 18 in order to generate huMJ 2-7 V1 VL. The humanized MJ 2-7 V2 was made by CDR grafting of CDRs MJ 2-7 heavy chain variable region onto DP54 human germline gene framework and CDRs of MJ 2-7 light chain variable region onto DPK9 human germline gene framework. The DP 54 clone belongs to human VH III germline subgroup and DPK9 is from the V kappa I subgroup of human germline genes. Antibody molecules that include VH III and V kappa I frameworks have high expression level in *E. coli* system and possess high stability and solubility in aqueous solutions (see, e.g., Stefan Ewert et al., *J. Mol. Biol.* (2003), 325; 531-553, Adrian Auf et al., *Methods* (2004) 34:215-224). We have used the combination of DP54/DPK9 human frameworks in the production of several recombinant antibodies and have achieved a high expression of antibody (>20 µg/ml) in the transient COS transfection experiments.

TABLE 2

| mAb | Expression, µg/ml |
| --- | --- |
| 3D6 | 10.166 |
| Ch MJ 2-7 pED6 (1) | 2.44 |
| Ch MJ 2-7pED6 (2) | 2.035 |
| h12A11 V2 | 1.639 |

The CDR grafted MJ 2-7 V1 and V2 VH and VL genes were subcloned into two mammalian expression vector systems (pED6kappa/pED6 IgG1mut and pSMEN2kappa/pSMED2IgG1mut), and the production of humanized MJ 2-7 antibodies was evaluated in transient COS transfection experiments as described above. In the first set of the experiments the effect of various combinations of huMJ 2-7 VL and VH on the antibody expression was evaluated (Table 3). Changing of MJ 2-7 VL framework regions to DKP9 increased the antibody production 8-10 fold, whereas VL V1 (CDR grafted onto DPK 18) showed only a moderate increase in antibody production. This effect was observed when humanized VL was combined with chimeric MJ 2-7 VH and humanized MJ 2-7 V1 and V2. The CDR grafted MJ 2-7 V2 had a 3-fold higher expression level then CDR grafted MJ 2-7 V1 in the same assay conditions.

TABLE 3

| mAb | Expression, µg/ml |
| --- | --- |
| ChMJ 2-7 | 1.83 |
| hVH V1/mVL | 3.04 |
| hVH V1/hVL V1 | 6.34 |
| hVH V1/hVL V2 | 15.4 |
| hVH-V2/mVL | 0.2 |
| mVH/hVL-V2 | 18.41 |
| hVH-V2/hVL-V1 | 5.13 |
| hVH-V2/hVL-V2 | 10.79 |

Similar experiments were performed with huMJ 2-7 V2 containing back mutations in the heavy chain variable regions (Table 4). The highest expression level was detected for huMJ 2-7 V2.11 that retained the antigen binding and neutralization properties of mouse MJ 2-7 antibody. Introduction of back mutations at the positions 48 and 49 (V48I and A49G) increased the production of huMJ 2-7 V2 antibody in COS cells, whereas the back mutations of amino acids at the positions 23, 24, 67 and 68 (A23T; A24G; R67K and F68A) had a negative impact on antibody expression.

TABLE 4

| mAb | Expression, µg/ml |
| --- | --- |
| V2 | 8.27 |
| V2.1 | 12.1 |
| V2.2 | 5.29 |
| V2.3 | 9.60 |
| V2.4 | 8.20 |
| V2.5 | 6.05 |
| V2.6 | 11.3 |
| V2.10 | 9.84 |
| V2.11 | 14.85 |
| V2.16 | 1.765 |

Example 14

Evaluation of Antigen Binding Properties of Humanized MJ 2-7 Antibodies by NHP IL-13 FLAG ELISA The ability of fully humanized MJ 2-7 mAb (V1, V2 v2) to compete with biotinylated mouse MJ 2-7 Ab for binding to NHP IL-13-FLAG was evaluated by ELISA. The microtiter plates (Costar) were coated with 1 μg/ml of anti-FLAG monoclonal antibody M2 (Sigma). The FLAG NHP IL-13 protein at concentration of 10 ng/ml was mixed with 10 ng/ml of biotin labeled mouse MJ 2-7 antibody and various concentrations of unlabeled mouse and humanized MJ 2-7 antibody. The mixture was incubated for 2 hours at room temperature and then added to the anti-FLAG antibody-coated plate. Binding of FLAG NHP-IL-13/bioMJ2-7 Ab complexes was detected with streptavidin-HRP and 3,3',5,5'-tetramethylbenzidine (TMB). The humanized MJ 2-7 V2 significantly lost activity whereas huMJ 2-7 V2.11 completely restored the antigen binding activity and was capable of competing with biotinylated MJ 2-7 mAb for binding to FLAG-NHP IL-13. BIACORE™ analysis also confirmed that NHP IL-13 had rapid binding to and slow dissociation to immobilized h1uMJ 2-7 v2.11.

Example 15

Molecular Modeling of Humanized MJ2-7 V2VH

Structure templates for modeling humanized MJ2-7 heavy chain version 2 (MJ2-7 V2VH) were selected based on BLAST homology searches against Protein Data Bank (PDB). Besides the two structures selected from the BLAST search output, an additional template was selected from an in-house database of protein structures. Model of MJ2-7 V2VH was built using the three template structures 1 JPS (co-crystal structure of human tissue factor in complex with humanized Fab D3h44), 1 N8Z (co-crystal structure of human Her2 in complex with Herceptin Fab) and F13.2 (IL-13 in complex with mouse antibody Fab fragment) as templates and the Homology module of InsightII (Accelrys, San Diego). The structurally conserved regions (SCRs) of 1JPS, 1N8Z and F13.2 (available from 16163-029001) were determined based on the Cα distance matrix for each molecule and the template structures were superimposed based on minimum RMS deviation of corresponding atoms in SCRs. The sequence of the target protein MJ2-7 V2VH was aligned to the sequences of the superimposed templates proteins and coordinates of the SCRs were assigned to the corresponding residues of the target protein. Based on the degree of sequence similarity between the target and the templates in each of the SCRs, coordinates from different templates were used for different SCRs. Coordinates for loops and variable regions not included in the SCRs were generated by Search Loop or Generate Loop methods as implemented in Homology module. Briefly, Search Loop method scans protein structures that would fit properly between two SCRs by comparing the Cα distance matrix of flanking SCR residues with a pre-calculated matrix derived from protein structures that have the same number of flanking residues and an intervening peptide segment of a given length. Generate Loop method that generate atom coordinates de novo was used in those cases where Search Loops did not produce desired results. Conformation of amino acid side chains was kept the same as that in the template if the amino acid residue was identical in the template and the target. However, a conformational search of rotamers was done and the energetically most favorable conformation was retained for those residues that are not identical in the template and target. This was followed by Splice Repair that sets up a molecular mechanics simulation to derive proper bond lengths and bond angles at junctions between two SCRs or between SCR and a variable region. Finally the model was subjected to energy minimization using Steepest Descents algorithm until a maximum derivative of 5 kcal/(mol Å) or 500 cycles and Conjugate Gradients algorithm until a maximum derivative of 5 kcal/(mol Å) or 2000 cycles. Quality of the model was evaluated using ProStat/Struct_Check command.

Molecular model of mouse MJ2-7 VH was built by following the procedure described for humanized MJ2-7 V2VH except the templates used were 1QBL and 1QBM, crystal structures for horse anti-cytochrome c antibody FabE8.

Potential differences in CDR-Framework H-bonds predicted by the models hMJ2-7 V2VH:G26-hMJ2-7 V2VH:A24
hMJ2-7 V2VH:Y109-hMJ2-7 V2VH:S25
mMJ2-7 VH:D61-mMJ2-7 VH:I48
mMJ2-7 VH:K63-mMJ2-7 VH:E46
mMJ2-7 VH:Y109-mMJ2-7 VH:R98

These differences suggested the following optional back mutations: A23T, A24G and V48I.

Other optional back mutations suggested based on significant RMS deviation of individual amino acids and differences in amino acid residues adjacent to these are: G9A, L115T and R87T.

Example 16

IL-13 Neutralization Activity of MJ2-7 and C65

Figure 2:
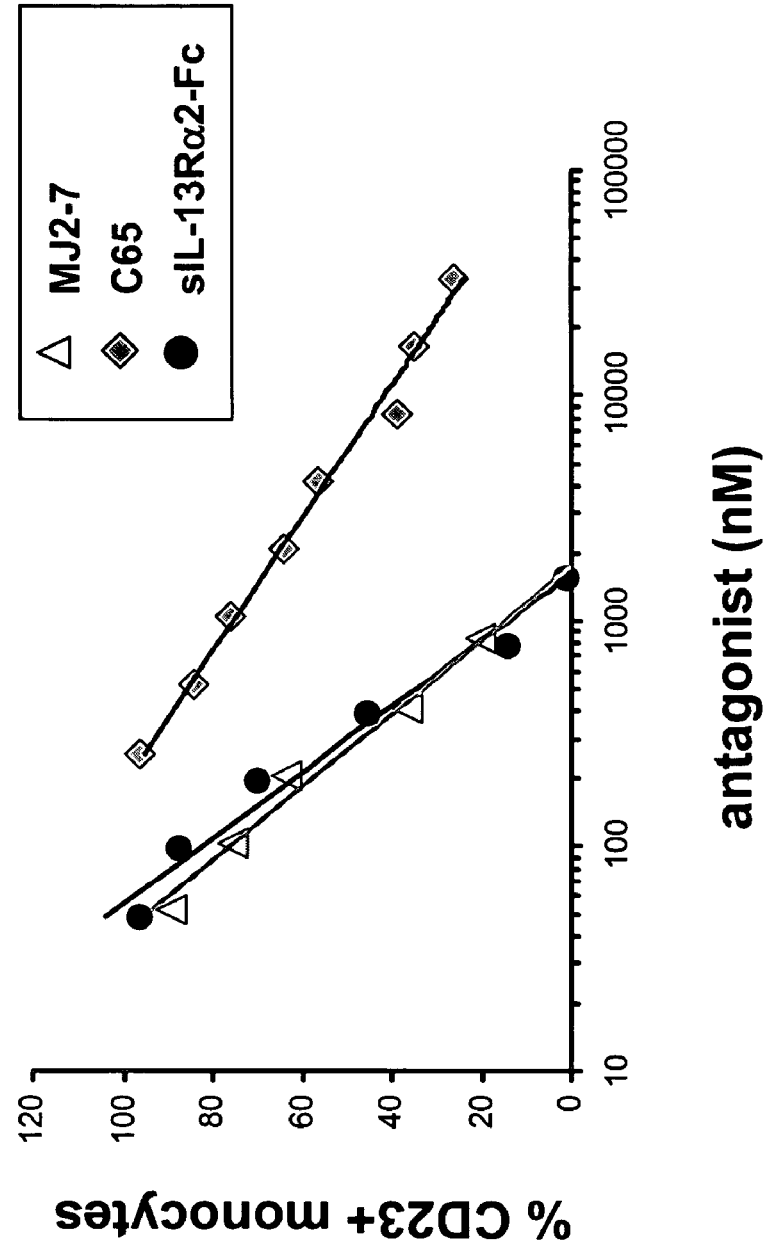
FIG. 2 is a graph depicting the neutralization of NHP IL-13 activity by various IL-13 binding agents, as measured by percentage of CD23$^+$ monocytes (y-axis). Concentration of MJ2-7 (Δ), C65 (♦), and sIL-13Rα2-Fc (●) are indicated on the x-axis.

The IL-13 neutralization capacities of MJ2-7 and C65 were tested in a series of bioassays. First, the ability of these antibodies to neutralize the bioactivity of NHP IL-13 was tested in a monocyte CD23 expression assay. Freshly isolated human PBMC were incubated overnight with 3 ng/ml NHP IL-13 in the presence of increasing concentrations of MJ2-7, C65, or sIL-13Rα2-Fc. Cells were harvested, stained with CYCHROME™-labeled antibody to the monocyte-specific marker, CD11b, and with PE-labeled antibody to CD23. In response to IL-13 treatment, CD23 expression is up-regulated on the surface of monocytes, which were gated based on expression of CD11b. MJ2-7, C65, and sIL13Rα2-Fc all were able to neutralize the acitivity of NHP IL-13 in this assay. The potencies of MJ2-7 and sIL-13Rα2-Fc were equivalent. C65 was approximately 20-fold less active (FIG. 2).

Figure 3:
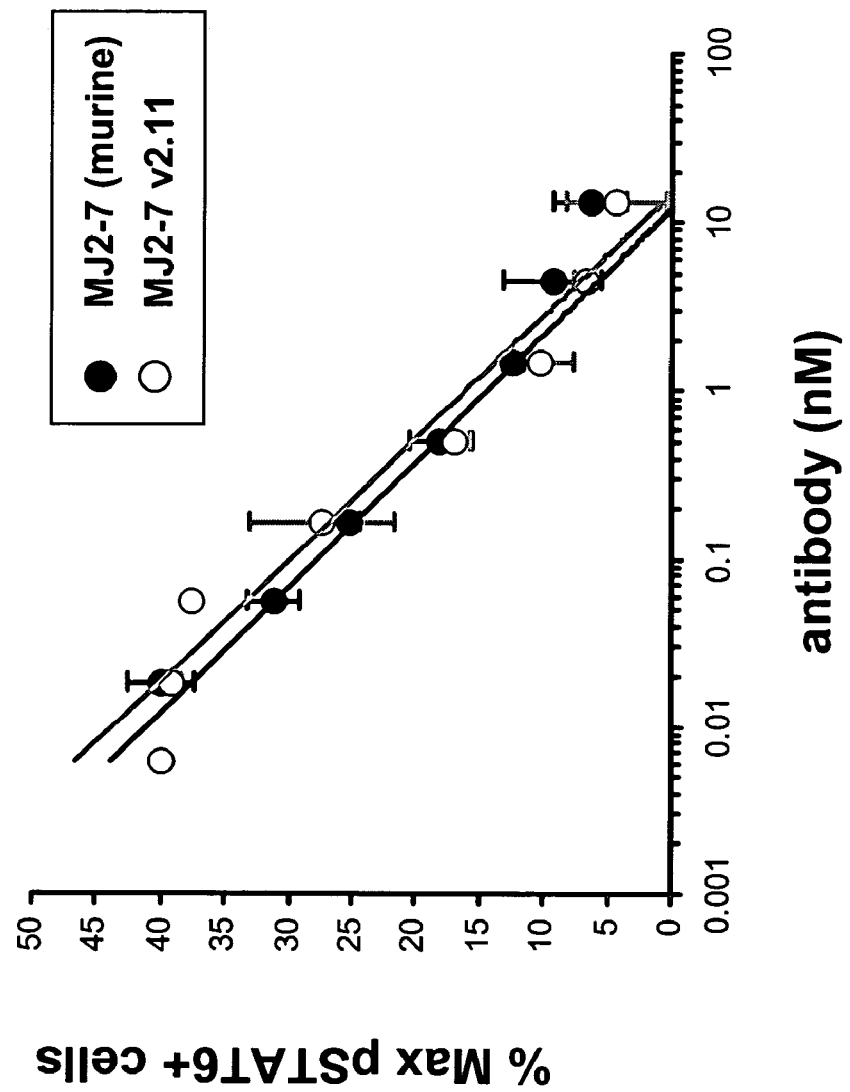
FIG. 3 is a graph depicting the neutralization of NHP IL-13 activity by MJ2-7 (murine; ●) or humanized MJ2-7 v2.11 (○). NHP IL-13 activity was measured by phosphorylation of STAT6 (y-axis) as a function of antibody concentration (x-axis).
Figure 4:
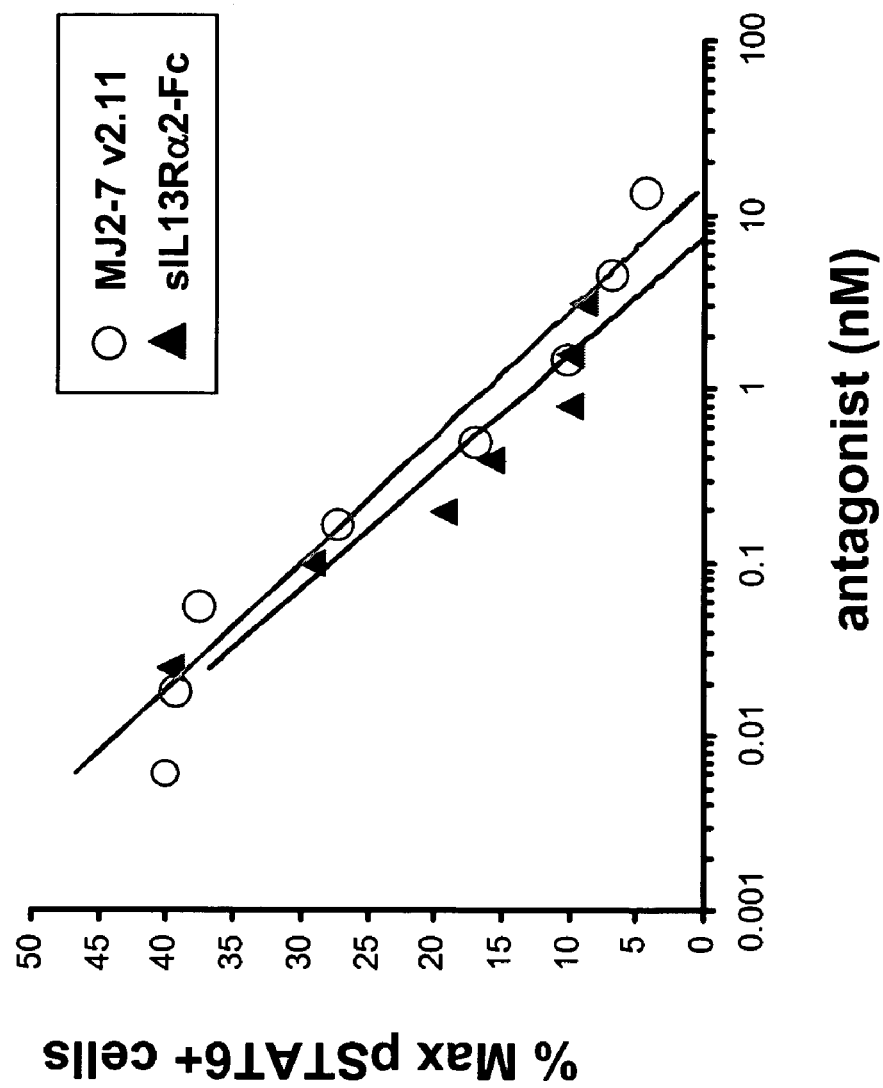
FIG. 4 is a graph depicting the neutralization of NHP IL-13 activity by MJ2-7 v2.11 (○) or sIL-13Rα2-Fc (▲). NHP IL-13 activity was measured by phosphorylation of STAT6 (y-axis) as a function of antagonist concentration (x-axis).
Figure 5:
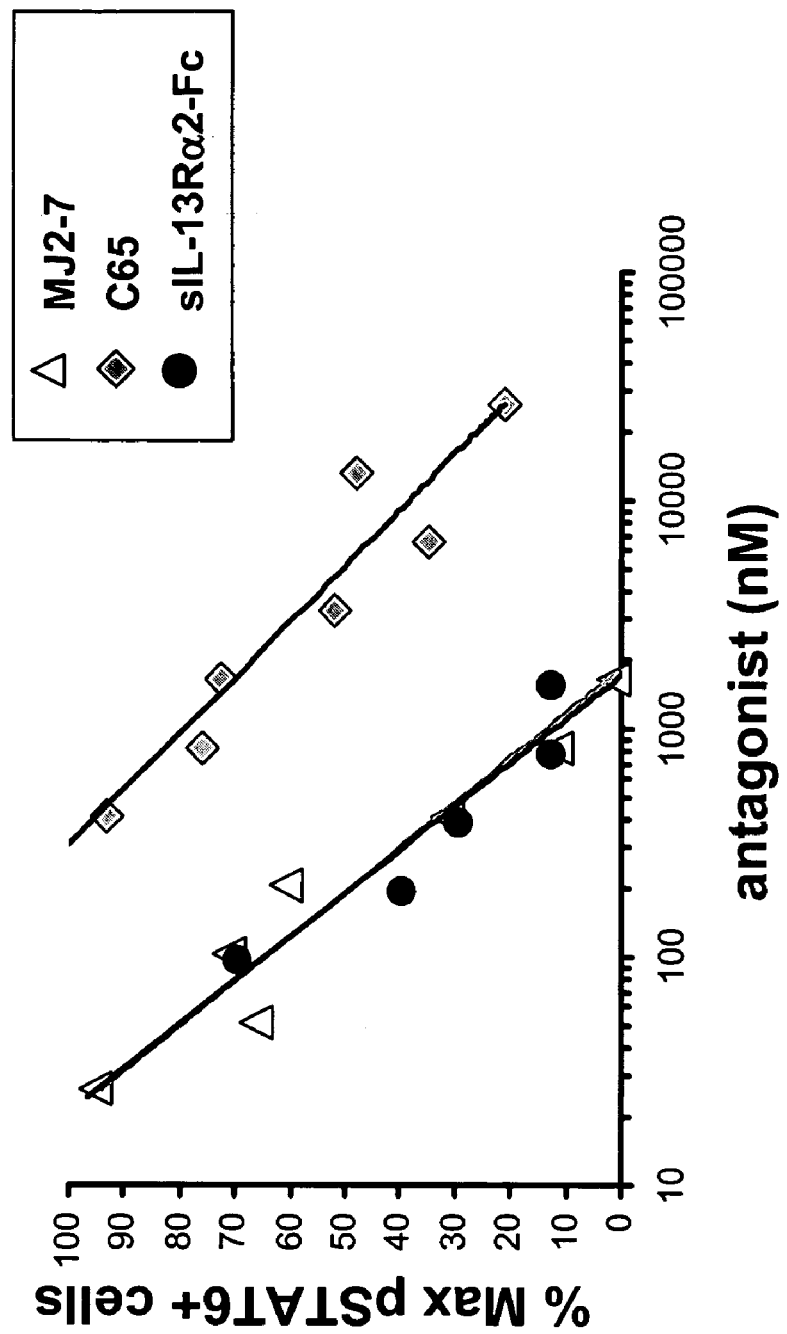
FIG. 5 is a graph depicting the neutralization of NHP IL-13 activity by MJ2-7 (Δ), C65 (♦), or sIL-13Rα2-Fc (●). NHP IL-13 activity was measured by phosphorylation of STAT6 (y-axis) as a function of antagonist concentration (x-axis).

In a second bioassay, the neutralization capacities of MJ2-7 and C65 for native human IL-13 were tested in a STAT6 phosphorylation assay. The HT-29 epithelial cell line was incubated with 0.3 ng/ml native human IL-13 in the presence of increasing concentrations of MJ2-7, C65, or sIL-13Rα2-Fc, for 30 minutes at 37° C. Cells were fixed, permeabilized, and stained with ALEXA™ Fluor 488-labeled antibody to phosphorylated STAT6. IL-13 treatment stimulated STAT6 phosphorylation. MJ2-7, C65, and sIL13Ra2-Fc all were able to neutralize the acitivity of native human IL-13 in this assay (FIG. 3). The IC50's for the murine MJ-27 antibody and the humanized form (V2.1 1) were 0.48 nM and 0.52 nM respectively. The potencies of MJ2-7 and sIL-13Rα2-Fc were approximately equivalent. The IC50 for sIL-13Ra2-Fc was 0.33 nM (FIG. 4). C65 was approximately 20-fold less active (FIG. 5).

Figure 6A:
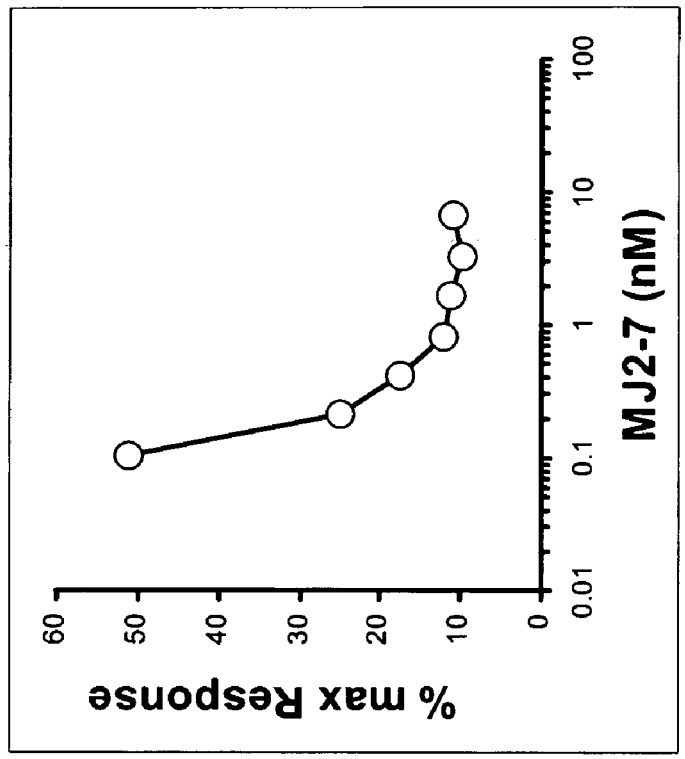
FIG. 6A is a graph depicting induction of tenascin production (y-axis) by native human IL-13 (x-axis).
Figure 6B:
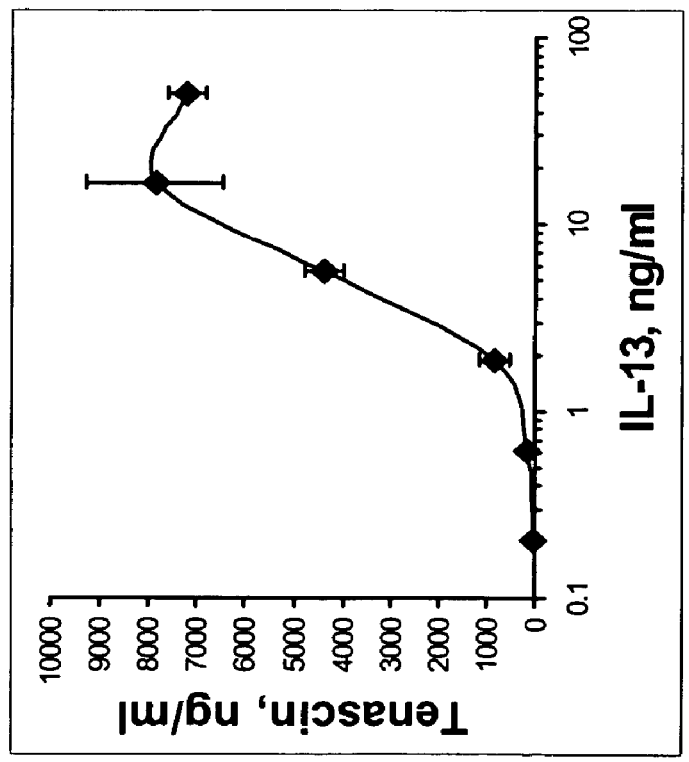
FIG. 6B is a graph depicting the neutralization of NHP IL-13 activity by MJ2-7, as measured by inhibition of induction of tenascin production (y-axis) as a function of antibody concentration (x-axis).

In a third bioassay, the ability of MJ2-7 to neutralize native human IL-13 was tested in a tenascin production assay. The human BEAS-2B lung epithelial cell line was incubated overnight with 3 ng/ml native human IL-13 in the presence of increasing concentrations of MJ2-7. Supernatants were harvested and tested for production of the extracellular matrix protein, tenascin C, by ELISA (FIG. 6A). MJ2-7 inhibited this response with IC50 of approximately 0.1 nM (FIG. 6B).

These results demonstrate that MJ2-7 is an effective neutralizer of both NHP IL-13 and native human IL-13. The IL-13 neutralization capacity of MJ2-7 is equivalent to that of sIL-13Rα2-Fc. MJ1-65 also has IL-13 neutralization activity, but is approximately 20-fold less potent than MJ2-7.

Example 17

Figure 7:
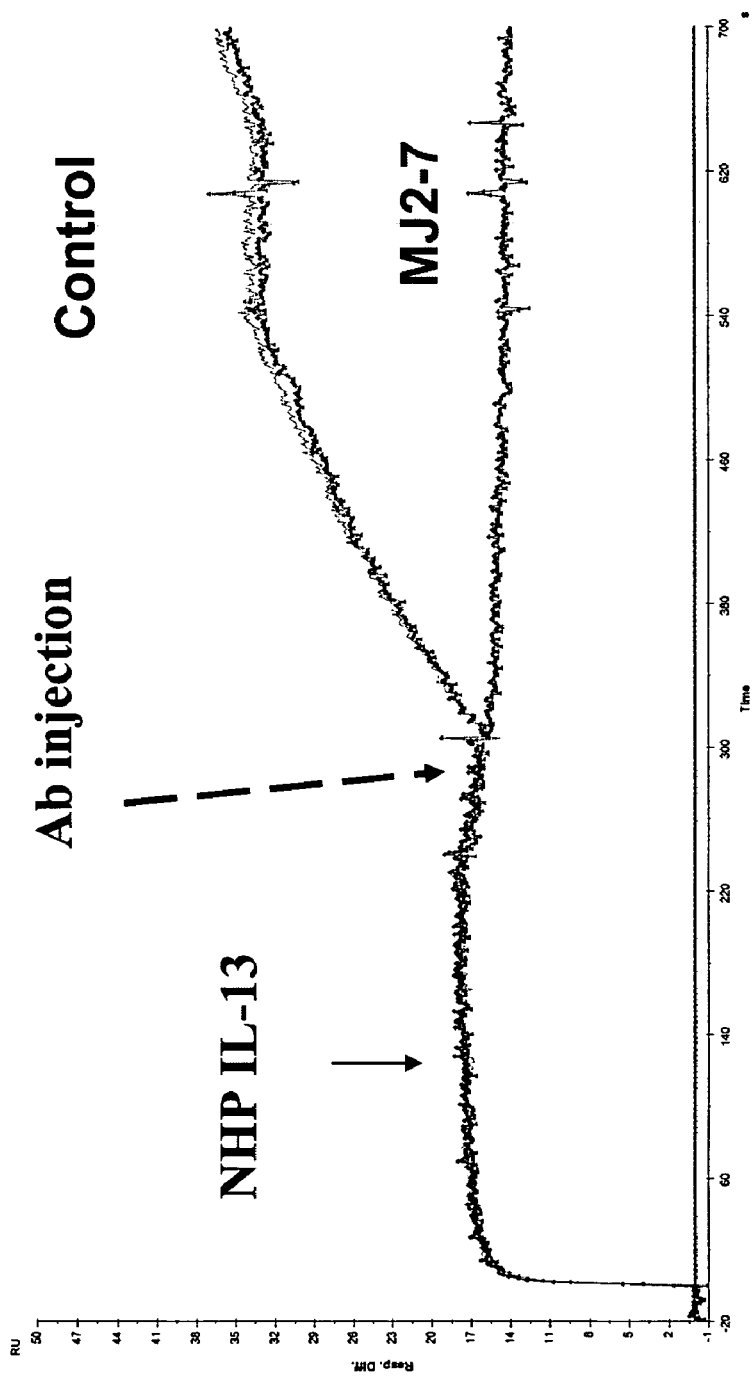
FIG. 7 is a graph depicting binding of MJ2-7 or control antibodies to NHP-IL-13 bound to sIL-13Rα2-Fc coupled to a SPR chip.

Epitope Mapping of MJ2-7 Antibody by SPR sIL-13Rα2-Fc was directly coated onto a CM5 chip by standard amine coupling. NHP-IL-13 at 100 nM concentration was injected, and its binding to the immobilized IL-13Rα2-Fc was detected by BIACORE™. An additional injection of 100 nM of anti IL-13 antibodies was added, and changes in binding were monitored. MJ2-7 antibody did not bind to NHP-IL-13 when it was in a complex with hu IL-13Rα2, whereas a positive control anti-IL-13 antibody did (FIG. 7). These results indicate that hu IL-13Rα2 and MJ2-7 bind to the same or overlapping epitopes of NHP IL-13.

Example 18

Measurement of Kinetic Rate Constants for the Interaction Between NHP-IL-13 and Humanized MJ2-7 V2-11 Antibody To prepare the biosensor surface, goat anti-human IgG Fc specific antibody was immobilized onto a research-grade carboxy methyl dextran chip (CM5) using amine coupling. The surface was activated with a mixture of 0.1 M 1-ethyl-3-(3-dimethylaminopropyl) carbodiimide (EDC) and 0.05 M N-Hydroxysuccinimide (NHS). The capturing antibody was injected at a concentration of 10 µg/ml in sodium acetate buffer (pH 5.5). Remaining activated groups were blocked with 1.0 M ethanolamine (pH 8.0). As a control, the first flow cell was used as a reference surface to correct for bulk refractive index, matrix effect,s and non-specific binding, the second, third and fourth flow cells were coated with the capturing molecule.

Figure 8:
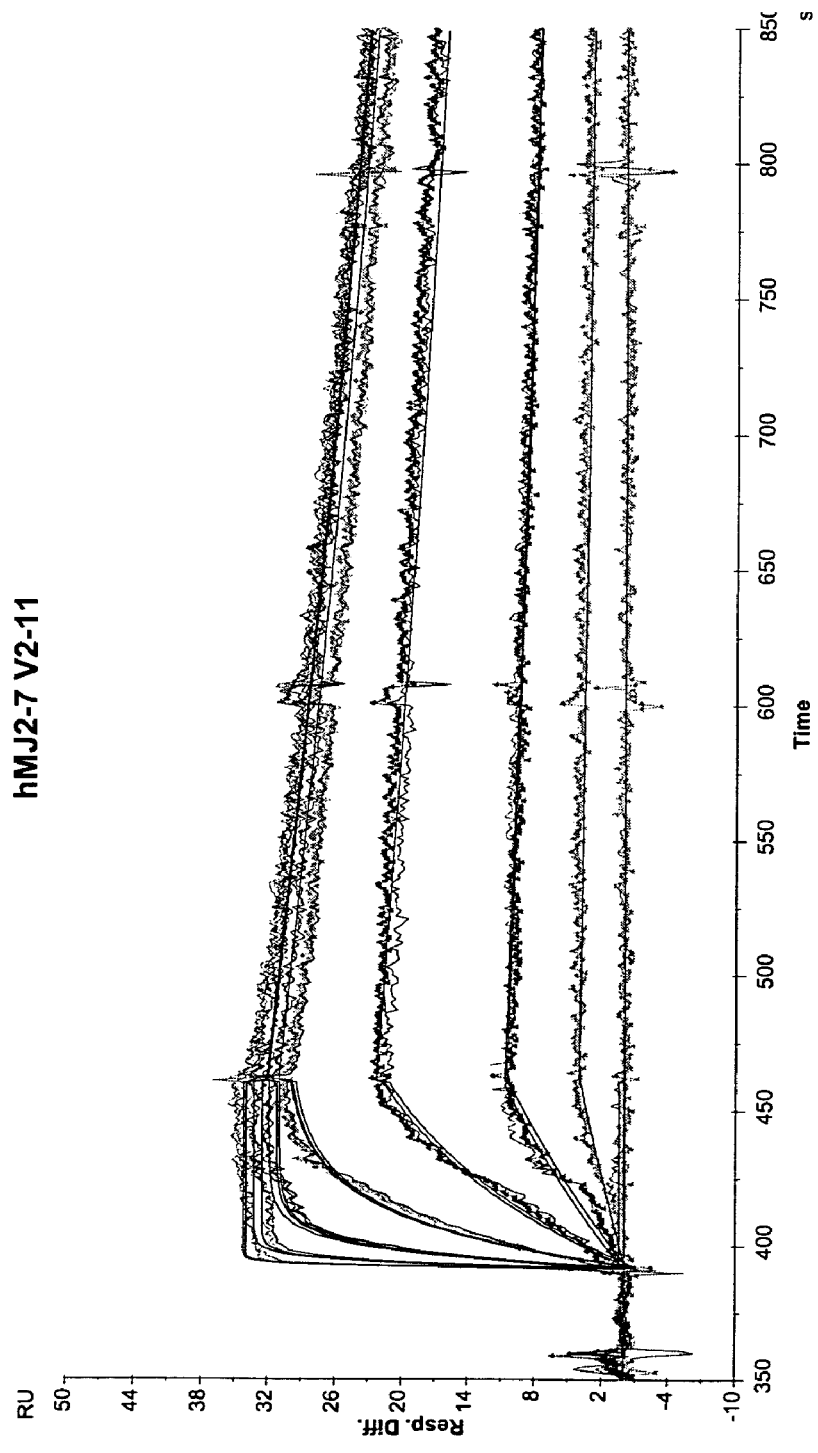
FIG. 8 is a graph depicting binding of varying concentrations (0.09-600 nM) of NHP IL-13 to captured hMJ2-7 V2-11 antibody.

For kinetic analysis, the monoclonal antibody hMJ2-7 V2-11 was captured onto the anti IgG antibody surface by injecting 40 µl of a 1 µg/ml solution. The net difference between the baseline and the point approximately 30 seconds after completion of injection was taken to represent the amount of target bound. Solutions of NHP-IL-13 at 600, 200, 66.6, 22.2, 7.4, 2.5, 0.8, 0.27, 0.09 and 0 nM concentrations were injected in triplicate at a flow rate of 100 μl per min for 2 minutes, and the amount of bound material as a function of time was recorded (FIG. 8). The dissociation phase was monitored in HBS/EP buffer (10 mM HEPES, pH 7.4, containing 150 mM NaCl, 3 mM EDTA and 0.005% (v/v) Surfactant P20) for 5 minutes at the same flow rate followed by two 5 μl injections of glycine, pH 1.5, to regenerate a fully active capturing surface. All kinetic experiments were done at 22.5° C. in HBS/EP buffer. Blank and buffer effects were subtracted for each sensorgram using double referencing.

The kinetic data were analyzed using BIAEVALUATION™ software 3.0.2 applied to a 1:1 model. The apparent dissociation (kd) and association (ka) rate constants were calculated from the appropriate regions of the sensorgrams using a global analysis. The affinity constant of the interaction between antibody and NHP IL-13 was calculated from the kinetic rate constants by the following formula: Kd=kd/ka. These results indicate that huMJ2-7 V2-11 has on and off-rates of $2.05 \times 10^7$ $M^{-1}s^{-1}$ and $8.89 \times 10^{-4}$ 1/s, respectively, resulting in an antibody with 43 pM affinity for NHP-IL-13.

Example 19

Inhibitory Activity of MJ2-7 Humanization Intermediates in Bioassays

Figure 9:
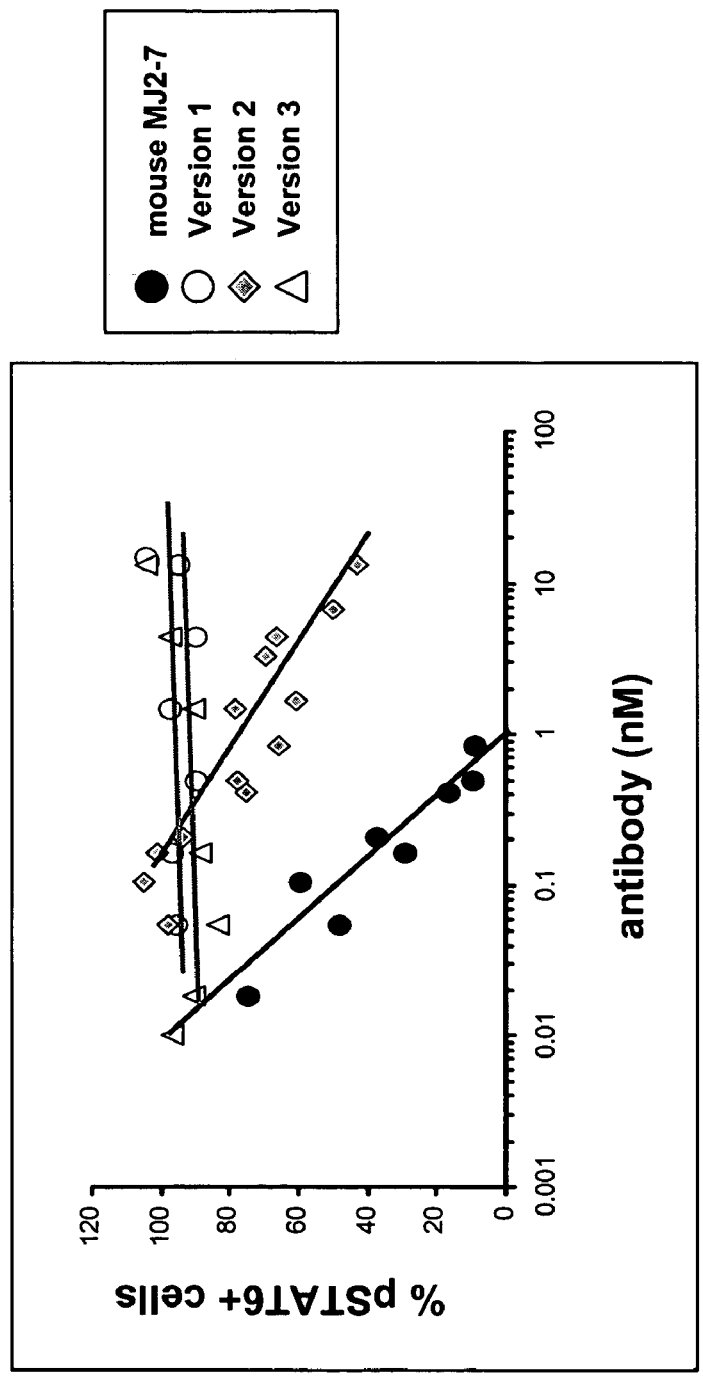
FIG. 9 is a graph depicting the neutralization of NHP IL-13 activity by mouse MJ2-7 (●) or humanized Version 1 (○), Version 2 (♦), or Version 3 (Δ) antibodies. NHP IL-13 activity was measured by phosphorylation of STAT6 (y-axis) as a function of antibody concentration (x-axis).
Figure 10:
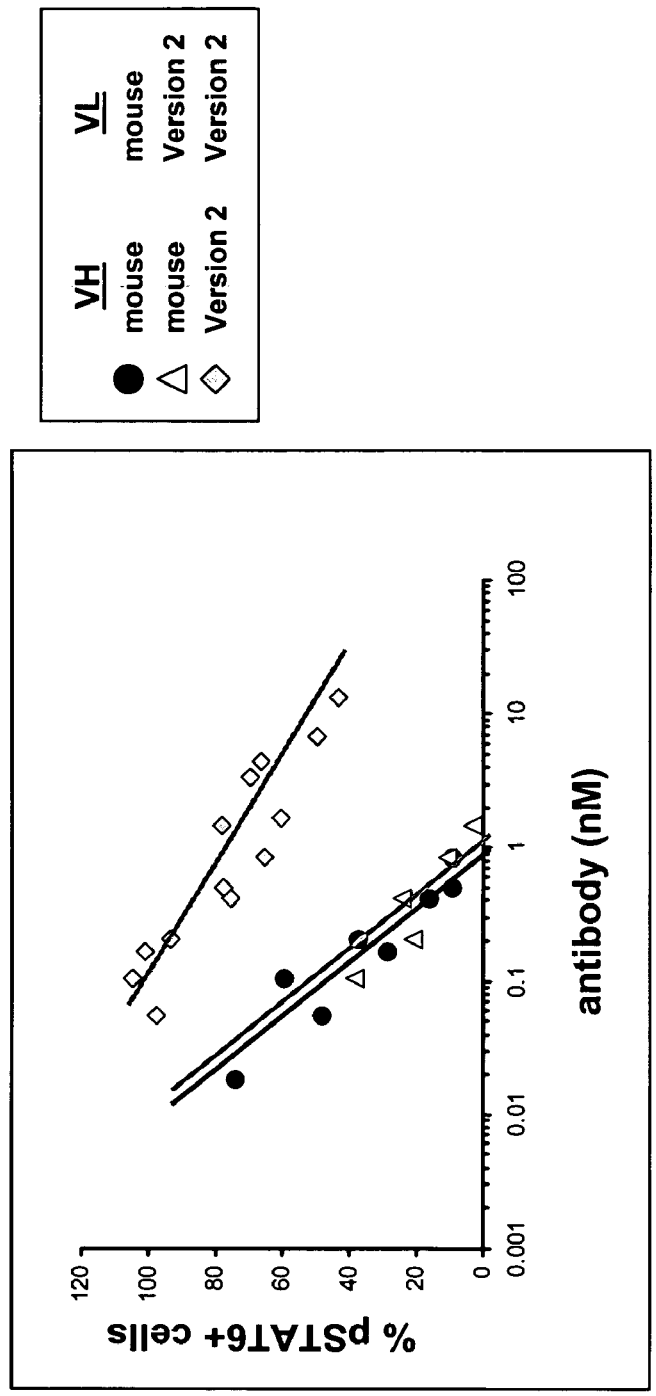
FIG. 10 is a graph depicting the neutralization of NHP IL-13 activity by antibodies including mouse MJ2-7 VH and VL (●), mouse VH and humanized Version 2 VL (Δ), or Version 2 VH and VL (♦). NHP IL-13 activity was measured by phosphorylation of STAT6 (y-axis) as a function of antibody concentration (x-axis).

The inhibitory activity of various intermediates in the humanization process was tested by STAT6 phosphorylation and tenascin production bioassays. A sub-maximal level of NHP IL-13 or native human IL-13 crude preparation was used to elicit the biological response, and the concentration of the humanized version of MJ2-7 required for half-maximal inhibition of the response was determined. Analysis hMJ2-7 V1, hMJ2-7 V2 and hMJ2-7 V3, expressed with the human IgG1, and kappa constant regions, showed that Version 2 retained neutralization activity against native human IL-13. This concentration of the Version 2 humanized antibody required for half-maximal inhibition of native human IL-13 bioactivity was approximately 110-fold greater than that of murine MJ2-7 (FIG. 9). Analysis of a semi-humanized form, in which the V1 or V2 VL was combined with murine MJ2-7 VH, demonstrated that the reduction of native human IL-13 neutralization activity was not due to to the humanized VL, but rather to the VH sequence (FIG. 10). Whereas the semi-humanized MJ2-7 antibody with VL V1 only partially retained the neutralization activity the version with humanized VL V2 was as active as parental mouse antibody. Therefore, a series of back-mutations were introduced into the V1 VH sequence to improve the native human IL-13 neutralization activity of murine MJ2-7.

Example 20

MJ2-7 blocks IL-13 Interaction with IL-13Rα1 and IL-13Rα2

MJ2-7 is specific for the C-terminal 19-mer of NHP IL-13, corresponding to amino acid residues 114-132 of the immature protein (SEQ ID NO:24), and residues 95-113 of the mature protein (SEQ ID NO:14). For human IL-13, this region, which forms part of the D alpha-helix of the protein, has been reported to contain residues important for binding to both IL-13Rα1 and IL-13Rα2. Analysis of human IL-13 mutants identified the A, C, and D-helices as containing important contacts site for the IL-13Rα1/IL-4Rα signaling complex (Thompson and Debinski (1999) *J. Biol. Chem.* 274: 29944-50). Alanine scanning mutagenesis of the D-helix identified residues K123, K124, and R127 (SEQ ID NO:24) as responsible for interaction with IL-13Rα2, and residues E110, E128, and L122 as important contacts for IL-13Rα1 (Madhankmuar et al. (2002) *J. Biol. Chem.* 277: 43194-205). High resolution solution structures of human IL-13 determined by NMR have predicted the IL-13 binding interactions based on similarities to related ligand-receptor pairs of known structure. These NMR studies have supported a key role for the IL-13 A and D-helices in making important contacts with IL-13Rα1 (Eisenmesser et al. (2001) *J. Mol. Biol.* 310:231-241; Moy et al. (2001) *J. Mol. Biol.* 310:219-230). Binding of MJ2-7 to this epitope located in the C-terminal, D-helix of IL-13 was predicted to disrupt interaction of IL-13 with IL-13Rα1 and IL-13Rα2.

The ability of MJ2-7 to inhibit binding of NHP IL-13 to IL-13Rα1 and IL-13Rα2 was tested by ELISA. Recombinant soluble forms of human IL-13Rα1-Fc and IL-13Rα2-Fc were coated onto ELISA plates. FLAG-tagged NHP IL-13 was added in the presence of increasing concentrations of MJ2-7. Results showed that MJ2-7 competed with both soluble receptor forms for binding to NHP IL-13 (FIGs. 11A and 11B). This provides a basis for the neutralization of IL-13 bioactivity by MJ2-7.

Example 21

The MJ 2-7 Light Chain CDRs Contribute to Antigen Binding

To evaluate if all three light chain CDR regions are required for the binding of MJ 2-7 antibody to NHP IL-13, two additional humanized versions of MJ 2-7 VL were constructed by CDR grafting. The VL version 3 was designed based on human germline clone DPK18, contained CDR1 and CDR2 of the human germline clone and CDR3 from mouse MJ2-7 antibody (FIG. 12). In the second construct (hMJ 2-7 V4), only CDR1 and CDR2 of MJ 2-7 antibody were grafted onto DPK 18 framework, and CDR3 was derived from irrelevant mouse monoclonal antibody.

The humanized MJ 2-7 V3 and V4 were produced in COS cells by combining hMJ 2-7 VH V1 with hMJ 2-7 VL V3 and V4. The antigen binding properties of the antibodies were examined by direct NHP IL-13 binding ELISA. The hMJ 2-7 V4 in which MJ 2-7 light chain CDR3 was absent retained the ability to bind NHP IL-13, whereas V3 that contained human germline CDR1 and CDR2 in the light chain did not bind to immobilized NHP IL-13. These results demonstrate that CDR1 and CDR2 of MJ 2-7 antibody light chain are most likely responsible for the antigen binding properties of this antibody.

Nucleotide sequence of hMJ 2-7 VL V3

```
  1 ATGCGGCTGC CCGCTCAGCT        (SEQ ID NO: 189)
    GCTGGGCCTG CTGATGCTGT
    GGGTGCCCGG

51 CTCTTCCGGC GACGTGGTGA
    TGACCCAGTC CCCTCTGTCT
    CTGCCCGTGA

101 CCCTGGGCCA GCCCGCTTCT
    ATCTCTTGCC GGTCCTCCCA
    GTCCCTGGTG
```

-continued

```
151 TACTCCGACG GCAACACCTA
    CCTGAACTGG TTCCAGCAGA
    GACCCGGCCA
201 GTCTCCTCGG CGGCTGATCT
    ACAAGGTGTC CAACCGCTTT
    TCCGGCGTGC
251 CCGATCGGTT CTCCGGCTCC
    GGCAGCGGCA CCGATTTCAC
    CCTGAAGATC
301 AGCCGCGTGG AGGCCGAGGA
    TGTGGGCGTG TACTACTGCT
    TCCAGGGCTC
351 CCACATCCCT TACACCTTTG
    GCGGCGGAAC CAAGGTGGAG ATCAAG
```

Amino acid sequence of hMJ 2-7 VL V3

MRLPAQLLGLLMLWVPGSSG- DVVMTQSPLSLPVTLGQPASISCRSSQSLVYSDGNTYLNW (SEQ ID NO: 190)

FQQRPGQSPRRLIYKVSNRFSGVPDRFSGSGSGTDFTLKISRVEAEDVGVYYCFQGSHIP

YTFGGGTKVEIK

Nucleotide sequence of hMJ 2-7 VL V4

GATGTTGTGATGACCCAATCTCCACTCTCCCTGCCTGTCACTCCTGGAGAGCCAGCCTCC (SEQ ID NO: 191)

ATCTCTTGCAGATCTAGTCAGAGCATTGTGCATAGTAATGGAAACACCTACCTGGAATGG

TACCTGCAGAAACCAGGCCAGTCTCCACAGCTCCTGATCTACAAAGTTTCCAACCGATTT

TCTGGGGTCCCAGACAGGTTCAGTGGCAGTGGATCAGGGACAGATTTCACACTCAAGATC

AGCAGAGTGGAGGCTGAGGATGTGGGAGTTTATTACTGCTTTCAAAGTTCACATGTTCCT

CTCACCTTCGGTCAGGGGACCAAGCTGGAGATCAAA

Amino acid sequence of hMJ 2-7 VL V4

DVVMTQSPLS LPVTPGEPAS ISCRSSQSIV (SEQ ID NO: 192)
HSNGNTYLEW YLQKPGQSPQ LLIYKVSNRF

SGVPDRFSGS GSGTDFTLKISRVEAEDVGV
YYCFQSSHVP LTFGQGTKLE IK

Those skilled in the art will recognize, or be able to ascertain using no more than routine experimentation, many equivalents of the specific embodiments described herein described herein. Other embodiments are within the following claims.

---

What is claimed is:

1. A purified molecule comprising a heavy chain immunoglobulin variable domain sequence and a light chain immunoglobulin variable domain that binds to IL-13 with a $K_D$ of less than $10^{-7}$ M, wherein the heavy chain variable domain comprises the amino acid sequence of:
   (i) G-(YF)-(NT)-I-K-D-T-Y-(MI)-H (SEQ ID NO:48), in CDR1,
   (ii) (WR)-I-D-P-(GA)-N-D-N-I-K-Y-(SD)-(PQ)-K-F-Q-G (SEQ ID NO:49), in CDR2, and
   (iii) SEENWYDFFDY (SEQ ID NO:17), in CDR3;
   and wherein the light chain variable domain comprises the amino acid sequence of:
   (i) (RK)-S-S-Q-S-(LI)-(KV)-H-S-(ND)-G-N-(TN)-Y-L-(EDNQYAS) (SEQ ID NO:25), in CDR1,
   (ii) K-(LVI)-S-(NY)-(RW)-(FD)-S (SEQ ID NO:27), in CDR2, and
   (iii) Q-(GSA)-(ST)-(HEQ)-I-P (SEQ ID NO:28), in CDR3.

2. The antibody molecule of claim 1, which has one or more of the following properties:
   (a) the antibody molecule competes with a monoclonal antibody having a heavy chain variable domain comprising the amino acid sequence of SEQ ID NO:130 and a light chain variable domain comprising the amino acid sequency of SEQ ID NO:133 for binding to a human IL-13, wherein the human IL-13 comprises the amino acid residues of SEQ ID NO:124;
   (b) the antibody molecule contacts one or more amino acid residues from IL-13 selected from the group consisting of residues 116, 117, 118, 122, 123, 124, 125, 126, 127, and 128 of non-human primate IL-13 (SEQ ID NO:24) or human IL-13 (SEQ ID NO:178);
   (c) the antibody molecule has a heavy chain variable domain comprising the same canonical structure as a monoclonal antibody having a heavy chain variable domain comprising the amino acid sequence of SEQ ID NO:130 and a light chain variable domain comprising the amino acid sequenced of SEQ ID NO:133 in hypervariable loops 1, 2, or 3; and
   (d) the antibody molecule has a light chain variable comprising the same canonical structure as a monoclonal antibody having a heavy chain variable domain comprising the amino acid sequenc of SEQ ID NO:130 and a light chain variable domain comprising the amino acid sequence of SEQ ID NO133 in hypervariable loops 1, 2 or 3.

3. The antibody molecule of claim 2, wherein the hypervariable loops of the heavy chain variable domain of the antibody molecule have the same canonical structures as the hypervariable loops 1, 2 and 3 of the monoclonal antibody having the heavy chain variable domain comprising the amino acid sequence of SEQ ID NO:130 and the light chain variable domain comprising the amino acid sequency of SEQ ID NO:133.

4. The antibody molecule of claim 1, wherein the heavy chain variable domain comprises:
   GFNIKDTYIH (SEQ ID NO:15), in CDR1,
   RIDPANDNIKYDPKFQG (SEQ ID NO:16), in CDR2, and
   SEENWYDFFDY (SEQ ID NO:17), in CDR3; and
wherein the light chain variable domain sequence comprises:
   RSSQSIVHSNGNTYLE (SEQ ID NO:18), in CDR1,
   KVSNRFS (SEQ ID NO:19), in CDR2, and
   FQGSHIPYT (SEQ ID NO:20), in CDR3.

5. The antibody molecule of claim 1 or 4 that is a recombinant IgG that includes an Fc domain.

6. The antibody molecule of claim 5, wherein the Fc domain is mutated to reduce on or more of Fc receptor binding, antibody glycosylation, number of cysteine residues, effector cell function or complement function.

7. The antibody molecule of claim 1 or 4 that is Fab or scFv.

8. The antibody molecule of claim 1 or 4 that comprises human framework regions, a human Fc region, or both.

9. The antibody molecule of claim 1 or 4, wherein the frameworks of the heavy chain domain sequence comprise:
   (i) at a position corresponding to 49, Gly;
   (ii) at a position corresponding to 72, Ala;
   (iii) at a position corresponding to 48, Ile, and to 49, Gly;
   (iv) at a position corresponding to 48, Ile, to 49, Gly, and to 72, Ala;
   (v) at a position corresponding to 67, Lys, to 68, Ala, and to 72, Ala; and/or (vi) at a position corresponding to 48, Ile, to 49, Gly, to 72, Ala, to 79, Ala.

10. The antibody molecule of claim 1 or 4 that has one or more properties chosen from:
(i) reduces the ability of IL-13 to bind to IL-13Rα1 or IL-13Rα2;
(ii) inhibits one or more IL-13-associated activities with an IC50 or 50 to 5 pM;
(iii) has a dissociation kinetics in the range or $10^{-2}$ to $10^{-6} s^{-1}$ determined using BIACORE; or
(iv) has a $K_D$ of less than $10^{-8}$ M, $10^{-9}$ M or $10^{-10}$ M determined using surface plasmon resonance (SPR).

11. The antibody molecule of claim 1 or 4 that binds to IL13 irrespective of the polymorphism present at position 130 in SEQ ID NO:24.

12. The antibody molecule of claim 1 that binds to one or both of: a peptide consisting of SEQ ID NO:1 and a peptide consisting of SEQ ID NO:2.

13. The antibody molecule of claim 1, wherein the heavy chain variable domain sequence comprises the amino acid sequence of one or more of:
GFNIKDTYIH (SEQ ID NO:15), in CDR1,
RIDPANDNIKYDPKFQG (SEQ ID NO:16), in CDR2, or
SEENWYDFFDY (SEQ ID NO:17), in CDR3.

14. The antibody molecule of claim 1, wherein the light chain variable domain sequence comprises the amino acid sequence of one more more of:
RSSQSIVHSNGNTYLE (SEQ ID NO:18), in CDR1,
KVSNRFS (SEQ ID NO:19), in CDR2, or
FQGSHIPYT (SEQ ID NO:20), in CDR3.

15. The antibody molecule of either of claim 1 or 4, wherein the antibody molecule is an isolated, recombiant IgG antibody that comprises two polypeptide chains: a light chain that comprises the light chain variable domain of V2.11 (SEQ ID NO:36) and a heavy chain that comprises the heavy chain variable domain of V2.1 (SEQ ID NO:71), V2.3 (SEQ ID NO:73), V2.4 (SEQ ID NO:74), V2.5 (SEQ ID NO:75), V2.6 (SEQ ID NO:76), V2.7 (SEQ ID NO:77), or V2.11 (SEQ ID NO:80).

16. The isolated, recombant IgG antibody of claim 15 wherein the heavy chain further comprises an Fc domain.

17. A pharmaceutical composition the antibody molecule of claim 1 and a pharmaceutically acceptable carrier.

18. The pharmaceutical composition of claim 17 that is adapted for subcutaneous, inhalotory, or topical admistration.

19. The antibody molecule of either of claim 1 or 4, wherein the antibody moleule is an isolated, recombinant antibody that comprises:
(i) a light chain that comprises the amino acid sequence of SEQ ID NO:177;
(ii) a heavy chain that comprises the amino acid sequence of SEQ ID NO:176.

20. The antibody molecule of claim 1, wherein the heavy chain immunoglobulin variable domain comprises an amino acid sequence encoded by a nucleotide sequence that hybridizes under hight stringency conditions in 6×SSC at about 45° C. followed by one or more washes in 0.2×SSC, 0.1% SDS at 65° C. to the complememt of the nucleotide sequence encoding a heavy chain variable domain of V2.11 (SEQ ID NO:80).

21. The antibody molecule of either of claim 1 or 20, wherein the light chain immunoglobulin variable domain comprises an amino acid sequence encoded by a nucleotide sequence that hybridizes under the hight stringency condition in 6×SSC at about 45° C. followed by one or more washes in 0.2×SSC, 0.1% SDS at 65° C. to the comlement of the nucleotide sequence encoding a light chain variable domain of V2.11 (SEQ ID NO:36).

22. The antibody molecule of claim 21, wherein the antibody molecule comprises a light chain variable domain framework region 4 (FR4) comprising the amino acid sequence of SEQ ID NO:47.

23. The antibody molecule of claim 1, wherein the heavy chain immunoglobulin variable domain comprises an amino acid sequence that is at least 90% identical to the amino acid sequence of the heavy chain variable domain of V2.11 (SEQ ID NO:80).

24. The antibody molecule of claim 23, wherein the light chain immunoglobulin variable domain comprises an amino acid sequence that is at least 90% indentical to the amino acid sequence of the light chain variable domain of V2.11 (SEQ ID NO:36).

25. The antibody moleucule of claim 24, wherein the antibody molecule comprises a heavy chain domain framework region 4 (FR4) comprising the amino acid sequence of SEQ ID NO:116 or SEQ ID NO117.

26. The antibody molecule of claim 1, wherein the light chain immunoglobulin variable domain comprises an amino acid sequence that is at least 90% indentical to the amino acid sequence of the light chain variable domain of V2.11 (SEQ ID NO:36).

27. The antibody molecule of claim 1, wherein the heavy chain immunoglobulin variable domain comprises the amino acid sequence of SEQ ID NO:80.

28. The antibody molecule of claim 27, wherein the heavy chain immunoglobulin variable domain further comprises a heavy chain variable domain framework region 4 (FR4) comprising the amino acid sequence of SEQ ID NO:116 or SEQ ID NO:117.

29. The antibody molecule of claim 27, wherein the light chain immunoglobulin variable domain comprises the amino acid sequence of SEQ ID NO:36.

30. The antibody molecule of claim 29, wherein the heavy chain immunoglobulin variable domain further comprises a heavy chain variable domain framework region 4 (FR4) comprising the amino acid sequence of SEQ ID NO:117.

31. The antibody molecule of claim 30, wherein the light chain immunoglobulin variable domain comprises a light chain variable domain framework region 4 (FR4) comprising the amino acid sequence of SEQ ID NO:47.

32. The antibody molecule of claim 31, wherein the antibody molecule comprises a heavy chain constant domain comprising the amino acid sequence of SEQ ID NO:128.

33. The antibody molecule of claim 32, wherein the antibody molecule comprises a light chain constant domain comprising residues 134-219 of SEQ ID NO:177.

34. The antibody molecule of claim 1, wherein the light chain immunoglobulin variable domain comprises the amino acid sequence of SEQ ID NO:36.

35. The antibody molecule of claim 34, wherein the light chain immunoglobulin variable domain further comprises a light chain variable domain framework region 4 (FR4) sequence comprising the amino acid sequence of SEQ ID NO:47.

36. The antibody molecule of claim 1, wherein the antibody molecule comprises a light chain that comprises an amino acide sequence that is at least 95% identical to the amino acid sequence of SEQ ID NO:177.

37. The antibody molecule of either of claim 1 or 36, wherein the antibody molecule comprises a heavy chain that comprises an amino acid sequence that is at least 95% identical to the amino acid sequence of SEQ ID NO:176.

38. The antibody molecule of claim 1, wherein the light chain immunoglobulin variable domain comprises an amino acid sequence that is at least 95% identical to the amino acid sequence of the lgiht chain variable domain of V2.11 (SEQ ID NO:36).

39. The antibody of claim 1, wherein the heavy chain immunoglobulin variable domain comprises an amino acid sequence that is at least 95% identical to the amino sequence of the heavy chain variable domain of V2.11 (SEQ ID NO:80).

40. The antibody molecule of claim 1, wherein the antibody molecule is a bispecific or a multispecific antibody molecule.

41. The antibody molecule of claim 1, wherein the antibody molecule is linked to a toxin, a radioisotope, a cytotoxic agent or a cytostatic agent.

* * * * *

SEQUENCE LISTING

<160> NUMBER OF SEQ ID NOS: 192

<210> SEQ ID NO 1
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 1

Phe Val Lys Asp Leu Leu Val His Leu Lys Lys Leu Phe Arg Glu Gly
1               5                   10                  15

Gln Phe Asn

```
<210> SEQ ID NO 2
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 2

Phe Val Lys Asp Leu Leu Val His Leu Lys Lys Leu Phe Arg Glu Gly
 1               5                   10                  15

Arg Phe Asn

<210> SEQ ID NO 3
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 3

Phe Val Lys Asp Leu Leu Leu His Leu Lys Lys Leu Phe Arg Glu Gly
 1               5                   10                  15

Gln Phe Asn

<210> SEQ ID NO 4
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 4

Phe Val Lys Asp Leu Leu Leu His Leu Lys Lys Leu Phe Arg Glu Gly
 1               5                   10                  15

Arg Phe Asn

<210> SEQ ID NO 5
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 5

Phe Val Lys Asp Leu Leu Val His Leu Lys Lys Leu Phe Arg Glu Gly
 1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 6

Phe Val Lys Asp Leu Leu Leu His Leu Lys Lys Leu Phe Arg Glu Gly
 1               5                   10                  15

<210> SEQ ID NO 7
<211> LENGTH: 17
<212> TYPE: PRT
<213> ORGANISM: Artificial Sequence
<220> FEATURE:
<223> OTHER INFORMATION: Synthetically generated peptide
```

```
<400> SEQUENCE: 7

Lys Asp Leu Leu Val His Leu Lys Lys Leu Phe Arg Glu Gly Gln Phe
1               5                   10                  15

Asn

<210> SEQ ID NO 8
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 8

Lys Asp Leu Leu Val His Leu Lys Lys Leu Phe Arg Glu Gly Arg Phe
1               5                   10                  15

Asn

<210> SEQ ID NO 9
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 9

Lys Asp Leu Leu Leu His Leu Lys Lys Leu Phe Arg Glu Gly Gln Phe
1               5                   10                  15

Asn

<210> SEQ ID NO 10
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 10

Lys Asp Leu Leu Leu His Leu Lys Lys Leu Phe Arg Glu Gly Arg Phe
1               5                   10                  15

Asn

<210> SEQ ID NO 11
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 11

Lys Asp Leu Leu Val His Leu Lys Lys Leu Phe Arg Glu
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 12

Lys Asp Leu Leu Leu His Leu Lys Lys Leu Phe Arg Glu
1               5                   10
```

<210> SEQ ID NO 13
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 13

His Leu Lys Lys Leu Phe Arg Glu
1               5

<210> SEQ ID NO 14
<211> LENGTH: 112
<212> TYPE: PRT
<213> ORGANISM: Macaca fascicularis

<400> SEQUENCE: 14

Ser Pro Val Pro Ser Thr Ala Leu Lys Glu Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Val Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Asn Gly Phe Cys Pro His Lys Val Ser Ala Gly Gln Phe Ser
65                  70                  75                  80

Ser Leu Arg Val Arg Asp Thr Lys Ile Glu Val Ala Gln Phe Val Lys
                85                  90                  95

Asp Leu Leu Val His Leu Lys Lys Leu Phe Arg Glu Gly Gln Phe Asn
            100                 105                 110

<210> SEQ ID NO 15
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 15

Gly Phe Asn Ile Lys Asp Thr Tyr Ile His
1               5                   10

<210> SEQ ID NO 16
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 16

Arg Ile Asp Pro Ala Asn Asp Asn Ile Lys Tyr Asp Pro Lys Phe Gln
1               5                   10                  15

Gly

<210> SEQ ID NO 17
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 17

```
Ser Glu Glu Asn Trp Tyr Asp Phe Phe Asp Tyr
1               5                   10
```

<210> SEQ ID NO 18
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 18

```
Arg Ser Ser Gln Ser Ile Val His Ser Asn Gly Asn Thr Tyr Leu Glu
1               5                   10                  15
```

<210> SEQ ID NO 19
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 19

```
Lys Val Ser Asn Arg Phe Ser
1               5
```

<210> SEQ ID NO 20
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 20

```
Phe Gln Gly Ser His Ile Pro Tyr Thr
1               5
```

<210> SEQ ID NO 21
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Arg or Lys
<220> FEATURE:
<221> NAME/KEY: VARIANT
<222> LOCATION: 6
<223> OTHER INFORMATION: Xaa = Leu or Ile
<220> FEATURE:
<221> NAME/KEY: VARIANT
<222> LOCATION: 7
<223> OTHER INFORMATION: Xaa = Lys or Val
<220> FEATURE:
<221> NAME/KEY: VARIANT
<222> LOCATION: 16
<223> OTHER INFORMATION: Xaa = Glu, Asp, Asn, Gln, Tyr, Ala or ser

<400> SEQUENCE: 21

```
Xaa Ser Ser Gln Ser Xaa Xaa His Ser Asn Gly Asn Thr Tyr Leu Xaa
1               5                   10                  15
```

<210> SEQ ID NO 22
<211> LENGTH: 7
<212> TYPE: PRT
<213> ORGANISM: Artificial Sequence
<220> FEATURE:
<223> OTHER INFORMATION: Synthetically generated peptide
<220> FEATURE:

```
<221> NAME/KEY: VARIANT
<222> LOCATION: 2
<223> OTHER INFORMATION: Xaa = Leu or Val
<220> FEATURE:
<221> NAME/KEY: VARIANT
<222> LOCATION: 4
<223> OTHER INFORMATION: Xaa = Asn or Tyr

<400> SEQUENCE: 22

Lys Xaa Ser Xaa Arg Phe Ser
 1               5

<210> SEQ ID NO 23
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 3
<223> OTHER INFORMATION: Xaa = Gly, Ser or Ala
<220> FEATURE:
<221> NAME/KEY: VARIANT
<222> LOCATION: 4
<223> OTHER INFORMATION: Xaa = Ser, Ile or Thr
<220> FEATURE:
<221> NAME/KEY: VARIANT
<222> LOCATION: 5
<223> OTHER INFORMATION: Xaa = His, Glu or Gln
<220> FEATURE:
<221> NAME/KEY: VARIANT
<222> LOCATION: 6
<223> OTHER INFORMATION: Xaa = Ile or Leu

<400> SEQUENCE: 23

Phe Gln Xaa Xaa Xaa Xaa Pro
 1               5

<210> SEQ ID NO 24
<211> LENGTH: 132
<212> TYPE: PRT
<213> ORGANISM: Macaca fascicularis

<400> SEQUENCE: 24

Met Ala Leu Leu Leu Thr Met Val Ile Ala Leu Thr Cys Leu Gly Gly
 1               5                  10                  15

Phe Ala Ser Pro Ser Pro Val Pro Pro Ser Thr Ala Leu Lys Glu Leu
                20                  25                  30

Ile Glu Glu Leu Val Asn Ile Thr Gln Asn Gln Lys Ala Pro Leu Cys
            35                  40                  45

Asn Gly Ser Met Val Trp Ser Ile Asn Leu Thr Ala Gly Val Tyr Cys
        50                  55                  60

Ala Ala Leu Glu Ser Leu Ile Asn Val Ser Gly Cys Ser Ala Ile Glu
65                  70                  75                  80

Lys Thr Gln Arg Met Leu Asn Gly Phe Cys Pro His Lys Val Ser Ala
                85                  90                  95

Gly Gln Phe Ser Ser Leu Arg Val Arg Asp Thr Lys Ile Glu Val Ala
            100                 105                 110

Gln Phe Val Lys Asp Leu Leu Val His Leu Lys Lys Leu Phe Arg Glu
        115                 120                 125

Gly Gln Phe Asn
        130

<210> SEQ ID NO 25
```

```
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Arg or Lys
<220> FEATURE:
<221> NAME/KEY: VARIANT
<222> LOCATION: 6
<223> OTHER INFORMATION: Xaa = Leu or Ile
<220> FEATURE:
<221> NAME/KEY: VARIANT
<222> LOCATION: 7
<223> OTHER INFORMATION: Xaa = Lys or Val
<220> FEATURE:
<221> NAME/KEY: VARIANT
<222> LOCATION: 10
<223> OTHER INFORMATION: Xaa = Asn or Asp
<220> FEATURE:
<221> NAME/KEY: VARIANT
<222> LOCATION: 13
<223> OTHER INFORMATION: Thr or Asn
<220> FEATURE:
<221> NAME/KEY: VARIANT
<222> LOCATION: 16
<223> OTHER INFORMATION: Xaa = Glu, Asp, Asn, gln, Tyr, Ala or Ser

<400> SEQUENCE: 25

Xaa Ser Ser Gln Ser Xaa Xaa His Ser Xaa Gly Asn Xaa Tyr Leu Xaa
 1               5                  10                  15

<210> SEQ ID NO 26
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Arg or Lys
<220> FEATURE:
<221> NAME/KEY: VARIANT
<222> LOCATION: 6
<223> OTHER INFORMATION: Xaa = Leu or Ile
<220> FEATURE:
<221> NAME/KEY: VARIANT
<222> LOCATION: 7
<223> OTHER INFORMATION: Xaa = Lys or  Val
<220> FEATURE:
<221> NAME/KEY: VARIANT
<222> LOCATION: 10
<223> OTHER INFORMATION: Xaa = Asn or Asp
<220> FEATURE:
<221> NAME/KEY: VARIANT
<222> LOCATION: 13
<223> OTHER INFORMATION: Xaa = Thr or Asn

<400> SEQUENCE: 26

Xaa Ser Ser Gln Ser Xaa Xaa His Ser Xaa Gly Asn Xaa Tyr Leu Glu
 1               5                  10                  15

<210> SEQ ID NO 27
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 2
<223> OTHER INFORMATION: Xaa = Leu, Val or Ile
```

```
<220> FEATURE:
<221> NAME/KEY: VARIANT
<222> LOCATION: 4
<223> OTHER INFORMATION: Xaa = Asn or Tyr
<220> FEATURE:
<221> NAME/KEY: VARIANT
<222> LOCATION: 5
<223> OTHER INFORMATION: Xaa = Arg or Trp
<220> FEATURE:
<221> NAME/KEY: VARIANT
<222> LOCATION: 6
<223> OTHER INFORMATION: Xaa = Phe or Asp

<400> SEQUENCE: 27

Lys Xaa Ser Xaa Xaa Xaa Ser
 1               5

<210> SEQ ID NO 28
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 2
<223> OTHER INFORMATION: Xaa = Gly, Ser or Ala
<220> FEATURE:
<221> NAME/KEY: VARIANT
<222> LOCATION: 3
<223> OTHER INFORMATION: Xaa = Ser or Thr
<220> FEATURE:
<221> NAME/KEY: VARIANT
<222> LOCATION: 4
<223> OTHER INFORMATION: Xaa = His, Glu or Gln

<400> SEQUENCE: 28

Gln Xaa Xaa Xaa Ile Pro
 1               5

<210> SEQ ID NO 29
<211> LENGTH: 9
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 3
<223> OTHER INFORMATION: Xaa = Gly, Ser or Ala
<220> FEATURE:
<221> NAME/KEY: VARIANT
<222> LOCATION: 4
<223> OTHER INFORMATION: xaa = Ser, Ile or Thr
<220> FEATURE:
<221> NAME/KEY: VARIANT
<222> LOCATION: 5
<223> OTHER INFORMATION: Xaa = His, Glu or Gln
<220> FEATURE:
<221> NAME/KEY: VARIANT
<222> LOCATION: 6
<223> OTHER INFORMATION: Xaa = Ile or Leu

<400> SEQUENCE: 29

Phe Gln Xaa Xaa Xaa Xaa Pro Tyr Thr
 1               5

<210> SEQ ID NO 30
<211> LENGTH: 102
<212> TYPE: PRT
<213> ORGANISM: Artificial Sequence
<220> FEATURE:
<223> OTHER INFORMATION: Synthetically generated peptide
```

```
<400> SEQUENCE: 30

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Tyr Thr
            100

<210> SEQ ID NO 31
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 31

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Tyr Thr
            100

<210> SEQ ID NO 32
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 32

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Phe Gln Gly
                85                  90                  95

Ser His Ile Pro Tyr Thr
            100
```

<210> SEQ ID NO 33
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 33

```
Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Pro
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Tyr Thr
            100
```

<210> SEQ ID NO 34
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 34

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Tyr Thr
            100
```

<210> SEQ ID NO 35
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 35

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Leu Gln Gln Arg Pro Gly Gln Pro
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Lys Ile
65              70                  75                  80

Ser Arg Val Glu Ala Glu Asp Val Gly Val Tyr Tyr Cys Phe Gln Gly
                85                  90                  95

Ser His Ile Pro Tyr Thr
            100
```

<210> SEQ ID NO 36
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 36

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Val His Ser
            20                  25                  30

Asn Gly Asn Thr Tyr Leu Glu Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65              70                  75                  80

Ser Ser Leu Gln Pro Glu Asp Phe Ala Thr Tyr Tyr Cys Phe Gln Gly
                85                  90                  95

Ser His Ile Pro Tyr Thr
            100
```

<210> SEQ ID NO 37
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 37

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Phe Gln Gly
                85                  90                  95
```

```
Ser His Ile Pro Tyr Thr
            100

<210> SEQ ID NO 38
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 38

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Ile Pro Tyr Thr
            100

<210> SEQ ID NO 39
<211> LENGTH: 100
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 24
<223> OTHER INFORMATION: Xaa = Arg or Lys
<220> FEATURE:
<221> NAME/KEY: VARIANT
<222> LOCATION: 29
<223> OTHER INFORMATION: Xaa = Leu or Ile
<220> FEATURE:
<221> NAME/KEY: VARIANT
<222> LOCATION: 30
<223> OTHER INFORMATION: Xaa = Lys or Val
<220> FEATURE:
<221> NAME/KEY: VARIANT
<222> LOCATION: 33
<223> OTHER INFORMATION: Xaa = Asn or Asp
<220> FEATURE:
<221> NAME/KEY: VARIANT
<222> LOCATION: 36
<223> OTHER INFORMATION: Xaa = Thr or Asn
<220> FEATURE:
<221> NAME/KEY: VARIANT
<222> LOCATION: 39
<223> OTHER INFORMATION: Xaa = Glu, Asp, Asn, Gln, Tyr, Ala or Ser
<220> FEATURE:
<221> NAME/KEY: VARIANT
<222> LOCATION: 56
<223> OTHER INFORMATION: Xaa = Leu, Val or Ile
<220> FEATURE:
<221> NAME/KEY: VARIANT
<222> LOCATION: 58
<223> OTHER INFORMATION: Xaa = Asn or Tyr
<220> FEATURE:
<221> NAME/KEY: VARIANT
<222> LOCATION: 59
<223> OTHER INFORMATION: Xaa = Arg or Trp
<220> FEATURE:
```

-continued

```
<221> NAME/KEY: VARIANT
<222> LOCATION: 60
<223> OTHER INFORMATION: Xaa = Phe or Asp
<220> FEATURE:
<221> NAME/KEY: VARIANT
<222> LOCATION: 96
<223> OTHER INFORMATION: Xaa = Gly, Ser or Ala
<220> FEATURE:
<221> NAME/KEY: VARIANT
<222> LOCATION: 97
<223> OTHER INFORMATION: Xaa = Ser, Ile or Thr
<220> FEATURE:
<221> NAME/KEY: VARIANT
<222> LOCATION: 98
<223> OTHER INFORMATION: Xaa = His, Glu or Gln
<220> FEATURE:
<221> NAME/KEY: VARIANT
<222> LOCATION: 99
<223> OTHER INFORMATION: Xaa = Ile or Leu

<400> SEQUENCE: 39

Asp Ile Val Met Thr Gln Thr Pro Leu Ser Leu Pro Val Thr Pro Gly
 1               5                  10                  15

Glu Pro Ala Ser Ile Ser Cys Xaa Ser Ser Gln Ser Xaa Xaa His Ser
            20                  25                  30

Xaa Gly Asn Xaa Tyr Leu Xaa Trp Tyr Leu Gln Lys Pro Gly Gln Ser
        35                  40                  45

Pro Gln Leu Leu Ile Tyr Lys Xaa Ser Xaa Xaa Xaa Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Xaa
                85                  90                  95

Xaa Xaa Xaa Pro
        100

<210> SEQ ID NO 40
<211> LENGTH: 100
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 24
<223> OTHER INFORMATION: Xaa = Arg or Lys
<220> FEATURE:
<221> NAME/KEY: VARIANT
<222> LOCATION: 29
<223> OTHER INFORMATION: Xaa = Leu or Ile
<220> FEATURE:
<221> NAME/KEY: VARIANT
<222> LOCATION: 30
<223> OTHER INFORMATION: Xaa =  Lys or Val
<220> FEATURE:
<221> NAME/KEY: VARIANT
<222> LOCATION: 33
<223> OTHER INFORMATION: Xaa = Asn or Asp
<220> FEATURE:
<221> NAME/KEY: VARIANT
<222> LOCATION: 36
<223> OTHER INFORMATION: Xaa = Thr or Asn
<220> FEATURE:
<221> NAME/KEY: VARIANT
<222> LOCATION: 39
<223> OTHER INFORMATION: Xaa = Glu, Asp, Asn, Gln, Tyr, Ala or Ser
<220> FEATURE:
<221> NAME/KEY: VARIANT
<222> LOCATION: 56
<223> OTHER INFORMATION: Xaa = Leu, Val  or Ile
<220> FEATURE:
```

```
<221> NAME/KEY: VARIANT
<222> LOCATION: 58
<223> OTHER INFORMATION: Xaa =  Asn or Tyr
<220> FEATURE:
<221> NAME/KEY: VARIANT
<222> LOCATION: 59
<223> OTHER INFORMATION: Xaa = Arg or Trp
<220> FEATURE:
<221> NAME/KEY: VARIANT
<222> LOCATION: 60
<223> OTHER INFORMATION: Xaa = Phe or Asp
<220> FEATURE:
<221> NAME/KEY: VARIANT
<222> LOCATION: (96)...(0)
<223> OTHER INFORMATION: Xaa = Gly, Ser or Ala
<220> FEATURE:
<221> NAME/KEY: VARIANT
<222> LOCATION: 97
<223> OTHER INFORMATION: Xaa = Ser, Ile or Thr
<220> FEATURE:
<221> NAME/KEY: VARIANT
<222> LOCATION: 98)
<223> OTHER INFORMATION: Xaa = His, Glu or Gln
<220> FEATURE:
<221> NAME/KEY: VARIANT
<222> LOCATION: 99
<223> OTHER INFORMATION: Xaa = Ile or Leu

<400> SEQUENCE: 40

Asp Val Val Met Thr Gln Ser Pro Leu Ser Leu Pro Val Thr Leu Gly
 1               5                  10                  15

Gln Pro Ala Ser Ile Ser Cys Xaa Ser Ser Gln Ser Xaa Xaa His Ser
            20                  25                  30

Xaa Gly Asn Xaa Tyr Leu Xaa Trp Phe Gln Gln Arg Pro Gly Gln Ser
        35                  40                  45

Pro Arg Arg Leu Ile Tyr Lys Xaa Ser Xaa Xaa Xaa Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Xaa
                85                  90                  95

Xaa Xaa Xaa Pro
           100

<210> SEQ ID NO 41
<211> LENGTH: 100
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 24
<223> OTHER INFORMATION: Xaa = Arg or Lys
<220> FEATURE:
<221> NAME/KEY: VARIANT
<222> LOCATION: 29
<223> OTHER INFORMATION: Xaa = Leu or Ile
<220> FEATURE:
<221> NAME/KEY: VARIANT
<222> LOCATION: 30
<223> OTHER INFORMATION: Xaa =  Lys or Val
<220> FEATURE:
<221> NAME/KEY: VARIANT
<222> LOCATION: 33
<223> OTHER INFORMATION: Xaa = Asn or Asp
<220> FEATURE:
<221> NAME/KEY: VARIANT
<222> LOCATION: 36
<223> OTHER INFORMATION: Xaa = Thr or Asn
<220> FEATURE:
```

```
<221> NAME/KEY: VARIANT
<222> LOCATION: 39
<223> OTHER INFORMATION: Xaa = Glu, Asp, Asn, Gln, Tyr, Ala or Ser
<220> FEATURE:
<221> NAME/KEY: VARIANT
<222> LOCATION: 56
<223> OTHER INFORMATION: Xaa = Leu, Val  or Ile
<220> FEATURE:
<221> NAME/KEY: VARIANT
<222> LOCATION: 58
<223> OTHER INFORMATION: Xaa =  Asn or Tyr
<220> FEATURE:
<221> NAME/KEY: VARIANT
<222> LOCATION: 59
<223> OTHER INFORMATION: Xaa = Arg or Trp
<220> FEATURE:
<221> NAME/KEY: VARIANT
<222> LOCATION: 60
<223> OTHER INFORMATION: Xaa = Phe or Asp
<220> FEATURE:
<221> NAME/KEY: VARIANT
<222> LOCATION: 96
<223> OTHER INFORMATION: Xaa = Gly, Ser or Ala
<220> FEATURE:
<221> NAME/KEY: VARIANT
<222> LOCATION: 97
<223> OTHER INFORMATION: Xaa = Ser, Ile or Thr
<220> FEATURE:
<221> NAME/KEY: VARIANT
<222> LOCATION: 98
<223> OTHER INFORMATION: Xaa = His, Glu or Gln
<220> FEATURE:
<221> NAME/KEY: VARIANT
<222> LOCATION: 99
<223> OTHER INFORMATION: Xaa = Ile or Leu

<400> SEQUENCE: 41

Asp Ile Val Met Thr Gln Thr Pro Leu Ser Leu Ser Val Thr Pro Gly
 1               5                  10                  15

Gln Pro Ala Ser Ile Ser Cys Xaa Ser Ser Gln Ser Xaa Xaa His Ser
             20                  25                  30

Xaa Gly Asn Xaa Tyr Leu Xaa Trp Tyr Leu Gln Lys Pro Gly Gln Ser
         35                  40                  45

Pro Gln Leu Leu Ile Tyr Lys Xaa Ser Xaa Xaa Xaa Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Xaa
                 85                  90                  95

Xaa Xaa Xaa Pro
            100

<210> SEQ ID NO 42
<211> LENGTH: 100
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 24
<223> OTHER INFORMATION: Xaa = Arg or Lys
<220> FEATURE:
<221> NAME/KEY: VARIANT
<222> LOCATION: 29
<223> OTHER INFORMATION: Xaa = Leu or Ile
<220> FEATURE:
<221> NAME/KEY: VARIANT
<222> LOCATION: 30
<223> OTHER INFORMATION: Xaa =  Lys or Val
<220> FEATURE:
```

```
<221> NAME/KEY: VARIANT
<222> LOCATION: 33
<223> OTHER INFORMATION: Xaa = Asn or Asp
<220> FEATURE:
<221> NAME/KEY: VARIANT
<222> LOCATION: 36
<223> OTHER INFORMATION: Xaa = Thr or Asn
<220> FEATURE:
<221> NAME/KEY: VARIANT
<222> LOCATION: 39
<223> OTHER INFORMATION: Xaa = Glu, Asp, Asn, Gln, Tyr, Ala or Ser
<220> FEATURE:
<221> NAME/KEY: VARIANT
<222> LOCATION: 56
<223> OTHER INFORMATION: Xaa = Leu, Val  or Ile
<220> FEATURE:
<221> NAME/KEY: VARIANT
<222> LOCATION: 58
<223> OTHER INFORMATION: Xaa =  Asn or Tyr
<220> FEATURE:
<221> NAME/KEY: VARIANT
<222> LOCATION: 59
<223> OTHER INFORMATION: Xaa = Arg or Trp
<220> FEATURE:
<221> NAME/KEY: VARIANT
<222> LOCATION: 60
<223> OTHER INFORMATION: Xaa = Phe or Asp
<220> FEATURE:
<221> NAME/KEY: VARIANT
<222> LOCATION: 96
<223> OTHER INFORMATION: Xaa = Gly, Ser or Ala
<220> FEATURE:
<221> NAME/KEY: VARIANT
<222> LOCATION: 97
<223> OTHER INFORMATION: Xaa = Ser, Ile or Thr
<220> FEATURE:
<221> NAME/KEY: VARIANT
<222> LOCATION: 98
<223> OTHER INFORMATION: Xaa = His, Glu or Gln
<220> FEATURE:
<221> NAME/KEY: VARIANT
<222> LOCATION: 99
<223> OTHER INFORMATION: Xaa = Ile or Leu

<400> SEQUENCE: 42

Asp Ile Val Met Thr Gln Thr Pro Leu Ser Leu Ser Val Thr Pro Gly
 1               5                  10                  15

Gln Pro Ala Ser Ile Ser Cys Xaa Ser Ser Gln Ser Xaa Xaa His Ser
             20                  25                  30

Xaa Gly Asn Xaa Tyr Leu Xaa Trp Tyr Leu Gln Lys Pro Gly Gln Pro
         35                  40                  45

Pro Gln Leu Leu Ile Tyr Lys Xaa Ser Xaa Xaa Xaa Ser Gly Val Pro
     50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Xaa
                 85                  90                  95

Xaa Xaa Xaa Pro
            100

<210> SEQ ID NO 43
<211> LENGTH: 100
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 24
<223> OTHER INFORMATION: Xaa = Arg or Lys
<220> FEATURE:
```

```
<221> NAME/KEY: VARIANT
<222> LOCATION: 29
<223> OTHER INFORMATION: Xaa = Leu or Ile
<220> FEATURE:
<221> NAME/KEY: VARIANT
<222> LOCATION: 30
<223> OTHER INFORMATION: Xaa =  Lys or Val
<220> FEATURE:
<221> NAME/KEY: VARIANT
<222> LOCATION: 33
<223> OTHER INFORMATION: Xaa = Asn or Asp
<220> FEATURE:
<221> NAME/KEY: VARIANT
<222> LOCATION: 36
<223> OTHER INFORMATION: Xaa = Thr or Asn
<220> FEATURE:
<221> NAME/KEY: VARIANT
<222> LOCATION: 39
<223> OTHER INFORMATION: Xaa = Glu, Asp, Asn, Gln, Tyr, Ala or Ser
<220> FEATURE:
<221> NAME/KEY: VARIANT
<222> LOCATION: 56
<223> OTHER INFORMATION: Xaa = Leu, Val  or Ile
<220> FEATURE:
<221> NAME/KEY: VARIANT
<222> LOCATION: 58
<223> OTHER INFORMATION: Xaa =  Asn or Tyr
<220> FEATURE:
<221> NAME/KEY: VARIANT
<222> LOCATION: 59
<223> OTHER INFORMATION: Xaa = Arg or Trp
<220> FEATURE:
<221> NAME/KEY: VARIANT
<222> LOCATION: 60
<223> OTHER INFORMATION: Xaa = Phe or Asp
<220> FEATURE:
<221> NAME/KEY: VARIANT
<222> LOCATION: 96
<223> OTHER INFORMATION: Xaa = Gly, Ser or Ala
<220> FEATURE:
<221> NAME/KEY: VARIANT
<222> LOCATION: 97
<223> OTHER INFORMATION: Xaa = Ser, Ile or Thr
<220> FEATURE:
<221> NAME/KEY: VARIANT
<222> LOCATION: 98
<223> OTHER INFORMATION: Xaa = His, Glu or Gln
<220> FEATURE:
<221> NAME/KEY: VARIANT
<222> LOCATION: 99
<223> OTHER INFORMATION: Xaa = Ile or Leu

<400> SEQUENCE: 43

Asp Ile Val Met Thr Gln Ser Pro Leu Ser Leu Pro Val Thr Pro Gly
 1               5                  10                  15

Glu Pro Ala Ser Ile Ser Cys Xaa Ser Ser Gln Ser Xaa Xaa His Ser
            20                  25                  30

Xaa Gly Asn Xaa Tyr Leu Xaa Trp Tyr Leu Gln Lys Pro Gly Gln Ser
        35                  40                  45

Pro Gln Leu Leu Ile Tyr Lys Xaa Ser Xaa Xaa Xaa Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Xaa
                85                  90                  95

Xaa Xaa Xaa Pro
        100

<210> SEQ ID NO 44
<211> LENGTH: 100
<212> TYPE: PRT
```

<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 24
<223> OTHER INFORMATION: Xaa = Arg or Lys
<220> FEATURE:
<221> NAME/KEY: VARIANT
<222> LOCATION: 29
<223> OTHER INFORMATION: Xaa = Leu or Ile
<220> FEATURE:
<221> NAME/KEY: VARIANT
<222> LOCATION: 30
<223> OTHER INFORMATION: Xaa = Lys or Val
<220> FEATURE:
<221> NAME/KEY: VARIANT
<222> LOCATION: 33
<223> OTHER INFORMATION: Xaa = Asn or Asp
<220> FEATURE:
<221> NAME/KEY: VARIANT
<222> LOCATION: 36
<223> OTHER INFORMATION: Xaa = Thr or Asn
<220> FEATURE:
<221> NAME/KEY: VARIANT
<222> LOCATION: 39
<223> OTHER INFORMATION: Xaa = Glu, Asp, Asn, Gln, Tyr, Ala or Ser
<220> FEATURE:
<221> NAME/KEY: VARIANT
<222> LOCATION: 56
<223> OTHER INFORMATION: Xaa = Leu, Val or Ile
<220> FEATURE:
<221> NAME/KEY: VARIANT
<222> LOCATION: 58
<223> OTHER INFORMATION: Xaa = Asn or Tyr
<220> FEATURE:
<221> NAME/KEY: VARIANT
<222> LOCATION: 59
<223> OTHER INFORMATION: Xaa = Arg or Trp
<220> FEATURE:
<221> NAME/KEY: VARIANT
<222> LOCATION: 60
<223> OTHER INFORMATION: Xaa = Phe or Asp
<220> FEATURE:
<221> NAME/KEY: VARIANT
<222> LOCATION: 96
<223> OTHER INFORMATION: Xaa = Gly, Ser or Ala
<220> FEATURE:
<221> NAME/KEY: VARIANT
<222> LOCATION: 97
<223> OTHER INFORMATION: Xaa = Ser, Ile or Thr
<220> FEATURE:
<221> NAME/KEY: VARIANT
<222> LOCATION: 98
<223> OTHER INFORMATION: Xaa = His, Glu or Gln
<220> FEATURE:
<221> NAME/KEY: VARIANT
<222> LOCATION: 99
<223> OTHER INFORMATION: Xaa = Ile or Leu

<400> SEQUENCE: 44

```
Asp Ile Val Met Thr Gln Thr Pro Leu Ser Ser Pro Val Thr Leu Gly
 1               5                  10                  15

Gln Pro Ala Ser Ile Ser Cys Xaa Ser Ser Gln Ser Xaa Xaa His Ser
             20                  25                  30

Xaa Gly Asn Xaa Tyr Leu Xaa Trp Leu Gln Gln Arg Pro Gly Gln Pro
         35                  40                  45

Pro Arg Leu Leu Ile Tyr Lys Xaa Ser Xaa Xaa Xaa Ser Gly Val Pro
     50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Phe Gln Xaa
                 85                  90                  95
```

```
Xaa Xaa Xaa Pro
          100

<210> SEQ ID NO 45
<211> LENGTH: 100
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 24
<223> OTHER INFORMATION: Xaa = Arg or Lys
<220> FEATURE:
<221> NAME/KEY: VARIANT
<222> LOCATION: 29
<223> OTHER INFORMATION: Xaa = Leu or Ile
<220> FEATURE:
<221> NAME/KEY: VARIANT
<222> LOCATION: 30
<223> OTHER INFORMATION: Xaa =  Lys or Val
<220> FEATURE:
<221> NAME/KEY: VARIANT
<222> LOCATION: 33
<223> OTHER INFORMATION: Xaa = Asn or Asp
<220> FEATURE:
<221> NAME/KEY: VARIANT
<222> LOCATION: 36
<223> OTHER INFORMATION: Xaa = Thr or Asn
<220> FEATURE:
<221> NAME/KEY: VARIANT
<222> LOCATION: 39
<223> OTHER INFORMATION: Xaa = Glu, Asp, Asn, Gln, Tyr, Ala or Ser
<220> FEATURE:
<221> NAME/KEY: VARIANT
<222> LOCATION: 56
<223> OTHER INFORMATION: Xaa = Leu, Val  or Ile
<220> FEATURE:
<221> NAME/KEY: VARIANT
<222> LOCATION: 58
<223> OTHER INFORMATION: Xaa =  Asn or Tyr
<220> FEATURE:
<221> NAME/KEY: VARIANT
<222> LOCATION: 59
<223> OTHER INFORMATION: Xaa = Arg or Trp
<220> FEATURE:
<221> NAME/KEY: VARIANT
<222> LOCATION: 60
<223> OTHER INFORMATION: Xaa = Phe or Asp
<220> FEATURE:
<221> NAME/KEY: VARIANT
<222> LOCATION: 96
<223> OTHER INFORMATION: Xaa = Gly, Ser or Ala
<220> FEATURE:
<221> NAME/KEY: VARIANT
<222> LOCATION: 97
<223> OTHER INFORMATION: Xaa = Ser, Ile or Thr
<220> FEATURE:
<221> NAME/KEY: VARIANT
<222> LOCATION: 98
<223> OTHER INFORMATION: Xaa = His, Glu or Gln
<220> FEATURE:
<221> NAME/KEY: VARIANT
<222> LOCATION: 99
<223> OTHER INFORMATION: Xaa = Ile or Leu

<400> SEQUENCE: 45

Asp Ile Gln Met Thr Gln Ser Pro Ser Ser Leu Ser Ala Ser Val Gly
 1               5                  10                  15

Asp Arg Val Thr Ile Thr Cys Xaa Ser Ser Gln Ser Xaa Xaa His Ser
            20                  25                  30

Xaa Gly Asn Xaa Tyr Leu Xaa Trp Tyr Gln Gln Lys Pro Gly Lys Ala
        35                  40                  45
```

```
Pro Lys Leu Leu Ile Tyr Lys Xaa Ser Xaa Xaa Xaa Ser Gly Val Pro
    50                  55                  60

Ser Arg Phe Ser Gly Ser Gly Ser Gly Thr Asp Phe Thr Leu Thr Ile
65              70                  75                  80

Ser Ser Leu Gln Pro Glu Asp Phe Ala Thr Tyr Tyr Cys Phe Gln Xaa
                85                  90                  95

Xaa Xaa Xaa Pro
        100
```

<210> SEQ ID NO 46
<211> LENGTH: 100
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 24
<223> OTHER INFORMATION: Xaa = Arg or Lys
<220> FEATURE:
<221> NAME/KEY: VARIANT
<222> LOCATION: 29
<223> OTHER INFORMATION: Xaa = Leu or Ile
<220> FEATURE:
<221> NAME/KEY: VARIANT
<222> LOCATION: 30
<223> OTHER INFORMATION: Xaa = Lys or Val
<220> FEATURE:
<221> NAME/KEY: VARIANT
<222> LOCATION: 33
<223> OTHER INFORMATION: Xaa = Asn or Asp
<220> FEATURE:
<221> NAME/KEY: VARIANT
<222> LOCATION: 36
<223> OTHER INFORMATION: Xaa = Thr or Asn
<220> FEATURE:
<221> NAME/KEY: VARIANT
<222> LOCATION: 39
<223> OTHER INFORMATION: Xaa = Glu, Asp, Asn, Gln, Tyr, Ala or Ser
<220> FEATURE:
<221> NAME/KEY: VARIANT
<222> LOCATION: 56
<223> OTHER INFORMATION: Xaa = Leu, Val or Ile
<220> FEATURE:
<221> NAME/KEY: VARIANT
<222> LOCATION: 58
<223> OTHER INFORMATION: Xaa = Asn or Tyr
<220> FEATURE:
<221> NAME/KEY: VARIANT
<222> LOCATION: 59
<223> OTHER INFORMATION: Xaa = Arg or Trp
<220> FEATURE:
<221> NAME/KEY: VARIANT
<222> LOCATION: 60
<223> OTHER INFORMATION: Xaa = Phe or Asp
<220> FEATURE:
<221> NAME/KEY: VARIANT
<222> LOCATION: 96
<223> OTHER INFORMATION: Xaa = Gly, Ser or Ala
<220> FEATURE:
<221> NAME/KEY: VARIANT
<222> LOCATION: 97
<223> OTHER INFORMATION: Xaa = Ser, Ile or Thr
<220> FEATURE:
<221> NAME/KEY: VARIANT
<222> LOCATION: 98
<223> OTHER INFORMATION: Xaa = His, Glu or Gln
<220> FEATURE:
<221> NAME/KEY: VARIANT
<222> LOCATION: 99
<223> OTHER INFORMATION: Xaa = Ile or Leu

<400> SEQUENCE: 46

Asp Val Leu Met Thr Gln Thr Pro Leu Ser Leu Pro Val Ser Leu Gly

```
                 1               5                   10                  15
Asp Gln Ala Ser Ile Ser Cys Xaa Ser Ser Gln Ser Xaa Xaa His Ser
                20                  25                  30

Xaa Gly Asn Xaa Tyr Leu Xaa Trp Tyr Leu Gln Lys Pro Gly Gln Ser
        35                  40                  45

Pro Lys Leu Leu Ile Tyr Lys Xaa Ser Xaa Xaa Xaa Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Xaa
                85                  90                  95

Xaa Xaa Xaa Pro
            100

<210> SEQ ID NO 47
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 47

Phe Gly Gly Gly Thr Lys Val Glu Ile Lys Arg
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 2
<223> OTHER INFORMATION: Xaa = Tyr or Phe
<220> FEATURE:
<221> NAME/KEY: VARIANT
<222> LOCATION: 3
<223> OTHER INFORMATION: Xaa = Asn or Thr
<220> FEATURE:
<221> NAME/KEY: VARIANT
<222> LOCATION: 9
<223> OTHER INFORMATION: Xaa = Met or Ile

<400> SEQUENCE: 48

Gly Xaa Xaa Ile Lys Asp Thr Tyr Xaa His
1               5                   10

<210> SEQ ID NO 49
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Trp or Arg
<220> FEATURE:
<221> NAME/KEY: VARIANT
<222> LOCATION: 5
<223> OTHER INFORMATION: Xaa = Gly or Ala
<220> FEATURE:
<221> NAME/KEY: VARIANT
<222> LOCATION: 12
<223> OTHER INFORMATION: Xaa = Ser or Asp
<220> FEATURE:
<221> NAME/KEY: VARIANT
```

```
<222> LOCATION: 13
<223> OTHER INFORMATION: Xaa = Pro or Gln

<400> SEQUENCE: 49

Xaa Ile Asp Pro Xaa Asn Asp Asn Ile Lys Tyr Xaa Xaa Lys Phe Gln
 1               5                   10                  15

Gly

<210> SEQ ID NO 50
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 50

Gln Val Gln Leu Val Gln Ser Gly Ala Glu Val Lys Lys Pro Gly Ala
 1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Arg Ile Asp Pro Ala Asn Asp Asn Ile Lys Tyr Asp Pro Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Ser Glu Glu Asn Trp Tyr Asp Phe Phe Asp Tyr
                100                 105

<210> SEQ ID NO 51
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 51

Gln Val Gln Leu Val Gln Ser Gly Ala Glu Val Lys Lys Pro Gly Ala
 1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Arg Leu Glu Trp Met
        35                  40                  45

Gly Arg Ile Asp Pro Ala Asn Asp Asn Ile Lys Tyr Asp Pro Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Glu Glu Asn Trp Tyr Asp Phe Phe Asp Tyr
                100                 105

<210> SEQ ID NO 52
<211> LENGTH: 109
<212> TYPE: PRT
<213> ORGANISM: Artificial Sequence
<220> FEATURE:
<223> OTHER INFORMATION: Synthetically generated peptide
```

<400> SEQUENCE: 52

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Thr Gly Gln Gly Leu Glu Trp Met
        35                  40                  45

Gly Arg Ile Asp Pro Ala Asn Asp Asn Ile Lys Tyr Asp Pro Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Glu Glu Asn Trp Tyr Asp Phe Phe Asp Tyr
            100                 105

<210> SEQ ID NO 53
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Arg Ile Asp Pro Ala Asn Asp Asn Ile Lys Tyr Asp Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Glu Glu Asn Trp Tyr Asp Phe Phe Asp Tyr
            100                 105

<210> SEQ ID NO 54
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Val Ser Gly Phe Asn Ile Lys Asp Thr
            20                  25                  30

Tyr Ile His Trp Val Arg Gln Ala Pro Gly Lys Gly Leu Glu Trp Met
        35                  40                  45

Gly Arg Ile Asp Pro Ala Asn Asp Asn Ile Lys Tyr Asp Pro Lys Phe
    50                  55                  60

Gln Gly Arg Val Thr Met Thr Glu Asp Thr Ser Thr Asp Thr Ala Tyr
65                  70                  75                  80

```
Met Glu Leu Ser Ser Leu Arg Ser Glu Asp Thr Ala Val Tyr Tyr Cys
                85                  90                  95

Ala Thr Ser Glu Glu Asn Trp Tyr Asp Phe Phe Asp Tyr
            100                 105

<210> SEQ ID NO 55
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 55

Gln Met Gln Leu Val Gln Ser Gly Ala Glu Val Lys Lys Thr Gly Ser
 1               5                  10                  15

Ser Val Lys Val Ser Cys Lys Ala Ser Gly Phe Asn Ile Lys Asp Thr
                20                  25                  30

Tyr Ile His Trp Val Arg Gln Ala Pro Gly Gln Ala Leu Glu Trp Met
            35                  40                  45

Gly Arg Ile Asp Pro Ala Asn Asp Asn Ile Lys Tyr Asp Pro Lys Phe
        50                  55                  60

Gln Gly Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Ser Glu Glu Asn Trp Tyr Asp Phe Phe Asp Tyr
            100                 105

<210> SEQ ID NO 56
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 56

Gln Val Gln Leu Val Gln Ser Gly Ala Glu Val Lys Lys Pro Gly Ala
 1               5                  10                  15

Ser Val Lys Val Ser Cys Lys Ala Ser Gly Phe Asn Ile Lys Asp Thr
                20                  25                  30

Tyr Ile His Trp Val Arg Gln Ala Pro Gly Gln Gly Leu Glu Trp Met
            35                  40                  45

Gly Arg Ile Asp Pro Ala Asn Asp Asn Ile Lys Tyr Asp Pro Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Glu Glu Asn Trp Tyr Asp Phe Phe Asp Tyr
            100                 105

<210> SEQ ID NO 57
<211> LENGTH: 107
<212> TYPE: PRT
<213> ORGANISM: Artificial Sequence
<220> FEATURE:
<223> OTHER INFORMATION: Synthetically generated peptide

<400> SEQUENCE: 57
```

Gln Met Gln Leu Val Gln Ser Gly Pro Glu Val Lys Lys Pro Gly Thr
1               5                   10                  15

Ser Val Lys Val Ser Cys Lys Ala Ser Gly Phe Asn Ile Lys Asp Thr
                20                  25                  30

Tyr Ile His Trp Val Arg Gln Arg Gln Arg Leu Glu Trp Ile Gly Arg
            35                  40                  45

Ile Asp Pro Ala Asn Asp Ile Lys Tyr Asp Pro Lys Phe Gln Gly
50                      55                  60

Arg Val Thr Ile Thr Arg Asp Met Ser Thr Ser Thr Ala Tyr Met Glu
65              70                  75                  80

Leu Ser Ser Leu Arg Ser Glu Asp Thr Ala Val Tyr Tyr Cys Ala Ala
                85                  90                  95

Ser Glu Glu Asn Trp Tyr Asp Phe Phe Asp Tyr
                100                 105

<210> SEQ ID NO 58
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Asp Pro Ala Asn Asp Asn Ile Lys Tyr Asp Pro Lys Phe
        50                  55                  60

Gln Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Val Tyr Tyr Cys
                85                  90                  95

Ala Arg Ser Glu Glu Asn Trp Tyr Asp Phe Phe Asp Tyr
            100                 105

<210> SEQ ID NO 59
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 59

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ser Arg Ile Asp Pro Ala Asn Asp Asn Ile Lys Tyr Asp Pro Lys Phe
        50                  55                  60

Gln Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Leu Tyr Tyr Cys
                85                  90                  95

```
Ala Lys Asp Ser Glu Glu Asn Trp Tyr Asp Phe Phe Asp Tyr
            100                 105                 110
```

<210> SEQ ID NO 60
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 60

```
Gln Val Gln Leu Val Glu Ser Gly Gly Gly Leu Val Lys Pro Gly Gly
  1               5                  10                  15

Ser Leu Arg Leu Ser Cys Ala Ala Ser Gly Phe Asn Ile Lys Asp Thr
             20                  25                  30

Tyr Ile His Trp Ile Arg Gln Ala Pro Gly Lys Gly Leu Glu Trp Val
             35                  40                  45

Ser Arg Ile Asp Pro Ala Asn Asp Asn Ile Lys Tyr Asp Pro Lys Phe
 50                  55                  60

Gln Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg Ser Glu Glu Asn Trp Tyr Asp Phe Phe Asp Tyr
            100                 105
```

<210> SEQ ID NO 61
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 61

```
Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
             35                  40                  45

Gly Arg Ile Asp Pro Ala Asn Asp Asn Ile Lys Tyr Asp Pro Lys Phe
 50                  55                  60

Gln Gly Arg Phe Thr Ile Ser Arg Asp Asp Ser Lys Asn Thr Leu Tyr
 65                  70                  75                  80

Leu Gln Met Asn Ser Leu Lys Thr Glu Asp Thr Ala Val Tyr Tyr Cys
             85                  90                  95

Thr Thr Ser Glu Glu Asn Trp Tyr Asp Phe Phe Asp Tyr
            100                 105
```

<210> SEQ ID NO 62
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 62

```
Glu Val Gln Leu Val Glu Ser Gly Gly Gly Val Val Arg Pro Gly Gly
  1               5                  10                  15
```

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ser Arg Ile Asp Pro Ala Asn Asp Asn Ile Lys Tyr Asp Pro Lys Phe
            50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
            85                  90                  95

Ala Arg Ser Glu Glu Asn Trp Tyr Asp Phe Phe Asp Tyr
            100                 105

<210> SEQ ID NO 63
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 63

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ser Arg Ile Asp Pro Ala Asn Asp Asn Ile Lys Tyr Asp Pro Lys Phe
            50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Ser Glu Glu Asn Trp Tyr Asp Phe Phe Asp Tyr
            100                 105

<210> SEQ ID NO 64
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ser Arg Ile Asp Pro Ala Asn Asp Asn Ile Lys Tyr Asp Pro Lys Phe
            50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Ser Glu Glu Asn Trp Tyr Asp Phe Phe Asp Tyr
            100                 105

<210> SEQ ID NO 65
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 65

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Asp Pro Ala Asn Asp Asn Ile Lys Tyr Asp Pro Lys Phe
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Glu Glu Asn Trp Tyr Asp Phe Phe Asp Tyr
            100                 105

<210> SEQ ID NO 66
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 66

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Asp Pro Ala Asn Asp Asn Ile Lys Tyr Asp Pro Lys Phe
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Glu Glu Asn Trp Tyr Asp Phe Phe Asp Tyr
            100                 105

<210> SEQ ID NO 67
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 67

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Asn Ile Lys Asp Thr
            20                  25                  30

```
Tyr Ile His Trp Val Arg Gln Ala Pro Gly Lys Gly Leu Glu Trp Val
            35                  40                  45

Ser Arg Ile Asp Pro Ala Asn Asp Asn Ile Lys Tyr Asp Pro Lys Phe
 50                      55                  60

Gln Gly Arg Phe Thr Ile Ser Arg Asp Asn Ser Lys Asn Ser Leu Tyr
 65                  70                  75                  80

Leu Gln Met Asn Ser Leu Arg Thr Glu Asp Thr Ala Leu Tyr Tyr Cys
                85                  90                  95

Ala Lys Asp Ser Glu Glu Asn Trp Tyr Asp Phe Phe Asp Tyr
                100                 105                 110

<210> SEQ ID NO 68
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 68

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ser Arg Ile Asp Pro Ala Asn Asp Asn Ile Lys Tyr Asp Pro Lys Phe
 50                      55                  60

Gln Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                85                  90                  95

Ala Arg Ser Glu Glu Asn Trp Tyr Asp Phe Phe Asp Tyr
                100                 105

<210> SEQ ID NO 69
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 69

Glu Val Gln Leu Val Glu Ser Gly Gly Gly Leu Val Gln Pro Gly Arg
 1               5                  10                  15

Ser Leu Arg Leu Ser Cys Thr Ala Ser Gly Phe Asn Ile Lys Asp Thr
                20                  25                  30

Tyr Ile His Trp Phe Arg Gln Ala Pro Gly Lys Gly Leu Glu Trp Val
            35                  40                  45

Gly Arg Ile Asp Pro Ala Asn Asp Asn Ile Lys Tyr Asp Pro Lys Phe
 50                      55                  60

Gln Gly Arg Phe Thr Ile Ser Arg Asp Gly Ser Lys Ser Ile Ala Tyr
 65                  70                  75                  80

Leu Gln Met Asn Ser Leu Lys Thr Glu Asp Thr Ala Val Tyr Tyr Cys
                85                  90                  95

Thr Arg Ser Glu Glu Asn Trp Tyr Asp Phe Phe Asp Tyr
                100                 105

<210> SEQ ID NO 70
```

<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 70

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Tyr Val
        35                  40                  45

Ser Arg Ile Asp Pro Ala Asn Asp Asn Ile Lys Tyr Asp Pro Lys Phe
50                  55                  60

Gln Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg Ser Glu Glu Asn Trp Tyr Asp Phe Phe Asp Tyr
            100                 105
```

<210> SEQ ID NO 71
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 71

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Ile
        35                  40                  45

Gly Arg Ile Asp Pro Ala Asn Asp Asn Ile Lys Tyr Asp Pro Lys Phe
50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Glu Glu Asn Trp Tyr Asp Phe Phe Asp Tyr
            100                 105
```

<210> SEQ ID NO 72
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 72

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45
```

-continued

Ala Arg Ile Asp Pro Ala Asn Asp Asn Ile Lys Tyr Asp Pro Lys Phe
        50                  55                  60

Gln Gly Lys Ala Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Glu Glu Asn Trp Tyr Asp Phe Phe Asp Tyr
                100                 105

<210> SEQ ID NO 73
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 73

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
                 20                  25                  30

Tyr Ile His Trp Val Arg Gln Ala Pro Gly Lys Gly Leu Glu Trp Val
             35                  40                  45

Ala Arg Ile Asp Pro Ala Asn Asp Asn Ile Lys Tyr Asp Pro Lys Phe
        50                  55                  60

Gln Gly Arg Phe Thr Ile Ser Ala Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Glu Glu Asn Trp Tyr Asp Phe Phe Asp Tyr
                100                 105

<210> SEQ ID NO 74
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 74

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
                 20                  25                  30

Tyr Ile His Trp Val Arg Gln Ala Pro Gly Lys Gly Leu Glu Trp Val
             35                  40                  45

Gly Arg Ile Asp Pro Ala Asn Asp Asn Ile Lys Tyr Asp Pro Lys Phe
        50                  55                  60

Gln Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Glu Glu Asn Trp Tyr Asp Phe Phe Asp Tyr
                100                 105

<210> SEQ ID NO 75
<211> LENGTH: 109
<212> TYPE: PRT
<213> ORGANISM: Artificial Sequence

```
<220> FEATURE:
<223> OTHER INFORMATION: Synthetically generated peptide

<400> SEQUENCE: 75

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Asp Pro Ala Asn Asp Asn Ile Lys Tyr Asp Pro Lys Phe
 50                  55                  60

Gln Gly Lys Ala Thr Ile Ser Ala Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Glu Glu Asn Trp Tyr Asp Phe Phe Asp Tyr
            100                 105

<210> SEQ ID NO 76
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 76

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Ile
        35                  40                  45

Gly Arg Ile Asp Pro Ala Asn Asp Asn Ile Lys Tyr Asp Pro Lys Phe
 50                  55                  60

Gln Gly Arg Phe Thr Ile Ser Ala Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Glu Glu Asn Trp Tyr Asp Phe Phe Asp Tyr
            100                 105

<210> SEQ ID NO 77
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 77

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Gly Arg Ile Asp Pro Ala Asn Asp Asn Ile Lys Tyr Asp Pro Lys Phe
 50                  55                  60
```

```
Gln Gly Arg Phe Thr Ile Ser Ala Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Glu Glu Asn Trp Tyr Asp Phe Phe Asp Tyr
            100                 105

<210> SEQ ID NO 78
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 78

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Asp Pro Ala Asn Asp Asn Ile Lys Tyr Asp Pro Lys Phe
 50                  55                  60

Gln Gly Arg Phe Thr Ile Ser Arg Asp Asn Ala Lys Asn Ser Ala Tyr
 65                  70                  75                  80

Leu Gln Met Asn Ser Leu Arg Ala Glu Asp Thr Ala Val Tyr Tyr Cys
                 85                  90                  95

Ala Arg Ser Glu Glu Asn Trp Tyr Asp Phe Phe Asp Tyr
            100                 105

<210> SEQ ID NO 79
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 79

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Gly Arg Ile Asp Pro Ala Asn Asp Asn Ile Lys Tyr Asp Pro Lys Phe
 50                  55                  60

Gln Gly Arg Phe Thr Ile Ser Ala Asp Asn Ala Lys Asn Ser Ala Tyr
 65                  70                  75                  80

Leu Gln Met Asn Ser Leu Arg Ala Glu Asp Thr Ala Val Tyr Tyr Cys
                 85                  90                  95

Ala Arg Ser Glu Glu Asn Trp Tyr Asp Phe Phe Asp Tyr
            100                 105

<210> SEQ ID NO 80
<211> LENGTH: 109
<212> TYPE: PRT
<213> ORGANISM: Artificial Sequence
<220> FEATURE:
<223> OTHER INFORMATION: Synthetically generated peptide
```

```
<400> SEQUENCE: 80

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Ile
        35                  40                  45

Gly Arg Ile Asp Pro Ala Asn Asp Asn Ile Lys Tyr Asp Pro Lys Phe
    50                  55                  60

Gln Gly Arg Phe Thr Ile Ser Ala Asp Asn Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Ser Glu Glu Asn Trp Tyr Asp Phe Phe Asp Tyr
            100                 105

<210> SEQ ID NO 81
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 81

Glu Val Gln Leu Val Glu Ser Gly Gly Gly Leu Val Gln Pro Gly Gly
 1               5                  10                  15

Ser Leu Arg Leu Ser Cys Thr Gly Ser Gly Phe Asn Ile Lys Asp Thr
            20                  25                  30

Tyr Ile His Trp Val Arg Gln Ala Pro Gly Lys Gly Leu Glu Trp Ile
        35                  40                  45

Gly Arg Ile Asp Pro Ala Asn Asp Asn Ile Lys Tyr Asp Pro Lys Phe
    50                  55                  60

Gln Gly Arg Phe Thr Ile Ser Ala Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Glu Glu Asn Trp Tyr Asp Phe Phe Asp Tyr
            100                 105

<210> SEQ ID NO 82
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 82

Glu Val Gln Leu Gln Gln Ser Gly Ala Glu Leu Val Lys Pro Gly Ala
 1               5                  10                  15

Ser Val Lys Leu Ser Cys Thr Gly Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Asp Asn Ile Lys Tyr Asp Pro Lys Phe
    50                  55                  60

Gln Gly Lys Ala Thr Ile Thr Ala Asp Thr Ser Ser Asn Thr Ala Tyr
65                  70                  75                  80
```

```
Leu Gln Leu Asn Ser Leu Thr Ser Glu Asp Thr Ala Val Tyr Tyr Cys
                85                  90                  95

Ala Arg Ser Glu Glu Asn Trp Tyr Asp Phe Phe Asp Tyr
            100                 105

<210> SEQ ID NO 83
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 83

Gln Val Gln Leu Val Gln Ser Gly Ala Glu Val Lys Lys Pro Gly Ala
 1               5                  10                  15

Ser Val Lys Val Ser Cys Lys Ala Ser Gly Xaa Xaa Ile Lys Asp Thr
            20                  25                  30

Tyr Xaa His Trp Val Arg Gln Ala Pro Gly Gln Gly Leu Glu Trp Met
        35                  40                  45

Gly Xaa Ile Asp Pro Xaa Asn Asp Asn Ile Lys Tyr Xaa Xaa Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Glu Glu Asn Trp Tyr Asp Phe Phe Asp Tyr
            100                 105

<210> SEQ ID NO 84
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
```

```
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 84

Gln Val Gln Leu Val Gln Ser Gly Ala Glu Val Lys Lys Pro Gly Ala
 1               5                  10                  15

Ser Val Lys Val Ser Cys Lys Ala Ser Gly Xaa Xaa Ile Lys Asp Thr
            20                  25                  30

Tyr Xaa His Trp Val Arg Gln Ala Pro Gly Gln Arg Leu Glu Trp Met
        35                  40                  45

Gly Xaa Ile Asp Pro Xaa Asn Asp Asn Ile Lys Tyr Xaa Xaa Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Glu Glu Asn Trp Tyr Asp Phe Phe Asp Tyr
                100                 105

<210> SEQ ID NO 85
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
```

<223> OTHER INFORMATION: Xaa = Pro or Gln

<400> SEQUENCE: 85

```
Gln Val Gln Leu Val Gln Ser Gly Ala Glu Val Lys Lys Pro Gly Ala
  1               5                  10                  15

Ser Val Lys Val Ser Cys Lys Ala Ser Gly Xaa Xaa Ile Lys Asp Thr
             20                  25                  30

Tyr Xaa His Trp Val Arg Gln Ala Thr Gly Gln Gly Leu Glu Trp Met
         35                  40                  45

Gly Xaa Ile Asp Pro Xaa Asn Asp Asn Ile Lys Tyr Xaa Xaa Lys Phe
     50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Glu Glu Asn Trp Tyr Asp Phe Phe Asp Tyr
            100                 105
```

<210> SEQ ID NO 86
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 86

```
Gln Val Gln Leu Val Gln Ser Gly Ala Glu Val Lys Lys Pro Gly Ala
  1               5                  10                  15

Ser Val Lys Val Ser Cys Lys Ala Ser Gly Xaa Xaa Ile Lys Asp Thr
             20                  25                  30

Tyr Xaa His Trp Val Arg Gln Ala Pro Gly Gln Gly Leu Glu Trp Met
         35                  40                  45

Gly Xaa Ile Asp Pro Xaa Asn Asp Asn Ile Lys Tyr Xaa Xaa Lys Phe
     50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
```

```
                    85                  90                  95

Ala Arg Ser Glu Glu Asn Trp Tyr Asp Phe Phe Asp Tyr
            100                 105

<210> SEQ ID NO 87
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 87

Gln Val Gln Leu Val Gln Ser Gly Ala Glu Val Lys Lys Pro Gly Ala
 1               5                  10                  15

Ser Val Lys Val Ser Cys Lys Val Ser Gly Xaa Xaa Ile Lys Asp Thr
            20                  25                  30

Tyr Xaa His Trp Val Arg Gln Ala Pro Gly Lys Gly Leu Glu Trp Met
        35                  40                  45

Gly Xaa Ile Asp Pro Xaa Asn Asp Asn Ile Lys Tyr Xaa Xaa Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ser Glu Glu Asn Trp Tyr Asp Phe Phe Asp Tyr
            100                 105

<210> SEQ ID NO 88
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
```

```
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 88

Gln Met Gln Leu Val Gln Ser Gly Ala Glu Val Lys Lys Thr Gly Ser
 1               5                  10                  15

Ser Val Lys Val Ser Cys Lys Ala Ser Gly Xaa Xaa Ile Lys Asp Thr
             20                  25                  30

Tyr Xaa His Trp Val Arg Gln Ala Pro Gly Gln Ala Leu Glu Trp Met
         35                  40                  45

Gly Xaa Ile Asp Pro Xaa Asn Asp Asn Ile Lys Tyr Xaa Xaa Lys Phe
     50                  55                  60

Gln Gly Arg Val Thr Ile Thr Arg Asp Arg Ser Met Ser Thr Ala Tyr
 65                  70                  75                  80

Met Glu Leu Ser Ser Leu Arg Ser Glu Asp Thr Ala Met Tyr Tyr Cys
                 85                  90                  95

Ala Arg Ser Glu Glu Asn Trp Tyr Asp Phe Phe Asp Tyr
                100                 105

<210> SEQ ID NO 89
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln
```

<400> SEQUENCE: 89

```
Gln Val Gln Leu Val Gln Ser Gly Ala Glu Val Lys Lys Pro Gly Ala
1               5                   10                  15

Ser Val Lys Val Ser Cys Lys Ala Ser Gly Xaa Xaa Ile Lys Asp Thr
            20                  25                  30

Tyr Xaa His Trp Val Arg Gln Ala Pro Gly Gln Gly Leu Glu Trp Met
        35                  40                  45

Gly Xaa Ile Asp Pro Xaa Asn Asp Asn Ile Lys Tyr Xaa Xaa Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Glu Glu Asn Trp Tyr Asp Phe Phe Asp Tyr
                100                 105
```

<210> SEQ ID NO 90
<211> LENGTH: 107
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 90

```
Gln Met Gln Leu Val Gln Ser Gly Pro Glu Val Lys Lys Pro Gly Thr
1               5                   10                  15

Ser Val Lys Val Ser Cys Lys Ala Ser Gly Xaa Xaa Ile Lys Asp Thr
            20                  25                  30

Tyr Xaa His Trp Val Arg Gln Arg Gln Arg Leu Glu Trp Ile Gly Xaa
        35                  40                  45

Ile Asp Pro Xaa Asn Asp Asn Ile Lys Tyr Xaa Xaa Lys Phe Gln Gly
    50                  55                  60

Arg Val Thr Ile Thr Arg Asp Met Ser Thr Ser Thr Ala Tyr Met Glu
65                  70                  75                  80

Leu Ser Ser Leu Arg Ser Glu Asp Thr Ala Val Tyr Tyr Cys Ala Ala
                85                  90                  95
```

```
Ser Glu Glu Asn Trp Tyr Asp Phe Phe Asp Tyr
            100                 105

<210> SEQ ID NO 91
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 91

Glu Val Gln Leu Val Glu Ser Gly Gly Gly Leu Val Gln Pro Gly Gly
 1               5                  10                  15

Ser Leu Arg Leu Ser Cys Ala Ala Ser Gly Xaa Xaa Ile Lys Asp Thr
            20                  25                  30

Tyr Xaa His Trp Val Arg Gln Ala Pro Gly Lys Gly Leu Glu Trp Val
        35                  40                  45

Ala Xaa Ile Asp Pro Xaa Asn Asp Asn Ile Lys Tyr Xaa Xaa Lys Phe
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Glu Glu Asn Trp Tyr Asp Phe Phe Asp Tyr
            100                 105

<210> SEQ ID NO 92
<211> LENGTH: 110
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
```

```
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 92

Glu Val Gln Leu Val Glu Ser Gly Gly Gly Leu Val Gln Pro Gly Arg
 1               5                  10                  15

Ser Leu Arg Leu Ser Cys Ala Ala Ser Gly Xaa Xaa Ile Lys Asp Thr
            20                  25                  30

Tyr Xaa His Trp Val Arg Gln Ala Pro Gly Lys Gly Leu Glu Trp Val
        35                  40                  45

Ser Xaa Ile Asp Pro Xaa Asn Asp Asn Ile Lys Tyr Xaa Xaa Lys Phe
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Glu Glu Asn Trp Tyr Asp Phe Phe Asp Tyr
            100                 105                 110

<210> SEQ ID NO 93
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln
```

<400> SEQUENCE: 93

```
Gln Val Gln Leu Val Glu Ser Gly Gly Gly Leu Val Lys Pro Gly Gly
 1               5                  10                  15

Ser Leu Arg Leu Ser Cys Ala Ala Ser Gly Xaa Xaa Ile Lys Asp Thr
            20                  25                  30

Tyr Xaa His Trp Ile Arg Gln Ala Pro Gly Lys Gly Leu Glu Trp Val
        35                  40                  45

Ser Xaa Ile Asp Pro Xaa Asn Asp Asn Ile Lys Tyr Xaa Xaa Lys Phe
    50                  55                  60

Gln Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Ser Glu Glu Asn Trp Tyr Asp Phe Phe Asp Tyr
            100                 105
```

<210> SEQ ID NO 94
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 94

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Xaa Xaa Ile Lys Asp Thr
            20                  25                  30

Tyr Xaa His Trp Val Arg Gln Ala Pro Gly Lys Gly Leu Glu Trp Val
        35                  40                  45

Gly Xaa Ile Asp Pro Xaa Asn Asp Asn Ile Lys Tyr Xaa Xaa Lys Phe
    50                  55                  60

Gln Gly Arg Phe Thr Ile Ser Arg Asp Asp Ser Lys Asn Thr Leu Tyr
 65                  70                  75                  80

Leu Gln Met Asn Ser Leu Lys Thr Glu Asp Thr Ala Val Tyr Tyr Cys
                85                  90                  95
```

```
Thr Thr Ser Glu Glu Asn Trp Tyr Asp Phe Phe Asp Tyr
            100                 105
```

<210> SEQ ID NO 95
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 95

```
Glu Val Gln Leu Val Glu Ser Gly Gly Gly Val Val Arg Pro Gly Gly
  1               5                  10                  15

Ser Leu Arg Leu Ser Cys Ala Ala Ser Gly Xaa Xaa Ile Lys Asp Thr
             20                  25                  30

Tyr Xaa His Trp Val Arg Gln Ala Pro Gly Lys Gly Leu Glu Trp Val
         35                  40                  45

Ser Xaa Ile Asp Pro Xaa Asn Asp Asn Ile Lys Tyr Xaa Xaa Lys Phe
 50                  55                  60

Gln Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr His Cys
             85                  90                  95

Ala Arg Ser Glu Glu Asn Trp Tyr Asp Phe Phe Asp Tyr
            100                 105
```

<210> SEQ ID NO 96
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT

```
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 96

Glu Val Gln Leu Val Glu Ser Gly Gly Gly Leu Val Lys Pro Gly Gly
 1               5                  10                  15

Ser Leu Arg Leu Ser Cys Ala Ala Ser Gly Xaa Xaa Ile Lys Asp Thr
            20                  25                  30

Tyr Xaa His Trp Val Arg Gln Ala Pro Gly Lys Gly Leu Glu Trp Val
        35                  40                  45

Ser Xaa Ile Asp Pro Xaa Asn Asp Asn Ile Lys Tyr Xaa Xaa Lys Phe
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Glu Glu Asn Trp Tyr Asp Phe Phe Asp Tyr
            100                 105

<210> SEQ ID NO 97
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 97
```

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Xaa Xaa Ile Lys Asp Thr
             20                  25                  30

Tyr Xaa His Trp Val Arg Gln Ala Pro Gly Lys Gly Leu Glu Trp Val
         35                  40                  45

Ser Xaa Ile Asp Pro Xaa Asn Asp Asn Ile Lys Tyr Xaa Xaa Lys Phe
     50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Glu Glu Asn Trp Tyr Asp Phe Phe Asp Tyr
                100                 105
```

<210> SEQ ID NO 98
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 98

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Xaa Xaa Ile Lys Asp Thr
             20                  25                  30

Tyr Xaa His Trp Val Arg Gln Ala Pro Gly Lys Gly Leu Glu Trp Val
         35                  40                  45

Ala Xaa Ile Asp Pro Xaa Asn Asp Asn Ile Lys Tyr Xaa Xaa Lys Phe
     50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Glu Glu Asn Trp Tyr Asp Phe Phe Asp Tyr
```

<210> SEQ ID NO 99
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 99

Gln Val Gln Leu Val Glu Ser Gly Gly Gly Val Val Gln Pro Gly Arg
 1               5                  10                  15

Ser Leu Arg Leu Ser Cys Ala Ala Ser Gly Xaa Xaa Ile Lys Asp Thr
            20                  25                  30

Tyr Xaa His Trp Val Arg Gln Ala Pro Gly Lys Gly Leu Glu Trp Val
        35                  40                  45

Ala Xaa Ile Asp Pro Xaa Asn Asp Asn Ile Lys Tyr Xaa Xaa Lys Phe
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Glu Glu Asn Trp Tyr Asp Phe Phe Asp Tyr
            100                 105

<210> SEQ ID NO 100
<211> LENGTH: 110
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34

```
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 100

Glu Val Gln Leu Val Glu Ser Gly Gly Val Val Gln Pro Gly Gly
 1               5                  10                  15

Ser Leu Arg Leu Ser Cys Ala Ala Ser Gly Xaa Xaa Ile Lys Asp Thr
            20                  25                  30

Tyr Xaa His Trp Val Arg Gln Ala Pro Gly Lys Gly Leu Glu Trp Val
            35                  40                  45

Ser Xaa Ile Asp Pro Xaa Asn Asp Asn Ile Lys Tyr Xaa Xaa Lys Phe
     50                  55                  60

Gln Gly Arg Phe Thr Ile Ser Arg Asp Asn Ser Lys Asn Ser Leu Tyr
 65                  70                  75                  80

Leu Gln Met Asn Ser Leu Arg Thr Glu Asp Thr Ala Leu Tyr Tyr Cys
                85                  90                  95

Ala Lys Asp Ser Glu Glu Asn Trp Tyr Asp Phe Phe Asp Tyr
                100                 105                 110

<210> SEQ ID NO 101
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 101
```

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Xaa Xaa Ile Lys Asp Thr
            20                  25                  30

Tyr Xaa His Trp Val Arg Gln Ala Pro Gly Lys Gly Leu Glu Trp Val
        35                  40                  45

Ser Xaa Ile Asp Pro Xaa Asn Asp Asn Ile Lys Tyr Xaa Xaa Lys Phe
 50                  55                  60

Gln Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                85                  90                  95

Ala Arg Ser Glu Glu Asn Trp Tyr Asp Phe Phe Asp Tyr
            100                 105
```

<210> SEQ ID NO 102
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 102

```
Glu Val Gln Leu Val Glu Ser Gly Gly Gly Leu Val Gln Pro Gly Arg
 1               5                  10                  15

Ser Leu Arg Leu Ser Cys Thr Ala Ser Gly Xaa Xaa Ile Lys Asp Thr
            20                  25                  30

Tyr Xaa His Trp Phe Arg Gln Ala Pro Gly Lys Gly Leu Glu Trp Val
        35                  40                  45

Gly Xaa Ile Asp Pro Xaa Asn Asp Asn Ile Lys Tyr Xaa Xaa Lys Phe
 50                  55                  60

Gln Gly Arg Phe Thr Ile Ser Arg Asp Gly Ser Lys Ser Ile Ala Tyr
 65                  70                  75                  80

Leu Gln Met Asn Ser Leu Lys Thr Glu Asp Thr Ala Val Tyr Tyr Cys
                85                  90                  95

Thr Arg Ser Glu Glu Asn Trp Tyr Asp Phe Phe Asp Tyr
            100                 105
```

<210> SEQ ID NO 103
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 103

Glu Val Gln Leu Val Glu Ser Gly Gly Gly Leu Val Gln Pro Gly Gly
1               5                   10                  15

Ser Leu Arg Leu Ser Cys Ala Ala Ser Gly Xaa Xaa Ile Lys Asp Thr
            20                  25                  30

Tyr Xaa His Trp Val Arg Gln Ala Pro Gly Lys Gly Leu Glu Tyr Val
        35                  40                  45

Ser Xaa Ile Asp Pro Xaa Asn Asp Asn Ile Lys Tyr Xaa Xaa Lys Phe
    50                  55                  60

Gln Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg Ser Glu Glu Asn Trp Tyr Asp Phe Phe Asp Tyr
            100                 105

<210> SEQ ID NO 104
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile

```
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 104

Glu Val Gln Leu Val Glu Ser Gly Gly Gly Leu Val Gln Pro Gly Gly
 1               5                  10                  15

Ser Leu Arg Leu Ser Cys Ala Ala Ser Gly Xaa Xaa Ile Lys Asp Thr
            20                  25                  30

Tyr Xaa His Trp Val Arg Gln Ala Pro Gly Lys Gly Leu Glu Trp Ile
        35                  40                  45

Gly Xaa Ile Asp Pro Xaa Asn Asp Asn Ile Lys Tyr Xaa Xaa Lys Phe
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Glu Glu Asn Trp Tyr Asp Phe Phe Asp Tyr
                100                 105

<210> SEQ ID NO 105
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 105

Glu Val Gln Leu Val Glu Ser Gly Gly Gly Leu Val Gln Pro Gly Gly
```

```
            1               5                  10                 15
Ser Leu Arg Leu Ser Cys Ala Ala Ser Gly Xaa Xaa Ile Lys Asp Thr
            20                 25                 30

Tyr Xaa His Trp Val Arg Gln Ala Pro Gly Lys Gly Leu Glu Trp Val
        35                 40                 45

Ala Xaa Ile Asp Pro Xaa Asn Asp Asn Ile Lys Tyr Xaa Xaa Lys Phe
        50                 55                 60

Gln Gly Lys Ala Thr Ile Ser Arg Asp Asn Ala Lys Asn Ser Leu Tyr
65                 70                 75                 80

Leu Gln Met Asn Ser Leu Arg Ala Glu Asp Thr Ala Val Tyr Tyr Cys
                85                 90                 95

Ala Arg Ser Glu Glu Asn Trp Tyr Asp Phe Phe Asp Tyr
            100                105

<210> SEQ ID NO 106
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 106

Glu Val Gln Leu Val Glu Ser Gly Gly Gly Leu Val Gln Pro Gly Gly
1               5                  10                 15

Ser Leu Arg Leu Ser Cys Ala Ala Ser Gly Xaa Xaa Ile Lys Asp Thr
            20                 25                 30

Tyr Xaa His Trp Val Arg Gln Ala Pro Gly Lys Gly Leu Glu Trp Val
        35                 40                 45

Ala Xaa Ile Asp Pro Xaa Asn Asp Asn Ile Lys Tyr Xaa Xaa Lys Phe
        50                 55                 60

Gln Gly Arg Phe Thr Ile Ser Ala Asp Asn Ala Lys Asn Ser Leu Tyr
65                 70                 75                 80

Leu Gln Met Asn Ser Leu Arg Ala Glu Asp Thr Ala Val Tyr Tyr Cys
                85                 90                 95

Ala Arg Ser Glu Glu Asn Trp Tyr Asp Phe Phe Asp Tyr
            100                105
```

```
<210> SEQ ID NO 107
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 107

Glu Val Gln Leu Val Glu Ser Gly Gly Gly Leu Val Gln Pro Gly Gly
 1               5                  10                  15

Ser Leu Arg Leu Ser Cys Ala Ala Ser Gly Xaa Xaa Ile Lys Asp Thr
            20                  25                  30

Tyr Xaa His Trp Val Arg Gln Ala Pro Gly Lys Gly Leu Glu Trp Val
        35                  40                  45

Gly Xaa Ile Asp Pro Xaa Asn Asp Asn Ile Lys Tyr Xaa Xaa Lys Phe
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Glu Glu Asn Trp Tyr Asp Phe Phe Asp Tyr
            100                 105

<210> SEQ ID NO 108
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
```

```
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 108
```

Glu Val Gln Leu Val Glu Ser Gly Gly Gly Leu Val Gln Pro Gly Gly
 1               5                  10                  15

Ser Leu Arg Leu Ser Cys Ala Ala Ser Gly Xaa Xaa Ile Lys Asp Thr
            20                  25                  30

Tyr Xaa His Trp Val Arg Gln Ala Pro Gly Lys Gly Leu Glu Trp Val
        35                  40                  45

Ala Xaa Ile Asp Pro Xaa Asn Asp Asn Ile Lys Tyr Xaa Xaa Lys Phe
    50                  55                  60

Gln Gly Lys Ala Thr Ile Ser Ala Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Glu Glu Asn Trp Tyr Asp Phe Phe Asp Tyr
            100                 105

```
<210> SEQ ID NO 109
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 109
```

Glu Val Gln Leu Val Glu Ser Gly Gly Gly Leu Val Gln Pro Gly Gly
 1               5                  10                  15

Ser Leu Arg Leu Ser Cys Ala Ala Ser Gly Xaa Xaa Ile Lys Asp Thr
            20                  25                  30

Tyr Xaa His Trp Val Arg Gln Ala Pro Gly Lys Gly Leu Glu Trp Ile
        35                  40                  45

Gly Xaa Ile Asp Pro Xaa Asn Asp Asn Ile Lys Tyr Xaa Xaa Lys Phe
        50                  55                  60

Gln Gly Arg Phe Thr Ile Ser Ala Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Ser Glu Glu Asn Trp Tyr Asp Phe Phe Asp Tyr
            100                 105

<210> SEQ ID NO 110
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 110

Glu Val Gln Leu Val Glu Ser Gly Gly Gly Leu Val Gln Pro Gly Gly
 1               5                  10                  15

Ser Leu Arg Leu Ser Cys Ala Ala Ser Gly Xaa Xaa Ile Lys Asp Thr
            20                  25                  30

Tyr Xaa His Trp Val Arg Gln Ala Pro Gly Lys Gly Leu Glu Trp Val
        35                  40                  45

Gly Xaa Ile Asp Pro Xaa Asn Asp Asn Ile Lys Tyr Xaa Xaa Lys Phe
        50                  55                  60

Gln Gly Arg Phe Thr Ile Ser Ala Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Ser Glu Glu Asn Trp Tyr Asp Phe Phe Asp Tyr
            100                 105

```
<210> SEQ ID NO 111
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 111

Glu Val Gln Leu Val Glu Ser Gly Gly Gly Leu Val Gln Pro Gly Gly
 1               5                  10                  15

Ser Leu Arg Leu Ser Cys Ala Ala Ser Gly Xaa Xaa Ile Lys Asp Thr
             20                  25                  30

Tyr Xaa His Trp Val Arg Gln Ala Pro Gly Lys Gly Leu Glu Trp Val
         35                  40                  45

Ala Xaa Ile Asp Pro Xaa Asn Asp Asn Ile Lys Tyr Xaa Xaa Lys Phe
     50                  55                  60

Gln Gly Arg Phe Thr Ile Ser Arg Asp Asn Ala Lys Asn Ser Ala Tyr
65                  70                  75                  80

Leu Gln Met Asn Ser Leu Arg Ala Glu Asp Thr Ala Val Tyr Tyr Cys
                 85                  90                  95

Ala Arg Ser Glu Glu Asn Trp Tyr Asp Phe Phe Asp Tyr
            100                 105

<210> SEQ ID NO 112
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
```

```
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 112

Glu Val Gln Leu Val Glu Ser Gly Gly Gly Leu Val Gln Pro Gly Gly
 1               5                  10                  15

Ser Leu Arg Leu Ser Cys Ala Ala Ser Gly Xaa Xaa Ile Lys Asp Thr
            20                  25                  30

Tyr Xaa His Trp Val Arg Gln Ala Pro Gly Lys Gly Leu Glu Trp Val
        35                  40                  45

Gly Xaa Ile Asp Pro Xaa Asn Asp Asn Ile Lys Tyr Xaa Xaa Lys Phe
    50                  55                  60

Gln Gly Arg Phe Thr Ile Ser Ala Asp Asn Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Ser Glu Glu Asn Trp Tyr Asp Phe Phe Asp Tyr
            100                 105

<210> SEQ ID NO 113
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 113

Glu Val Gln Leu Val Glu Ser Gly Gly Gly Leu Val Gln Pro Gly Gly
 1               5                  10                  15
```

```
Ser Leu Arg Leu Ser Cys Ala Ala Ser Gly Xaa Xaa Ile Lys Asp Thr
             20                  25                  30

Tyr Xaa His Trp Val Arg Gln Ala Pro Gly Lys Gly Leu Glu Trp Ile
         35                  40                  45

Gly Xaa Ile Asp Pro Xaa Asn Asp Asn Ile Lys Tyr Xaa Xaa Lys Phe
     50                  55                  60

Gln Gly Arg Phe Thr Ile Ser Ala Asp Asn Ala Lys Asn Ser Ala Tyr
 65                  70                  75                  80

Leu Gln Met Asn Ser Leu Arg Ala Glu Asp Thr Ala Val Tyr Tyr Cys
                 85                  90                  95

Ala Arg Ser Glu Glu Asn Trp Tyr Asp Phe Phe Asp Tyr
                100                 105
```

<210> SEQ ID NO 114
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 114

```
Glu Val Gln Leu Val Glu Ser Gly Gly Gly Leu Val Gln Pro Gly Gly
 1               5                  10                  15

Ser Leu Arg Leu Ser Cys Thr Gly Ser Gly Xaa Xaa Ile Lys Asp Thr
             20                  25                  30

Tyr Xaa His Trp Val Arg Gln Ala Pro Gly Lys Gly Leu Glu Trp Ile
         35                  40                  45

Gly Xaa Ile Asp Pro Xaa Asn Asp Asn Ile Lys Tyr Xaa Xaa Lys Phe
     50                  55                  60

Gln Gly Arg Phe Thr Ile Ser Ala Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Glu Glu Asn Trp Tyr Asp Phe Phe Asp Tyr
                100                 105
```

<210> SEQ ID NO 115

```
<211> LENGTH: 109
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 27
<223> OTHER INFORMATION: Xaa = Tyr or Phe
<220> FEATURE:
<221> NAME/KEY: VARIANT
<222> LOCATION: 28
<223> OTHER INFORMATION: Xaa = Asn or Thr
<220> FEATURE:
<221> NAME/KEY: VARIANT
<222> LOCATION: 34
<223> OTHER INFORMATION: Xaa = Met or Ile
<220> FEATURE:
<221> NAME/KEY: VARIANT
<222> LOCATION: 50
<223> OTHER INFORMATION: Xaa = Trp or Arg
<220> FEATURE:
<221> NAME/KEY: VARIANT
<222> LOCATION: 54
<223> OTHER INFORMATION: Xaa = Gly or Ala
<220> FEATURE:
<221> NAME/KEY: VARIANT
<222> LOCATION: 61
<223> OTHER INFORMATION: Xaa = Ser or Asp
<220> FEATURE:
<221> NAME/KEY: VARIANT
<222> LOCATION: 62
<223> OTHER INFORMATION: Xaa = Pro or Gln

<400> SEQUENCE: 115

Glu Val Gln Leu Gln Gln Ser Gly Ala Glu Leu Val Lys Pro Gly Ala
 1               5                  10                  15

Ser Val Lys Leu Ser Cys Thr Gly Ser Gly Xaa Xaa Ile Lys Asp Thr
            20                  25                  30

Tyr Xaa His Trp Val Lys Gln Arg Pro Glu Gln Gly Leu Glu Trp Ile
        35                  40                  45

Gly Xaa Ile Asp Pro Xaa Asn Asp Asn Ile Lys Tyr Xaa Xaa Lys Phe
    50                  55                  60

Gln Gly Lys Ala Thr Ile Thr Ala Asp Thr Ser Ser Asn Thr Ala Tyr
65                  70                  75                  80

Leu Gln Leu Asn Ser Leu Thr Ser Glu Asp Thr Ala Val Tyr Tyr Cys
                85                  90                  95

Ala Arg Ser Glu Glu Asn Trp Tyr Asp Phe Phe Asp Tyr
            100                 105

<210> SEQ ID NO 116
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 116

Trp Gly Gln Gly Thr Thr Leu Thr Val Ser Ser
 1               5                  10

<210> SEQ ID NO 117
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 117
```

```
Trp Gly Gln Gly Thr Leu Val Thr Val Ser Ser
 1               5                  10
```

<210> SEQ ID NO 118
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 118

```
Gln Ala Ser Gln Gly Thr Ser Ile Asn Leu Asn
 1               5                  10
```

<210> SEQ ID NO 119
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 119

```
Gly Ala Ser Asn Leu Glu Asp
 1               5
```

<210> SEQ ID NO 120
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 120

```
Leu Gln His Ser Tyr Leu Pro Trp Thr
 1               5
```

<210> SEQ ID NO 121
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 121

```
Gly Phe Ser Leu Thr Gly Tyr Gly Val Asn
 1               5                  10
```

<210> SEQ ID NO 122
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 122

```
Ile Ile Trp Gly Asp Gly Ser Thr Asp Tyr Asn Ser Ala Leu
 1               5                  10
```

<210> SEQ ID NO 123
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 123

```
Asp Lys Thr Phe Tyr Tyr Asp Gly Phe Tyr Arg Gly Arg Met Asp Tyr
 1               5                  10                  15
```

<210> SEQ ID NO 124
<211> LENGTH: 113
<212> TYPE: PRT
<213> ORGANISM: Homo sapiens

<400> SEQUENCE: 124

```
Pro Gly Pro Val Pro Ser Thr Ala Leu Arg Glu Leu Ile Glu Glu
 1               5                  10                  15

Leu Val Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
                35                  40                  45

Glu Ser Leu Ile Asn Val Ser Gly Cys Ser Ala Ile Glu Lys Thr Gln
                50                  55                  60

Arg Met Leu Ser Gly Phe Cys Pro His Lys Val Ser Ala Gly Gln Phe
65                  70                  75                  80

Ser Ser Leu His Val Arg Asp Thr Lys Ile Glu Val Ala Gln Phe Val
                85                  90                  95

Lys Asp Leu Leu Leu His Leu Lys Lys Leu Phe Arg Glu Gly Arg Phe
                100                 105                 110

Asn
```

<210> SEQ ID NO 125
<211> LENGTH: 427
<212> TYPE: PRT
<213> ORGANISM: Homo sapiens

<400> SEQUENCE: 125

```
Met Glu Trp Pro Ala Arg Leu Cys Gly Leu Trp Ala Leu Leu Leu Cys
 1               5                  10                  15

Ala Gly Gly Gly Gly Gly Gly Gly Ala Ala Pro Thr Glu Thr Gln
                20                  25                  30

Pro Pro Val Thr Asn Leu Ser Val Ser Val Glu Asn Leu Cys Thr Val
                35                  40                  45

Ile Trp Thr Trp Asn Pro Pro Glu Gly Ala Ser Ser Asn Cys Ser Leu
                50                  55                  60

Trp Tyr Phe Ser His Phe Gly Asp Lys Gln Asp Lys Lys Ile Ala Pro
65                  70                  75                  80

Glu Thr Arg Arg Ser Ile Glu Val Pro Leu Asn Glu Arg Ile Cys Leu
                85                  90                  95

Gln Val Gly Ser Gln Cys Ser Thr Asn Glu Ser Glu Lys Pro Ser Ile
                100                 105                 110

Leu Val Glu Lys Cys Ile Ser Pro Pro Glu Gly Asp Pro Glu Ser Ala
                115                 120                 125

Val Ile Glu Leu Gln Cys Ile Trp His Asn Leu Ser Tyr Met Lys Cys
                130                 135                 140

Ser Trp Leu Pro Gly Arg Asn Thr Ser Pro Asp Thr Asn Tyr Thr Leu
145                 150                 155                 160

Tyr Tyr Trp His Arg Ser Leu Glu Lys Ile His Gln Cys Glu Asn Ile
                165                 170                 175

Phe Arg Glu Gly Gln Tyr Phe Gly Cys Ser Phe Asp Leu Thr Lys Val
                180                 185                 190

Lys Asp Ser Ser Phe Glu Gln His Ser Val Gln Ile Met Val Lys Asp
```

-continued

```
                195                 200                 205
Asn Ala Gly Lys Ile Lys Pro Ser Phe Asn Ile Val Pro Leu Thr Ser
    210                 215                 220
Arg Val Lys Pro Asp Pro Pro His Ile Lys Asn Leu Ser Phe His Asn
225                 230                 235                 240
Asp Leu Tyr Val Gln Trp Glu Asn Pro Gln Asn Phe Ile Ser Arg
            245                 250                 255
Cys Leu Phe Tyr Glu Val Glu Val Asn Asn Ser Gln Thr Glu Thr His
                260                 265                 270
Asn Val Phe Tyr Val Gln Glu Ala Lys Cys Glu Asn Pro Glu Phe Glu
                275                 280                 285
Arg Asn Val Glu Asn Thr Ser Cys Phe Met Val Pro Gly Val Leu Pro
290                 295                 300
Asp Thr Leu Asn Thr Val Arg Ile Arg Val Lys Thr Asn Lys Leu Cys
305                 310                 315                 320
Tyr Glu Asp Asp Lys Leu Trp Ser Asn Trp Ser Gln Glu Met Ser Ile
                325                 330                 335
Gly Lys Lys Arg Asn Ser Thr Leu Tyr Ile Thr Met Leu Leu Ile Val
                340                 345                 350
Pro Val Ile Val Ala Asp Ala Ile Ile Val Leu Leu Leu Tyr Leu Lys
                355                 360                 365
Arg Leu Lys Ile Ile Ile Phe Pro Pro Ile Pro Asp Pro Gly Lys Ile
            370                 375                 380
Phe Lys Glu Met Phe Gly Asp Gln Asn Asp Asp Thr Leu His Trp Lys
385                 390                 395                 400
Lys Tyr Asp Ile Tyr Glu Lys Gln Thr Lys Glu Glu Thr Asp Ser Val
                405                 410                 415
Val Leu Ile Glu Asn Leu Lys Lys Ala Ser Gln
                420                 425

<210> SEQ ID NO 126
<211> LENGTH: 101
<212> TYPE: PRT
<213> ORGANISM: Homo sapiens

<400> SEQUENCE: 126

Asp Val Val Met Thr Gln Ser Pro Leu Ser Leu Pro Val Thr Leu Gly
  1               5                  10                  15
Gln Pro Ala Ser Ile Ser Cys Arg Ser Ser Gln Ser Leu Val Tyr Ser
                20                  25                  30
Asp Gly Asn Thr Tyr Leu Asn Trp Phe Gln Gln Arg Pro Gly Gln Ser
            35                  40                  45
Pro Arg Arg Leu Ile Tyr Lys Val Ser Asn Arg Phe Ser Gly Val Pro
        50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Gly
                85                  90                  95
Thr His Trp Pro Pro
            100

<210> SEQ ID NO 127
<211> LENGTH: 20
<212> TYPE: PRT
<213> ORGANISM: Macaca fascicularis
```

<400> SEQUENCE: 127

Met Ala Leu Leu Leu Thr Met Val Ile Ala Leu Thr Cys Leu Gly Gly
1               5                   10                  15

Phe Ala Ser Pro
            20

<210> SEQ ID NO 128
<211> LENGTH: 329
<212> TYPE: PRT
<213> ORGANISM: Artificial Sequence
<220> FEATURE:
<223> OTHER INFORMATION: Synthetically generated peptide

<400> SEQUENCE: 128

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Lys
                85                  90                  95

Val Glu Pro Lys Ser Cys Asp Lys Thr His Thr Cys Pro Pro Cys Pro
            100                 105                 110

Ala Pro Glu Ala Leu Gly Ala Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys

<210> SEQ ID NO 129
<211> LENGTH: 360
<212> TYPE: DNA
<213> ORGANISM: Mus musculus

<400> SEQUENCE: 129
gaggttcagc tgcagcagtc tggggcagag cttgtgaagc caggggcctc agtcaagttg     60
tcctgcacag gttctggctt caacattaaa gacacctata tacactgggt gaagcagagg    120
cctgaacagg gcctggagtg gattggaagg attgatcctg cgaatgataa tattaaatat    180
gacccgaagt tccagggcaa ggccactata acagcagaca catcctccaa cacagcctac    240
ctacagctca acagcctgac atctgaggac actgccgtct attactgtgc tagatctgag    300
gaaaattggt acgactttt tgactactgg ggccaaggca ccactctcac agtctcctca    360

<210> SEQ ID NO 130
<211> LENGTH: 120
<212> TYPE: PRT
<213> ORGANISM: Mus musculus

<400> SEQUENCE: 130

Glu Val Gln Leu Gln Gln Ser Gly Ala Glu Leu Val Lys Pro Gly Ala
 1               5                  10                  15

Ser Val Lys Leu Ser Cys Thr Gly Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Asp Asn Ile Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Asn Ser Leu Thr Ser Glu Asp Thr Ala Val Tyr Tyr Cys
                85                  90                  95

Ala Arg Ser Glu Glu Asn Trp Tyr Asp Phe Phe Asp Tyr Trp Gly Gln
            100                 105                 110

Gly Thr Thr Leu Thr Val Ser Ser
        115                 120

<210> SEQ ID NO 131
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 131

Met Lys Cys Ser Trp Val Ile Phe Phe Leu Met Ala Val Val Thr Gly
 1               5                  10                  15

Val Asn Ser

<210> SEQ ID NO 132
<211> LENGTH: 336
<212> TYPE: DNA
<213> ORGANISM: Mus musculus

<400> SEQUENCE: 132
gatgttttga tgacccaaac tccactctcc ctgcctgtca gtcttggaga tcaagcctcc     60

```
atctcttgca ggtctagtca gagcattgta catagtaatg gaaacaccta tttagaatgg    120
tacctgcaga aaccaggcca gtctccaaag ctcctgatct acaaagtttc caaccgattt    180
tctggggtcc cagacaggtt cagtggcagt ggatcaggga cagatttcac actcaagatt    240
agcagagtgg aggctgagga tctgggagtt tattactgct ttcaaggttc acatattccg    300
tacacgttcg gaggggggac caagctggaa ataaaa                              336
```

<210> SEQ ID NO 133
<211> LENGTH: 112
<212> TYPE: PRT
<213> ORGANISM: Mus musculus

<400> SEQUENCE: 133

Asp Val Leu Met Thr Gln Thr Pro Leu Ser Leu Pro Val Ser Leu Gly
1               5                   10                  15
Asp Gln Ala Ser Ile Ser Cys Arg Ser Ser Gln Ser Ile Val His Ser
            20                  25                  30
Asn Gly Asn Thr Tyr Leu Glu Trp Tyr Leu Gln Lys Pro Gly Gln Ser
        35                  40                  45
Pro Lys Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Gly
                85                  90                  95
Ser His Ile Pro Tyr Thr Phe Gly Gly Gly Thr Lys Leu Glu Ile Lys
            100                 105                 110

<210> SEQ ID NO 134
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 134

Met Lys Leu Pro Val Arg Leu Leu Val Leu Met Phe Trp Ile Pro Ala
1               5                   10                  15
Ser Ser Ser

<210> SEQ ID NO 135
<211> LENGTH: 429
<212> TYPE: DNA
<213> ORGANISM: Mus musculus

<400> SEQUENCE: 135

```
atggctgtcc tggcattact cttctgcctg gtaacattcc caagctgtat cctttcccag     60
gtgcagctga aggagtcagg acctggcctg gtggcgccct cacagagcct gtccatcaca    120
tgcaccgtct cagggttctc attaaccggc tatggtgtaa actgggttcg ccagcctcca    180
ggaaagggtc tggagtggct gggaataatt tggggtgatg aagcacaga ctataattca    240 gctctcaaat ccagactgat catcaacaag acaactcca agagccaagt tttcttaaaa    300
atgaacagtc tgcaaactga tgacacagcc aggtacttct gtgccagaga taagactttt    360
tactacgatg gtttctacag gggcaggatg gactactggg gtcaaggaac ctcagtcacc    420
gtctcctca                                                            429
```

```
<210> SEQ ID NO 136
<211> LENGTH: 124
<212> TYPE: PRT
<213> ORGANISM: Mus musculus

<400> SEQUENCE: 136

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Ile Ile Trp Gly Asp Gly Ser Thr Asp Tyr Asn Ser Ala Leu Lys
    50                  55                  60

Ser Arg Leu Ile Ile Asn Lys Asp Asn Ser Lys Ser Gln Val Phe Leu
65                  70                  75                  80

Lys Met Asn Ser Leu Gln Thr Asp Asp Thr Ala Arg Tyr Phe Cys Ala
                85                  90                  95

Arg Asp Lys Thr Phe Tyr Tyr Asp Gly Phe Tyr Arg Gly Arg Met Asp
            100                 105                 110

Tyr Trp Gly Gln Gly Thr Ser Val Thr Val Ser Ser
        115                 120

<210> SEQ ID NO 137
<211> LENGTH: 124
<212> TYPE: PRT
<213> ORGANISM: Artificial Sequence
<220> FEATURE:
<223> OTHER INFORMATION: Synthetically generated peptide

<400> SEQUENCE: 137

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Ile Ile Trp Gly Asp Gly Ser Thr Asp Tyr Asn Ser Ala Leu Lys
    50                  55                  60

Ser Arg Leu Ile Ile Asn Lys Asp Asn Ser Lys Ser Gln Val Phe Leu
65                  70                  75                  80

Lys Met Asn Ser Leu Gln Thr Asp Asp Thr Ala Arg Tyr Phe Cys Ala
                85                  90                  95

Arg Asp Lys Thr Phe Tyr Tyr Asp Gly Phe Tyr Arg Gly Arg Met Asp
            100                 105                 110

Tyr Trp Gly Gln Gly Thr Ser Val Thr Val Ser Ser
        115                 120

<210> SEQ ID NO 138
<211> LENGTH: 387
<212> TYPE: DNA
<213> ORGANISM: Mus musculus

<400> SEQUENCE: 138
atgaacacga gggcccctgc tgagttcctt gggttcctgt tgctctggtt tttaggtgcc      60
agatgtgatg tccagatgat tcagtctcca tcctccctgt ctgcatcttt gggagacatt     120
gtcaccatga cttgccaggc aagtcagggc actagcatta atttaaactg gtttcagcaa     180
```

```
aaaccaggga aagctcctaa gctcctgatc tttggtgcaa gcaacttgga agatggggtc    240
ccatcaaggt tcagtggcag tagatatggg acaaatttca ctctcaccat cagcagcctg    300
gaggatgaag atatggcaac ttatttctgt ctacagcata gttatctccc gtggacgttc    360
ggtggcggca ccaaactgga aatcaaa                                        387
```

```
<210> SEQ ID NO 139
<211> LENGTH: 107
<212> TYPE: PRT
<213> ORGANISM: Mus musculus

<400> SEQUENCE: 139
```

Asp Val Gln Met Ile Gln Ser Pro Ser Ser Leu Ser Ala Ser Leu Gly
1               5                   10                  15

Asp Ile Val Thr Met Thr Cys Gln Ala Ser Gln Gly Thr Ser Ile Asn
            20                  25                  30

Leu Asn Trp Phe Gln Gln Lys Pro Gly Lys Ala Pro Lys Leu Leu Ile
        35                  40                  45

Phe Gly Ala Ser Asn Leu Glu Asp Gly Val Pro Ser Arg Phe Ser Gly
    50                  55                  60

Ser Arg Tyr Gly Thr Asn Phe Thr Leu Thr Ile Ser Ser Leu Glu Asp
65                  70                  75                  80

Glu Asp Met Ala Thr Tyr Phe Cys Leu Gln His Ser Tyr Leu Pro Trp
                85                  90                  95

Thr Phe Gly Gly Gly Thr Lys Leu Glu Ile Lys
            100                 105

```
<210> SEQ ID NO 140
<211> LENGTH: 22
<212> TYPE: PRT
<213> ORGANISM: Artificial Sequence
<220> FEATURE:
<223> OTHER INFORMATION: Synthetically generated peptide

<400> SEQUENCE: 140
```

Met Asn Thr Arg Ala Pro Ala Glu Phe Leu Gly Phe Leu Leu Trp
1               5                   10                  15

Phe Leu Gly Ala Arg Cys
            20

```
<210> SEQ ID NO 141
<211> LENGTH: 329
<212> TYPE: PRT
<213> ORGANISM: Homo sapiens

<400> SEQUENCE: 141
```

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Lys
                85                  90                  95

-continued

Val Glu Pro Lys Ser Cys Asp Lys Thr His Thr Cys Pro Pro Cys Pro
              100                 105                 110
Ala Pro Glu Ala Leu Gly Ala Pro Ser Val Phe Leu Phe Pro Pro Lys
          115                 120                 125
Pro Lys Asp Thr Leu Met Ile Ser Arg Thr Pro Glu Val Thr Cys Val
    130                 135                 140
Val Val Asp Val Ser His Glu Asp Pro Glu Val Lys Phe Asn Trp Tyr
145                 150                 155                 160
Val Asp Gly Val Glu Val His Asn Ala Lys Thr Lys Pro Arg Glu Glu
                165                 170                 175
Gln Tyr Asn Ser Thr Tyr Arg Val Val Ser Val Leu Thr Val Leu His
            180                 185                 190
Gln Asp Trp Leu Asn Gly Lys Glu Tyr Lys Cys Lys Val Ser Asn Lys
        195                 200                 205
Ala Leu Pro Ala Pro Ile Glu Lys Thr Ile Ser Lys Ala Lys Gly Gln
    210                 215                 220
Pro Arg Glu Pro Gln Val Tyr Thr Leu Pro Pro Ser Arg Glu Glu Met
225                 230                 235                 240
Thr Lys Asn Gln Val Ser Leu Thr Cys Leu Val Lys Gly Phe Tyr Pro
                245                 250                 255
Ser Asp Ile Ala Val Glu Trp Glu Ser Asn Gly Gln Pro Glu Asn Asn
            260                 265                 270
Tyr Lys Thr Thr Pro Pro Val Leu Asp Ser Asp Gly Ser Phe Phe Leu
        275                 280                 285
Tyr Ser Lys Leu Thr Val Asp Lys Ser Arg Trp Gln Gln Gly Asn Val
    290                 295                 300
Phe Ser Cys Ser Val Met His Glu Ala Leu His Asn His Tyr Thr Gln
305                 310                 315                 320
Lys Ser Leu Ser Leu Ser Pro Gly Lys
                325

<210> SEQ ID NO 142
<211> LENGTH: 417
<212> TYPE: DNA
<213> ORGANISM: Mus musculus

<400> SEQUENCE: 142
atgaaatgca gctgggttat cttcttcctg atggcagtgg ttacaggggt caattcagag    60
gttcagctgc agcagtctgg ggcagagctt gtgaagccag ggcctcagt caagttgtcc   120
tgcacaggtt ctggcttcaa cattaaagac acctatatac actgggtgaa gcagaggcct   180
gaacagggcc tggagtggat tggaaggatt gatcctgcga atgataatat taaatatgac   240
ccgaagttcc agggcaaggc cactataaca gcagacacat cctccaacac agcctaccta   300
cagctcaaca gcctgacatc tgaggacact gccgtctatt actgtgctag atctgaggaa   360
aattggtacg acttttttga ctactggggc caaggcacca ctctcacagt ctcctca     417

<210> SEQ ID NO 143
<211> LENGTH: 139
<212> TYPE: PRT
<213> ORGANISM: Mus musculus

<400> SEQUENCE: 143

Met Lys Cys Ser Trp Val Ile Phe Phe Leu Met Ala Val Val Thr Gly
  1               5                  10                  15
Val Asn Ser Glu Val Gln Leu Gln Gln Ser Gly Ala Glu Leu Val Lys

-continued

```
                 20                  25                  30
Pro Gly Ala Ser Val Lys Leu Ser Cys Thr Gly Ser Gly Phe Asn Ile
             35                  40                  45

Lys Asp Thr Tyr Ile His Trp Val Lys Gln Arg Pro Glu Gln Gly Leu
 50                  55                  60

Glu Trp Ile Gly Arg Ile Asp Pro Ala Asn Asp Asn Ile Lys Tyr Asp
 65                  70                  75                  80

Pro Lys Phe Gln Gly Lys Ala Thr Ile Thr Ala Asp Thr Ser Ser Asn
                 85                  90                  95

Thr Ala Tyr Leu Gln Leu Asn Ser Leu Thr Ser Glu Asp Thr Ala Val
                100                 105                 110

Tyr Tyr Cys Ala Arg Ser Glu Glu Asn Trp Tyr Asp Phe Phe Asp Tyr
                115                 120                 125

Trp Gly Gln Gly Thr Thr Leu Thr Val Ser Ser
                130                 135
```

<210> SEQ ID NO 144
<211> LENGTH: 393
<212> TYPE: DNA
<213> ORGANISM: Mus musculus

<400> SEQUENCE: 144

```
atgaagttgc ctgttaggct gttggtgctg atgttctgga ttcctgcttc cagcagtgat    60
gttttgatga cccaaactcc actctccctg cctgtcagtc ttggagatca agcctccatc   120
tcttgcaggt ctagtcagag cattgtacat agtaatggaa acacctattt agaatggtac   180
ctgcagaaac caggccagtc tccaaagctc ctgatctaca agtttccaa ccgattttct    240
ggggtcccag acaggttcag tggcagtgga tcagggacag atttcacact caagattagc   300
agagtggagg ctgaggatct gggagtttat tactgctttc aaggttcaca tattccgtac   360
acgttcggag gggggaccaa gctggaaata aaa                                 393
```

<210> SEQ ID NO 145
<211> LENGTH: 131
<212> TYPE: PRT
<213> ORGANISM: Mus musculus

<400> SEQUENCE: 145

```
Met Lys Leu Pro Val Arg Leu Leu Val Leu Met Phe Trp Ile Pro Ala
 1               5                  10                  15

Ser Ser Ser Asp Val Leu Met Thr Gln Thr Pro Leu Ser Leu Pro Val
                 20                  25                  30

Ser Leu Gly Asp Gln Ala Ser Ile Ser Cys Arg Ser Ser Gln Ser Ile
             35                  40                  45

Val His Ser Asn Gly Asn Thr Tyr Leu Glu Trp Tyr Leu Gln Lys Pro
 50                  55                  60

Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Val Tyr Tyr Cys
                100                 105                 110

Phe Gln Gly Ser His Ile Pro Tyr Thr Phe Gly Gly Gly Thr Lys Leu
                115                 120                 125

Glu Ile Lys
                130
```

<210> SEQ ID NO 146
<211> LENGTH: 417
<212> TYPE: DNA
<213> ORGANISM: Artificial Sequence
<220> FEATURE:
<223> OTHER INFORMATION: Synthetically generated oligonucleotide

<400> SEQUENCE: 146

```
atggattgga cctggcgcat cctgttcctg gtggccgctg ccaccggcgc tcactctcag    60
gtgcagctgg tgcagtctgg cgccgaggtg aagaagcctg gcgcttccgt gaaggtgtcc   120
tgtaaggcct ccggcttcaa catcaaggac acctacatcc actgggtgcg gcaggctccc   180
ggccagcggc tggagtggat gggccggatc gatcctgcca acgacaacat caagtacgac   240
cccaagtttc agggccgcgt gaccatcacc cgcgatacct ccgcttctac cgcctacatg   300
gagctgtcta gcctgcggag cgaggatacc gccgtgtact actgcgcccg ctccgaggag   360
aactggtacg acttcttcga ctactgggc agggcaccc tggtgaccgt gtcctct        417
```

<210> SEQ ID NO 147
<211> LENGTH: 144
<212> TYPE: PRT
<213> ORGANISM: Artificial Sequence
<220> FEATURE:
<223> OTHER INFORMATION: Synthetically generated peptide

<400> SEQUENCE: 147

```
Met Asp Trp Thr Trp Arg Ile Leu Phe Leu Val Ala Ala Thr Gly
  1               5                  10                  15

Ala His Ser Gln Val Gln Leu Val Gln Ser Gly Ala Glu Val Lys Lys
                 20                  25                  30

Pro Gly Ala Ser Val Lys Val Ser Cys Lys Ala Ser Gly Phe Asn Ile
             35                  40                  45

Lys Asp Thr Tyr Ile His Trp Val Arg Gln Ala Pro Gly Gln Arg Leu
     50                  55                  60

Glu Trp Met Gly Arg Ile Asp Pro Ala Asn Asp Asn Ile Lys Tyr Asp
 65                  70                  75                  80

Pro Lys Phe Gln Gly Arg Val Thr Ile Thr Arg Asp Thr Ser Ala Ser
                 85                  90                  95

Thr Ala Tyr Met Glu Leu Ser Ser Leu Arg Ser Glu Asp Thr Ala Val
            100                 105                 110

Tyr Tyr Cys Ala Arg Ser Glu Glu Asn Trp Tyr Asp Phe Phe Asp Tyr
        115                 120                 125

Trp Gly Gln Gly Thr Leu Val Thr Val Ser Ser Gly Glu Ser Cys Arg
    130                 135                 140
```

<210> SEQ ID NO 148
<211> LENGTH: 396
<212> TYPE: DNA
<213> ORGANISM: Artificial Sequence
<220> FEATURE:
<223> OTHER INFORMATION: Synthetically generated oligonucleotide

<400> SEQUENCE: 148

```
atgcggctgc ccgctcagct gctgggcctg ctgatgctgt gggtgccgg ctcttccggc     60
gacgtggtga tgacccagtc ccctctgtct ctgcccgtga cctgggcca gccgcttct    120
atctcttgcc ggtcctccca gtccatcgtg cactccaacg gcaacaccta cctggagtgg   180
tttcagcaga gacccggcca gtctcctcgg cggctgatct acaaggtgtc caaccgcttt   240
```

```
tccggcgtgc ccgatcggtt ctccggcagc ggctccggca ccgatttcac cctgaagatc      300
agccgcgtgg aggccgagga tgtgggcgtg tactactgct tccagggctc ccacatccct      360
tacacctttg gcggcggaac caaggtggag atcaag                                396
```

<210> SEQ ID NO 149
<211> LENGTH: 132
<212> TYPE: PRT
<213> ORGANISM: Artificial Sequence
<220> FEATURE:
<223> OTHER INFORMATION: Synthetically generated peptide

<400> SEQUENCE: 149

```
Met Arg Leu Pro Ala Gln Leu Leu Gly Leu Leu Met Leu Trp Val Pro
 1               5                  10                  15

Gly Ser Ser Gly Asp Val Val Met Thr Gln Ser Pro Leu Ser Leu Pro
            20                  25                  30

Val Thr Leu Gly Gln Pro Ala Ser Ile Ser Cys Arg Ser Ser Gln Ser
        35                  40                  45

Ile Val His Ser Asn Gly Asn Thr Tyr Leu Glu Trp Phe Gln Gln Arg
    50                  55                  60

Pro Gly Gln Ser Pro Arg Arg Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
           100                 105                 110

Cys Phe Gln Gly Ser His Ile Pro Tyr Thr Phe Gly Gly Gly Thr Lys
       115                 120                 125

Val Glu Ile Lys
       130
```

<210> SEQ ID NO 150
<211> LENGTH: 417
<212> TYPE: DNA
<213> ORGANISM: Artificial Sequence
<220> FEATURE:
<223> OTHER INFORMATION: Synthetically generated oligonucleotide

<400> SEQUENCE: 150

```
atggagctgg gcctgtcttg ggtgttcctg gtggctatcc tggagggcgt gcagtgcgag      60
gtgcagctgg tggagtctgg cggcggactg gtgcagcctg gcggctctct gcggctgtct     120
tgcgccgctt ccggcttcaa catcaaggac acctacatcc actgggtgcg gcaggctccc     180
ggcaagggcc tggagtgggt ggcccggatc gatcctgcca cgacaacat caagtacgac      240 cccaagttcc agggccggtt caccatctct gcgacaacg ccaagaactc cctgtacctc      300
cagatgaact ctctgcgcgc cgaggatacc gccgtgtact actgcgcccg gagcgaggag      360
aactggtacg acttcttcga ctactggggc cagggcaccc tggtgaccgt gtcctct        417
```

<210> SEQ ID NO 151
<211> LENGTH: 139
<212> TYPE: PRT
<213> ORGANISM: Artificial Sequence
<220> FEATURE:
<223> OTHER INFORMATION: Synthetically generated peptide

<400> SEQUENCE: 151

Met Glu Leu Gly Leu Ser Trp Val Phe Leu Val Ala Ile Leu Glu Gly

```
                1               5                  10                  15
        Val Gln Cys Glu Val Gln Leu Val Glu Ser Gly Gly Gly Leu Val Gln
                            20                  25                  30

Pro Gly Gly Ser Leu Arg Leu Ser Cys Ala Ala Ser Gly Phe Asn Ile
                        35                  40                  45

Lys Asp Thr Tyr Ile His Trp Val Arg Gln Ala Pro Gly Lys Gly Leu
                    50                  55                  60

Glu Trp Val Ala Arg Ile Asp Pro Ala Asn Asp Asn Ile Lys Tyr Asp
        65                  70                  75                  80

Pro Lys Phe Gln Gly Arg Phe Thr Ile Ser Arg Asp Asn Ala Lys Asn
                            85                  90                  95

Ser Leu Tyr Leu Gln Met Asn Ser Leu Arg Ala Glu Asp Thr Ala Val
                        100                 105                 110

Tyr Tyr Cys Ala Arg Ser Glu Glu Asn Trp Tyr Asp Phe Phe Asp Tyr
                    115                 120                 125

Trp Gly Gln Gly Thr Leu Val Thr Val Ser Ser
                130                 135

<210> SEQ ID NO 152
<211> LENGTH: 405
<212> TYPE: DNA
<213> ORGANISM: Artificial Sequence
<220> FEATURE:
<223> OTHER INFORMATION: Synthetically generated oligonucleotide

<400> SEQUENCE: 152
atggatatgc gcgtgcccgc tcagctgctg ggcctgctgc tgctgtggct gcgcggagcc      60
cgctgcgata tccagatgac ccagtcccct tcttctctgt ccgcctctgt gggcgatcgc     120
gtgaccatca cctgtcggtc ctcccagtcc atcgtgcact ccaacggcaa cacctacctg     180
gagtggtatc agcagaagcc cggcaaggcc cctaagctgc tgatctacaa ggtgtccaac     240
cgcttttccg gcgtgccttc tcggttctcc ggctccggct ccggcaccga tttcaccctg     300
accatctcct ccctccagcc cgaggatttc gccacctact actgcttcca gggctcccac     360
atcccttaca cctttggcgg cggaaccaag gtggagatca agcgt                      405

<210> SEQ ID NO 153
<211> LENGTH: 135
<212> TYPE: PRT
<213> ORGANISM: Artificial Sequence
<220> FEATURE:
<223> OTHER INFORMATION: Synthetically generated peptide

<400> SEQUENCE: 153

Met Asp Met Arg Val Pro Ala Gln Leu Leu Gly Leu Leu Leu Leu Trp
        1               5                  10                  15

Leu Arg Gly Ala Arg Cys Asp Ile Gln Met Thr Gln Ser Pro Ser Ser
                            20                  25                  30

Leu Ser Ala Ser Val Gly Asp Arg Val Thr Ile Thr Cys Arg Ser Ser
                        35                  40                  45

Gln Ser Ile Val His Ser Asn Gly Asn Thr Tyr Leu Glu Trp Tyr Gln
                    50                  55                  60

Gln Lys Pro Gly Lys Ala Pro Lys Leu Leu Ile Tyr Lys Val Ser Asn
        65                  70                  75                  80

Arg Phe Ser Gly Val Pro Ser Arg Phe Ser Gly Ser Gly Ser Gly Thr
                            85                  90                  95

Asp Phe Thr Leu Thr Ile Ser Ser Leu Gln Pro Glu Asp Phe Ala Thr
```

```
              100                 105                 110
Tyr Tyr Cys Phe Gln Gly Ser His Ile Pro Tyr Thr Phe Gly Gly Gly
        115                 120                 125

Thr Lys Val Glu Ile Lys Arg
    130                 135

<210> SEQ ID NO 154
<211> LENGTH: 360
<212> TYPE: DNA
<213> ORGANISM: Artificial Sequence
<220> FEATURE:
<223> OTHER INFORMATION: Synthetically generated oligonucleotide

<400> SEQUENCE: 154
gaggtgcagc tggtggagtc tggcggcgga ctggtgcagc ctggcggctc tctgcggctg      60
tcttgcgccg cttccggctt caacatcaag gacacctaca tccactgggt gcggcaggct    120
cccggcaagg gcctggagtg gatcggccgg atcgatcctg ccaacgacaa catcaagtac    180
gaccccaagt tccagggccg gttcaccatc tctcgcgaca cgccaagaa ctccctgtac     240 ctccagatga actctctgcg cgccgaggat accgccgtgt actactgcgc ccggagcgag    300
gagaactggt acgacttctt cgactactgg ggccagggca ccctggtgac cgtgtcctct    360

<210> SEQ ID NO 155
<211> LENGTH: 120
<212> TYPE: PRT
<213> ORGANISM: Artificial Sequence
<220> FEATURE:
<223> OTHER INFORMATION: Synthetically generated peptide

<400> SEQUENCE: 155

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Ile
         35                  40                  45

Gly Arg Ile Asp Pro Ala Asn Asp Asn Ile Lys Tyr Asp Pro Lys Phe
     50                  55                  60

Gln Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Glu Glu Asn Trp Tyr Asp Phe Phe Asp Tyr Trp Gly Gln
            100                 105                 110

Gly Thr Leu Val Thr Val Ser Ser
        115                 120

<210> SEQ ID NO 156
<211> LENGTH: 360
<212> TYPE: DNA
<213> ORGANISM: Artificial Sequence
<220> FEATURE:
<223> OTHER INFORMATION: Synthetically generated oligonucleotide

<400> SEQUENCE: 156
gaggtgcagc tggtggagtc tggcggcgga ctggtgcagc ctggcggctc tctgcggctg      60
tcttgcgccg cttccggctt caacatcaag gacacctaca tccactgggt gcggcaggct    120
cccggcaagg gcctggagtg ggtggcccgg atcgatcctg ccaacgacaa catcaagtac    180
```

-continued

```
gaccccaagt tccagggcaa ggccaccatc tctcgcgaca acgccaagaa ctccctgtac    240
ctccagatga actctctgcg cgccgaggat accgccgtgt actactgcgc cggagcgag    300 gagaactggt acgacttctt cgactactgg ggccagggca ccctggtgac cgtgtcctct   360
```

<210> SEQ ID NO 157
<211> LENGTH: 120
<212> TYPE: PRT
<213> ORGANISM: Artificial Sequence
<220> FEATURE:
<223> OTHER INFORMATION: Synthetically generated peptide

<400> SEQUENCE: 157

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Asp Pro Ala Asn Asp Asn Ile Lys Tyr Asp Pro Lys Phe
     50                  55                  60

Gln Gly Lys Ala Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Glu Glu Asn Trp Tyr Asp Phe Phe Asp Tyr Trp Gly Gln
            100                 105                 110

Gly Thr Leu Val Thr Val Ser Ser
        115                 120
```

<210> SEQ ID NO 158
<211> LENGTH: 360
<212> TYPE: DNA
<213> ORGANISM: Artificial Sequence
<220> FEATURE:
<223> OTHER INFORMATION: Synthetically generated oligonucleotide

<400> SEQUENCE: 158

```
gaggtgcagc tggtggagtc tggcggcgga ctggtgcagc ctggcggctc tctgcggctg    60
tcttgcgccg cttccggctt caacatcaag gacacctaca tccactgggt gcggcaggct   120
cccggcaagg gcctggagtg ggtggcccgg atcgatcctg ccaacgacaa catcaagtac   180
gaccccaagt tccagggccg gttcaccatc tctgccgaca cgccaagaa ctccctgtac    240 ctccagatga actctctgcg cgccgaggat accgccgtgt actactgcgc cggagcgag    300 gagaactggt acgacttctt cgactactgg ggccagggca ccctggtgac cgtgtcctct   360
```

<210> SEQ ID NO 159
<211> LENGTH: 120
<212> TYPE: PRT
<213> ORGANISM: Artificial Sequence
<220> FEATURE:
<223> OTHER INFORMATION: Synthetically generated peptide

<400> SEQUENCE: 159

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
             20                  25                  30
```

```
Tyr Ile His Trp Val Arg Gln Ala Pro Gly Lys Gly Leu Glu Trp Val
        35                  40                  45

Ala Arg Ile Asp Pro Ala Asn Asp Asn Ile Lys Tyr Asp Pro Lys Phe
 50                  55                  60

Gln Gly Arg Phe Thr Ile Ser Ala Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Glu Glu Asn Trp Tyr Asp Phe Phe Asp Tyr Trp Gly Gln
            100                 105                 110

Gly Thr Leu Val Thr Val Ser Ser
            115                 120
```

<210> SEQ ID NO 160
<211> LENGTH: 360
<212> TYPE: DNA
<213> ORGANISM: Artificial Sequence
<220> FEATURE:
<223> OTHER INFORMATION: Synthetically generated oligonucleotide

<400> SEQUENCE: 160

```
gaggtgcagc tggtggagtc tggcggcgga ctggtgcagc ctggcggctc tctgcggctg      60
tcttgcgccg cttccggctt caacatcaag gacacctaca tccactgggt gcggcaggct     120
cccggcaagg gcctggagtg ggtgggccgg atcgatcctg ccaacgacaa catcaagtac     180
gaccccaagt tccagggccg gttcaccatc tctgcgaca acgccaagaa ctccctgtac      240
ctccagatga actctctgcg cgccgaggat accgccgtgt actactgcgc ccggagcgag     300
gagaactggt acgacttctt cgactactgg ggccagggca ccctggtgac cgtgtcctct     360
```

<210> SEQ ID NO 161
<211> LENGTH: 120
<212> TYPE: PRT
<213> ORGANISM: Artificial Sequence
<220> FEATURE:
<223> OTHER INFORMATION: Synthetically generated peptide

<400> SEQUENCE: 161

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Gly Arg Ile Asp Pro Ala Asn Asp Asn Ile Lys Tyr Asp Pro Lys Phe
 50                  55                  60

Gln Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Glu Glu Asn Trp Tyr Asp Phe Phe Asp Tyr Trp Gly Gln
            100                 105                 110

Gly Thr Leu Val Thr Val Ser Ser
            115                 120
```

<210> SEQ ID NO 162
<211> LENGTH: 360
<212> TYPE: DNA
<213> ORGANISM: Artificial Sequence
<220> FEATURE:
<223> OTHER INFORMATION: Synthetically generated oligonucleotide

<400> SEQUENCE: 162

```
gaggtgcagc tggtggagtc tggcggcgga ctggtgcagc ctggcggctc tctgcggctg    60
tcttgcgccg cttccggctt caacatcaag gacacctaca tccactgggt gcggcaggct   120
cccggcaagg gcctggagtg ggtggcccgg atcgatcctg ccaacgacaa catcaagtac   180
gaccccaagt tccagggcaa ggccaccatc tctgccgaca cgccaagaa ctccctgtac    240
ctccagatga actctctgcg cgccgaggat accgccgtgt actactgcgc ccggagcgag   300
gagaactggt acgacttctt cgactactgg ggccagggca cctggtgac cgtgtcctct    360
```

<210> SEQ ID NO 163
<211> LENGTH: 120
<212> TYPE: PRT
<213> ORGANISM: Artificial Sequence
<220> FEATURE:
<223> OTHER INFORMATION: Synthetically generated peptide

<400> SEQUENCE: 163

```
Glu Val Gln Leu Val Glu Ser Gly Gly Gly Leu Val Gln Pro Gly Gly
  1               5                  10                  15
Ser Leu Arg Leu Ser Cys Ala Ala Ser Gly Phe Asn Ile Lys Asp Thr
             20                  25                  30
Tyr Ile His Trp Val Arg Gln Ala Pro Gly Lys Gly Leu Glu Trp Val
         35                  40                  45
Ala Arg Ile Asp Pro Ala Asn Asp Asn Ile Lys Tyr Asp Pro Lys Phe
     50                  55                  60
Gln Gly Lys Ala Thr Ile Ser Ala Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg Ser Glu Glu Asn Trp Tyr Asp Phe Phe Asp Tyr Trp Gly Gln
            100                 105                 110
Gly Thr Leu Val Thr Val Ser Ser
        115                 120
```

<210> SEQ ID NO 164
<211> LENGTH: 360
<212> TYPE: DNA
<213> ORGANISM: Artificial Sequence
<220> FEATURE:
<223> OTHER INFORMATION: Synthetically generated oligonucleotide

<400> SEQUENCE: 164

```
gaggtgcagc tggtggagtc tggcggcgga ctggtgcagc ctggcggctc tctgcggctg    60
tcttgcgccg cttccggctt caacatcaag gacacctaca tccactgggt gcggcaggct   120
cccggcaagg gcctggagtg gatcggccgg atcgatcctg ccaacgacaa catcaagtac   180
gaccccaagt tccagggccg gttcaccatc tctgccgaca cgccaagaa ctccctgtac    240
ctccagatga actctctgcg cgccgaggat accgccgtgt actactgcgc ccggagcgag   300
gagaactggt acgacttctt cgactactgg ggccagggca cctggtgac cgtgtcctct    360
```

<210> SEQ ID NO 165
<211> LENGTH: 120
<212> TYPE: PRT
<213> ORGANISM: Artificial Sequence
<220> FEATURE:

<223> OTHER INFORMATION: Synthetically generated peptide

<400> SEQUENCE: 165

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Ile
        35                  40                  45
Gly Arg Ile Asp Pro Ala Asn Asp Asn Ile Lys Tyr Asp Pro Lys Phe
    50                  55                  60
Gln Gly Arg Phe Thr Ile Ser Ala Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Ser Glu Glu Asn Trp Tyr Asp Phe Phe Asp Tyr Trp Gly Gln
            100                 105                 110
Gly Thr Leu Val Thr Val Ser Ser
        115                 120
```

<210> SEQ ID NO 166
<211> LENGTH: 360
<212> TYPE: DNA
<213> ORGANISM: Artificial Sequence
<220> FEATURE:
<223> OTHER INFORMATION: Synthetically generated oligonucleotide

<400> SEQUENCE: 166

```
gaggtgcagc tggtggagtc tggcggcgga ctggtgcagc ctggcggctc tctgcggctg      60
tcttgcgccg cttccggctt caacatcaag gacacctaca tccactgggt gcggcaggct     120
cccggcaagg gcctggagtg ggtgggccgg atcgatcctg ccaacgacaa catcaagtac     180
gaccccaagt tccagggccg gttcaccatc tctgccgaca acgccaagaa ctccctgtac     240
ctccagatga actctctgcg cgccgaggat accgccgtgt actactgcgc ccggagcgag     300
gagaactggt acgacttctt cgactactgg ggccagggca cctggtgac cgtgtcctct     360
```

<210> SEQ ID NO 167
<211> LENGTH: 120
<212> TYPE: PRT
<213> ORGANISM: Artificial Sequence
<220> FEATURE:
<223> OTHER INFORMATION: Synthetically generated peptide

<400> SEQUENCE: 167

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
        35                  40                  45
Gly Arg Ile Asp Pro Ala Asn Asp Asn Ile Lys Tyr Asp Pro Lys Phe
    50                  55                  60
Gln Gly Arg Phe Thr Ile Ser Ala Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Ser Glu Glu Asn Trp Tyr Asp Phe Phe Asp Tyr Trp Gly Gln
```

<210> SEQ ID NO 168
<211> LENGTH: 360
<212> TYPE: DNA
<213> ORGANISM: Artificial Sequence
<220> FEATURE:
<223> OTHER INFORMATION: Synthetically generated oligonucleotide

<400> SEQUENCE: 168

```
gaggtgcagc tggtggagtc tggcggcgga ctggtgcagc ctggcggctc tctgcggctg      60
tcttgcgccg cttccggctt caacatcaag gacacctaca tccactgggt gcggcaggct     120
cccggcaagg gcctggagtg ggtggcccgg atcgatcctg ccaacgacaa catcaagtac     180
gaccccaagt tccagggccg gttcaccatc tctcgcgaca cgccaagaa ctccgcctac     240
ctccagatga actctctgcg cgccgaggat accgccgtgt actactgcgc ccggagcgag     300
gagaactggt acgacttctt cgactactgg ggccagggca ccctggtgac cgtgtcctct     360
```

<210> SEQ ID NO 169
<211> LENGTH: 120
<212> TYPE: PRT
<213> ORGANISM: Artificial Sequence
<220> FEATURE:
<223> OTHER INFORMATION: Synthetically generated peptide

<400> SEQUENCE: 169

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Asp Pro Ala Asn Asp Asn Ile Lys Tyr Asp Pro Lys Phe
    50                  55                  60

Gln Gly Arg Phe Thr Ile Ser Arg Asp Asn Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Ser Glu Glu Asn Trp Tyr Asp Phe Phe Asp Tyr Trp Gly Gln
            100                 105                 110

Gly Thr Leu Val Thr Val Ser Ser
        115                 120

<210> SEQ ID NO 170
<211> LENGTH: 360
<212> TYPE: DNA
<213> ORGANISM: Artificial Sequence
<220> FEATURE:
<223> OTHER INFORMATION: Synthetically generated oligonucleotide

<400> SEQUENCE: 170

```
gaggtgcagc tggtggagtc tggcggcgga ctggtgcagc ctggcggctc tctgcggctg      60
tcttgcgccg cttccggctt caacatcaag gacacctaca tccactgggt gcggcaggct     120
cccggcaagg gcctggagtg ggtgggccgg atcgatcctg ccaacgacaa catcaagtac     180
gaccccaagt tccagggccg gttcaccatc tctgccgaca cgccaagaa ctccgcctac     240
```

```
ctccagatga actctctgcg cgccgaggat accgccgtgt actactgcgc cggagcgag    300 gagaactggt acgacttctt cgactactgg ggccagggca ccctggtgac cgtgtcctct    360
```

<210> SEQ ID NO 171
<211> LENGTH: 120
<212> TYPE: PRT
<213> ORGANISM: Artificial Sequence
<220> FEATURE:
<223> OTHER INFORMATION: Synthetically generated peptide

<400> SEQUENCE: 171

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Gly Arg Ile Asp Pro Ala Asn Asp Asn Ile Lys Tyr Asp Pro Lys Phe
    50                  55                  60

Gln Gly Arg Phe Thr Ile Ser Ala Asp Asn Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Ser Glu Glu Asn Trp Tyr Asp Phe Phe Asp Tyr Trp Gly Gln
            100                 105                 110

Gly Thr Leu Val Thr Val Ser Ser
        115                 120

<210> SEQ ID NO 172
<211> LENGTH: 360
<212> TYPE: DNA
<213> ORGANISM: Artificial Sequence
<220> FEATURE:
<223> OTHER INFORMATION: Synthetically generated oligonucleotide

<400> SEQUENCE: 172

```
gaggtgcagc tggtggagtc tggcggcgga ctggtgcagc ctggcggctc tctgcggctg     60
tcttgcgccg cttccggctt caacatcaag gacacctaca tccactgggt gcggcaggct    120 ccccggcaagg gcctggagtg gatcggccgg atcgatcctg ccaacgacaa catcaagtac    180
gaccccaagt tccagggccg gttcaccatc tctgccgaca acgccaagaa ctccgcctac    240
ctccagatga actctctgcg cgccgaggat accgccgtgt actactgcgc cggagcgag    300 gagaactggt acgacttctt cgactactgg ggccagggca ccctggtgac cgtgtcctct    360
```

<210> SEQ ID NO 173
<211> LENGTH: 120
<212> TYPE: PRT
<213> ORGANISM: Artificial Sequence
<220> FEATURE:
<223> OTHER INFORMATION: Synthetically generated peptide

<400> SEQUENCE: 173

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Ile
        35                  40                  45

```
Gly Arg Ile Asp Pro Ala Asn Asp Asn Ile Lys Tyr Asp Pro Lys Phe
    50                  55                  60

Gln Gly Arg Phe Thr Ile Ser Ala Asp Asn Ala Lys Asn Ser Ala Tyr
 65                  70                  75                  80

Leu Gln Met Asn Ser Leu Arg Ala Glu Asp Thr Ala Val Tyr Tyr Cys
                 85                  90                  95

Ala Arg Ser Glu Glu Asn Trp Tyr Asp Phe Phe Asp Tyr Trp Gly Gln
                100                 105                 110

Gly Thr Leu Val Thr Val Ser Ser
            115                 120

<210> SEQ ID NO 174
<211> LENGTH: 360
<212> TYPE: DNA
<213> ORGANISM: Artificial Sequence
<220> FEATURE:
<223> OTHER INFORMATION: Synthetically generated oligonucleotide

<400> SEQUENCE: 174
gaggtgcagc tggtggagtc tggcggcgga ctggtgcagc ctggcggctc tctgcggctg      60
tcttgcaccg gctccggctt caacatcaag gacacctaca tccactgggt gcggcaggct     120
cccggcaagg gcctggagtg gatcggccgg atcgatcctg ccaacgacaa catcaagtac     180
gaccccaagt tccagggccg gttcaccatc tctgccgaca acgccaagaa ctccctgtac     240
ctccagatga actctctgcg cgccgaggat accgccgtgt actactgcgc ccggagcgag     300
gagaactggt acgacttctt cgactactgg ggccagggca ccctggtgac cgtgtcctct     360

<210> SEQ ID NO 175
<211> LENGTH: 120
<212> TYPE: PRT
<213> ORGANISM: Artificial Sequence
<220> FEATURE:
<223> OTHER INFORMATION: Synthetically generated peptide

<400> SEQUENCE: 175

Glu Val Gln Leu Val Glu Ser Gly Gly Gly Leu Val Gln Pro Gly Gly
  1               5                  10                  15

Ser Leu Arg Leu Ser Cys Thr Gly Ser Gly Phe Asn Ile Lys Asp Thr
                 20                  25                  30

Tyr Ile His Trp Val Arg Gln Ala Pro Gly Lys Gly Leu Glu Trp Ile
             35                  40                  45

Gly Arg Ile Asp Pro Ala Asn Asp Asn Ile Lys Tyr Asp Pro Lys Phe
    50                  55                  60

Gln Gly Arg Phe Thr Ile Ser Ala Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Glu Glu Asn Trp Tyr Asp Phe Phe Asp Tyr Trp Gly Gln
                100                 105                 110

Gly Thr Leu Val Thr Val Ser Ser
            115                 120

<210> SEQ ID NO 176
<211> LENGTH: 450
<212> TYPE: PRT
<213> ORGANISM: Artificial Sequence
<220> FEATURE:
<223> OTHER INFORMATION: Synthetically generated peptide
```

```
<400> SEQUENCE: 176

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Ile
        35                  40                  45

Gly Arg Ile Asp Pro Ala Asn Asp Asn Ile Lys Tyr Asp Pro Lys Phe
    50                  55                  60

Gln Gly Arg Phe Thr Ile Ser Ala Asp Asn Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Ser Glu Glu Asn Trp Tyr Asp Phe Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Leu Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 177
<211> LENGTH: 219
<212> TYPE: PRT
<213> ORGANISM: Artificial Sequence
<220> FEATURE:
<223> OTHER INFORMATION: Synthetically generated peptide

<400> SEQUENCE: 177

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Val His Ser
            20                  25                  30

Asn Gly Asn Thr Tyr Leu Glu Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser His Ile Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 178
<211> LENGTH: 132
<212> TYPE: PRT
<213> ORGANISM: Homo sapiens

<400> SEQUENCE: 178

Met Ala Leu Leu Leu Thr Thr Val Ile Ala Leu Thr Cys Leu Gly Gly
1               5                   10                  15

Phe Ala Ser Pro Gly Pro Val Pro Pro Ser Thr Ala Leu Arg Glu Leu
            20                  25                  30

Ile Glu Glu Leu Val Asn Ile Thr Gln Asn Gln Lys Ala Pro Leu Cys
        35                  40                  45
```

-continued

```
Asn Gly Ser Met Val Trp Ser Ile Asn Leu Thr Ala Gly Met Tyr Cys
 50                  55                  60
Ala Ala Leu Glu Ser Leu Ile Asn Val Ser Gly Cys Ser Ala Ile Glu
 65                  70                  75                  80
Lys Thr Gln Arg Met Leu Ser Gly Phe Cys Pro His Lys Val Ser Ala
                 85                  90                  95
Gly Gln Phe Ser Ser Leu His Val Arg Asp Thr Lys Ile Glu Val Ala
            100                 105                 110
Gln Phe Val Lys Asp Leu Leu Leu His Leu Lys Lys Leu Phe Arg Glu
        115                 120                 125
Gly Arg Phe Asn
        130

<210> SEQ ID NO 179
<211> LENGTH: 13
<212> TYPE: PRT
<213> ORGANISM: Macaca fascicularis

<400> SEQUENCE: 179

Met Ala Leu Leu Leu Thr Met Val Ile Ala Leu Thr Cys
 1               5                  10

<210> SEQ ID NO 180
<211> LENGTH: 12
<212> TYPE: PRT
<213> ORGANISM: Macaca fascicularis

<400> SEQUENCE: 180

Leu Gly Gly Phe Ala Ser Pro Ser Pro Val Pro Pro
 1               5                  10

<210> SEQ ID NO 181
<211> LENGTH: 17
<212> TYPE: PRT
<213> ORGANISM: Macaca fascicularis

<400> SEQUENCE: 181

Ser Pro Ser Pro Val Pro Pro Ser Thr Ala Leu Lys Glu Leu Ile Glu
 1               5                  10                  15
Glu

<210> SEQ ID NO 182
<211> LENGTH: 19
<212> TYPE: PRT
<213> ORGANISM: Macaca fascicularis

<400> SEQUENCE: 182

Thr Ala Leu Lys Glu Leu Ile Glu Glu Leu Val Asn Ile Thr Gln Asn
 1               5                  10                  15
Gln Lys Ala

<210> SEQ ID NO 183
<211> LENGTH: 22
<212> TYPE: PRT
<213> ORGANISM: Macaca fascicularis

<400> SEQUENCE: 183

Asn Gln Lys Ala Pro Leu Cys Asn Gly Ser Met Val Trp Ser Ile Asn
 1               5                  10                  15
Leu Thr Ala Gly Val Tyr
            20
```

<210> SEQ ID NO 184
<211> LENGTH: 21
<212> TYPE: PRT
<213> ORGANISM: Macaca fascicularis

<400> SEQUENCE: 184

Ile Asn Leu Thr Ala Gly Val Tyr Cys Ala Ala Leu Glu Ser Leu Ile
1               5                   10                  15

Asn Val Ser Gly Cys
            20

<210> SEQ ID NO 185
<211> LENGTH: 21
<212> TYPE: PRT
<213> ORGANISM: Macaca fascicularis

<400> SEQUENCE: 185

Ser Leu Ile Asn Val Ser Gly Cys Ser Ala Ile Glu Lys Thr Gln Arg
1               5                   10                  15

Met Ile Asn Gly Phe
            20

<210> SEQ ID NO 186
<211> LENGTH: 18
<212> TYPE: PRT
<213> ORGANISM: Macaca fascicularis

<400> SEQUENCE: 186

Gly Phe Cys Pro His Lys Val Ser Ala Gly Gln Phe Ser Ser Leu Arg
1               5                   10                  15

Val Arg

<210> SEQ ID NO 187
<211> LENGTH: 20
<212> TYPE: PRT
<213> ORGANISM: Macaca fascicularis

<400> SEQUENCE: 187

Val Arg Asp Thr Lys Ile Glu Val Ala Gln Phe Val Lys Asp Leu Leu
1               5                   10                  15

Val His Leu Lys
            20

<210> SEQ ID NO 188
<211> LENGTH: 19
<212> TYPE: PRT
<213> ORGANISM: Macaca fascicularis

<400> SEQUENCE: 188

Phe Val Lys Asp Leu Leu Val His Leu Lys Lys Leu Phe Arg Glu Gly
1               5                   10                  15

Gln Phe Asn

<210> SEQ ID NO 189
<211> LENGTH: 396
<212> TYPE: DNA
<213> ORGANISM: Artificial Sequence
<220> FEATURE:
<223> OTHER INFORMATION: Synthetically generated oligonucleotide

<400> SEQUENCE: 189

```
atgcggctgc cgctcagct gctgggcctg ctgatgctgt gggtgcccgg ctcttccggc    60
gacgtggtga tgacccagtc ccctctgtct ctgcccgtga ccctgggcca gcccgcttct   120
atctcttgcc ggtcctccca gtccctggta tactccgacg gcaacaccta cctgaactgg   180
ttccagcaga gacccggcca gtctcctcgg cggctgatct acaaggtgtc caaccgcttt   240
tccggcgtgc ccgatcggtt ctccggctcc ggcagcggca ccgatttcac cctgaagatc   300
agccgcgtgg aggccgagga tgtgggcgtg tactactgct ccagggctc ccacatccct   360 tacacctttg gcggcggaac caaggtggag atcaag                             396
```

<210> SEQ ID NO 190
<211> LENGTH: 132
<212> TYPE: PRT
<213> ORGANISM: Artificial Sequence
<220> FEATURE:
<223> OTHER INFORMATION: Synthetically generated peptide

<400> SEQUENCE: 190

```
Met Arg Leu Pro Ala Gln Leu Leu Gly Leu Leu Met Leu Trp Val Pro
  1               5                  10                  15

Gly Ser Ser Gly Asp Val Val Met Thr Gln Ser Pro Leu Ser Leu Pro
             20                  25                  30

Val Thr Leu Gly Gln Pro Ala Ser Ile Ser Cys Arg Ser Ser Gln Ser
         35                  40                  45

Leu Val Tyr Ser Asp Gly Asn Thr Tyr Leu Asn Trp Phe Gln Gln Arg
     50                  55                  60

Pro Gly Gln Ser Pro Arg Arg Leu Ile Tyr Lys Val Ser Asn Arg Phe
 65                  70                  75                  80

Ser Gly Val Pro Asp Arg Phe Ser Gly Ser Gly Ser Gly Thr Asp Phe
                 85                  90                  95

Thr Leu Lys Ile Ser Arg Val Glu Ala Glu Asp Val Gly Val Tyr Tyr
            100                 105                 110

Cys Phe Gln Gly Ser His Ile Pro Tyr Thr Phe Gly Gly Gly Thr Lys
        115                 120                 125

Val Glu Ile Lys
        130
```

<210> SEQ ID NO 191
<211> LENGTH: 336
<212> TYPE: DNA
<213> ORGANISM: Artificial Sequence
<220> FEATURE:
<223> OTHER INFORMATION: Synthetically generated oligonucleotide

<400> SEQUENCE: 191

```
gatgttgtga tgacccaatc tccactctcc ctgcctgtca ctcctggaga gccagcctcc    60
atctcttgca gatctagtca gagcattgtg catagtaatg aaacacccta cctgaatgg   120 tacctgcaga aaccaggcca gtctccacag ctcctgatct acaaagtttc caaccgattt   180
tctggggtcc cagacaggtt cagtggcagt ggatcaggga cagatttcac actcaagatc   240
agcagagtgg aggctgagga tgtgggagtt tattactgct ttcaaagttc acatgttcct   300
ctcaccttcg gtcaggggac caagctggag atcaaa                             336
```

<210> SEQ ID NO 192
<211> LENGTH: 112
<212> TYPE: PRT
<213> ORGANISM: Artificial Sequence
<220> FEATURE:

-continued

```
<223> OTHER INFORMATION: Synthetically generated peptide

<400> SEQUENCE: 192

Asp Val Val Met Thr Gln Ser Pro Leu Ser Leu Pro Val Thr Pro Gly
 1               5                  10                  15

Glu Pro Ala Ser Ile Ser Cys Arg Ser Ser Gln Ser Ile Val His Ser
             20                  25                  30

Asn Gly Asn Thr Tyr Leu Glu Trp Tyr Leu Gln Lys Pro Gly Gln Ser
         35                  40                  45

Pro Gln Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Ser
             85                  90                  95

Ser His Val Pro Leu Thr Phe Gly Gln Gly Thr Lys Leu Glu Ile Lys
            100                 105                 110
```